(12) United States Patent
Flynn et al.

(10) Patent No.: US 9,133,183 B2
(45) Date of Patent: Sep. 15, 2015

(54) IMIDAZOLIDINONES AND ANALOGS EXHIBITING ANTI-CANCER AND ANTI-PROLIFERATIVE ACTIVITIES

(71) Applicant: Deciphera Pharmaceuticals, LLC, Lawrence, KS (US)

(72) Inventors: Daniel L. Flynn, Lawrence, KS (US); Michael D. Kaufman, Lawrence, KS (US); Thiwanka Samarakoon, Quincy, MA (US); Timothy Malcolm Caldwell, Fishers, IN (US); Lakshminarayana Vogeti, Arlington, MA (US); YuMi Ahn, Lawrence, KS (US); William C. Patt, Lawrence, KS (US); Karen M. Yates, Fishers, IN (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

(21) Appl. No.: 14/214,134

(22) Filed: Mar. 14, 2014

(65) Prior Publication Data

US 2014/0315917 A1    Oct. 23, 2014

Related U.S. Application Data

(60) Provisional application No. 61/788,374, filed on Mar. 15, 2013.

(51) Int. Cl.
| | |
|---|---|
| *A61K 31/497* | (2006.01) |
| *C07D 417/14* | (2006.01) |
| *C07D 401/14* | (2006.01) |
| *C07D 405/14* | (2006.01) |
| *C07D 413/14* | (2006.01) |

(52) U.S. Cl.
CPC ............ *C07D 417/14* (2013.01); *C07D 401/14* (2013.01); *C07D 405/14* (2013.01); *C07D 413/14* (2013.01)

(58) Field of Classification Search
None
See application file for complete search history.

(56) References Cited

U.S. PATENT DOCUMENTS

| | | |
|---|---|---|
| 2008/0214544 A1 | 9/2008 | Bellon et al. |
| 2008/0255155 A1 | 10/2008 | Raeppel et al. |

FOREIGN PATENT DOCUMENTS

| | | |
|---|---|---|
| WO | WO2010/051373 A1 | 5/2010 |

OTHER PUBLICATIONS

PCT International Search Report from corresponding International Application No. PCT/US2014/029650 dated Oct. 29, 2014.

*Primary Examiner* — Heidi Reese
(74) *Attorney, Agent, or Firm* — Cooley LLP

(57) ABSTRACT

Described are compounds of Formula I

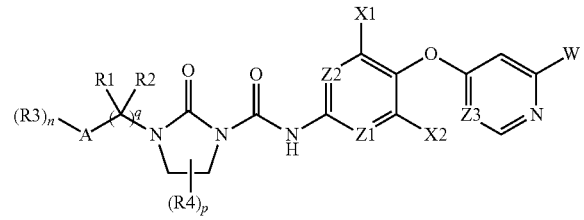

Formula I which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

32 Claims, No Drawings

SEQUENCE LISTING

```
<160> NUMBER OF SEQ ID NOS: 3

<210> SEQ ID NO 1
<211> LENGTH: 435
<212> TYPE: PRT
<213> ORGANISM: Homo sapiens

<400> SEQUENCE: 1

Tyr Lys Tyr Lys Gln Lys Pro Lys Tyr Gln Val Arg Trp Lys Ile Ile
1               5                   10                  15

Glu Ser Tyr Glu Gly Asn Ser Tyr Thr Phe Ile Asp Pro Thr Gln Leu
            20                  25                  30

Pro Tyr Asn Glu Lys Trp Glu Phe Pro Arg Asn Asn Leu Gln Phe Gly
        35                  40                  45

Lys Thr Leu Gly Ala Gly Ala Phe Gly Lys Val Val Glu Ala Thr Ala
    50                  55                  60

Phe Gly Leu Gly Lys Glu Asp Ala Val Leu Lys Val Ala Val Lys Met
65                  70                  75                  80

Leu Lys Ser Thr Ala His Ala Asp Glu Lys Glu Ala Leu Met Ser Glu
                85                  90                  95

Leu Lys Ile Met Ser His Leu Gly Gln His Glu Asn Ile Val Asn Leu
            100                 105                 110

Leu Gly Ala Cys Thr His Gly Gly Pro Val Leu Val Ile Thr Glu Tyr
        115                 120                 125

Cys Cys Tyr Gly Asp Leu Leu Asn Phe Leu Arg Arg Lys Ala Glu Ala
130                 135                 140

Met Leu Gly Pro Ser Leu Ser Pro Gly Gln Asp Pro Glu Gly Gly Val
145                 150                 155                 160

Asp Tyr Lys Asn Ile His Leu Glu Lys Lys Tyr Val Arg Arg Asp Ser
                165                 170                 175

Gly Phe Ser Ser Gln Gly Val Asp Thr Tyr Val Glu Met Arg Pro Val
            180                 185                 190

Ser Thr Ser Ser Asn Asp Ser Phe Ser Glu Gln Asp Leu Asp Lys Glu
        195                 200                 205

Asp Gly Arg Pro Leu Glu Leu Arg Asp Leu Leu His Phe Ser Ser Gln
    210                 215                 220

Val Ala Gln Gly Met Ala Phe Leu Ala Ser Lys Asn Cys Ile His Arg
225                 230                 235                 240

Asp Val Ala Ala Arg Asn Val Leu Leu Thr Asn Gly His Val Ala Lys
                245                 250                 255

Ile Gly Asp Phe Gly Leu Ala Arg Asp Ile Met Asn Asp Ser Asn Tyr
            260                 265                 270

Ile Val Lys Gly Asn Ala Arg Leu Pro Val Lys Trp Met Ala Pro Glu
        275                 280                 285

Ser Ile Phe Asp Cys Val Tyr Thr Val Gln Ser Asp Val Trp Ser Tyr
    290                 295                 300

Gly Ile Leu Leu Trp Glu Ile Phe Ser Leu Gly Leu Asn Pro Tyr Pro
305                 310                 315                 320

Gly Ile Leu Val Asn Ser Lys Phe Tyr Lys Leu Val Lys Asp Gly Tyr
                325                 330                 335
```

```
Gln Met Ala Gln Pro Ala Phe Ala Pro Lys Asn Ile Tyr Ser Ile Met
            340                 345                 350

Gln Ala Cys Trp Ala Leu Glu Pro Thr His Arg Pro Thr Phe Gln Gln
        355                 360                 365

Ile Cys Ser Phe Leu Gln Glu Gln Ala Gln Glu Asp Arg Arg Glu Arg
    370                 375                 380

Asp Tyr Thr Asn Leu Pro Ser Ser Arg Ser Gly Gly Ser Gly Ser
385                 390                 395                 400

Ser Ser Ser Glu Leu Glu Glu Ser Ser Glu His Leu Thr Cys
                405                 410                 415

Cys Glu Gln Gly Asp Ile Ala Gln Pro Leu Leu Gln Pro Asn Asn Tyr
            420                 425                 430

Gln Phe Cys
        435

<210> SEQ ID NO 2
<211> LENGTH: 676
<212> TYPE: PRT
<213> ORGANISM: Homo sapiens

<400> SEQUENCE: 2

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
    130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
    210                 215                 220

Tyr Lys Lys Ala Gly Ser Ala Ala Val Leu Glu Gly Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270
```

```
Pro Thr Gln Leu Pro Tyr Asp His Lys Trp Glu Phe Pro Arg Asn Arg
            275                 280                 285

Leu Ser Phe Gly Lys Thr Leu Gly Ala Gly Ala Phe Gly Lys Val Val
290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
            325                 330                 335

Leu Met Ser Glu Leu Lys Val Leu Ser Tyr Leu Gly Asn His Met Asn
            340                 345                 350

Ile Val Asn Leu Leu Gly Ala Cys Thr Ile Gly Gly Pro Thr Leu Val
            355                 360                 365

Ile Thr Glu Tyr Cys Cys Tyr Gly Asp Leu Leu Asn Phe Leu Arg Arg
            370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
            405                 410                 415

Ser Thr Asn Glu Tyr Met Asp Met Lys Pro Gly Val Ser Tyr Val Val
            420                 425                 430

Pro Thr Lys Ala Asp Lys Arg Arg Ser Val Arg Ile Gly Ser Tyr Ile
            435                 440                 445

Glu Arg Asp Val Thr Pro Ala Ile Met Glu Asp Asp Glu Leu Ala Leu
450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
            485                 490                 495

Asn Ile Leu Leu Thr His Gly Arg Ile Thr Lys Ile Cys Asp Phe Gly
            500                 505                 510

Leu Ala Arg Asp Ile Lys Asn Asp Ser Asn Tyr Val Val Lys Gly Asn
            515                 520                 525

Ala Arg Leu Pro Val Lys Trp Met Ala Pro Glu Ser Ile Phe Asn Cys
            530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
            565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
            595                 600                 605

Ala Asp Pro Leu Lys Arg Pro Thr Phe Lys Gln Ile Val Gln Leu Ile
610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
            645                 650                 655

Ile Asn Ser Val Gly Ser Thr Ala Ser Ser Ser Gln Pro Leu Leu Val
            660                 665                 670

His Asp Asp Val
            675
```

<210> SEQ ID NO 3
<211> LENGTH: 550
<212> TYPE: PRT
<213> ORGANISM: Homo sapiens

<400> SEQUENCE: 3

Gln Lys Lys Pro Arg Tyr Glu Ile Arg Trp Lys Val Ile Glu Ser Val
1               5                   10                  15

Ser Ser Asp Gly His Glu Tyr Ile Tyr Val Asp Pro Met Gln Leu Pro
            20                  25                  30

Tyr Asp Ser Thr Trp Glu Leu Pro Arg Asp Gln Leu Val Leu Gly Arg
        35                  40                  45

Thr Leu Gly Ser Gly Ala Phe Gly Gln Val Val Glu Ala Thr Ala His
50                  55                  60

Gly Leu Ser His Ser Gln Ala Thr Met Lys Val Ala Val Lys Met Leu
65                  70                  75                  80

Lys Ser Thr Ala Arg Ser Ser Glu Lys Gln Ala Leu Met Ser Glu Leu
                85                  90                  95

Lys Ile Met Ser His Leu Gly Pro His Leu Asn Val Val Asn Leu Leu
            100                 105                 110

Gly Ala Cys Thr Lys Gly Gly Pro Ile Tyr Ile Ile Thr Glu Tyr Cys
        115                 120                 125

Arg Tyr Gly Asp Leu Val Asp Tyr Leu His Arg Asn Lys His Thr Phe
130                 135                 140

Leu Gln His His Ser Asp Lys Arg Arg Pro Pro Ser Ala Glu Leu Tyr
145                 150                 155                 160

Ser Asn Ala Leu Pro Val Gly Leu Pro Leu Pro Ser His Val Ser Leu
                165                 170                 175

Thr Gly Glu Ser Asp Gly Gly Tyr Met Asp Met Ser Lys Asp Glu Ser
            180                 185                 190

Val Asp Tyr Val Pro Met Leu Asp Met Lys Gly Asp Val Lys Tyr Ala
        195                 200                 205

Asp Ile Glu Ser Ser Asn Tyr Met Ala Pro Tyr Asp Asn Tyr Val Pro
210                 215                 220

Ser Ala Pro Glu Arg Thr Cys Arg Ala Thr Leu Ile Asn Glu Ser Pro
225                 230                 235                 240

Val Leu Ser Tyr Met Asp Leu Val Gly Phe Ser Tyr Gln Val Ala Asn
                245                 250                 255

Gly Met Glu Phe Leu Ala Ser Lys Asn Cys Val His Arg Asp Leu Ala
            260                 265                 270

Ala Arg Asn Val Leu Ile Cys Glu Gly Lys Leu Val Lys Ile Cys Asp
        275                 280                 285

Phe Gly Leu Ala Arg Asp Ile Met Arg Asp Ser Asn Tyr Ile Ser Lys
290                 295                 300

Gly Ser Thr Phe Leu Pro Leu Lys Trp Met Ala Pro Glu Ser Ile Phe
305                 310                 315                 320

Asn Ser Leu Tyr Thr Thr Leu Ser Asp Val Trp Ser Phe Gly Ile Leu
                325                 330                 335

Leu Trp Glu Ile Phe Thr Leu Gly Gly Thr Pro Tyr Pro Glu Leu Pro
            340                 345                 350

Met Asn Glu Gln Phe Tyr Asn Ala Ile Lys Arg Gly Tyr Arg Met Ala
        355                 360                 365

Gln Pro Ala His Ala Ser Asp Glu Ile Tyr Glu Ile Met Gln Lys Cys
370                 375                 380

```
Trp Glu Glu Lys Phe Glu Ile Arg Pro Pro Phe Ser Gln Leu Val Leu
385                 390                 395                 400

Leu Leu Glu Arg Leu Leu Gly Glu Gly Tyr Lys Lys Lys Tyr Gln Gln
            405                 410                 415

Val Asp Glu Glu Phe Leu Arg Ser Asp His Pro Ala Ile Leu Arg Ser
        420                 425                 430

Gln Ala Arg Leu Pro Gly Phe His Gly Leu Arg Ser Pro Leu Asp Thr
        435                 440                 445

Ser Ser Val Leu Tyr Thr Ala Val Gln Pro Asn Glu Gly Asp Asn Asp
    450                 455                 460

Tyr Ile Ile Pro Leu Pro Asp Pro Lys Pro Glu Val Ala Asp Glu Gly
465                 470                 475                 480

Pro Leu Glu Gly Ser Pro Ser Leu Ala Ser Ser Thr Leu Asn Glu Val
            485                 490                 495

Asn Thr Ser Ser Thr Ile Ser Cys Asp Ser Pro Leu Glu Pro Gln Asp
            500                 505                 510

Glu Pro Glu Pro Glu Pro Gln Leu Glu Leu Gln Val Glu Pro Glu Pro
        515                 520                 525

Glu Leu Glu Gln Leu Pro Asp Ser Gly Cys Pro Ala Pro Arg Ala Glu
    530                 535                 540

Ala Glu Asp Ser Phe Leu
545             550
```

IMIDAZOLIDINONES AND ANALOGS EXHIBITING ANTI-CANCER AND ANTI-PROLIFERATIVE ACTIVITIES

PRIORITY

This application claims the benefit of U.S. Provisional Application No. 61/788,374, filed Mar. 15, 2013. The entire disclosure of this application is relied on and incorporated into this application by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: DECP_053_01US_SeqList_ST25.txt, date recorded: Mar. 12, 2014, file size 18 kilobytes).

FIELD OF THE INVENTION

Disclosed are compounds which find utility in the treatment of cancer, autoimmune diseases and metabolic bone disorders through inhibition of c-FMS (CSF-1R), c-KIT, and/or PDGFR kinases. These compounds also find utility in the treatment of other mammalian diseases mediated by c-FMS, c-KIT, or PDGFR kinases.

BACKGROUND

Autoimmune diseases, including autoimmune arthritis, represent significant human diseases of high morbidity and prevalence. Rheumatoid arthritis affects ~0.6% of the world population (Firestein, G. S., Nature (2003) 423: 356). While the adaptive immune response, involving generation of autoantibodies which react with tissue antigen, is involved in the etiology and initial propagation of these diseases (Edwards, J. C. et al., New England Journal of Medicine (2004) 350: 2572; Genovese, M. C. et al., New England Journal of Medicine (2005) 353: 1114), the chronic manifestations of tissue and joint damage are mediated in large part by cellular events mediated by the innate immune response (Firestein, G. S., Nature (2003) 423: 356; Paniagua, R. T. et al., Arthritis Research & Therapy (2010) 12: R32). Contributing cell types from the innate immune response which mediate chronic tissue damage include fibroblast-like synoviocytes, macrophages, mast cells, and osteoclasts.

Kinases represent a protein family that play critical roles in mammalian cell function, including cell proliferation, survival, motility, response to growth factors, and secretion of cytokines and other proinflammatory, proangiogenic, and immunomodulatory substances. Thus, elucidation of kinases which mediate these events in fibroblast-like synoviocytes, macrophages, mast cells, and osteoclasts represents a rational approach to new therapies for the treatment of autoimmune diseases.

Imatinib is a marketed kinase inhibitor for the treatment of the cancer chronic myelogenous leukemia (CML, Druker, B. J. et al., New England Journal of Medicine (2001) 344: 1031) and for the treatment of gastrointestinal stromal tumors (GIST, Demetri, G. D., et al., New England Journal of Medicine (2002) 347: 472). Imatinib has also shown benefit in cancer patients co-presenting with autoimmune diseases such as rheumatoid arthritis (Ihara, M. K. et al., Clinical Rheumatology (2003) 22: 362; Eklund, K. K. and Joensuu, H., Ann Medicine (2003) 35: 362; Ames, P. R. et al., Journal of Rheumatology (2008) 35: 1682). The kinases inhibited by imatinib which confer its efficacy in the treatment of CML and GIST are BCR-ABL kinase and c-KIT kinase, respectively. Beyond these two kinases, other kinases inhibited by imatinib include c-FMS, PDGFR-alpha, and PDGFR-beta (Dewer, A. L. et al., Blood (2005) 105: 3127; Fabian, M. A. et al., Nature Biotechnology (2005) 23: 329.

Recent research disclosures have identified c-FMS kinase to be associated with activation of synovial macrophages, PDGFR kinase to be associated with activation of fibroblast-like synoviocytes, and c-KIT kinase to be associated with activation of mast cells (Paniagua, R. T., et al Journal of Clinical Investigation (2006) 116: 2633). c-FMS kinase has also been associated with the proliferation and differentiation of monocytes into macrophages and osteoclasts, which are recruited to mediate joint damage in rheumatoid arthritis (Paniagua, R. T. et al., Arthritis Research & Therapy (2010) 12: R32; Yao, Z. et al., Journal of Biological Chemistry (2006) 281: 11846; Patel, S, and Player, M. R. Current Topics in Medicinal Chemistry (2009) 9: 599; Pixley, F. J. et al., Trends in Cell Biology (2004) 14: 628).

In recent years, the importance of the tumor microenvironment in cancer motility, invasion, and metastasis has become more clearly defined. Specifically, the role of tumor-associated macrophages (TAMs) in tumor progression has been studied. These host (stromal) macrophages are recruited to tumor sites or to pre-metastatic niches to modify the tumor environment and render that environment more conducive to tumor motility, invasion and metastasis. These TAMs are known to express c-FMS receptor tyrosine kinase (also known as CSF-1R) on their surfaces and to rely on signaling through this kinase by binding to the activating ligands CSF-1 (also known as macrophage colony stimulating factor, or MCSF) and interleukin-34 (IL-34). Activation of this c-FMS/MCSF (CSF1-R/CSF-1) signaling axis stimulates monocyte proliferation, differentiation into tumor associated macrophages, and promotion of macrophage cell survival. By stimulating the TAM component of the tumor microenvironment, c-FMS kinase activation is associated with tumor cell migration, invasion, and metastasis (J. Condeelis and J. W. Pollard, Cell (2006) 124: 263; S. Patel and M. R. Player, Current Topics in Medicinal Chemistry (2009) 9: 599). Ablation of CSF-1, the ligand for c-FMS kinase, in mice reduced tumor progression and significantly reduced metastasis in a murine model of breast cancer; whereas overexpression of CSF-1 accelerated metastasis in this model (E. Y. Lin et al., Journal of Experimental Medicine (2001) 193: 727). Furthermore, an interaction between tumor cells and macrophages has been described, wherein macrophage secretion of the tumor growth factor EGF and tumor cell secretion of CSF-1 establish a paracrine loop that promotes tumor migration and invasiveness. This paracrine loop was blocked by administration of an antibody to the c-FMS kinase (J. Wyckoff et al., Cancer Research (2004) 64: 7022). Correlative clinical data have also shown that overexpression of CSF-1 in tumors is a predictor of poor prognosis (R. D. Leek and A. L. Harris, Journal of Mammary Gland Biology Neoplasia (2002) 7: 177; E. Y. Lin et al., Journal of Mammary Gland Biology Neoplasia (2002) 7: 147). c-FMS kinase activation is also required for osteoclast differentiation and activation. Its involvement in mediating bone metastases of various cancers, including breast and prostate cancers, has been reported (S. Patel and M. R. Player, Current Topics in Medicinal Chemistry (2009) 9: 599). High plasma concentrations of CSF-1 have been reported in bone metastatic prostate cancer, implicating activation of osteoclast c-FMS kinase in prostate cancer bone metastases (H. Ide, et al., Human Cell (2008) 21:1). c-FMS inhibitors have been reported to reduce radiographic bone lesions when evaluated in models of metastatic bone disease (C. L. Manthey, et al., Molecular Cancer Therapy (2009) 8: 3151; H. Ohno et al., Mol. Cancer. Therapy (2006) 5: 2634). MCSF-mediated activation of both LYVE-1+ and LYVE1− macrophages also mediates pathological angiogenesis and lymphangiogenesis in murine models of cancer, and blockade of c-FMS signaling resulted in suppression of tumor angiogenesis/lymphangiogenesis (Y. Kubota et al., Journal of Experimental Medicine (2009) 206: 1089). Administration of a CSF-1R inhibitor blocked the recruitment of bone marrow derived TAMs and also bone marrow derived monocytic myeloid-derived suppressor cells (MDSCs) to tumor sites; this blockade led to a significant decrease in tumor angiogenesis and when combined with anti-VEGFR-2 therapy synergistically suppressed tumor growth (S. J. Priceman, et al., Blood (2010) 115: 1461). Irradiation of glioblastoma tumors in mice was shown to cause a temporary decrease in tumor size only to be followed by a rebound tumor vasculogenesis mediated by the recruitment of bone marrow derived monocytes expressing CD11b and F4/80 surface antigens (M. Kioi et al., Journal of Clinical Investigation (2010) 120: 694). CD11b+ and F4/80+ monocytes are also known to express functional c-FMS receptors. Hence, blockade of tumor infiltrating c-FMS+ bone marrow derived monocytes by the use of c-FMS kinase inhibitors offers the potential to prevent tumor rebound vasculogenesis and glioblastoma tumor progression. CSF-1R blockade has also been shown to reverse immunotolerance mechanisms in an immunocompetent murine breast cancer model and promote the appearance of anti-tumor immune programs by upregulating CD8+ T-cell-mediated tumor suppression. Restoration of an anti-tumor immune program was mechanistically linked to c-FMS inhibitor blockade of TAM-mediated Programmed Death Ligand-1 (PDL-1) immunotolerance (D. G. DeNardo, et al., Cancer Discovery (2011) 1: OF52).

Hence, small molecule inhibitors of c-FMS kinase, c-KIT kinase, or PDGFR kinases provide a rational approach to new therapies for the treatment of autoimmune diseases, and to particularly block the chronic tissue destruction mediated by the innate immune system. Inhibition of c-FMS kinase also provides a rational approach to new therapies for the treatment of cancers, especially for the treatment of cancer invasiveness, cancer angiogenesis or vasculogenesis, cancer metastasis, cancer immunotolerance, and for the treatment of cancers prone to bone metastases.

There is a need to provide kinase inhibitors which selectively inhibit kinases causative of the chronic tissue destruction in autoimmune disease (c-FMS, c-KIT, PDGFR), without inhibiting other kinases targeted by marketed cancer therapeutics (ABL, BCR-ABL, KDR, SRC, LCK, LYN, FGFR and other kinases). The present invention discloses novel inhibitors that inhibit c-FMS, c-KIT, and/or PDGFR kinases for the treatment of autoimmune diseases which also exhibit selectivity by not potently inhibiting other kinases including ABL, BCR-ABL, KDR, SRC, LCK, LYN, FGFR, MET and other kinases. The inhibitors of the present invention also find utility in the treatment of other mammalian diseases, including human diseases, mediated by c-FMS, c-KIT, or PDGFR kinases.

Such diseases include, without limitation, cancers, autoimmune diseases, and bone resorptive diseases.

SUMMARY OF THE INVENTION

In one aspect, compounds of the Formula I are described:

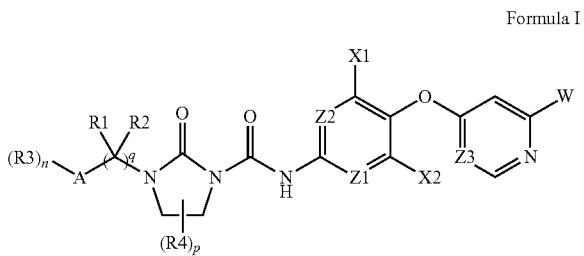

Formula I and pharmaceutically acceptable salts, enantiomers, stereoisomers, or tautomers thereof, wherein A is selected from the group consisting of C1-C6 alkyl, deutero-C1-C6 alkyl wherein the alkyl chain is partially or completely deuterated, branched C3-C8alkyl, fluoroC1-C6alkyl wherein the alkyl is fully or partially fluorinated, C3-C8-carbocyclyl, and a 4-8 membered heterocyclic ring, and wherein the A moiety may be further substituted with one, two, or three R3 moieties;

W is C5-C6heteroaryl, —NHC(O)R6, —NHC(O)R7, —NHC(O)N(R8)R9, —C(O)R11 or phenyl, wherein the C5-C6heteroaryl and phenyl moieties are optionally substituted by one, two, or three R5;

each X1, X2, X3 and X4 are individually and independently hydrogen, C1-C6 alkyl, halogen or fluoro-C1-C6 alkyl wherein the alkyl chain is partially or completely fluorinated;

Z1 is N or CX3;

Z2 is CX4 or N;

Z3 is CH or N;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen, C1-C6 alkyl, or branched C3-C8 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—C(O)R6, —(CH$_2$)$_m$—CN, —(CH$_2$)$_m$—OR8, —(CH$_2$)$_m$—NR8(R9), or —(CH$_2$)$_m$—R7, wherein each alkylene may be further substituted with one or more C1-C6alkyl;

each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkylene may be further substituted with one or more C1-C6alkyl;

each R7 is independently and individually selected from the group consisting of and wherein the symbol (##) is the point of attachment to respective R5 or R6 moieties containing a R7 moiety;

each R7 is optionally substituted with —(R10)$_p$;

each R8 and R9 is individually and independently H, C1-C6 alkyl, fluoro-C1-C6 alkyl wherein the alkyl chain is partially or completely fluorinated, or branched C3-C8 alkyl;

each R10 is individually and independently C1-C6 alkyl, —(CH$_2$)$_m$—CN, —(CH$_2$)$_m$—OR3, —(CH$_2$)$_m$—NR8(R9), or —(CH$_2$)$_m$—C(O)—R6, wherein each alkyl or alkylene is optionally substituted with one or two C1-C6 alkyl;

R11 is —N(R8)R9 or R7;

each m is individually and independently 0, 1, 2, or 3;

each n is individually and independently 0, 1, 2, or 3;

each p is individually and independently 0, 1, 2, or 3; and each q is individually and independently 0, 1, 2, or 3.

In one embodiment of Formula I, A is C1-C6alkyl.

In one embodiment of Formula I, A is branched C3-C8alkyl.

In one embodiment of Formula I, A is fluoroC1-C6alkyl wherein the alkyl is fully or partially fluorinated.

In one embodiment of Formula I, A is C3-C8-carbocyclyl.

In one embodiment of Formula I, A is a 4-8 membered heterocyclic ring.

In one embodiment of Formula I, W is C5-C6heteroaryl optionally substituted by one, two, or three R5.

In one embodiment of Formula I, W is —NHC(O)R6, —NHC(O)R7, or —NHC(O)N(R8)R9.

In one embodiment of Formula I, W is —NHC(O)R6.

In one embodiment of Formula I, W is —NHC(O)R7.

In one embodiment of Formula I, W is —NHC(O)N(R8)R9.

In one embodiment of Formula I, W is —C(O)R11.

In one embodiment of Formula I, W is phenyl optionally substituted by one, two, or three R5.

In one embodiment of Formula I, Z1 is N, Z2 is CX4, and X1, X2 and X4 are individually and independently hydrogen, C1-C6 alkyl, halogen or fluoro-C1-C6 alkyl wherein the alkyl chain is partially or completely fluorinated.

In one embodiment of Formula I, Z1 is N, Z2 is CX4, and X1, X2 and X4 are individually and independently hydrogen or C1-C6 alkyl.

In one embodiment of Formula I, Z1 is N, Z2 is CX4, and X1, X2 and X4 are hydrogen.

In one embodiment of Formula I, Z1 is N, Z2 is CX4, X4 is hydrogen, and one of X1 and X2 is hydrogen and the other is C1-C6alkyl.

In one embodiment of Formula I, Z1 is CX3, Z2 is CX4, and X1, X2, X3 and X4 are individually and independently hydrogen, C1-C6 alkyl, halogen or fluoro-C1-C6 alkyl wherein the alkyl chain is partially or completely fluorinated.

In one embodiment of Formula I, Z1 is CX3, Z2 is CX4, and X1, X2, X3 and X4 are individually and independently hydrogen or halogen.

In one embodiment of Formula I, Z1 is CX3, Z2 is CX4, X1 and X3 are halogen, and X2 and X4 are hydrogen.

In one embodiment of Formula I, Z1 and Z2 are N, and X1 and X2 are individually and independently hydrogen or C1-C6 alkyl.

In one embodiment of Formula I, Z1 and Z2 are N, and X1 and X2 are hydrogen.

In one embodiment of Formula I, Z3 is CH.

In one embodiment of Formula I, Z3 is N.

In one embodiment, the compound of Formula I is a compound of Formula Ia

Formula Ia wherein A, X1, X2, W, Z1, R3, R4, n, and p are described above.

In one embodiment of Formula Ia, A is methyl and R3 is H.

In one embodiment of Formula Ia, A is ethyl and R3 is H.

In one embodiment of Formula Ia, A is branched C3-C8alkyl.

In one embodiment of Formula Ia, A is isopropyl and R3 is H.

In one embodiment of Formula Ia, A is tert-butyl and R3 is H.

In one embodiment of Formula Ia, A is fluoroC1-C6alkyl wherein the alkyl is fully or partially fluorinated and R3 is H.

In one embodiment of Formula Ia, A is 2,2,2-trifluoroethyl and R3 is H.

In one embodiment of Formula Ia, A is C3-C8-carbocyclyl.

In one embodiment of Formula Ia, A is cyclopropyl.

In one embodiment of Formula Ia, A is cyclobutyl.

In one embodiment of Formula Ia, A is cyclopentyl.

In one embodiment of Formula Ia, A is cyclohexyl.

In one embodiment of Formula Ia, A is a 4-8 membered heterocyclic ring.

In one embodiment of Formula Ia, A is a oxetanyl.

In one embodiment of Formula Ia, A is a tetrahydrofuranyl.

In one embodiment of Formula Ia, A is a tetrahydropyranyl.

In one embodiment of Formula Ia, W is C5-C6heteroaryl optionally substituted by one, two, or three R5.

In one embodiment of Formula Ia, W is pyrazolyl, imidazolyl, isoxazolyl, oxazolyl, thiazolyl, triazolyl, or pyridinyl and wherein each W is optionally substituted by one, two, or three R5.

In one embodiment of Formula Ia, W is pyrazolyl optionally substituted by one, two, or three R5.

In one embodiment of Formula Ia, W is imidazolyl optionally substituted by one, two, or three R5.

In one embodiment of Formula Ia, W is isoxazolyl optionally substituted by one or two R5.

In one embodiment of Formula Ia, W is oxazolyl optionally substituted by one or two R5.

In one embodiment of Formula Ia, W is thiazolyl optionally substituted by one or two R5.

In one embodiment of Formula Ia, W is triazolyl optionally substituted by one or two R5.

In one embodiment of Formula Ia, W is pyridinyl optionally substituted by one, two, or three R5.

In one embodiment of Formula Ia, W is —NHC(O)R6, —NHC(O)R7, or —NHC(O)N(R8)R9.

In one embodiment of Formula Ia, W is —NHC(O)R6.

In one embodiment of Formula Ia, W is —NHC(O)R7.

In one embodiment of Formula Ia, W is —NHC(O)N(R8)R9.

In one embodiment of Formula Ia, W is —C(O)R11.

In one embodiment of Formula Ia, W is phenyl optionally substituted by one, two, or three R5.

In one embodiment of Formula Ia, Z1 is N, and X1 and X2 are individually and independently hydrogen, C1-C6 alkyl, halogen or fluoro-C1-C6 alkyl wherein the alkyl chain is partially or completely fluorinated.

In one embodiment of Formula Ia, Z1 is N, and X1 and X2 are individually and independently hydrogen or C1-C6 alkyl.

In one embodiment of Formula Ia is, Z1 is N, and X1 and X2 are hydrogen.

In one embodiment of Formula Ia, Z1 is N, and one of X1 and X2 is hydrogen and the other is C1-C6alkyl.

In one embodiment of Formula Ia, Z1 is CX3, and X1 and X2 and X3 are individually and independently hydrogen, C1-C6 alkyl, halogen or fluoro-C1-C6 alkyl wherein the alkyl chain is partially or completely fluorinated.

In one embodiment of Formula Ia, Z1 is CX3, and X1 and X2 and X3 are individually and independently hydrogen or halogen.

In one embodiment of Formula Ia, Z1 is CX3, and X1 and X3 are halogen, and X2 is hydrogen.

In one embodiment of Formula Ia, A is C1-C6 alkyl, branched C3-C8alkyl, or C3-C8-carbocyclyl, and W is pyrazolyl, imidazolyl, or pyridinyl, and Z1 is N, and X1 is H, and X2 is C1-C6alkyl, and each R3 is independently H, C1-C6alkyl or C1-C6alkoxy.

In one embodiment of Formula Ia, A is C1-C6 alkyl, branched C3-C8alkyl, or C3-C8-carbocyclyl, and W is pyrazolyl, imidazolyl, or pyridinyl, and Z1 is N, and X2 is H, and X1 is C1-C6alkyl, and each R3 is independently H, C1-C6alkyl or C1-C6alkoxy.

In one embodiment of Formula Ia, A is C1-C6 alkyl, branched C3-C8alkyl, or C3-C8-carbocyclyl, and W is pyrazolyl, imidazolyl, or pyridinyl, and Z1 is N, and X1 and X2 are H, and each R3 is independently H, C1-C6alkyl or C1-C6alkoxy.

In one embodiment of Formula Ia, A is C1-C6 alkyl, branched C3-C8alkyl, or C3-C8-carbocyclyl, and W is pyrazolyl, imidazolyl, or pyridinyl, and Z1 is CX3, and X2 is H and X1 and X3 are independently halogen or H, and each R3 is independently H, C1-C6alkyl or C1-C6alkoxy.

In another embodiment, the compound of Formula I is a compound of Formula Ib

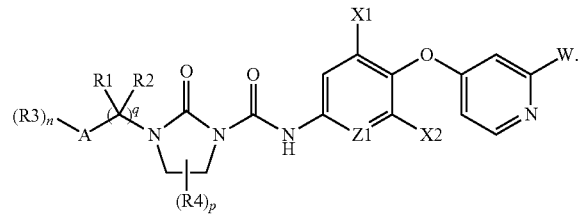

Formula Ib wherein A, X1, X2, W, Z1, R1, R2, R3, R4, n, p, and q are described above.

In one embodiment of Formula Ib, A is methyl.

In one embodiment of Formula Ib, A is ethyl.

In one embodiment of Formula Ib, A is branched C3-C8alkyl.

In one embodiment of Formula Ib, A is isopropyl.

In one embodiment of Formula Ib, A is tert-butyl.

In one embodiment of Formula Ib, A is fluoroC1-C6alkyl wherein the alkyl is fully or partially fluorinated.

In one embodiment of Formula Ib, A is C3-C8-carbocyclyl.

In one embodiment of Formula Ib, A is cyclopropyl.

In one embodiment of Formula Ib, A is cyclobutyl.

In one embodiment of Formula Ib, A is cyclopentyl.

In one embodiment of Formula Ib, A is cyclohexyl.

In one embodiment of Formula Ib, A is a 4-8 membered heterocyclic ring.

In one embodiment of Formula Ib, A is a oxetanyl.

In one embodiment of Formula Ib, A is a tetrahydrofuranyl.

In one embodiment of Formula Ib, A is tetrahydropyranyl.

In one embodiment of Formula Ib, W is C5-C6heteroaryl optionally substituted by one, two, or three R5.

In one embodiment of Formula Ib, W is pyrazolyl, imidazolyl, isoxazolyl, oxazolyl, thiazolyl, triazolyl, pyridinyl and wherein each W is optionally substituted by one, two, or three R5.

In one embodiment of Formula Ib, W is pyrazolyl optionally substituted by one, two, or three R5.

In one embodiment of Formula Ib, W is imidazolyl optionally substituted by one, two, or three R5.

In one embodiment of Formula Ib, W is isoxazolyl optionally substituted by one or two R5.

In one embodiment of Formula Ib, W is oxazolyl optionally substituted by one or two R5.

In one embodiment of Formula Ib, W is thiazolyl optionally substituted by one or two R5.

In one embodiment of Formula Ib, W is triazolyl optionally substituted by one or two R5.

In one embodiment of Formula Ib, W is pyridinyl optionally substituted by one, two, or three R5.

In one embodiment of Formula Ib, W is —NHC(O)R6, —NHC(O)R7, or —NHC(O)N(R8)R9.

In one embodiment of Formula Ib, W is —NHC(O)R6.

In one embodiment of Formula Ib, W is —NHC(O)R7.

In one embodiment of Formula Ib, W is —NHC(O)N(R8)R9.

In one embodiment of Formula Ib, W is —C(O)R11.

In one embodiment of Formula Ib, W is phenyl optionally substituted by one, two, or three R5.

In one embodiment of Formula Ib, Z1 is N, and X1 and X2 are individually and independently hydrogen, C1-C6 alkyl, halogen or fluoro-C1-C6 alkyl wherein the alkyl chain is partially or completely fluorinated.

In one embodiment of Formula Ib, Z1 is N, and X1 and X2 are individually and independently hydrogen or C1-C6 alkyl.

In one embodiment of Formula Ib, Z1 is N, and X1 and X2 are hydrogen.

In one embodiment of Formula Ib, Z1 is N, and one of X1 and X2 is hydrogen and the other is C1-C6alkyl.

In one embodiment of Formula Ib, Z1 is CX3, and X1 and X2 and X3 are individually and independently hydrogen, C1-C6 alkyl, halogen or fluoro-C1-C6 alkyl wherein the alkyl chain is partially or completely fluorinated.

In one embodiment of Formula Ib, Z1 is CX3, and X1 and X2 and X3 are individually and independently hydrogen or halogen.

In one embodiment of Formula Ib, Z1 is CX3, and X1 and X3 are halogen, and X2 is hydrogen.

In one embodiment of Formula Ib, R1 and R2 are individually and independently H, C1-C6 alkyl, or fluoroC1-C6alkyl wherein the alkyl is fully or partially fluorinated.

In one embodiment of Formula Ib, R1 and R2 are H.

In one embodiment of Formula Ib, R1 and R2 are C1-C6alkyl.

In one embodiment of Formula Ib, R1 is H and R2 is C1-C6alkyl.

In one embodiment of Formula Ib, R3 is H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano.

In one embodiment of Formula Ib, R3 is H.

In one embodiment of Formula Ib, R3 is C1-C6 alkoxy.

In one embodiment of Formula Ib, R3 is fluoro-C1-C6 alkoxy wherein the alkyl chain is partially or completely fluorinated.

In one embodiment of Formula Ib, A is C1-C6 alkyl, branched C3-C8alkyl, or C3-C8carbocyclyl, and q is 0 or 1, and W is pyrazolyl, imidazolyl, or pyridinyl, and Z1 is N, and X1 is H, and X2 is C1-C6alkyl, and R3 is H or C1-C6alkoxy.

In one embodiment of Formula Ib, A is C1-C6 alkyl, branched C3-C8alkyl, or C3-C8carbocyclyl, and q is 0 or 1, and W is pyrazolyl, imidazolyl, or pyridinyl, and Z1 is N, and X2 is H, and X1 is C1-C6alkyl, and R3 is H or C1-C6alkoxy.

In one embodiment of Formula Ib, A is C1-C6 alkyl, branched C3-C8alkyl, or C3-C8carbocyclyl, and q is 0 or 1, and W is pyrazolyl, imidazolyl, or pyridinyl, and Z1 is N, and X1 and X2 are H, and R3 is H or C1-C6alkoxy.

In one embodiment of Formula Ib, A is C1-C6 alkyl, branched C3-C8alkyl, or C3-C8carbocyclyl, and q is 0 or 1, and W is pyrazolyl, imidazolyl, or pyridinyl, and Z1 is CX3, and X2 is H and X1 and X3 are independently halogen or H, and R3 is H or C1-C6alkoxy.

In another embodiment, the compound of Formula I is a compound of Formula Ic:

Formula Ic

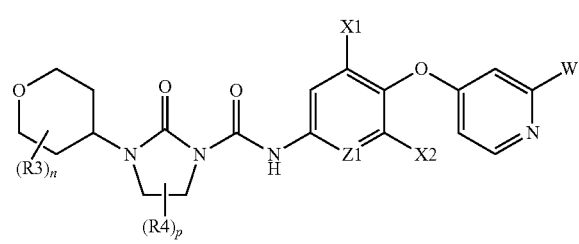

wherein X1, X2, W, Z1, R3, R4, n, and p are described above.

In one embodiment of Formula Ic, W is pyrazolyl, imidazolyl, isoxazolyl, oxazolyl, thiazolyl, triazolyl, or pyridinyl and wherein each W is optionally substituted by one, two, or three R5.

In one embodiment of Formula Ic, W is pyrazolyl optionally substituted by one, two, or three R5.

In one embodiment of Formula Ic, W is imidazolyl optionally substituted by one, two, or three R5.

In one embodiment Formula Ic, W is isoxazolyl optionally substituted by one or two R5.

In one embodiment of Formula Ic, W is oxazolyl optionally substituted by one or two R5.

In one embodiment of Formula Ic, W is thiazolyl optionally substituted by one or two R5.

In one embodiment of Formula Ic, W is triazolyl optionally substituted by one or two R5; or a pharmaceutically acceptable salt, enantiomer, stereoisomer, or tautomer thereof.

In one embodiment of Formula Ic, W is pyridinyl optionally substituted by one, two, or three R5.

In one embodiment of Formula Ic, W is —NHC(O)R6, —NHC(O)R7, or —NHC(O)N(R8)R9.

In one embodiment of Formula Ic W is —NHC(O)R6.

In one embodiment of Formula Ic, W is —NHC(O)R7.

In one embodiment of Formula Ic, W is —NHC(O)N(R8)R9.

In one embodiment of Formula Ic, W is —C(O)R11.

In one embodiment of Formula Ic, W is phenyl optionally substituted by one, two, or three R5.

In one embodiment of Formula Ic, Z1 is N, and X1 and X2 are individually and independently hydrogen, C1-C6 alkyl, halogen or fluoro-C1-C6 alkyl wherein the alkyl chain is partially or completely fluorinated.

In one embodiment of Formula Ic, Z1 is N, and X1 and X2 are individually and independently hydrogen or C1-C6 alkyl.

In one embodiment of Formula Ic, Z1 is N, and X1 and X2 are hydrogen.

In one embodiment of Formula Ic, Z1 is N, and one of X1 and X2 is hydrogen and the other is C1-C6alkyl.

In one embodiment of Formula Ic, Z1 is CX3, and X1 and X2 and X3 are individually and independently hydrogen, C1-C6 alkyl, halogen or fluoro-C1-C6 alkyl wherein the alkyl chain is partially or completely fluorinated.

In one embodiment of Formula Ic, Z1 is CX3, and X1 and X2 and X3 are individually and independently hydrogen or halogen.

In one embodiment of Formula Ic, Z1 is CX3, and X1 and X3 are halogen, and X2 is hydrogen.

In one embodiment of Formula Ic, W is pyrazolyl, imidazolyl, or pyridinyl, and Z1 is N, and X1 is H, and X2 is C1-C6alkyl, and R3 is H or C1-C6alkyl.

In one embodiment of Formula Ic, W is pyrazolyl, imidazolyl, or pyridinyl, and Z1 is N, and X2 is H, and X1 is C1-C6alkyl, and R3 is H or C1-C6alkyl.

In one embodiment of Formula Ic, W is pyrazolyl, imidazolyl, or pyridinyl, and Z1 is N, and X1 and X2 are H, and R3 is H or C1-C6alkyl.

In one embodiment of Formula Ic, W is pyrazolyl, imidazolyl, or pyridinyl, and Z1 is CX3, and X2 is H and X1 and X3 are independently halogen or H, and R3 is H or C1-C6alkyl.

In another embodiment, the compound of Formula I is a compound of Formula Id:

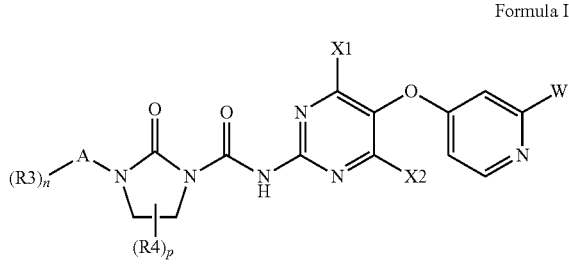

Formula Id wherein A, X1, X2, W, R3, R4, n, and p are described above.

In one embodiment of Formula Id, A is methyl and R3 is H.
In one embodiment of Formula Id, A is ethyl.
In one embodiment of Formula Id, A is branched C3-C8alkyl.
In one embodiment of Formula Id, A is isopropyl.
In one embodiment of Formula Id, A is tert-butyl.
In one embodiment of Formula Id, A is fluoroC1-C6alkyl wherein the alkyl is fully or partially fluorinated.
In one embodiment of Formula Id, A is 2,2,2-trifluoroethyl.
In one embodiment of Formula Id, A is C3-C8carbocyclyl.
In one embodiment of Formula Id, A is cyclopropyl.
In one embodiment of Formula Id A is cyclobutyl.
In one embodiment of Formula Id, A is cyclopentyl.
In one embodiment of Formula Id, A is cyclohexyl.
In one embodiment of Formula Id, A is a 4-8 membered heterocyclic ring.
In one embodiment of Formula Id, A is a oxetanyl.
In one embodiment of Formula Id, A is a tetrahydrofuranyl.
In one embodiment of Formula Id, A is a tetrahydropyranyl.
In one embodiment of Formula Id, W is C5-C6heteroaryl optionally substituted by one, two, or three R5.
In one embodiment of Formula Id, W is pyrazolyl, imidazolyl, isoxazolyl, oxazolyl, thiazolyl, triazolyl, or pyridinyl and wherein each W is optionally substituted by one, two, or three R5.
In one embodiment of Formula Id, W is pyrazolyl optionally substituted by one, two, or three R5.
In one embodiment of Formula Id, W is imidazolyl optionally substituted by one, two, or three R5.
In one embodiment of Formula Id, W is isoxazolyl optionally substituted by one or two R5.
In one embodiment of Formula Id, W is oxazolyl optionally substituted by one or two R5.
In one embodiment of Formula Id, W is thiazolyl optionally substituted by one or two R5.
In one embodiment of Formula Id, W is triazolyl optionally substituted by one or two R5.
In one embodiment of Formula Id, W is pyridinyl optionally substituted by one, two, or three R5.
In one embodiment of Formula Id, W is —NHC(O)R6, —NHC(O)R7, or —NHC(O)N(R8)R9.
In one embodiment of Formula Id, W is —NHC(O)R6.
In one embodiment of Formula Id, W is —NHC(O)R7.
In one embodiment of Formula Id, W is —NHC(O)N(R8)R9.
In one embodiment of Formula Id, W is —C(O)R11.
In one embodiment of Formula Id, W is phenyl optionally substituted by one, two, or three R5.

In one embodiment of Formula Id, X1 and X2 are individually and independently hydrogen, C1-C6 alkyl, halogen or fluoro-C1-C6 alkyl wherein the alkyl chain is partially or completely fluorinated.

In one embodiment of Formula Id, X1 and X2 are hydrogen.

In some embodiments, the invention comprises a compound selected from the group consisting of N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(6-methyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-ethyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(H-pyrazol-4-yl)pyridin-4-yl)oxy)pyridin-2-yl)-2-oxo-3-(tetrahydro-2H-pyran-4-yl)imidazolidine-1-carboxamide, 2-oxo-3-(tetrahydro-2H-pyran-4-yl)-N-(5-((2-(1-(trideuteromethyl)-1H-pyrazol-4-yl)pyridin-4-yl)oxy)pyridin-2-yl)imidazolidine-1-carboxamide, N-(5-((2-(3-methylisoxazol-5-yl)pyridin-4-yl)oxy)pyridin-2-yl)-2-oxo-3-(tetrahydro-2H-pyran-4-yl)imidazolidine-1-carboxamide, N-(5-((6-(1-methyl-1H-pyrazol-4-yl)pyrimidin-4-yl)oxy)pyridin-2-yl)-2-oxo-3-(tetrahydro-2H-pyran-4-yl)imidazolidine-1-carboxamide, N-(5-((2-(1H-pyrazol-4-yl)pyridin-4-yl)oxy)-6-methylpyridin-2-yl)-2-oxo-3-(tetrahydro-2H-pyran-4-yl)imidazolidine-1-carboxamide, 3-(2-methoxyethyl)-N-(5-((2-(1-methyl-1H-pyrazol-4-yl)pyridin-4-yl)oxy)pyridin-2-yl)-2-oxoimidazolidine-1-carboxamide, 3-(3-methoxypropyl)-N-(5-((2-(1-methyl-1H-pyrazol-4-yl)pyridin-4-yl)oxy)pyridin-2-yl)-2-oxoimidazolidine-1-carboxamide, (S)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(2,2-dimethyltetrahydro-2H-pyran-4-yl)-N-(5-((2-(1-methyl-1H-pyrazol-4-yl)pyridin-4-yl)oxy)pyridin-2-yl)-2-oxoimidazolidine-1-carboxamide, N-(6-methyl-5-((2-(3-methylisoxazol-5-yl)pyridin-4-yl)oxy)pyridin-2-yl)-2-oxo-3-(tetrahydro-2H-pyran-4-yl)imidazolidine-1-carboxamide, 3-cyclohexyl-N-(5-((2-(1-methyl-1H-pyrazol-4-yl)pyridin-4-yl)oxy)pyridin-2-yl)-2-oxoimidazolidine-1-carboxamide, (S)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide, 3-(2-(1-methoxycyclopropyl)ethyl)-N-(5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide, 3-(3-methoxypropyl)-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2-(1-methyl-1H-pyrazol-4-yl)pyridin-4-yl)oxy)pyridin-2-yl)-2-oxo-3-(2-(trifluoromethoxy)ethyl)imidazolidine-1-carboxamide, 3-cyclohexyl-N-(6-methyl-5-((2-(1-methyl-1H-pyrazol-4-yl)pyridin-4-yl)oxy)pyridin-2-yl)-2-oxoimidazolidine-1-carboxamide, (S)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(3-methoxy-3-methylbutyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(6-methyl-5-

((2-(1-methyl-1H-pyrazol-4-yl)pyridin-4-yl)oxy)pyridin-2-yl)-2-oxoimidazolidine-1-carboxamide, (R)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, (R)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-cyclopentyl-N-(6-methyl-5-((2-(1-methyl-1H-pyrazol-4-yl)pyridin-4-yl)oxy)pyridin-2-yl)-2-oxoimidazolidine-1-carboxamide, 3-cyclopentyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(6-methyl-5-((2-(1-methyl-1H-pyrazol-4-yl)pyridin-4-yl)oxy)pyridin-2-yl)-2-oxoimidazolidine-1-carboxamide 3-(tert-butyl)-N-(5-((2-(1-methyl-1H-pyrazol-4-yl)pyridin-4-yl)oxy)pyridin-2-yl)-2-oxoimidazolidine-1-carboxamide, 3-isopropyl-N-(6-methyl-5-((2-(1-methyl-1H-pyrazol-4-yl)pyridin-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyridin-2-yl)-2-oxoimidazolidine-1-carboxamide, (R)—N-(6-methyl-5-((2-(1-(trideuteromethyl)-1H-pyrazol-4-yl)pyridin-4-yl)oxy)pyridin-2-yl)-2-oxo-3-(tetrahydrofuran-3-yl)imidazolidine-1-carboxamide, (S)-3-(1-methoxypropan-2-yl)-N-(6-methyl-5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-(trideuteromethyl)-1H-pyrazol-4-yl)pyridin-4-yl)oxy)pyridin-2-yl)-2-oxoimidazolidine-1-carboxamide, 4-methyl-N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, 3-methyl-N-(6-methyl-5-((2-(1-methyl-1H-pyrazol-4-yl)pyridin-4-yl)oxy)pyridin-2-yl)-2-oxoimidazolidine-1-carboxamide, 3-ethyl-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-methyl-N-(5-((2-(1-methyl-1H-pyrazol-4-yl)pyridin-4-yl)oxy)pyridin-2-yl)-2-oxoimidazolidine-1-carboxamide, 3-ethyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(1-methyl-1H-pyrazol-4-yl)pyridin-4-yl)oxy)pyridin-2-yl)-2-oxoimidazolidine-1-carboxamide, N-(5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, N-(6-ethyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2'-methyl-[2,4'-bipyridin]-4-yl)oxy)pyridin-2-yl)-2-oxo-3-(tetrahydro-2H-pyran-4-yl)imidazolidine-1-carboxamide, N-(5-((6'-methyl-[2,3'-bipyridin]-4-yl)oxy)pyridin-2-yl)-2-oxo-3-(tetrahydro-2H-pyran-4-yl)imidazolidine-1-carboxamide, N-(6-methyl-5-((6'-methyl-[2,3'-bipyridin]-4-yl)oxy)pyridin-2-yl)-2-oxo-3-(2,2,2-trifluoroethyl)imidazolidine-1-carboxamide, N-(6-methyl-5-((6'-methyl-[2,3'-bipyridin]-4-yl)oxy)pyridin-2-yl)-2-oxo-3-(tetrahydro-2H-pyran-4-yl)imidazolidine-1-carboxamide, 3-(cyanomethyl)-N-(5-((2-(1-methyl-1H-pyrazol-4-yl)pyridin-4-yl)oxy)pyridin-2-yl)-2-oxoimidazolidine-1-carboxamide, N-(6-ethyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-cyclopentyl-N-(6-ethyl-5-((2-(1-methyl-1H-pyrazol-4-yl)pyridin-4-yl)oxy)pyridin-2-yl)-2-oxoimidazolidine-1-carboxamide, 3-cyclopropyl-N-(6-ethyl-5-((2-(1-methyl-1H-pyrazol-4-yl)pyridin-4-yl)oxy)pyridin-2-yl)-2-oxoimidazolidine-1-carboxamide, (R)-3-(1-methoxypropan-2-yl)-N-(5-((2-(1-methyl-11H-pyrazol-4-yl)pyridin-4-yl)oxy)pyridin-2-yl)-2-oxoimidazolidine-1-carboxamide, N-(5-((2-(2-methylthiazol-5-yl)pyridin-4-yl)oxy)pyridin-2-yl)-2-oxo-3-(tetrahydro-2H-pyran-4-yl)imidazolidine-1-carboxamide, 3-ethyl-N-(6-methyl-5-((2-(4-(1-methylpiperidin-4-yl)phenyl)pyridin-4-yl)oxy)pyridin-2-yl)-2-oxoimidazolidine-1-carboxamide, 3-(2-methoxyethyl)-N-(5-((2-(2-methylthiazol-5-yl)pyridin-4-yl)oxy)pyridin-2-yl)-2-oxoimidazolidine-1-carboxamide, N-(6-ethyl-5-((6'-methyl-[2,3'-bipyridin]-4-yl)oxy)pyridin-2-yl)-2-oxo-3-(tetrahydro-2H-pyran-4-yl)imidazolidine-1-carboxamide, N-(6-ethyl-5-((2'-methyl-[2,4'-bipyridin]-4-yl)oxy)pyridin-2-yl)-2-oxo-3-(tetrahydro-2H-pyran-4-yl)imidazolidine-1-carboxamide, 3-cyclopropyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(tetrahydro-2H-pyran-4-yl)imidazolidine-1-carboxamide, 3-(2-methoxyethyl)-N-(6-methyl-5-((2-(2-methylthiazol-5-yl)pyridin-4-yl)oxy)pyridin-2-yl)-2-oxoimidazolidine-1-carboxamide, 3-ethyl-N-(6-methyl-5-((2-(4-(4-methylpiperazin-1-yl)phenyl)pyridin-4-yl)oxy)pyridin-2-yl)-2-oxoimidazolidine-1-carboxamide, 3-ethyl-N-(5-((2-(2-methylthiazol-5-yl)pyridin-4-yl)oxy)pyridin-2-yl)-2-oxoimidazolidine-1-carboxamide, 3-ethyl-N-(6-methyl-5-((2-(2-methylthiazol-5-yl)pyridin-4-yl)oxy)pyridin-2-yl)-2-oxoimidazolidine-1-carboxamide, 3-cyclopropyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-cyclopentyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-methyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(2,2,2-trifluoroethyl)imidazolidine-1-carboxamide, 3-cyclopentyl-N-(6-methyl-5-((2-(2-methylthiazol-5-yl)pyridin-4-yl)oxy)pyridin-2-yl)-2-oxoimidazolidine-1-carboxamide, N-(5-((2-(4-methyl-1H-imidazol-1-yl)pyridin-4-yl)oxy)pyridin-2-yl)-2-oxo-3-(2,2,2-trifluoroethyl)imidazolidine-1-carboxamide, N-(5-((2-(4-methyl-1H-imidazol-1-yl)pyridin-4-yl)oxy)pyridin-2-yl)-2-oxo-3-(tetrahydro-2H-pyran-4-yl)imidazolidine-1-carboxamide, 3-cyclopentyl-N-(6-ethyl-5-((2-(2-methylthiazol-5-yl)pyridin-4-yl)oxy)pyridin-2-yl)-2-oxoimidazolidine-1-carboxamide, 3-ethyl-N-(5-((2-(4-methyl-1H-imidazol-1-yl)pyridin-4-yl)oxy)pyridin-2-yl)-2-oxoimidazolidine-1-carboxamide, 3-(2-methoxyethyl)-N-(6-methyl-5-((2-(4-(1-methylpiperidin-4-yl)phenyl)pyridin-4-yl)oxy)pyridin-2-yl)-2-oxoimidazolidine-1-carboxamide, 3-(2-methoxyethyl)-N-(6-methyl-5-((2-(1-methyl-1H-imidazol-4-yl)pyridin-4-yl)oxy)pyridin-2-yl)-2-oxoimidazolidine-1-carboxamide, 3-ethyl-N-(5-((2-(1-methyl-1H-imidazol-4-yl)pyridin-4-yl)oxy)pyridin-2-yl)-2-oxoimidazolidine-1-carboxamide, N-(5-((2-(1-methyl-1H-imidazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-imidazol-4-yl)pyridin-4-yl)oxy)pyridin-2-yl)-2-oxo-3-(2,2,2-trifluoroethyl)imidazolidine-1-carboxamide, 3-methyl-N-(4-methyl-5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(4-(1-methylpiperidin-4-yl)phenyl)pyridin-4-yl)oxy)pyridin-2-yl)-2-oxoimidazolidine-1-carboxamide, N-(6-methyl-5-((2'-methyl-[2,4'-bipyridin]-4-yl)oxy)pyridin-2-yl)-2-oxo-3-(tetrahydro-2H-pyran-4-yl)imidazolidine-1-carboxamide, 3-ethyl-N-(4-methyl-5-((2-(4-methyl-1H-imidazol-1-yl)pyridin-4-yl)oxy)pyridin-2-yl)-2-oxoimidazolidine-1-carboxamide, 3-methyl-N-(4-methyl-5-((2-(4-methyl-1H-imidazol-1-yl)pyridin-4-yl)oxy)pyridin-2-yl)-2-oxoimidazolidine-1-carboxamide, 4-((6-(3-(tert-butyl)-2-oxoimidazolidine-1-carboxamido)pyridin-3-yl)oxy)-N-methylpicolinamide, N-(2,5-difluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(2-fluoro-3-methyl-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(4-((2-(1H-pyrazol-4-yl)pyridin-4-yl)oxy)-5-chloro-2-fluorophenyl)-2-oxo-3-(tetrahydro-2H-pyran-4-yl)imidazolidine-1-carboxamide, N-(2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(3-chloro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(4-((2-acetamidopyridin-4-yl)oxy)-5-chloro-2-fluorophenyl)-2-oxo-3-(tetrahydro-2H-pyran-4-yl)imidazolidine-1-carboxamide, N-(2,5-difluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-(1-methoxycyclopropyl)ethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-4-((2-(3,3-dimethylureido)pyridin-4-yl)oxy)-2-fluorophenyl)-2-oxo-3-(tetrahydro-2H-pyran-4-yl)imidazolidine-1-carboxamide, N-(3-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(3-methoxypropyl)-2-oxoimidazolidine-1-carboxamide, N-(5-chloro-2-fluoro-4-((2-(1-methyl-1H-pyrazol-4-yl)pyridin-4-yl)oxy)phenyl)-3-(oxetan-3-yl)-2-oxoimidazolidine-1-carboxamide, (S)—N-(5-chloro-2-fluoro-4-((2-(1-methyl-1H-pyrazol-4-yl)pyridin-4-yl)oxy)phenyl)-3-(1-methoxypropan-2-yl)-2-oxoimidazolidine-1-carboxamide, N-(5-chloro-2-fluoro-4-((2-(1-methyl-1H-pyrazol-4-yl)pyridin-4-yl)oxy)phenyl)-2-oxo-3-(2-(trifluoromethoxy)ethyl)imidazolidine-1-carboxamide, N-(5-chloro-2-fluoro-4-((2-(1-methyl-1H-pyrazol-4-yl)pyridin-4-yl)oxy)phenyl)-3-cyclohexyl-2-oxoimidazolidine-1-carboxamide, N-(5-chloro-2-fluoro-4-((2-(1-methyl-1H-pyrazol-4-yl)pyridin-4-yl)oxy)phenyl)-3-(3-methoxy-3-methylbutyl)-2-oxoimidazolidine-1-carboxamide, N-(5-bromo-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(4,4-difluorocyclohexyl)-2-oxoimidazolidine-1-carboxamide, N-(5-chloro-2-fluoro-4-((2-(1-methyl-1H-pyrazol-4-yl)pyridin-4-yl)oxy)phenyl)-3-cyclopentyl-2-oxoimidazolidine-1-carboxamide, N-(5-chloro-2-fluoro-4-((2-(1-methyl-1H-pyrazol-4-yl)pyridin-4-yl)oxy)phenyl)-3-(2-hydroxy-3,3-dimethylbutyl)-2-oxoimidazolidine-1-carboxamide, N-(3-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-4-((2-(2-cyanoacetamido)pyridin-4-yl)oxy)-2-fluorophenyl)-2-oxo-3-(tetrahydro-2H-pyran-4-yl)imidazolidine-1-carboxamide, 4-((6-(3-ethyl-2-oxoimidazolidine-1-carboxamido)pyridin-3-yl)oxy)-N-methylpicolinamide, N-(5-((2-(3,3-dimethylureido)pyridin-4-yl)oxy)pyridin-2-yl)-3-(2-methoxyethyl)-2-oxoimidazolidine-1-carboxamide, 3-ethyl-N-(5-((2-(2-methyloxazol-5-yl)pyridin-4-yl)oxy)pyridin-2-yl)-2-oxoimidazolidine-1-carboxamide, 3-ethyl-N-(6-methyl-5-((2'-methyl-[2,4'-bipyridin]-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyrimidin-2-yl)-2-oxoimidazolidine-1-carboxamide, N-(5-((2-acetamidopyridin-4-yl)oxy)pyridin-2-yl)-2-oxo-3-(tetrahydro-2H-pyran-4-yl)imidazolidine-1-carboxamide, N-(5-((2-(3,3-dimethylureido)pyridin-4-yl)oxy)pyridin-2-yl)-2-oxo-3-(tetrahydro-2H-pyran-4-yl)imidazolidine-1-carboxamide, N-(5-((2-acetamidopyridin-4-yl)oxy)-6-methylpyridin-2-yl)-2-oxo-3-(tetrahydro-2H-pyran-4-yl)imidazolidine-1-carboxamide, and N-(5-((2-acetamidopyridin-4-yl)oxy)-6-methylpyridin-2-yl)-3-ethyl-2-oxoimidazolidine-1-carboxamide.

In certain embodiments, the invention comprises a method of treating mammalian disease at least partially mediated by the kinase activity of c-FMS, PDGFR-b, or c-KIT kinases, wherein the kinase is a wildtype form, a mutant oncogenic form, an aberrant fusion protein form or a polymorph thereof. The method comprises administering to a mammal in need thereof an effective amount of a compound of Formula I as described herein.

In other embodiments, the present invention comprises a pharmaceutical composition, comprising a compound of Formula I and a pharmaceutically acceptable carrier.

In certain embodiments, the composition comprises an additive selected from adjuvants, excipients, diluents, or stabilizers.

In some embodiments, the invention includes a method of treating cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of Formula I.

In some embodiments, the invention includes a method of treating glioblastomas, breast cancers, pancreatic cancers, metastasis of primary tumor sites, or cancers that are metastatic to bone, the method comprising administering to a patient in need thereof an effective amount of a compound of Formula I.

In certain embodiments of the present methods, the compound is administered orally, parenterally, by inhalation, or subcutaneously.

In some embodiments, the invention provides the use of a compound of Formula I, or a pharmaceutically acceptable salt thereof, in the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia, the method comprising administering to a patient in need thereof an effective amount of a compound of Formula I.

In some embodiments, the invention provides the use of a compound of Formula I, or a pharmaceutically acceptable salt thereof, in the treatment of glioblastomas, breast cancers, pancreatic cancers, metastasis of primary tumor sites, or cancers that are metastatic to bone, the method comprising administering to a patient in need thereof an effective amount of a compound of Formula I.

In some embodiments, the invention provides for the use of a compound of Formula I, or a pharmaceutically acceptable salt thereof, for the manufacture of a medicament for the treatment of cancer, gastrointestinal stromal tumors, hyperproliferative diseases, metabolic diseases, neurodegenerative diseases, solid tumors, melanomas, glioblastomas, ovarian cancer, pancreatic cancer, prostate cancer, lung cancers, breast cancers, renal cancers, hepatic cancers, osteosarcomas, multiple myelomas, cervical carcinomas, metastasis of primary tumor sites, cancers that are metastatic to bone, papillary thyroid carcinoma, non-small cell lung cancer, colonic cancers, rheumatoid arthritis, osteoarthritis, multiple sclerosis, autoimmune nephritis, lupus, Crohn's disease, asthma, chronic obstructive pulmonary disease, osteoporosis, mastocytosis, or mast cell leukemia.

In certain embodiments, the invention provides for the use of a compound of Formula I, or a pharmaceutically acceptable salt thereof, for the manufacture of a medicament for the treatment of glioblastomas, breast cancers, pancreatic cancers, metastasis of primary tumor sites, or cancers that are metastatic to bone.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, and pharmaceutically acceptable salts. Thus, the terms "compound", "compounds", "test compound" or "test compounds" as used in this disclosure refer to the compounds of this disclosure and any and all possible isomers, stereoisomers, enantiomers, diastereomers, tautomers, and pharmaceutically acceptable salts thereof.

DEFINITIONS

The term "alkyl" as used herein refers to a straight chain alkyl, wherein alkyl chain length is indicated by a range of numbers. In exemplary embodiments, "alkyl" refers to an alkyl chain as defined above containing 1, 2, 3, 4, 5, or 6 carbons (i.e., C1-C6 alkyl). Examples of an alkyl group include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing from 3, 4, 5, 6, 7, or 8 carbons (i.e., branched C3-C8 alkyl). Examples of a branched alkyl group include, but are not limited to, iso-propyl, iso-butyl, secondary-butyl, and tertiary-butyl, 2-pentyl, 3-pentyl, 2-hexyl, and 3-hexyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to —$CH_2$—, —$CH_2CH_2$—, and —$CH_2CH_2CH_2$—. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands through which the heterocyclyl ring is connected to an adjacent moiety. For example, in some embodiments, a ring N atom from the heterocyclyl is the bonding atom of the heterocylic moiety. In exemplary embodiments, "heterocyclyl" refers to a monocyclic hydrocarbon containing 4, 5, 6, 7 or 8 ring atoms (i.e., C4-C8 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands through which the heteroaryl ring is connected to an adjacent moiety. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. *Handbook of Pharmaceutical Salts: Properties, Selection and Use*; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, feline, horse, cow, pig, monkey, chimpanzee, baboon, or rhesus monkey.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder.

Structural, chemical and stereochemical definitions are broadly taken from IUPAC recommendations, and more specifically from Glossary of Terms used in Physical Organic Chemistry (IUPAC Recommendations 1994) as summarized by Müller, P. *Pure Appl. Chem.* 1994, 66, pp. 1077-1184 and Basic Terminology of Stereochemistry (IUPAC Recommendations 1996) as summarized by Moss, G. P. *Pure Appl. Chem.* 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

G-X—Y=Z ⇌ X=Y—Z-G where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is H[+], is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19th ed., Mack Publishing Co., 1995).

The compounds of Formula I, or pharmaceutically acceptable salts thereof, may be prepared by a variety of procedures known in the art, as well as those described below. The specific synthetic steps may be combined in different ways to prepare the Formula I compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5th Edition, Michael B. Smith and Jerry March, Wiley Interscience, 2001; Advanced Organic Chemistry, 4th Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate "conc." is concentrated, "DBU" is 1,8-diazabicyclo[5.4.0]undec-7-ene, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphryl azide, "ESI" is electrospray ionization, "Et$_2$O" is diethylether, "EtOAc" is ethyl acetate, "EtOH" is ethanol, "GST" is glutathione S-transferase, "h" is hour or hours, "Hex" is hexane, "IC$_{50}$" is half maximal inhibitory concentration, "LiMHDS" is lithium bis(trimethylsilyl)amide, "MeCN" is acetonitrile, "MeOH" is methanol, "Me$_4$tBuXPhos" is di-tert-butyl(2',4',6'-triisopropyl-3,4,5,6-tetramethyl-[1,1'-biphenyl]-2-yl)phosphine, "MHz" is megahertz, "min" is minute or minutes, "MS" is mass spectrometry, "MTBE" is methyl tert-butyl ether, "NADH" is nicotinamide adenine dinucleotide, "NBS" is N-bromosuccinimide, "NMR" is nuclear magnetic resonance, "PBS" is phosphate buffered saline, "Pd/C" is palladium on carbon, "Pd$_2$(dba)$_3$" is tris(dibenzylideneacetone)dipalladium(0), "Pd(PPh$_3$)$_4$" is tetrakis(triphenylphosphine)palladium (0), "prep-HPLC" is preparative high performance liquid chromatography, "RT" is room temperature which is also known as "ambient temp," which will be understood to consist of a range of normal laboratory temperatures ranging from 15-25° C., "satd." is saturated, "TEA" is triethylamine, "TFA" is trifluoroacetic acid, "THF" is tetrahydrofuran, "Tris" is tris (hydroxymethyl)aminomethane, "Xantphos" is 4,5-bis (diphenylphosphino)-9,9-dimethylxanthene, and "X-Phos" is 2-dicyclohexylphosphino-2',4',6'-triisopropylbiphenyl.

General Chemistry

The compounds of Formula I are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula I is dependent upon the particular compound being synthesized, the starting compound, and the relative lability of the substituted moieties, as is well appreciated by the ordinary skilled chemist. All substituents, unless otherwise indicated, are as defined above.

The compounds of Formula I may contain —NH or —OH moieties in the W, R1, R2, R3, R5, R6, R7, R8 and R9 positions. It will be understood by those skilled in the art that in some instances it may be advantageous to use an amine protecting group during synthesis to temporarily mask one or more —NH moieties. Said protecting group can be removed from any subsequent intermediate leading to the synthesis of compound 1, using standard conditions that effect removal of said protecting group, said conditions of which will be familiar to those skilled in the art. When not specified in a scheme, it will be understood that the W, R1, R2, R3, R5, R6, R7, R8 and R9 moieties represented in the schemes below may optionally contain standard amino or hydroxyl protecting groups that can be removed at any opportune time in the synthetic sequence.

Compounds 1 of the invention can be prepared as illustrated in Scheme 1. In one embodiment, cyclic ureas of formula 2 are reacted with phosgene (or an equivalent, such as diphosgene or triphosgene) in the presence of a base, for example pyridine, to provide an intermediate carbonyl chloride 3. Intermediate 3 may be isolated or may be generated and used in situ. Further reaction of carbonyl chloride 3 with general amine 4 in the presence of a base such as pyridine or triethylamine provides compounds of formula I. In another embodiment, intermediate 3 is reacted with amine 5 to provide intermediate 6. Further conversion of 6 to 1 is effected by reaction of 6 with reagent M-W (7), wherein M is H (when W is —NHC(O)R6, —NHC(O)R7, —NHC(O)N(R8)R9, or an N-linked heteroaryl), or alternately (when W is heteroaryl) wherein M is trialkylstanyl or a boronic acid or boronate ester. Conditions for the transformation of 6 to 1 are dependent on the nature of the W-moiety, but generally include the use of palladium catalysts, for example $Pd(PPh_3)_4$ or $Pd_2(dba)_3$, optionally in the presence of additional ligands, for example Xantphos. General conditions to accomplish these transformation (including Suzuki coupling, Stille coupling, Buchwald amidation) are well known to those skilled in the art.

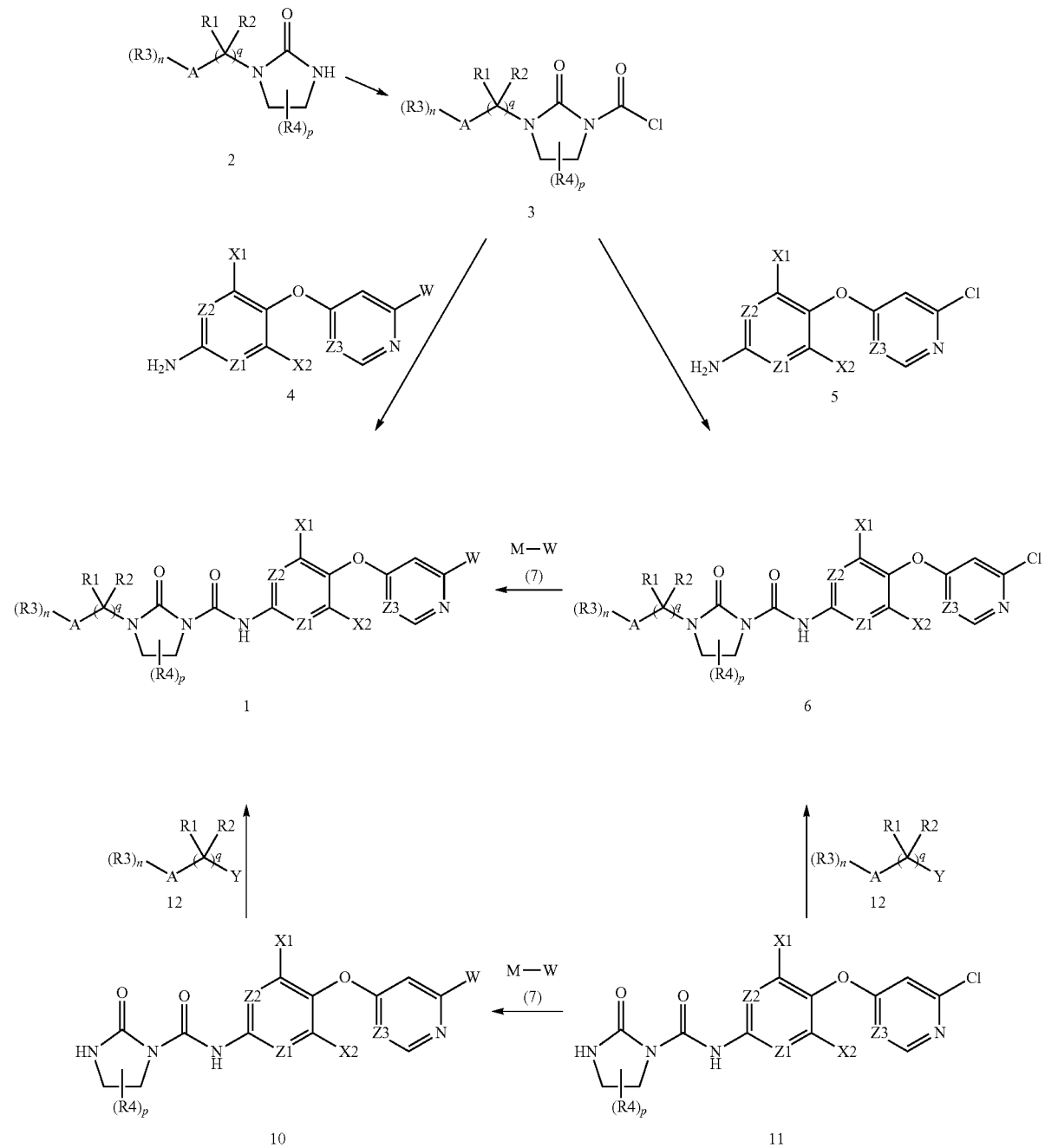

Scheme 1

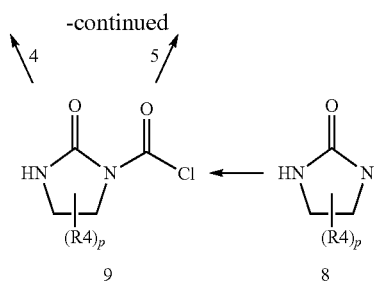

Alternately, compounds of Formula 1 can be prepared directly from intermediate 10 by N-alkylation with an appropriate alkylating agent. In one embodiment, the alkylating agent is intermediate 12 wherein Y is a halide or a sulfonate, for example a mesylate, triflate or tosylate. Similarly, intermediate 6 can also be prepared by alkylation of 11 with 12. In another embodiment, the alkylating agent is an A-substituted oxirane. Intermediates 10 and 11 can be prepared by reaction of 9 with 4 or 5 respectively, as described above for the reaction of 3 with 4 or 5. Intermediate 9 is in turn prepared from imidazolidin-2-one 8 by treatment with phosgene or an equivalent such as triphosogene.

General amines 4 and 5 can be synthesized according to methods commonly known to those skilled in the art as illustrated in Schemes 2-4. Scheme 2 illustrates the preparation of general amines 4 and 5. In one embodiment, amine 5 can be prepared directly from the reaction of 13 with dichloride 14. Suitable conditions include combining 13, 14 and potassium tert-butoxide in a solvent, for example dimethylacetamide, and heating said mixture at a temp of 80-120° C. In another embodiment, amine 5 can be prepared from nitro compound 17 by reduction under standard conditions, for example by treatment with zinc dust in the presence of ammonium chloride or by hydrogenation over Raney nickel. Nitro compound 17 is in turn prepared from the reaction of 16 with compound 15, wherein Y is a halide. Suitable conditions to effect said transformation include combining 15 and 16 with a base, for example potassium carbonate, and heating said mixture at a temp of 80-120° C. in a solvent such as dimethylformamide to effect ether formation. In another embodiment, nitro 17 is obtained by the reaction of 18 with dichloride 14. In one embodiment, by analogy to Scheme 1, further conversion of 5 to 4 is effected by reaction of 5 with reagent M-W (7), wherein M is H (when W is —NHC(O)R6, —NHC(O)R7, —NHC(O)N(R8)R9, or an N-linked heteroaryl), or alternately (when W is heteroaryl) wherein M is trialkylstannyl or a boronic acid or boronate ester. Conditions for the transformation of 5 to 4 are dependent on the nature of the W-moiety, but generally include the use of palladium catalysts, as further illustrated in the accompanying examples. In another embodiment, intermediate 17 can first be transformed to intermediate 19. Further reduction of the nitro group of 19 provides general amine 4.

Scheme 2

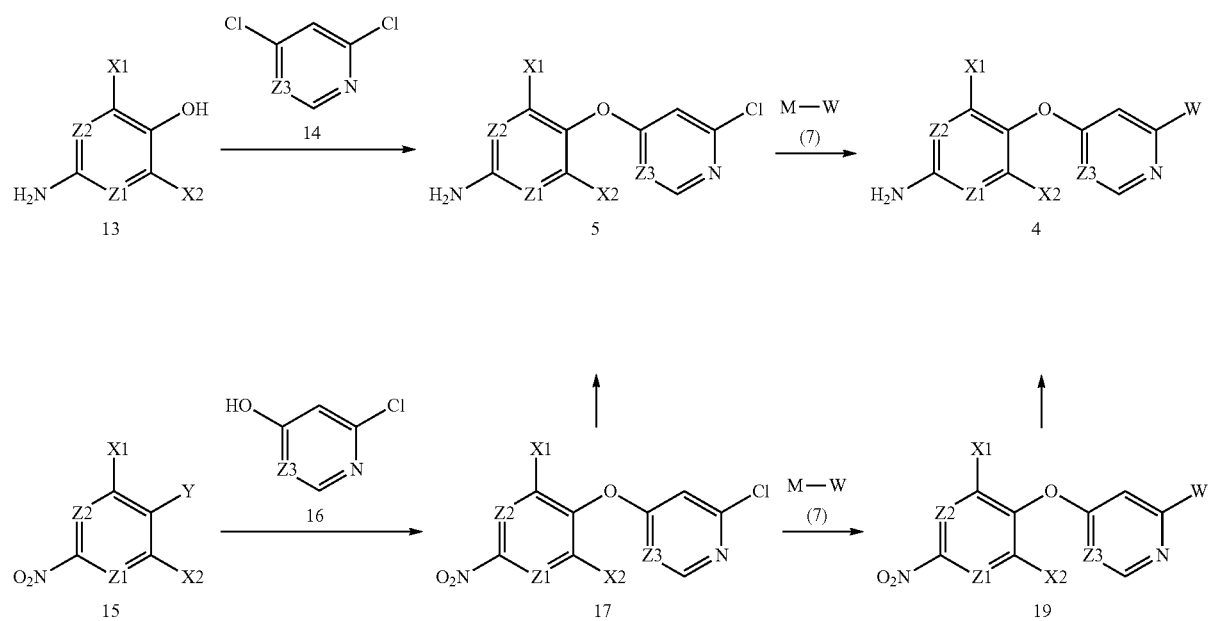

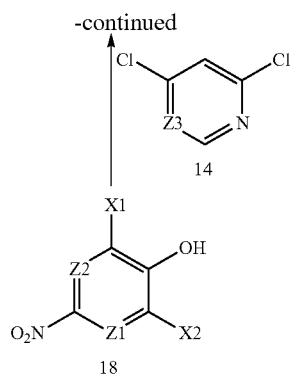

Scheme 3 illustrates the synthesis of amine 24, a variant of general amine 4 wherein W is isoxazol-5-yl. Reaction of amine 5 to with trimethylsilylacetylene (20) in the presence of a palladium catalyst affords 21. Removal of the trimethylsilyl group affords 22. Conversion of 22 to isoxazole 24 is accomplished by [3+2]cycloaddition with the reagent derived from oxime 23, N-chlorosuccinimide, and triethylamine. Alternately, amine 24 can be prepared by reduction of the nitro moiety of 27, in turn available by a similar sequence of reactions commencing with nitro-chloride 17.

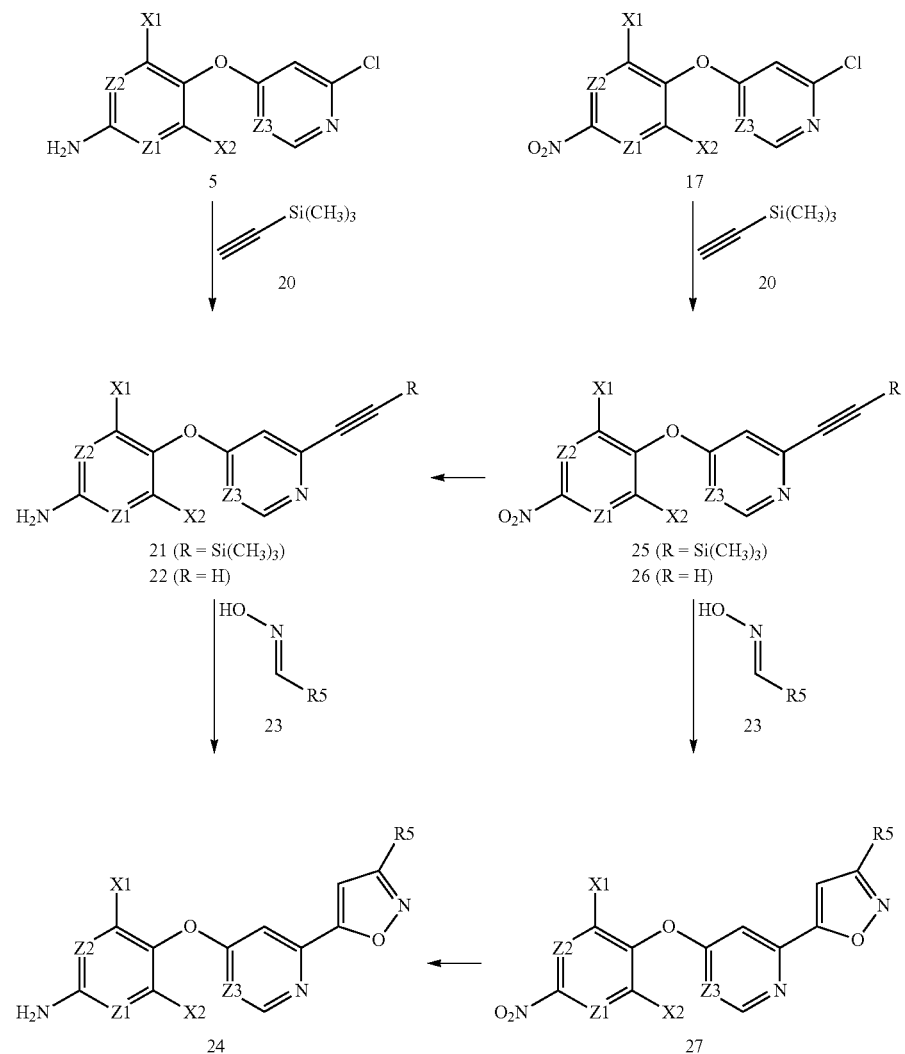

Scheme 4 illustrates the synthesis of amine 31, a variant of general amine 4 wherein W is —C(O)NR(R9).

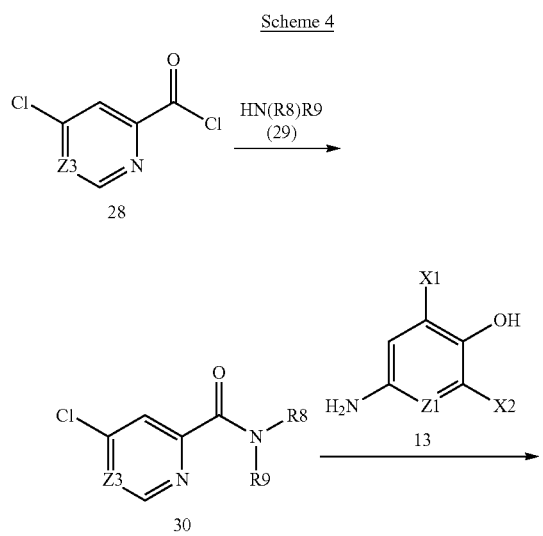

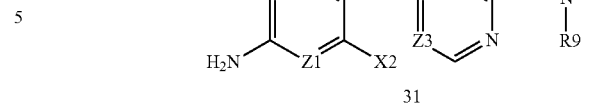

Scheme 5 illustrates an alternate preparation of general amine 38 (amine 4 wherein Z1 is N and Z3 is CH) from iodide 33. Following Scheme 2, hydroxypyridine 33 and dichloride 14 are combined with heating in the presence of a base such as potassium carbonate to provide iodo ether 34. Further reaction of 34 with an aminocarbonyl reagent 35, $Cs_2CO_3$ (2.115 g, 6.46 mmol), X-Phos, and tris(dibenzylideneacetone)dipalladium [$Pd_2(dba)_3$] with heating in a suitable solvent, such as dioxane, provides 36. Suitable R-groups of 35 and 36 include alkyl or alkoxy. Using the methods described in Schemes 2 and 3, above, the chloride of 36 can be converted to a W-moiety to provide 37. Removal of the RC(O)-protecting group of 37, for example by treatment with acid, provides amine 38, an example of general amine 4. In a similar manner, the RC(O)-protecting group of 36 can be directly removed to provide general intermediate 39, an example of general intermediate 5 wherein Z1 is N and Z3 is CH.

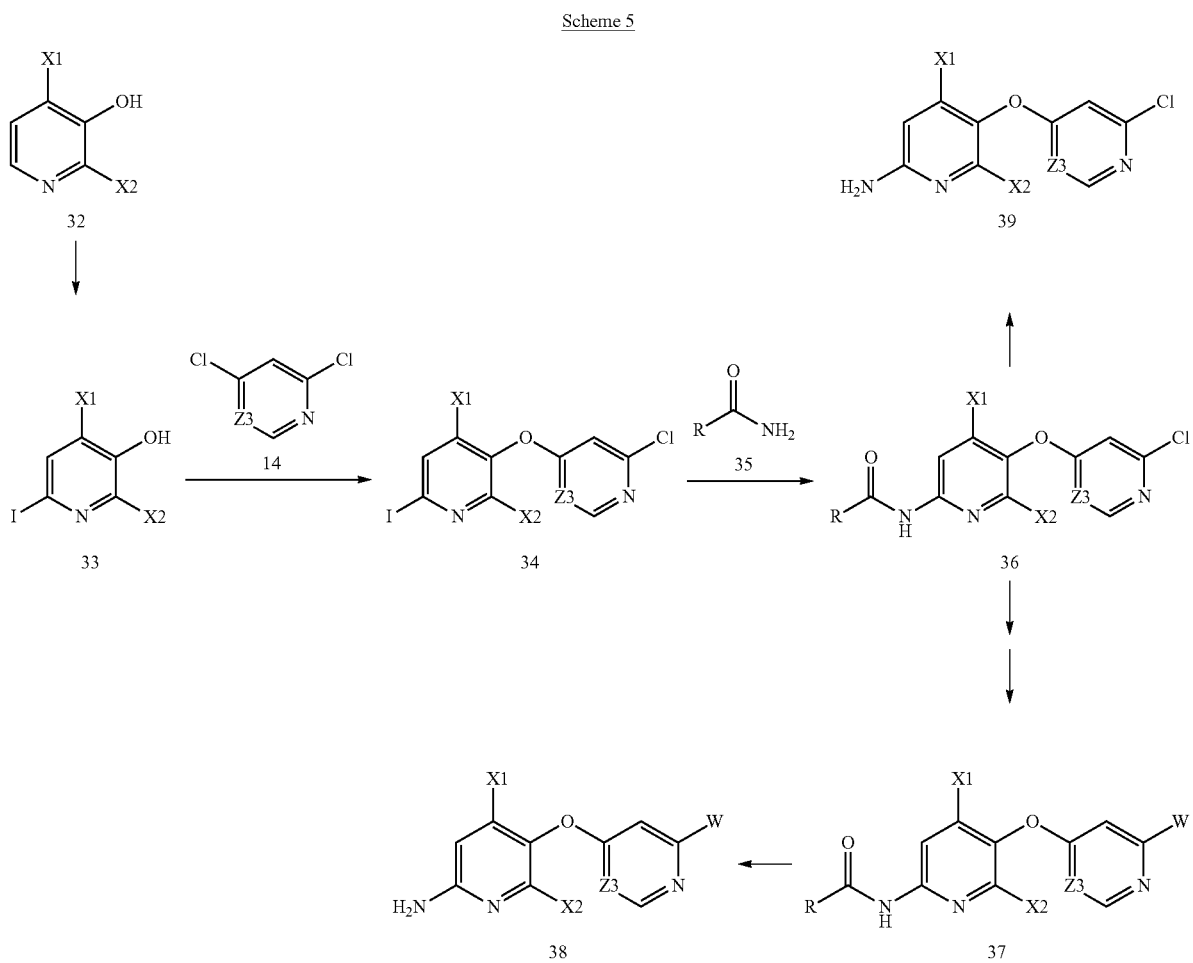

General ureas of formula 2 useful for the invention can be prepared by the general methods of Schemes 6-8. In one embodiment, urea 46 is prepared according to Scheme 6 commencing with isocyanate 40 (Y is halo). Reaction of 40 with amine 41 provides urea 42. Treatment of 42 with a base, for example sodium hydride, in an aprotic solvent, for example THF, optionally while heating the reaction mixture, effects an intramolecular alkylation to form the cyclic urea 46. In some embodiments the conversion of 40 to 46 can be performed without the isolation of 42. In other embodiments, intermediate 42 can be prepared by reaction of amine 43 (Y is halo) with isocyanate 44. In other embodiments, intermediate 42 can be prepared by reaction of amine 43 (Y is halo) with acid 45 in the presence of diphenylphosphoryl azide (DPPA) and heating said mixture to effect a Curtius rearrangement [in situ generation of isocyanate 44]. It will be understood in Schemes 6 and 7 that the R3 and R4 groups are independently variable within each compound and may also be hydrogen.

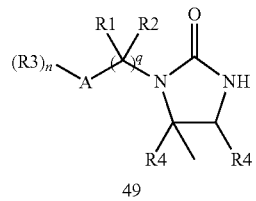

49

In another embodiment, urea 2 is prepared from imidazolidin-2-one 8 by alkylation with intermediate 12 wherein Y is a halide or a sulfonate (for example a mesylate, triflate or tosylate), as shown in Scheme 8. Conditions include the addition of a base, for example lithium bis(trimethylsilyl)amide, optionally with heating.

Scheme 6

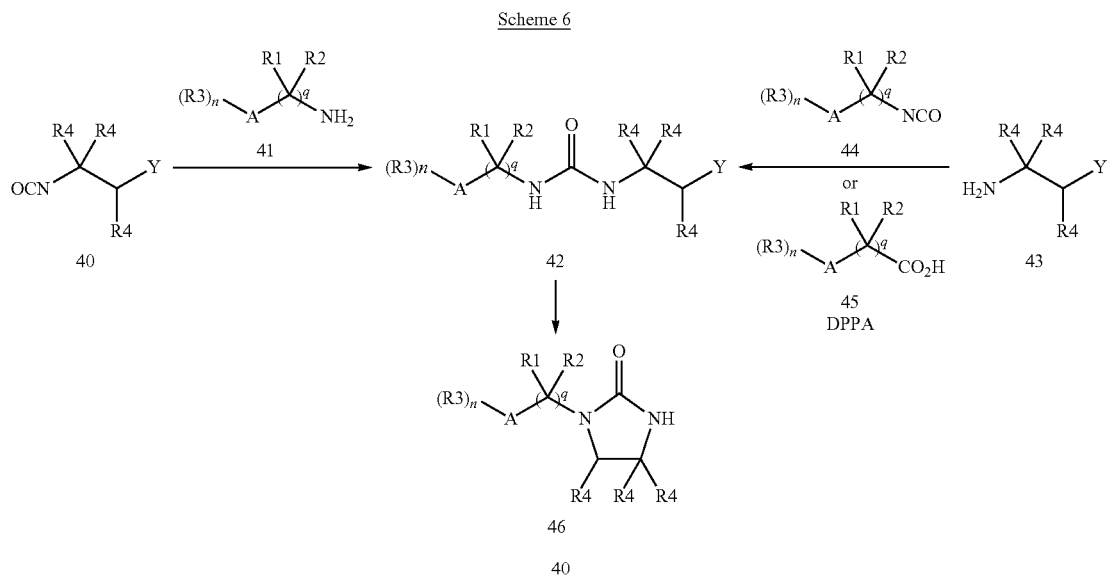

In another embodiment, urea 49 is prepared as shown in Scheme 7 by the reaction of allylic amine 47 with isocyanate 44 to provide 48. Treatment of allylic urea 48 with an acid, for example trifluoroacetic acid, effects cyclization to form urea 49.

Scheme 7

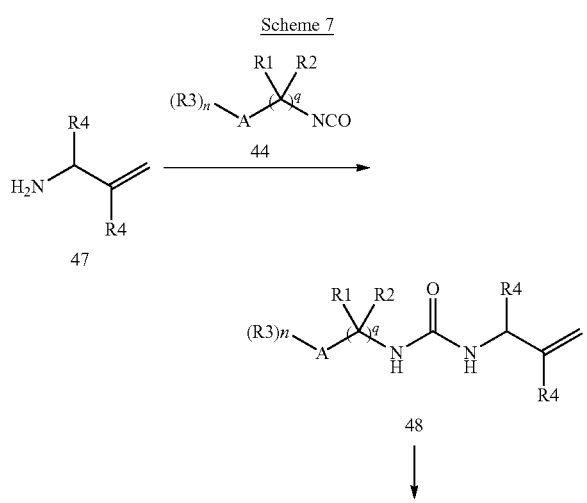

Scheme 8

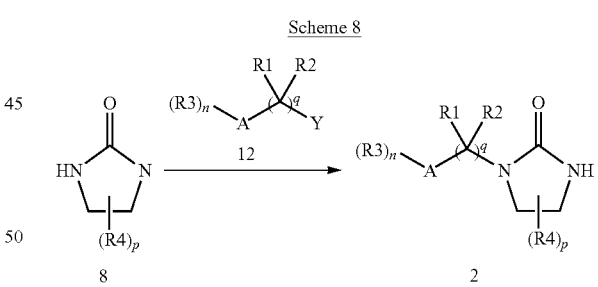

Using the synthetic procedures and methods described herein and methods known to those skilled in the art, the following compounds were made: N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(6-methyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-ethyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1H-pyrazol-4-yl)pyridin-4-yl)oxy)pyridin-2-yl)-2-oxo-3-(tetrahydro-2H-pyran-4-yl)imidazolidine-1-carboxamide, 2-oxo-3-(tetrahydro-2H-pyran-4-yl)-N-(5-((2-(1-(trideuteromethyl)-1H-pyrazol-4-yl)pyridin-4-yl)oxy) pyridin-2-yl)imidazolidine-1-carboxamide, N-(5-((2-(3- methylisoxazol-5-yl)pyridin-4-yl)oxy)pyridin-2-yl)-2-oxo-3-(tetrahydro-2H-pyran-4-yl)imidazolidine-1-carboxamide, N-(5-((6-(1-methyl-1H-pyrazol-4-yl)pyrimidin-4-yl)oxy) pyridin-2-yl)-2-oxo-3-(tetrahydro-2H-pyran-4-yl)imidazolidine-1-carboxamide, N-(5-((2-(1H-pyrazol-4-yl)pyridin-4-yl)oxy)-6-methylpyridin-2-yl)-2-oxo-3-(tetrahydro-2H-pyran-4-yl)imidazolidine-1-carboxamide, 3-(2-methoxyethyl)-N-(5-((2-(1-methyl-1H-pyrazol-4-yl)pyridin-4-yl)oxy)pyridin-2-yl)-2-oxoimidazolidine-1-carboxamide, 3-(3-methoxypropyl)-N-(5-((2-(1-methyl-1H-pyrazol-4-yl)pyridin-4-yl)oxy)pyridin-2-yl)-2-oxoimidazolidine-1-carboxamide, (S)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(2,2-dimethyltetrahydro-2H-pyran-4-yl)-N-(5-((2-(1-methyl-1H-pyrazol-4-yl)pyridin-4-yl)oxy)pyridin-2-yl)-2-oxoimidazolidine-1-carboxamide, N-(6-methyl-5-((2-(3-methylisoxazol-5-yl)pyridin-4-yl)oxy)pyridin-2-yl)-2-oxo-3-(tetrahydro-2H-pyran-4-yl)imidazolidine-1-carboxamide, 3-cyclohexyl-N-(5-((2-(1-methyl-1H-pyrazol-4-yl)pyridin-4-yl)oxy)pyridin-2-yl)-2-oxoimidazolidine-1-carboxamide, (S)-3-(1-methoxypropan-2-yl)-N-(5-((2-(1-methyl-11H-pyrazol-4-yl)pyridin-4-yl)oxy)pyridin-2-yl)-2-oxoimidazolidine-1-carboxamide, 3-(2-(1-methoxycyclopropyl)ethyl)-N-(5-((2-(1-methyl-1H-pyrazol-4-yl)pyridin-4-yl)oxy) pyridin-2-yl)-2-oxoimidazolidine-1-carboxamide, 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide, 3-(3-methoxypropyl)-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2-(1-methyl-1H-pyrazol-4-yl)pyridin-4-yl)oxy)pyridin-2-yl)-2-oxo-3-(2-(trifluoromethoxy)ethyl)imidazolidine-1-carboxamide, 3-cyclohexyl-N-(6-methyl-5-((2-(1-methyl-1H-pyrazol-4-yl)pyridin-4-yl)oxy)pyridin-2-yl)-2-oxoimidazolidine-1-carboxamide, (S)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(3-methoxy-3-methylbutyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(6-methyl-5-((2-(1-methyl-1H-pyrazol-4-yl)pyridin-4-yl)oxy)pyridin-2-yl)-2-oxoimidazolidine-1-carboxamide, (R)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, (R)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-cyclopentyl-N-(6-methyl-5-((2-(1-methyl-1H-pyrazol-4-yl)pyridin-4-yl)oxy)pyridin-2-yl)-2-oxoimidazolidine-1-carboxamide, 3-cyclopentyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(5-((2-(1-methyl-1H-pyrazol-4-yl)pyridin-4-yl)oxy)pyridin-2-yl)-2-oxoimidazolidine-1-carboxamide, 3-isopropyl-N-(6-methyl-5-((2-(1-methyl-1H-pyrazol-4-yl)pyridin-4-yl)oxy) pyridin-2-yl)-2-oxoimidazolidine-1-carboxamide, 3-isopropyl-N-(5-((2-(1-methyl-1H-pyrazol-4-yl)pyridin-4-yl)oxy)pyridin-2-yl)-2-oxoimidazolidine-1-carboxamide, (R)—N-(6-methyl-5-((2-(1-(trideuteromethyl)-1H-pyrazol-4-yl)pyridin-4-yl)oxy)pyridin-2-yl)-2-oxo-3-(tetrahydrofuran-3-yl)imidazolidine-1-carboxamide, (S)-3-(1-methoxypropan-2-yl)-N-(6-methyl-5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-(trideuteromethyl)-1H-pyrazol-4-yl)pyridin-4-yl)oxy) pyridin-2-yl)-2-oxoimidazolidine-1-carboxamide, 4-methyl-N-(5-((2-(1-methyl-1H-pyrazol-4-yl)pyridin-4-yl)oxy) pyridin-2-yl)-2-oxo-3-(tetrahydro-2H-pyran-4-yl) imidazolidine-1-carboxamide, 3-methyl-N-(6-methyl-5-((2-(1-methyl-1H-pyrazol-4-yl)pyridin-4-yl)oxy)pyridin-2-yl)-2-oxoimidazolidine-1-carboxamide, 3-ethyl-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-methyl-N-(5-((2-(1-methyl-1H-pyrazol-4-yl)pyridin-4-yl)oxy)pyridin-2-yl)-2-oxoimidazolidine-1-carboxamide, 3-ethyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(1-methyl-1H-pyrazol-4-yl)pyridin-4-yl)oxy)pyridin-2-yl)-2-oxoimidazolidine-1-carboxamide, N-(5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, N-(6-ethyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2'-methyl-[2,4'-bipyridin]-4-yl)oxy)pyridin-2-yl)-2-oxo-3-(tetrahydro-2H-pyran-4-yl)imidazolidine-1-carboxamide, N-(5-((6'-methyl-[2,3'-bipyridin]-4-yl)oxy) pyridin-2-yl)-2-oxo-3-(tetrahydro-2H-pyran-4-yl) imidazolidine-1-carboxamide, N-(6-methyl-5-((6'-methyl-[2,3'-bipyridin]-4-yl)oxy)pyridin-2-yl)-2-oxo-3-(2,2,2-trifluoroethyl)imidazolidine-1-carboxamide, N-(6-methyl-5-((6'-methyl-[2,3'-bipyridin]-4-yl)oxy)pyridin-2-yl)-2-oxo-3-(tetrahydro-2H-pyran-4-yl)imidazolidine-1-carboxamide, 3-(cyanomethyl)-N-(5-((2-(1-methyl-1H-pyrazol-4-yl)pyridin-4-yl)oxy)pyridin-2-yl)-2-oxoimidazolidine-1-carboxamide, N-(6-ethyl-5-((2-(1-methyl-1H-pyrazol-4-yl)pyridin-4-yl)oxy)pyridin-2-yl)-2-oxo-3-(2,2,2-trifluoroethyl) imidazolidine-1-carboxamide, 3-cyclopentyl-N-(6-ethyl-5-((2-(1-methyl-1H-pyrazol-4-yl)pyridin-4-yl)oxy)pyridin-2-yl)-2-oxoimidazolidine-1-carboxamide, 3-cyclopropyl-N-(6-ethyl-5-((2-(1-methyl-1H-pyrazol-4-yl)pyridin-4-yl)oxy) pyridin-2-yl)-2-oxoimidazolidine-1-carboxamide, (R)-3-(1-methoxypropan-2-yl)-N-(5-((2-(1-methyl-11H-pyrazol-4-yl)pyridin-4-yl)oxy)pyridin-2-yl)-2-oxoimidazolidine-1-carboxamide, N-(5-((2-(2-methylthiazol-5-yl)pyridin-4-yl) oxy)pyridin-2-yl)-2-oxo-3-(tetrahydro-2H-pyran-4-yl) imidazolidine-1-carboxamide, 3-ethyl-N-(6-methyl-5-((2-(4-(1-methylpiperidin-4-yl)phenyl)pyridin-4-yl)oxy) pyridin-2-yl)-2-oxoimidazolidine-1-carboxamide, 3-(2-methoxyethyl)-N-(5-((2-(2-methylthiazol-5-yl)pyridin-4-yl) oxy)pyridin-2-yl)-2-oxoimidazolidine-1-carboxamide, N-(6-ethyl-5-((6'-methyl-[2,3'-bipyridin]-4-yl)oxy)pyridin-2-yl)-2-oxo-3-(tetrahydro-2H-pyran-4-yl)imidazolidine-1-carboxamide, N-(6-ethyl-5-((2'-methyl-[2,4'-bipyridin]-4-yl)oxy)pyridin-2-yl)-2-oxo-3- (tetrahydro-2H-pyran-4-yl)

imidazolidine-1-carboxamide, 3-cyclopropyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(tetrahydro-2H-pyran-4-yl)imidazolidine-1-carboxamide, 3-(2-methoxyethyl)-N-(6-methyl-5-((2-(2-methylthiazol-5-yl)pyridin-4-yl)oxy)pyridin-2-yl)-2-oxoimidazolidine-1-carboxamide, 3-ethyl-N-(6-methyl-5-((2-(4-(4-methylpiperazin-1-yl)phenyl)pyridin-4-yl)oxy)pyridin-2-yl)-2-oxoimidazolidine-1-carboxamide, 3-ethyl-N-(5-((2-(2-methylthiazol-5-yl)pyridin-4-yl)oxy)pyridin-2-yl)-2-oxoimidazolidine-1-carboxamide, 3-ethyl-N-(6-methyl-5-((2-(2-methylthiazol-5-yl)pyridin-4-yl)oxy)pyridin-2-yl)-2-oxoimidazolidine-1-carboxamide, 3-cyclopropyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-cyclopentyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-methyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(2,2,2-trifluoroethyl)imidazolidine-1-carboxamide, 3-cyclopentyl-N-(6-methyl-5-((2-(2-methylthiazol-5-yl)pyridin-4-yl)oxy)pyridin-2-yl)-2-oxoimidazolidine-1-carboxamide, N-(5-((2-(4-methyl-1H-imidazol-1-yl)pyridin-4-yl)oxy)pyridin-2-yl)-2-oxo-3-(2,2,2-trifluoroethyl)imidazolidine-1-carboxamide, N-(5-((2-(4-methyl-1H-imidazol-1-yl)pyridin-4-yl)oxy)pyridin-2-yl)-2-oxo-3-(tetrahydro-2H-pyran-4-yl)imidazolidine-1-carboxamide, 3-cyclopentyl-N-(6-ethyl-5-((2-(2-methylthiazol-5-yl)pyridin-4-yl)oxy)pyridin-2-yl)-2-oxoimidazolidine-1-carboxamide, 3-ethyl-N-(5-((2-(4-methyl-1H-imidazol-1-yl)pyridin-4-yl)oxy)pyridin-2-yl)-2-oxoimidazolidine-1-carboxamide, 3-(2-methoxyethyl)-N-(6-methyl-5-((2-(4-(1-methylpiperidin-4-yl)phenyl)pyridin-4-yl)oxy)pyridin-2-yl)-2-oxoimidazolidine-1-carboxamide, 3-(2-methoxyethyl)-N-(6-methyl-5-((2-(1-methyl-1H-imidazol-4-yl)pyridin-4-yl)oxy)pyridin-2-yl)-2-oxoimidazolidine-1-carboxamide, 3-ethyl-N-(5-((2-(1-methyl-1H-imidazol-4-yl)pyridin-4-yl)oxy)pyridin-2-yl)-2-oxoimidazolidine-1-carboxamide, N-(5-((2-(1-methyl-1H-imidazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-imidazol-4-yl)oxy)pyridin-4-yl)oxy)pyridin-2-yl)-2-oxo-3-(2,2,2-trifluoroethyl)imidazolidine-1-carboxamide, 3-methyl-N-(4-methyl-5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(4-(1-methylpiperidin-4-yl)phenyl)pyridin-4-yl)oxy)pyridin-2-yl)-2-oxoimidazolidine-1-carboxamide, N-(6-methyl-5-((2'-methyl-[2,4'-bipyridin]-4-yl)oxy)pyridin-2-yl)-2-oxo-3-(tetrahydro-2H-pyran-4-yl)imidazolidine-1-carboxamide, 3-ethyl-N-(4-methyl-5-((2-(4-methyl-1H-imidazol-1-yl)pyridin-4-yl)oxy)pyridin-2-yl)-2-oxoimidazolidine-1-carboxamide, 3-methyl-N-(4-methyl-5-((2-(4-methyl-1H-imidazol-1-yl)pyridin-4-yl)oxy)pyridin-2-yl)-2-oxoimidazolidine-1-carboxamide, 4-((6-(3-(tert-butyl)-2-oxoimidazolidine-1-carboxamido)pyridin-3-yl)oxy)-N-methylpicolinamide, N-(2,5-difluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(2-fluoro-3-methyl-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(4-((2-(1H-pyrazol-4-yl)pyridin-4-yl)oxy)-5-chloro-2-fluorophenyl)-2-oxo-3-(tetrahydro-2H-pyran-4-yl)imidazolidine-1-carboxamide, N-(2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(3-chloro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(4-((2-acetamidopyridin-4-yl)oxy)-5-chloro-2-fluorophenyl)-2-oxo-3-(tetrahydro-2H-pyran-4-yl)imidazolidine-1-carboxamide, N-(2,5-difluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-(1-methoxycyclopropyl)ethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-4-((2-(3,3-dimethylureido)pyridin-4-yl)oxy)-2-fluorophenyl)-2-oxo-3-(tetrahydro-2H-pyran-4-yl)imidazolidine-1-carboxamide, N-(3-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(3-methoxypropyl)-2-oxoimidazolidine-1-carboxamide, N-(5-chloro-2-fluoro-4-((2-(1-methyl-1H-pyrazol-4-yl)pyridin-4-yl)oxy)phenyl)-3-(oxetan-3-yl)-2-oxoimidazolidine-1-carboxamide, (S)—N-(5-chloro-2-fluoro-4-((2-(1-methyl-1H-pyrazol-4-yl)pyridin-4-yl)oxy)phenyl)-3-(1-methoxypropan-2-yl)-2-oxoimidazolidine-1-carboxamide, N-(5-chloro-2-fluoro-4-((2-(1-methyl-1H-pyrazol-4-yl)pyridin-4-yl)oxy)phenyl)-2-oxo-3-(2-(trifluoromethoxy)ethyl)imidazolidine-1-carboxamide, N-(5-chloro-2-fluoro-4-((2-(1-methyl-1H-pyrazol-4-yl)pyridin-4-yl)oxy)phenyl)-3-cyclohexyl-2-oxoimidazolidine-1-carboxamide, N-(5-chloro-2-fluoro-4-((2-(1-methyl-1H-pyrazol-4-yl)pyridin-4-yl)oxy)phenyl)-3-(3-methoxy-3-methylbutyl)-2-oxoimidazolidine-1-carboxamide, N-(5-bromo-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(4,4-difluorocyclohexyl)-2-oxoimidazolidine-1-carboxamide, N-(5-chloro-2-fluoro-4-((2-(1-methyl-1H-pyrazol-4-yl)pyridin-4-yl)oxy)phenyl)-3-cyclopentyl-2-oxoimidazolidine-1-carboxamide, N-(5-chloro-2-fluoro-4-((2-(1-methyl-1H-pyrazol-4-yl)pyridin-4-yl)oxy)phenyl)-3-(2-hydroxy-3,3-dimethylbutyl)-2-oxoimidazolidine-1-carboxamide, N-(3-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-4-((2-(2-cyanoacetamido)pyridin-4-yl)oxy)-2-fluorophenyl)-2-oxo-3-(tetrahydro-2H-pyran-4-yl)imidazolidine-1-carboxamide, 4-((6-(3-ethyl-2-oxoimidazolidine-1-carboxamido)pyridin-3-yl)oxy)-N-methylpicolinamide, N-(5-((2-(3,3-dimethylureido)pyridin-4-yl)oxy)pyridin-2-yl)-3-(2-methoxyethyl)-2-oxoimidazolidine-1-carboxamide, 3-ethyl-N-(5-((2-(2-methyloxazol-5-yl)pyridin-4-yl)oxy)pyridin-2-yl)-2-oxoimidazolidine-1-carboxamide, 3-ethyl-N-(6-methyl-5-((2'-methyl-[2,4'-bipyridin]-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyrimidin-2-yl)-2-oxoimidazolidine-1-carboxamide, N-(5-((2-acetamidopyridin-4-yl)oxy)pyridin-2-yl)-2-oxo-3-(tetrahydro-2H-pyran-4-yl)imidazolidine-1-carboxamide, N-(5-((2-(3,3-dimethylureido)pyridin-4-yl)oxy)pyridin-2-yl)-2-oxo-3-(tetrahydro-2H-pyran-4-yl)imidazolidine-1-carboxamide, N-(5-((2-acetamidopyridin-4-yl)oxy)-6-methylpyridin-2-yl)-2-oxo-3-(tetrahydro-2H-pyran-4-yl) imidazolidine-1-carboxamide, and N-(5-((2-acetamidopyridin-4-yl)oxy)-6-methylpyridin-2-yl)-3-ethyl-2-oxoimidazolidine-1-carboxamide.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

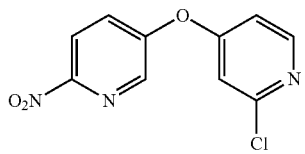 [SMILES: O=[N+]([O-])c1ccc(Oc2ccnc(Cl)c2)cn1]

Example A1

A solution of 5-bromo-2-nitropyridine (15 g, 73.9 mmol) in DMF (300 mL) was sparged with Ar, treated with $Cs_2CO_3$ (48.2 g, 148 mmol) and 2-chloro-4-hydroxypyridine (10.53 g, 81 mmol), sparged again with Ar and heated at 85° C. overnight. The mixture was cooled to RT, filtered through a bed of silica gel, washed thoroughly with EtOAc, and the filtrate treated with 5% LiCl and stirred overnight. The layers were separated, the aqueous layer extracted with additional EtOAc (4×) and the combined organics were dried over $Na_2SO_4$ and concentrated to dryness. The residue was dissolved in EtOAc, treated with 5% LiCl, stirred for 1 h, the layers separated and the aqueous layer extracted with EtOAc (3×). The combined organics were dried over $Na_2SO_4$, concentrated to dryness and purified via silica gel chromatography (EtOAc/Hex). The material was suspended in MTBE, sonicated and the resulting solid collected via filtration to afford 2-chloro-4-((6-nitropyridin-3-yl)oxy)pyridine (6.06 g, 33%). $^1$H NMR (400 MHz, DMSO-$d_6$): δ 8.62 (d, J=2.4, 1 H), 8.43-8.39 (m, 2 H), 8.06 (dd, J=8.8, 2.8 Hz, 1 H), 7.36 (d, J=2.0 Hz, 1 H), 7.23 (dd, J=5.6, 2.0 Hz, 1 H); MS (ESI) m/z: 252.0 (M+H+).

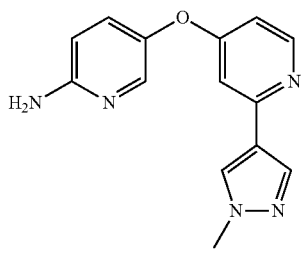 [SMILES: Cn1cc(-c2cc(Oc3ccc(N)nc3)ccn2)cn1]

Example A2

A suspension of Example A1 (14.38 g, 57.1 mmol), 1-methyl-4-(4,4,5,5-tetramethyl-1,3,2-dioxaborolan-2-yl)-1H-pyrazole (13.08 g, 62.9 mmol) and $Cs_2CO_3$ (55.9 g, 171 mmol) in DMF (150 mL) was sparged with Ar, treated with $Pd(PPh_3)_4$ (6.60 g, 5.71 mmol), sparged again with Ar and heated at 90° C. overnight. The mixture was cooled to RT, the solids removed via filtration through diatomaceous earth, washed with EtOAc and the filtrate concentrated to near-dryness. The residue was treated with EtOAc, washed with 5% LiCl (1×) and the aqueous layer back-extracted with EtOAc (4×). The combined organics were dried over $Na_2SO_4$, concentrated to dryness and purified via silica gel chromatography (MeOH/DCM) to afford 2-(1-methyl-1H-pyrazol-4-yl)-4-((6-nitropyridin-3-yl)oxy)pyridine (12.28 g, 72%). $^1$H NMR (400 MHz, DMSO-$d_6$): δ 8.59 (d, J=2.8 Hz, 1 H), 8.49 (d, J=5.6 Hz, 1 H), 8.41 (d, J=8.9 Hz, 1 H), 8.29 (s, 1 H), 8.00 (d, J=0.7 Hz, 1 H), 7.97 (dd, J=8.9, 2.8 Hz, 1 H), 7.44 (d, J=2.4 Hz, 1 H), 6.97 (dd, J=5.6, 2.4 Hz, 1 H), 3.85 (s, 3 H); MS (ESI) m/z: 298.1 (M+H+).

A mixture of 2-(1-methyl-1H-pyrazol-4-yl)-4-((6-nitropyridin-3-yl)oxy)pyridine (11.88 g, 40.0 mmol) and $NH_4Cl$ (22.4 g, 419 mmol) in EtOH (200 mL) and water (200 mL) was treated portion-wise with iron powder (22.4 g, 401 mmol), stirred for 0.5 h, treated with additional $NH_4Cl$ (22.4 g, 419 mmol) and iron powder (22.4 g, 401 mmol) and stirred at RT for 3 h. The solids were removed via filtration through diatomaceous earth and washed with EtOAc and DCM. The filtrate was washed with water, the aqueous layer back-extracted with DCM (4×) and the combined organics were dried over $Na_2SO_4$, concentrated to dryness and purified via silica gel chromatography (MeOH/DCM) to afford 5-((2-(1-methyl-1H-pyrazol-4-yl)pyridin-4-yl)oxy)pyridin-2-amine (6.4 g, 60%). MS (ESI) m/z: 268.1 (M+H+).

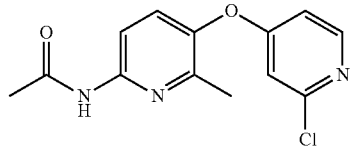 [SMILES: CC(=O)Nc1ccc(Oc2ccnc(Cl)c2)c(C)n1]

Example A3

A solution of 3-hydroxy-2-methylpyridine (20.0 g, 183 mmol) and $Na_2CO_3$ (38.8 g, 367 mmol) in $H_2O$ (320 mL) and MeOH (200 mL) was treated with $I_2$ (46.5 g, 183 mmol) and stirred at RT for 1 h. The mixture was acidified with HCl (2 M), extracted with EtOAc (2×) and the combined organics were washed with brine, dried over $Na_2SO_4$ and concentrated to dryness. The material was suspended in 1:1 EtOAc/Hex, sonicated and the solid collected via filtration and dried. The filtrate was concentrated to dryness, treated with DCM, the solid collected via filtration and combined with the first solid to afford 6-iodo-2-methylpyridin-3-ol (20.5 g, 48%). MS (ESI) m/z: 236.0 (M+H$^+$).

A mixture of 6-iodo-2-methylpyridin-3-ol (6.8 g, 28.9 mmol), 2,4-dichloro pyridine (8.56 g, 57.9 mmol) and $K_2CO_3$ (4.00 g, 28.9 mmol) in DMA (50 mL) was heated at 110° C. for 16 h under argon. The mixture was cooled to RT, treated with $H_2O$, extracted with EtOAc (2×) and the combined organics were washed with $H_2O$, then brine, dried over $Na_2SO_4$, concentrated to dryness and purified via silica gel chromatography (EtOAc/Hex) to afford 3-((2-chloropyridin-4-yl)oxy)-6-iodo-2-methylpyridine (7.35 g, 73%) as a white solid. MS (ESI) m/z: 346.9 (M+H$^+$).

A solution of 3-((2-chloropyridin-4-yl)oxy)-6-iodo-2-methylpyridine (8.5 g, 24.53 mmol) in dioxane (100 mL) was sparged with argon, treated with acetamide (5.07 g, 86 mmol), Cs$_2$CO$_3$ (11.99 g, 36.8 mmol), X-Phos (0.585 g, 1.226 mmol) and Pd$_2$(dba)$_3$ (1.123 g, 1.226 mmol) and heated at 83° C. for 16 h. The mixture was cooled to RT, treated with EtOAc, solids removed via filtration through diatomaceous earth, rinsed well with EtOAc, and the filtrate washed with H$_2$O, then brine, dried over Na$_2$SO$_4$, concentrated to dryness and purified via silica gel chromatography (EtOAc/Hex) to afford N-(5-((2-chloropyridin-4-yl)oxy)-6-methylpyridin-2-yl)acetamide (3.8 g, 56%) as an off-white solid. MS (ESI) m/z: 278.0 (M+H$^+$).

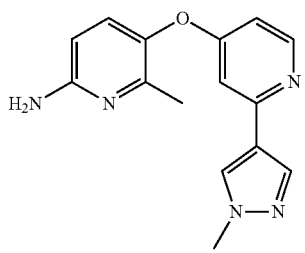 [SMILES: Cc1nc(N)ccc1Oc1ccnc(-c2cnn(C)c2)c1]

Example A4

Method 1: A solution of Example A3 (3.83 g, 13.79 mmol) in dioxane (50 mL) was sparged with argon, treated with a solution of K$_2$CO$_3$ (3.81 g, 27.6 mmol) in H$_2$O (10 mL), 1-methyl-4-(4,4,5,5-tetramethyl-1,3,2-dioxaborolan-2-yl)-1H-pyrazole (3.44 g, 16.55 mmol) and Pd(PPh$_3$)$_4$ (0.637 g, 0.552 mmol) and heated at 80° C. for 16 h. The mixture was cooled to RT, treated with H$_2$O, extracted with EtOAc (2×) and the combined organics washed with H$_2$O, then brine, dried over Na$_2$SO$_4$ and concentrated to dryness. The material was suspended in 3:2 EtOAc/Hex, sonicated and the resulting solid collected via filtration and dried. The filtrate was concentrated to dryness, purified via silica gel chromatography (MeOH/DCM) and combined with the isolated solid to afford N-(6-methyl-5-((2-(1-methyl-1H-pyrazol-4-yl)pyridin-4-yl)oxy)pyridin-2-yl)acetamide (3.88 g, 87%) as a white solid. $^1$H NMR (400 MHz, DMSO-d$_6$): δ 10.60 (s, 1 H), 8.34 (d, J=5.7 Hz, 1 H), 8.25 (s, 1 H), 8.01 (d, J=8.8 Hz, 1 H), 7.95 (s, 1 H), 7.57 (d, J=8.8 Hz, 1 H), 7.17 (d, J=2.4 Hz, 1 H), 6.58 (dd, J=5.7, 2.4 Hz, 1 H), 3.84 (s, 3 H), 2.25 (s, 3 H), 2.08 (s, 3 H); MS (ESI) m/z: 324.1 (M+H$^+$).

A solution of N-(6-methyl-5-((2-(1-methyl-1H-pyrazol-4-yl)pyridin-4-yl)oxy)pyridin-2-yl)acetamide (3.88 g, 12.00 mmol) in THF (30 mL) was treated with 2M HCl (30 mL, 60 mmol), heated at 65° C. for 6 h, cooled to RT and concentrated to dryness. The mixture was treated with H$_2$O, neutralized with solid NaHCO$_3$, extracted with EtOAc (2×) and the combined organics were washed with brine, dried over Na$_2$SO$_4$ and concentrated to dryness. The material was suspended in 3:2 EtOAc/Hex, sonicated and the resulting solid collected via filtration and dried to afford 6-methyl-5-((2-(1-methyl-1H-pyrazol-4-yl)pyridin-4-yl)oxy)pyridin-2-amine (3.1 g, 92%) as a white solid. MS (ESI) m/z: 282.1 (M+H$^+$).

Method 2: A mixture of Example A7 (4.42 g, 18.76 mmol), 1-methyl-4-(4,4,5,5-tetramethyl-1,3,2-dioxaborolan-2-yl)-1H-pyrazole (5.07 g, 24.38 mmol), and K$_2$CO$_3$ in dioxane (60 mL) and water (15 mL) was sparged with Ar, treated with Pd(PPh$_3$)$_4$ (1.084 g, 0.938 mmol), sparged with Ar again and heated at 90° C. for 6 h. The reaction was cooled to RT, treated with saturated brine, and extracted with EtOAc (3×). The organics were dried over Na$_2$SO$_4$ and concentrated to dryness. The residue was treated with EtOAc (30 mL) and briefly sonicated. The solids were collected by filtration, washed with EtOAc (10 mL) and dried under vacuum to obtain the product (4.15 g, 79% yield) of suitable NMR purity. This material (4.15 g, 14.75 mmol) was dissolved in THF (300 mL) and MeOH (15 mL) and treated with thiol-modified silica gel (1.2 mmol thiol/g, 4.92 g, 5.90 mmol). The mixture was stirred at RT for 4 h, filtered through a pad of diatomaceous earth and washed with EtOAc (300 mL) and THF (400 mL). The filtrate was concentrated to dryness. The residue was treated with EtOAc (30 mL) and the solid was collected by filtration, washed with EtOAc and dried under vacuum at 80° C. to obtain 5-((2-(1-methyl-1H-pyrazol-4-yl)pyridin-4-yl)oxy)pyridin-2-amine (3.6 g, 87% yield). $^1$H NMR (400 MHz, DMSO-d$_6$): δ 8.30 (d, J=5.7 Hz, 1 H), 8.22 (s, 1 H), 7.93 (d, J=0.7 Hz, 1 H), 7.17 (d, J=8.7 Hz, 1 H), 7.10 (d, J=2.4 Hz, 1 H), 6.49 (dd, J=5.7, 2.4 Hz, 1 H), 6.34 (d, J=8.7 Hz, 1 H), 5.93 (s, 2 H), 3.84 (s, 3 H), 2.06 (s, 3 H); MS (ESI) m/z: 282.1 (M+H$^+$).

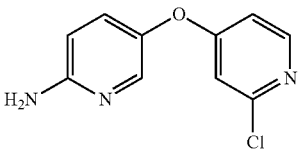

Example A5

A mixture of Example A1 (2.55 g, 10.13 mmol) and NH$_4$Cl (5.42 g, 101 mmol) in THF (250 mL) and MeOH (250 mL) was treated with zinc dust (6.63 g, 101 mmol), stirred at RT for 3 h, the solids removed via filtration and the filtrate concentrated to dryness and purified by silica gel chromatography to provide 5-((2-chloropyridin-4-yl)oxy)pyridin-2-amine (1.41 g, 63% yield).

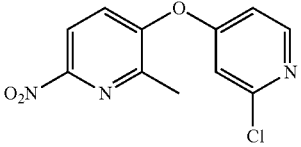 [SMILES: Cc1nc([N+](=O)[O-])ccc1Oc1ccnc(Cl)c1]

Example A6

A 0° C. solution of sulfuric acid (125 mL) was treated drop-wise with H$_2$O$_2$ (30%, 63.1 mL, 2058 mmol), stirred for 15 min, treated drop-wise with a cold solution of 6-amino-3-bromo-2-picoline (35 g, 187 mmol) in sulfuric acid (125 mL), allowed to warm to RT and stirred for 4 h. The mixture was poured onto ice (1.2 kg) and the resulting solid collected via filtration, dissolved in DCM, washed with brine, dried over Na$_2$SO$_4$ and concentrated to dryness. The aqueous filtrate and washes were combined, extracted with DCM (2×) and the combined organics were dried over Na$_2$SO$_4$, concentrated to dryness, purified via silica gel chromatography (EtOAc/Hex) and combined with the above-isolated solid to afford 3-bromo-2-methyl-6-nitropyridine (25.59 g, 63%). MS (ESI) m/z: 218.9 (M+H$^+$).

A solution of 3-bromo-2-methyl-6-nitropyridine (25.59 g, 118 mmol), K$_2$CO$_3$ (48.9 g, 354 mmol) and 2-chloro-4-hydroxy-pyridine (30.6 g, 236 mmol) in DMF (160 mL) was sparged with Ar, heated at 100° C. overnight, then cooled to RT. The mixture was treated with water and EtOAc, the solids removed via filtration through diatomaceous earth and washed with water, EtOAc, then DCM. The aqueous filtrate was extracted with EtOAc (2×) and the organic extracts were combined with the organic filtrates, washed with water, then brine, dried over $Na_2SO_4$ and concentrated to dryness. The residue was treated with MTBE, sonicated and the resulting solid collected via filtration to afford 3-((2-chloropyridin-4-yl)oxy)-2-methyl-6-nitropyridine (17.16 g, 55%). $^1$H NMR (400 MHz, DMSO-$d_6$): δ 8.38 (d, J=5.7 Hz, 1 H), 8.25 (d, J=8.7 Hz, 1 H), 7.95 (d, J=8.7 Hz, 1 H), 7.29 (d, J=2.3 Hz, 1 H), 7.16 (dd, J=5.7, 2.3 Hz, 1 H), 2.46 (s, 3 H); MS (ESI) m/z: 266.0 (M+H$^+$).

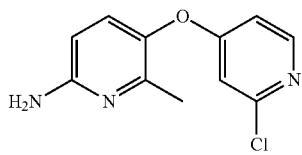 [SMILES: Cc1nc(N)ccc1Oc1ccnc(Cl)c1]

Example A7

Method A: Example A6 (5.0 g, 18.82 mmol) and ammonium chloride (30.2 g, 565 mmol) were suspended in a mixture of MeOH:THF (1:1, 100 mL). Zinc (12.31 g, 188 mmol) was added portionwise over 10 min and then the mixture was stirred at RT overnight. The reaction mixture was diluted with EtOAc (500 mL) and filtered. The filtrate was concentrated in vacuo and the residue was purified by silica gel chromatography to obtain 5-((2-chloropyridin-4-yl)oxy)-6-methylpyridin-2-amine (3.72 g, 84%). $^1$H NMR (400 MHz, DMSO-$d_6$): δ 8.24 (d, J=5.7 Hz, 1 H), 7.20 (d, J=8.7 Hz, 1 H), 6.89 (d, J=2.2 Hz, 1 H), 6.85 (dd, J=5.8, 2.3 Hz, 1 H), 6.35 (d, J=8.7 Hz, 1 H), 6.02 (s, 2 H), 2.05 (s, 3 H); MS (ESI) m/z: 236.1 (M+H$^+$).

Method B: A solution of Example A6 (1 g, 3.76 mmol) in EtOH (38 mL) was treated with tin(II) chloride dihydrate (4.25 g, 18.8 mmol), heated at 80° C. for 30 h, then cooled to RT and treated slowly with satd. $NaHCO_3$. The mixture was stirred for several minutes, the solids removed via filtration through diatomaceous earth and the filtrate was dried over $Na_2SO_4$ and concentrated to dryness to afford crude 5-((2-chloropyridin-4-yl)oxy)-6-methylpyridin-2-amine (645 mg, 73%) which was used without further purification. MS (ESI) m/z: 236.1 (M+H$^+$).

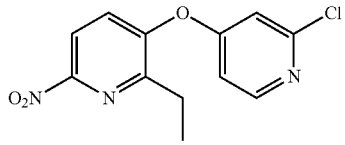 [SMILES: CCc1nc([N+](=O)[O-])ccc1Oc1ccnc(Cl)c1]

Example A8

A 0° C. solution of 6-ethylpyridin-2-amine (3.37 g, 27.6 mmol) in CHCl3 (30 mL) was treated portion-wise with NBS (4.91 g, 27.6 mmol) over 30 min, stirred for 45 min, then concentrated to dryness. The residue was treated with EtOAc (8 mL), filtered to remove solids and purified via silica gel chromatography (EtOAc/Hex) to afford 5-bromo-6-ethylpyridin-2-amine (3.79 g, 68%). $^1$H NMR (400 MHz, DMSO-$d_6$): δ 7.43 (d, J=8.6 Hz, 1 H), 6.21 (d, J=8.7 Hz, 1 H), 6.03 (s, 2 H), 2.61 (q, J=7.5 Hz, 2 H), 1.11 (t, J=7.5 Hz, 3 H); MS (ESI) m/z: 201.0 (M+H$^+$).

A 0° C. solution of $H_2SO_4$ (11 mL) was slowly treated with $H_2O_2$ (30%, 5.5 mL), in an open flask, stirred for 5 min, treated drop-wise with a solution of 5-bromo-6-ethylpyridin-2-amine (3.79 g, 18.85 mmol) in $H_2SO_4$ (10 mL) warmed to RT as the cooling bath expired and stirred overnight. The solution was poured into ice water (200 mL), treated with DCM, cooled to 0° C. and treated slowly with 50% NaOH until pH=10. The layers were separated, the aqueous layer extracted with additional DCM (1×) and the combined organics were washed with brine, dried over $Na_2SO_4$ and concentrated to dryness to afford crude 3-bromo-2-ethyl-6-nitropyridine (3.168 g, 71%) which was used without further purification. $^1$H NMR (400 MHz, DMSO-$d_6$): δ 8.44 (d, J=8.5 Hz, 1 H), 8.05 (d, J=8.5 Hz, 1 H), 2.97 (q, J=7.5 Hz, 2 H), 1.24 (t, J=7.5 Hz, 3 H); MS (ESI) m/z: 231.0 (M+H$^+$).

A mixture of 3-bromo-2-ethyl-6-nitropyridine (3.168 g, 13.71 mmol), 2-chloro-4-hydroxypyridine (3.55 g, 27.4 mmol) and $K_2CO_3$ (5.69 g, 41.1 mmol) in DMA (25 mL) was sparged with Ar and heated at 105° C. overnight. The mixture was cooled to RT, treated with EtOAc, washed successively with 10% $K_2CO_3$, 5% LiCl, then brine, dried over $Na_2SO_4$, concentrated to dryness and purified via silica gel chromatography (EtOAc/Hex) to afford 3-((2-chloropyridin-4-yl)oxy)-2-ethyl-6-nitropyridine (1.102 g, 28%). MS (ESI) m/z: 280.0 (M+H$^+$).

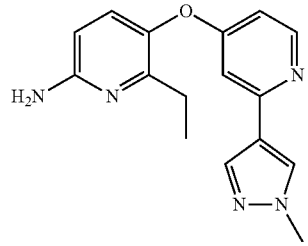 [SMILES: CCc1nc(N)ccc1Oc1ccnc(-c2cnn(C)c2)c1]

Example A9

A mixture of Example A8 (1.10 g, 3.93 mmol), 1-methyl-4-(4,4,5,5-tetramethyl-1,3,2-dioxaborolan-2-yl)-1H-pyrazole (1.06 g, 5.11 mmol), $K_2CO_3$ (1.631 g, 11.80 mmol) and Pd(PPh$_3$)$_4$ (227 mg, 0.197 mmol) in dioxane (8 mL) and water (2 mL) was sparged with Ar and heated at 80° C. for 24 h. The mixture was cooled to RT, treated with EtOAc, washed with satd. $NaHCO_3$, then brine, dried over $Na_2SO_4$ and concentrated to dryness to afford crude 2-ethyl-3-((2-(1-methyl-1H-pyrazol-4-yl)pyridin-4-yl)oxy)-6-nitropyridine (100% yield assumed) without further purification. MS (ESI) m/z: 326.1 (M+H$^+$).

A solution of crude 2-ethyl-3-((2-(1-methyl-1H-pyrazol-4-yl)pyridin-4-yl)oxy)-6-nitropyridine (1.280 g, 3.93 mmol) in MeOH (15 mL) and THF (15 mL) was treated with $NH_4Cl$ (8.42 g, 157 mmol), cooled to 0° C., treated portion-wise with zinc dust (2.57 g, 39.3 mmol), warmed to RT as the cooling bath expired and stirred overnight. The mixture was diluted with EtOAc, the solids removed via filtration through diatomaceous earth, washed with warm 2:1 EtOAc/MeOH and the filtrate concentrated to dryness. The residue was treated with EtOAc, heated to reflux, cooled to RT and the solids removed via filtration. The filtrate was again treated with EtOAc, heated to reflux and the solid collected via hot filtration. The filtrate was concentrated to dryness, purified via silica gel chromatography (MeOH/EtOAc) and combined with the above-isolated solid to afford 6-ethyl-5-((2-(1-methyl-1H-pyrazol-4-yl)pyridin-4-yl)oxy)pyridin-2-amine (929 mg, 80%). $^1$H NMR (400 MHz, DMSO-d$_6$): δ 8.30 (d, J=5.8 Hz, 1 H), 8.22 (s, 1 H), 7.93 (s, 1 H), 7.18 (d, J=8.7 Hz, 1 H), 7.12 (d, J=2.4 Hz, 1 H), 6.51 (dd, J=5.7, 2.4 Hz, 1 H), 6.36 (d, J=8.7 Hz, 1 H), 5.97 (s, 2 H), 3.84-3.83 (m, 3 H), 2.39 (q, J=7.6 Hz, 2 H), 1.04 (t, J=7.5 Hz, 3 H); MS (ESI) m/z: 296.1 (M+H$^+$).

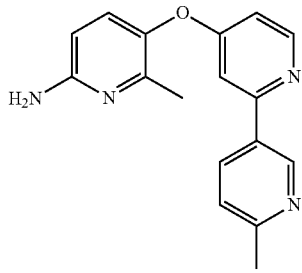 [SMILES: Cc1ccc(-c2cc(Oc3ccc(N)nc3C)ccn2)cn1]

Example A10

A mixture of Example A7 (2.8 g, 11.88 mmol), 2-methyl-5-(4,4,5,5-tetramethyl-1,3,2-dioxaborolan-2-yl)pyridine (3.38 g, 15.45 mmol) and K$_2$CO$_3$ (3.28 g, 23.76 mmol) in dioxane 48 mL) and water (12 mL) was sparged with Ar, treated with Pd(PPh$_3$)$_4$ (1.373 g, 1.188 mmol) and heated at 85° C. overnight. The mixture was cooled to RT, diluted with EtOAc, the solids removed via filtration through diatomaceous earth and the filtrate concentrated to dryness and purified via silica gel chromatography (MeOH/DCM). The material was treated with MeCN, the solid collected via filtration and re-purified via silica gel chromatography (MeOH/DCM) to afford 6-methyl-5-((6'-methyl-[2,3'-bipyridin]-4-yl)oxy)pyridin-2-amine (3.08 g, 89%). $^1$H NMR (400 MHz, DMSO-d$_6$): δ 9.56 (d, J=2.4 Hz, 1 H), 8.96 (d, J=5.7 Hz, 1 H), 8.71 (dd, J=8.1, 2.4 Hz, 1 H), 7.86 (d, J=2.4 Hz, 1 H), 7.76 (d, J=8.1 Hz, 1 H), 7.66 (d, J=8.7 Hz, 1 H), 7.18 (dd, J=5.7, 2.4 Hz, 1 H), 6.94 (dd, J=8.6, 0.7 Hz, 1 H), 5.86 (s, 2 H), 2.97 (s, 3 H), 2.59 (s, 3 H); MS (ESI) m/z: 293.1 (M+H$^+$).

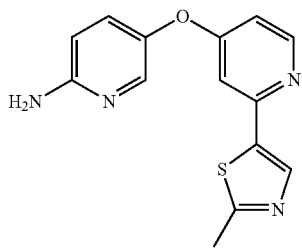 [SMILES: Cc1ncc(-c2cc(Oc3ccc(N)nc3)ccn2)s1]

Example A11

A suspension of Pd(PPh$_3$)$_4$ (0.092 g, 0.079 mmol), K$_2$CO$_3$ (0.659 g, 4.77 mmol), 2-methyl-5-(4,4,5,5-tetramethyl-1,3,2-dioxaborolan-2-yl)thiazole (0.429 g, 1.908 mmol) and Example A1 (0.4 g, 1.590 mmol) in dioxane (6 mL) and water (1.5 mL) was sparged with Ar and heated at 90° C. overnight. The mixture was cooled to RT, treated with brine, extracted with EtOAc (3×) and the combined organics were dried over Na$_2$SO$_4$, concentrated to dryness and purified via silica gel chromatography (EtOAc/Hex) to afford 2-methyl-5-(4-((6-nitropyridin-3-yl)oxy)pyridin-2-yl)thiazole (191 mg, 38%). $^1$H NMR (400 MHz, DMSO-d$_6$): δ 8.61 (d, J=2.8 Hz, 1 H), 8.52 (d, J=5.7 Hz, 1 H), 8.42 (d, J=8.9 Hz, 1 H), 8.35 (s, 1 H), 8.02 (dd, J=8.9, 2.8 Hz, 1 H), 7.79 (d, J=2.4 Hz, 1 H), 7.10 (dd, J=5.7, 2.4 Hz, 1 H), 2.65 (s, 3 H); MS (ESI) m/z: 315.1 (M+H$^+$).

A 0° C. solution of 2-methyl-5-(4-((6-nitropyridin-3-yl)oxy)pyridin-2-yl)thiazole (0.191 g, 0.608 mmol) in THF (3 mL) and MeOH (3 mL) was treated with NH$_4$Cl (1.3 g, 24.31 mmol) followed by the slow addition of zinc dust (0.397 g, 6.08 mmol), the mixture allowed to warm to RT and stirred for 2 h. The mixture was treated with THF, the solids removed via filtration through diatomaceous earth, washed well with THF, the filtrate treated with EtOAc, washed with 1:1 brine/satd. NaHCO$_3$, dried over Na$_2$SO$_4$ and concentrated to dryness to afford 5-((2-(2-methylthiazol-5-yl)pyridin-4-yl)oxy)pyridin-2-amine (164 mg, 95%). $^1$H NMR (400 MHz, DMSO-d$_6$): δ 8.34 (d, J=5.8 Hz, 1 H), 8.28 (s, 1 H), 7.82 (d, J=2.9 Hz, 1 H), 7.50 (d, J=2.4 Hz, 1 H), 7.29 (dd, J=8.9, 3.0 Hz, 1 H), 6.67 (dd, J=5.8, 2.4 Hz, 1 H), 6.51 (d, J=8.9 Hz, 1 H), 6.03 (s, 2 H), 2.64 (s, 3 H); MS (ESI) m/z: 285.1 (M+H$^+$).

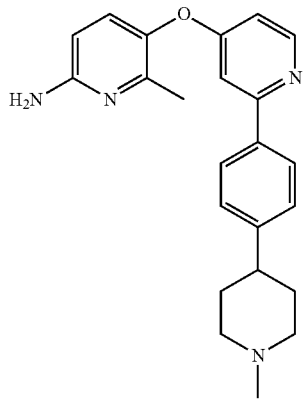 [SMILES: Cc1nc(N)ccc1Oc1ccnc(-c2ccc(C3CCN(C)CC3)cc2)c1]

Example A12

A mixture of Example C7 (1.185 g, 3.93 mmol), Example A6 (0.746 g, 2.81 mmol), K$_2$CO$_3$ (1.165 g, 8.43 mmol) and Pd(PPh$_3$)$_4$ (0.325 g, 0.281 mmol) in dioxane (11 mL) and water (3 mL) was sparged with Ar and heated at 90° C. overnight. The mixture was cooled to RT, treated with EtOAc and brine and the solids removed via filtration through diatomaceous earth. The layers of the filtrate were separated, the aqueous layer extracted with additional EtOAc (3×) and the combined organics were dried over Na$_2$SO$_4$, concentrated to dryness and purified via silica gel chromatography (MeOH/DCM) to afford 2-methyl-3-((2-(4-(1-methylpiperidin-4-yl)phenyl)pyridin-4-yl)oxy)-6-nitropyridine (553 mg, 49%). MS (ESI) m/z: 405.2 (M+H$^+$).

A solution of 2-methyl-3-((2-(4-(1-methylpiperidin-4-yl)phenyl)pyridin-4-yl)oxy)-6-nitropyridine (0.553 g, 1.367 mmol) in MeOH (20 mL) was treated with 10% Pd/C (50% w/w water, 146 mg, 0.137 mmol) and hydrogenated (1 atm) overnight. The solids were removed via filtration, washed with MeOH and the filtrate concentrated to dryness to afford 6-methyl-5-((2-(4-(1-methylpiperidin-4-yl)phenyl)pyridin-4-yl)oxy)pyridin-2-amine (446 mg, 87%). MS (ESI) m/z: 375.2 (M+H$^+$).

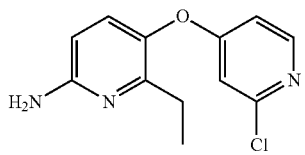 [SMILES: CCc1nc(N)ccc1Oc1ccnc(Cl)c1]

Example A13

A suspension of Example A8 (1.3 g, 4.65 mmol) and NH₄Cl (7.5 g, 140 mmol) in MeOH (24 mL) and THF (24 mL) was treated portion-wise with zinc dust (3 g, 45.9 mmol) and stirred at RT overnight. The solids were removed via filtration through diatomaceous earth and the filtrate concentrated to dryness to afford 5-((2-chloropyridin-4-yl)oxy)-6-ethylpyridin-2-amine (1.1 g, 85%). MS (ESI) m/z: 250.1 (M+H⁺).

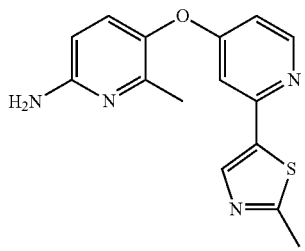 [SMILES: Cc1ncc(-c2cc(Oc3ccc(N)nc3C)ccn2)s1]

Example A14

A mixture of Example C6 (2 g, 5.15 mmol), Example A6 (1.053 g, 3.96 mmol) and Pd(PPh₃)₄ (0.229 g, 0.198 mmol) in toluene (20 mL), sparged with Ar and heated at 105° C. overnight. The mixture was cooled to RT, treated 10% KF (aq) and EtOAc and stirred at RT for 2 h. The solids were removed via filtration through diatomaceous earth, washed with EtOAc and the filtrate was washed with satd. NaHCO₃, then brine, dried over Na₂SO₄, concentrated to dryness and purified via silica gel chromatography (EtOAc/Hex) to afford 2-methyl-5-(4-((2-methyl-6-nitropyridin-3-yl)oxy)pyridin-2-yl)thiazole (1.06 g, 81%). ¹H NMR (400 MHz, DMSO-d₆): δ 8.50 (d, J=5.7 Hz, 1 H), 8.34 (s, 1 H), 8.24 (d, J=8.7 Hz, 1 H), 7.88 (d, J=8.7 Hz, 1 H), 7.72 (d, J=2.4 Hz, 1 H), 7.02 (dd, J=5.7, 2.4 Hz, 1 H), 2.65 (s, 3 H), 2.50 (s, 3 H); MS (ESI) m/z: 329.1 (M+H⁺).

A solution of 2-methyl-5-(4-((2-methyl-6-nitropyridin-3-yl)oxy)pyridin-2-yl)thiazole (1.06 g, 3.23 mmol) in MeOH (40 mL) was treated with 10% Pd/C (50% w/w water, 0.344 g, 0.323 mmol) and hydrogenated (50 psi) overnight. Additional 10% Pd/C (50% w/w water, 0.344 g, 0.323 mmol) was added and the mixture hydrogenated (50 psi) for an additional 24 h. The solids were removed via filtration through diatomaceous earth, washed with MeOH and the filtrate concentrated to dryness. The material was treated with MTBE, the solid collected via filtration and dried to afford 6-methyl-5-((2-(2-methylthiazol-5-yl)pyridin-4-yl)oxy)pyridin-2-amine (860 mg, 89%). ¹H NMR (400 MHz, DMSO-d₆): δ 8.34 (d, J=5.8 Hz, 1 H), 8.28 (s, 1 H), 7.49 (d, J=2.4 Hz, 1 H), 7.19 (d, J=8.7 Hz, 1 H), 6.58 (dd, J=5.8, 2.4 Hz, 1 H), 6.35 (d, J=8.7 Hz, 1 H), 5.96 (s, 2 H), 2.65 (s, 3 H), 2.07 (s, 3 H); MS (ESI) m/z: 299.1 (M+H⁺).

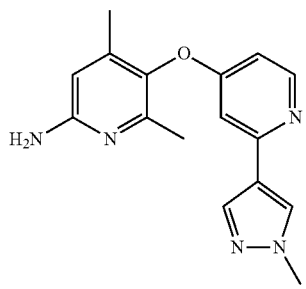 [SMILES: Cc1cc(N)nc(C)c1Oc1ccnc(-c2cnn(C)c2)c1]

Example A15

A mixture of 2,4-dimethyl-3-hydroxypyridine (3.00 g, 24.36 mmol) and Na₂CO₃ (5.16 g, 48.7 mmol) in MeOH (40 mL) and water (24 mL) was treated with iodine (6.18 g, 24.36 mmol) and stirred at RT for 1 h. Additional iodine (0.4 g) was added, the mixture stirred at RT for 3 h, then acidified to pH=5 with 3M HCl. The mixture was treated with brine, extracted with EtOAc (2×) and the combined organics were washed with brine, dried over Na₂SO₄ and concentrated to dryness to afford 6-iodo-2,4-dimethylpyridin-3-ol (5.1 g, 84%). MS (ESI) m/z: 250.0 (M+H⁺).

A solution of 6-iodo-2,4-dimethylpyridin-3-ol (5.10 g, 20.48 mmol) in DMA (60 mL) was sparged with Ar, treated with 2,4-dichloropyridine (3.94 g, 26.60 mmol) and K₂CO₃ (3.40 g, 24.57 mmol) and heated at 105° C. overnight. The mixture was cooled to RT, treated with EtOAc and water, filtered to remove solids, then treated with charcoal, warmed to reflux, cooled to RT and filtered through diatomaceous earth. The layers of the filtrate were separated, the aqueous layer extracted with additional EtOAc (1×) and the combined organics were washed with brine, dried over Na₂SO₄, concentrated to dryness and purified via silica gel chromatography (EtOAc/Hex) to afford 3-((2-chloropyridin-4-yl)oxy)-6-iodo-2,4-dimethylpyridine (1.476 g, 20%). ¹H NMR (400 MHz, DMSO-d₆): δ 8.27 (d, J=5.8 Hz, 1 H), 7.75 (s, 1 H), 7.05 (d, J=2.3 Hz, 1 H), 6.89 (dd, J=5.8, 2.3 Hz, 1 H), 2.20 (s, 3 H), 2.02 (s, 3 H); MS (ESI) m/z: 361.0 (M+H⁺).

A mixture of 3-((2-chloropyridin-4-yl)oxy)-6-iodo-2,4-dimethylpyridine (1.45 g, 4.02 mmol), acetamide (950 mg, 16.09 mmol), Cs₂CO₃ (1.965 g, 6.03 mmol) and X-phos (96 mg, 0.201 mmol) in dioxane (25 mL) was sparged with Ar, treated with Pd₂(dba)₃ (184 mg, 0.201 mmol), sparged again with Ar and heated at 85° C. overnight. The mixture was cooled to RT, diluted with EtOAc and the solids removed via filtration through diatomaceous earth. The filtrate was washed with water, then brine, dried over Na₂SO₄, concentrated to dryness and purified via silica gel chromatography (EtOAc/Hex) to afford N-(5-((2-chloropyridin-4-yl)oxy)-4,6-dimethylpyridin-2-yl)acetamide (598 mg, 51%). ¹H NMR (400 MHz, DMSO-d₆): δ 10.53 (s, 1 H), 8.26 (d, J=5.8 Hz, 1 H), 7.94 (s, 1 H), 6.99 (d, J=2.3 Hz, 1 H), 6.85 (dd, J=5.8, 2.3 Hz, 1 H), 2.17 (s, 3 H), 2.06 (d, J=1.7 Hz, 6 H); MS (ESI) m/z: 292.1 (M+H⁺).

A mixture of N-(5-((2-chloropyridin-4-yl)oxy)-4,6-dimethylpyridin-2-yl)acetamide (598 mg, 2.05 mmol), 1-methyl-4-(4,4,5,5-tetramethyl-1,3,2-dioxaborolan-2-yl)-1H-pyrazole (554 mg, 2.66 mmol), K₂CO₃ (850 mg, 6.15 mmol) and Pd(PPh₃)₄ (118 mg, 0.102 mmol) in dioxane (8 mL) and water (2 mL) was sparged with Ar and heated at 80° C. overnight. The mixture was cooled to RT, diluted with EtOAc, washed with satd. NaHCO₃, then brine, dried over Na₂SO₄ and concentrated to dryness to afford crude N-(4,6-dimethyl- 5-((2-(1-methyl-1H-pyrazol-4-yl)pyridin-4-yl)oxy)pyridin-2-yl)acetamide (100% yield assumed) which was used without further purification. MS (ESI) m/z: 338.1 (M+H⁺).

A solution of N-(4,6-dimethyl-5-((2-(1-methyl-1H-pyrazol-4-yl)pyridin-4-yl)oxy)pyridin-2-yl)acetamide (692 mg, 2.051 mmol) in THF (25 mL) was treated with HCl (3 M, 3.4 mL, 10.2 mmol) and warmed at 40° C. for 17 h. The mixture was treated with satd. NaHCO₃, extracted with EtOAc (2×) and the combined organics were dried over Na₂SO₄, concentrated to dryness and purified via silica gel chromatography (MeOH/EtOAc) to afford 4,6-dimethyl-5-((2-(1-methyl-1H-pyrazol-4-yl)pyridin-4-yl)oxy)pyridin-2-amine (446 mg, 73%). ¹H NMR (400 MHz, DMSO-d₆): δ 8.30 (d, J=5.7 Hz, 1 H), 8.23 (s, 1 H), 7.93 (d, J=0.7 Hz, 1 H), 7.10 (d, J=2.4 Hz, 1 H), 6.44 (dd, J=5.7, 2.4 Hz, 1 H), 6.22 (s, 1 H), 5.81 (s, 2 H), 3.84 (s, 3 H), 2.02 (s, 3 H), 1.92 (s, 3 H); MS (ESI) m/z: 296.1 (M+H⁺).

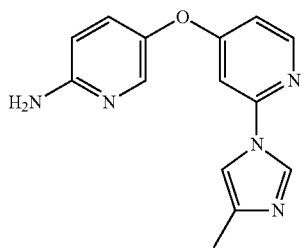 [SMILES: Cc1cn(-c2cc(Oc3ccc(N)nc3)ccn2)cn1]

Example A16

A mixture of toluene (60 mL) and dioxane (12 mL) was sparged with Ar, treated with Pd₂(dba)₃ (0.255 g, 0.278 mmol) and Me₄tBuXPhos [di-tert-butyl(2',4',6'-triisopropyl-3,4,5,6-tetramethyl-[1,1'-biphenyl]-2-yl)phosphine] (0.267 g, 0.556 mmol) and heated at 120° C. for 15 min, partially cooled, treated with Example A1 (3.5 g, 13.91 mmol), K₃PO₄ (5.91 g, 27.8 mmol) and 4-methylimidazole (3.43 g, 41.7 mmol) and heated at 120° C. overnight. The mixture was cooled to RT, treated with brine and extracted with EtOAc (2×). The combined organics were washed with brine (2×), dried over MgSO₄, concentrated to dryness and purified via silica gel chromatography (EtOAc/Hex) to afford 2-(4-methyl-1H-imidazol-1-yl)-4-((6-nitropyridin-3-yl)oxy)pyridine (1.3 g, 31%). ¹H NMR (400 MHz, DMSO-d₆): δ 8.64-8.63 (m, 1 H), 8.44-8.43 (m, 2 H), 8.41 (d, J=1.4 Hz, 1 H), 8.06 (dd, J=8.9, 2.8 Hz, 1 H), 7.65 (t, J=1.3 Hz, 1 H), 7.56 (d, J=2.2 Hz, 1 H), 7.12 (dd, J=5.7, 2.2 Hz, 1 H), 2.13 (d, J=1.0 Hz, 3 H); MS (ESI) m/z: 298.1 (M+H⁺).

A solution of 2-(4-methyl-1H-imidazol-1-yl)-4-((6-nitropyridin-3-yl)oxy)pyridine (1.3 g, 4.37 mmol) in MeOH (20 mL)/THF (20 mL) was treated sequentially with NH₄Cl (7.02 g, 131 mmol) and zinc dust (2.86 g, 43.7 mmol) and stirred at RT for 2 h. The mixture was diluted with THF, the solids removed via filtration through diatomaceous earth, washed with THF and the filtrate concentrated to dryness. The material was treated with THF, the solids removed via filtration and the filtrate concentrated to dryness, treated with DCM and sonicated. The resulting solid was collected via filtration and dried to afford 5-((2-(4-methyl-1H-imidazol-1-yl)pyridin-4-yl)oxy)pyridin-2-amine (800 mg, 68%). ¹H NMR (400 MHz, DMSO-d₆): δ 8.39 (d, J=1.4 Hz, 1 H), 8.28 (d, J=5.8 Hz, 1 H), 7.83 (d, J=2.9 Hz, 1 H), 7.63 (s, 1 H), 7.31-7.30 (m, 2 H), 6.70 (dd, J=5.8, 2.2 Hz, 1 H), 6.51 (d, J=8.9 Hz, 1 H), 6.05 (s, 2 H), 2.14 (d, J=1.0 Hz, 3 H); MS (ESI) m/z: 268.2 (M+H⁺).

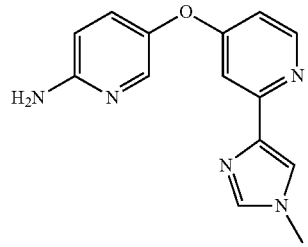 [SMILES: Cn1cnc(-c2cc(Oc3ccc(N)nc3)ccn2)c1]

Example A17

A mixture of Example A1 (1.5 g, 5.96 mmol), N-methyl-4-(tributylstannyl)imidazole (3.32 g, 8.94 mmol) and Pd(PPh₃)₄ (0.344 g, 0.298 mmol) in toluene (30 mL) sparged with Ar and heated at 110° C. overnight. The mixture was cooled to RT, treated with 10% KF and EtOAc, stirred at RT for 2 h, the solids removed via filtration through diatomaceous earth and washed with 5% MeOH/DCM. The layers of the filtrate were separated and the organic layer was washed with brine, dried over Na₂SO₄, concentrated to dryness and purified via silica gel chromatography (MeOH/DCM). The material was washed with a small amount of Et₂O and dried to afford 2-(1-methyl-1H-imidazol-4-yl)-4-((6-nitropyridin-3-yl)oxy)pyridine (1.61 g, 91%). MS (ESI) m/z: 298.1 (M+H⁺).

A solution of 2-(1-methyl-1H-imidazol-4-yl)-4-((6-nitropyridin-3-yl)oxy)pyridine (1.61 g, 5.42 mmol) in MeOH (30 mL) was treated with 10% Pd/C (50% w/w water, 0.576 g, 0.542 mmol) and hydrogenated (50 psi) overnight. The solids were removed via filtration through diatomaceous earth, washed with warm MeOH and the filtrate was concentrated to dryness to afford 5-((2-(1-methyl-1H-imidazol-4-yl)pyridin-4-yl)oxy)pyridin-2-amine (1.311 g, 91%). ¹H NMR (400 MHz, DMSO-d₆): δ 8.31 (d, J=5.7 Hz, 1 H), 7.81 (d, J=2.9 Hz, 1 H), 7.65 (d, J=1.3 Hz, 1 H), 7.58 (s, 1 H), 7.29 (dd, J=8.9, 3.0 Hz, 1 H), 7.19 (d, J=2.6 Hz, 1 H), 6.73 (dd, J=5.7, 2.6 Hz, 1 H), 6.52 (d, J=8.9 Hz, 1 H), 6.03 (s, 2 H), 3.67 (s, 3 H); MS (ESI) m/z: 268.1 (M+H⁺).

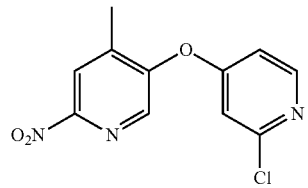 [SMILES: Cc1cc([N+](=O)[O-])ncc1Oc1ccnc(Cl)c1]

Example A18

A 0° C. solution of H₂SO₄ (12 mL) was treated with H₂O₂ (9.72 mL, 95 mmol), stirred for 10 min, treated with a solution of 2-amino-5-fluoro-4-methylpyridine (2 g, 15.86 mmol) in H₂SO₄ (8 mL), stirred for 15 min, then warmed to RT and stirred for 3 h. The mixture was re-cooled to 0° C., neutralized slowly with solid NaHCO₃ and the resulting solid collected via filtration and dried to afford 5-fluoro-4-methyl-2-nitropyridine (2 g, 81%). ¹H NMR (400 MHz, DMSO-d₆): δ 8.57 (s, 1 H), 8.42 (d, J=5.3 Hz, 1 H), 2.42 (d, J=1.9 Hz, 3 H); MS (ESI) m/z: 157.1 (M+H⁺).

A mixture of 5-fluoro-4-methyl-2-nitropyridine (2 g, 12.81 mmol) and 2-chloro-4-hydroxypyridine (1.66 g, 12.81 mmol) in DMF (26 mL) was sparged with Ar, treated with K₂CO₃ (2.66 g, 19.22 mmol), heated at 88° C. for 24 h, then at 50° C. for 2 days. The mixture was treated with water and the resulting solid collected via filtration and dried to afford 5-((2-chloropyridin-4-yl)oxy)-4-methyl-2-nitropyridine (2.72 g, 80%). ¹H NMR (400 MHz, DMSO-d₆): δ 8.49 (s, 1 H), 8.47 (s, 1 H), 8.35 (d, J=5.7 Hz, 1 H), 7.24 (d, J=2.3 Hz, 1 H), 7.12 (dd, J=5.7, 2.3 Hz, 1 H), 2.32 (s, 3 H); MS (ESI) m/z: 266.0 (M+H⁺).

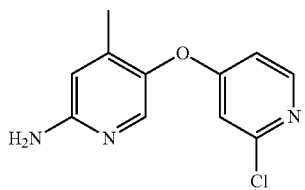

Example A19

A mixture of Example A18 (0.48 g, 1.807 mmol) and NH₄Cl (2.90 g, 54.2 mmol) in MeOH (4.5 mL) and THF (4.5 mL) was treated portion-wise with zinc dust (1.182 g, 18.07 mmol) and stirred at RT for 1 h. The mixture was diluted with EtOAc, the solids removed via filtration through diatomaceous earth and the filtrate concentrated to dryness to afford 5-((2-chloropyridin-4-yl)oxy)-4-methylpyridin-2-amine (400 mg, 94%). MS (ESI) m/z: 236.1 (M+H⁺).

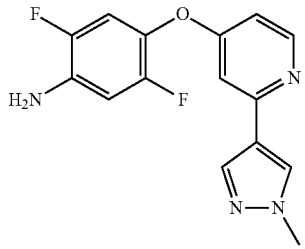 [SMILES: Cn1cc(-c2cc(Oc3cc(F)c(N)cc3F)ccn2)cn1]

Example A20

Anhydrous DMF (150 mL) was added to 60% NaH in mineral oil (2.72 g, 67.9 mmol) under an Ar atmosphere, cooled in an ice bath, treated portion-wise with a solution of 2-chloropyridin-4-ol (8 g, 61.8 mmol) in DMF (30 mL) and stirred cold for 5 minutes. The cooling bath was removed and the mixture was warmed to RT and stirred for 20 minutes. 1,2,4-Trifluoro-5-nitrobenzene (13.12 g, 74.1 mmol) was added and the reaction mixture heated at 90° C. for 3 h. The reaction mixture was cooled to RT, concentrated to dryness, treated with EtOH (50 mL) and MeOH (20 mL), warmed gently, then cooled to RT. The yellow solid was collected by filtration, rinsed with EtOH (50 mL) and hexanes (20 mL) and dried under vacuum overnight to provide 2-chloro-4-(2,5-difluoro-4-nitrophenoxy)pyridine as a yellow solid (11.68 g, 63% yield). ¹H NMR (400 MHz, DMSO-d): δ 8.48 (dd, J=10.2, 7.0 Hz, 1 H), 8.41 (d, J=5.6 Hz, 1 H), 7.90 (dd, J=11.6, 6.7 Hz, 1 H), 7.41 (d, J=2.1 Hz, 1 H), 7.26 (dd, J=5.6, 2.4 Hz, 1 H); MS (ESI): m/z 287.0 [M+H]

A solution of 2-chloro-4-(2,5-difluoro-4-nitrophenoxy)pyridine (11.68 g, 40.8 mmol) in MeOH (200 mL) was treated with Raney Ni (50% wet, 0.955 g, 8.15 mmol) and hydrogenated (10-20 psi) for 4 h. The mixture was filtered through a pad of diatomaceous earth and the filtrate was concentrated to dryness to provide 4-(2-chloropyridin-4-yloxy)-2,5-difluoroaniline (8.2 g, 72% yield). ¹H NMR (400 MHz, DMSO-d₆): δ 8.28 (d, J=5.9 Hz, 1 H), 7.25 (dd, J=11.2, 7.5 Hz, 1 H), 7.02 (dd, J=2.2 Hz, 1 H), 6.95 (dd, J=5.8, 2.0 Hz, 1 H), 6.74 (dd, J=12.3, 8.3 Hz, 1 H), 5.57 (s, 2 H); MS (ESI): m/z 257.0 [M+H]⁺

A solution of 4-(2-chloropyridin-4-yloxy)-2,5-difluoroaniline (450 mg, 1.76 mmol) and 1-methyl-4-(4,4,5,5-tetramethyl-1,3,2-dioxaborolan-2-yl)-1H-pyrazole (400 mg, 1.9 mmol) in DMF (30 mL) was treated with tetrakis(triphenylphosphine)palladium(0) [Pd(PPh₃)₄](105 mg, 0.09 mmol) and an aqueous solution of potassium phosphate (2 M, 1.8 mL). The mixture was flushed with nitrogen for 10 min, and then heated at 90° C. overnight. After cooling to RT, the mixture was treated with water, extracted with EtOAc (4×) and the combined organics were washed with brine, dried (Na₂SO₄), concentrated under reduced pressure and purified by silica gel chromatography to give 2,5-difluoro-4-((2-(1-methyl-1H-pyrazol-4-yl)pyridin-4-yl)oxy)aniline (335 mg, 63% yield). ¹H NMR (300 MHz, DMSO-d₆): δ 8.35 (d, J=5.7 Hz, 1 H), 8.27 (s, 1 H), 7.98 (s, 1 H), 7.24-7.18 (m, 2 H), 6.75 (dd, J=1 2.3, 8.1 Hz, 1 H), 6.62 (dd, J=5.4, 2.1 Hz, 1 H), 5.53 (br s, 2 H), 3.87 (s, 3 H); MS (ESI): m/z 303.1 [M+1]⁺.

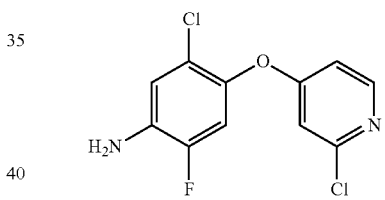

Example A21

A 0° C. suspension of NaH (60% in mineral oil, 0.620 g, 15.5 mmol) in DMF (30 mL) was treated portion-wise with of 2-chloro-4-hydroxypyridine (1.339 g, 10.33 mmol), stirred at 0° C. for 0.5 h, slowly warmed to RT, treated with a solution of 5-chloro-2,4-difluoronitrobenzene (2 g, 10.33 mmol) in DMF (4.4 mL) and heated at 90° C. for 15 h. The mixture was cooled to RT, diluted with EtOAc, washed with 10% LiCl (3×), then brine (2×), dried over MgSO₄, concentrated to dryness and purified via silica gel chromatography (EtOAc/Hex) to afford 2-chloro-4-(2-chloro-5-fluoro-4-nitrophenoxy)pyridine (1.415 g, 45%). ¹H NMR (400 MHz, DMSO-d₆): δ 8.56 (dd, 1 H), 8.35 (dd, 1 H), 7.88 (dd, 1 H), 7.32 (dd, 1 H), 7.18 (m, 1H); MS (ESI) m/z: 303.0 (M+H⁺).

A mixture of 2-chloro-4-(2-chloro-5-fluoro-4-nitrophenoxy)pyridine (1.306 g, 4.31 mmol) and NH₄Cl (2.305 g, 43.1 mmol) in THF (108 mL) and MeOH (108 mL) was treated with zinc dust (2.82 g, 43.1 mmol) and stirred at RT for 1 h. The solids were removed via filtration through diatomaceous earth and the filtrate concentrated under reduced pressure to afford 5-chloro-4-((2-chloropyridin-4-yl)oxy)-2-fluoroaniline (100% yield assumed) as a brown solid which was used without purification. MS (ESI) m/z: 273.0 (M+H⁺).

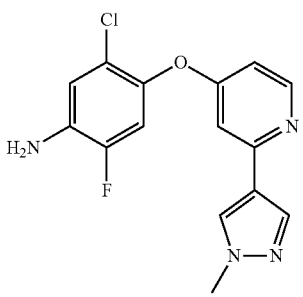 [SMILES: Cn1cc(-c2cc(Oc3cc(F)c(N)cc3Cl)ccn2)cn1]

Example A22

A solution of Example A21 (1.177 g, 4.31 mmol) and 1-methyl(4,4,5,5-tetramethyl-1,3,2-dioxaborolan-2-yl)-1H-pyrazole (1.166 g, 5.60 mmol) in DMF (16 mL) was treated with Cs$_2$CO$_3$ (4.21 g, 12.93 mmol) and water (5 mL), sparged with Ar, treated with Pd(PPh$_3$)$_4$ (0.249 g, 0.215 mmol) and heated at 90° C. for 4 h. The mixture was cooled to RT, diluted with 4:1 EtOAc/THF, washed with 10% LiCl (2×), then brine (1×), dried over MgSO$_4$, evaporated under reduced pressure and purified via silica gel chromatography (EtOAc/Hex) to yield 5-chloro-2-fluoro-4-((2-(1-methyl-1H-pyrazol-4-yl)pyridin-4-yl)oxy)aniline as a tan solid (1.062 g, 77%). $^1$H NMR (400 MHz, DMSO-d$_6$): δ 8.31 (d, 1 H), 8.24 (s, 1 H), 7.95 (s, 1 H), 7.20 (d, 1 H), 7.13 (d, 1 H), 6.92 (d, 1 H), 6.52 (dd, 1 H), 5.49 (s, 2 H), 3.84 (s, 3H); MS (ESI) m/z: 319.1 (M+H$^+$).

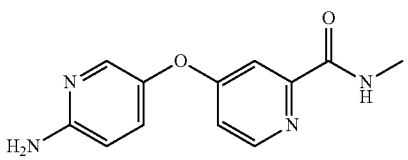 [SMILES: CNC(=O)c1cc(Oc2ccc(N)nc2)ccn1]

Example A23

DMF (25 mL) was slowly treated with SOCl$_2$ (125 mL) to maintain a temperature of 40-50° C. The mixture was then treated portion-wise with pyridine-2-carboxylic acid (25 g, 0.2 mol) over 0.5 h, then heated at reflux for 16 h, cooled to RT, diluted with toluene (80 mL) and concentrated to dryness (this process was repeated three times). The resulting residue was washed with toluene and dried under reduced pressure to yield 4-chloro-pyridine-2-carbonyl chloride (27.6 g, 79% yield), which was used in the next step without purification.

A 0° C. solution of 4-chloro-pyridine-2-carbonyl chloride (27.6 g, 0.16 mol) in THF (100 mL) at was treated drop-wise with a solution of MeNH$_2$ in EtOH, stirred at 3° C. for 4 h, then concentrated to dryness. The material was suspended in EtOAc, the solids removed via filtration and the filtrate was washed with brine (2×), dried and concentrated to yield 4-chloro-N-methylpicolinamide (16.4 g, 60%) as a yellow solid. $^1$H NMR (400 MHz, DMSO-d$_6$) δ 8.78 (br s, 1 H), 8.55 (d, J=5.2 Hz, 1 H), 7.97 (d, J=2.0 Hz, 1 H), 7.66 (m, 1 H), 2.82 (d, J=4.8 Hz, 3H); MS (ESI) m/z: 171.0 (M+H$^+$).

A solution of 2-amino-5-hydroxypyridine (0.968 g, 8.79 mmol) in DMA (15 mL) was treated with potassium tert-butoxide (0.987 g, 8.79 mmol), stirred at RT for 3 h, treated with 4-chloro-N-methylpicolinamide (1.5 g, 8.79 mmol) and stirred at RT for 2 days. The mixture was concentrated to dryness, treated with water, extracted with EtOAc (3×) and the combined organics were washed with brine, dried over Na$_2$SO$_4$, concentrated to dryness and purified via silica gel chromatography (EtOAc, MeOH/DCM) to afford 4-((6-aminopyridin-3-yl)oxy)-N-methylpicolinamide (1.3 g, 61%). $^1$H NMR (400 MHz, DMSO-d$_6$): δ 8.75 (m, 1 H), 8.46 (d, J=5.6 Hz, 1 H), 7.82 (d, J=2.9 Hz, 1 H), 7.34 (d, J=2.6 Hz, 1 H), 7.30 (dd, J=8.9, 3.0 Hz, 1 H), 7.10 (dd, J=5.6, 2.7 Hz, 1 H), 6.53 (d, J=8.9 Hz, 1 H), 6.07 (s, 2 H), 2.77 (d, J=4.8 Hz, 3 H); MS (ESI) m/z: 245.1 (M+H$^+$).

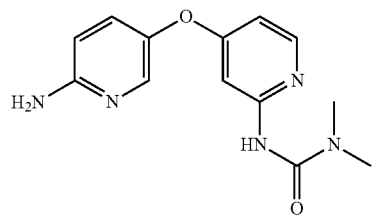 [SMILES: CN(C)C(=O)Nc1cc(Oc2ccc(N)nc2)ccn1]

Example A24

A mixture of Example A1 (1 g, 3.97 mmol) in dioxane (20 mL) was sparged with Ar, treated with N,N-dimethyl urea (0.700 g, 7.95 mmol) and Cs$_2$CO$_3$ (1.942 g, 5.96 mmol), sparged with Ar, treated with dppf [1,1'-bis(diphenylphosphino)ferrocene] (12.38 g, 22.33 mmol) and Pd$_2$(dba)$_3$ (0.182 g, 0.199 mmol), sparged once again with Ar and heated at 95° C. overnight. The mixture was cooled to RT, treated with EtOAc and the solids removed via filtration through silica gel. The filtrate was concentrated to dryness and purified twice via silica gel chromatography (MeOH/DCM) to afford 1,1-dimethyl-3-(4-((6-nitropyridin-3-yl)oxy)pyridin-2-yl)urea (616 mg, 51%). MS (ESI) m/z: 304.1 (M+H$^+$).

A solution of 1,1-dimethyl-3-(4-((6-nitropyridin-3-yl)oxy)pyridin-2-yl)urea (0.631 g, 2.081 mmol) in MeOH (20 mL) was treated with NH$_4$Cl (3.34 g, 62.4 mmol) followed by zinc dust (1.361 g, 20.81 mmol) and stirred at RT overnight. The solids were removed via filtration, washed with THF and the filtrate concentrated to dryness to afford 3-(4-((6-aminopyridin-3-yl)oxy)pyridin-2-yl)-1,1-dimethylurea (560 mg, 98%). MS (ESI) m/z: 274.1 (M+H$^+$).

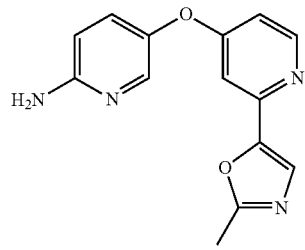 [SMILES: Cc1ncc(-c2cc(Oc3ccc(N)nc3)ccn2)o1]

Example A25

A mixture of Example A1 (600 mg, 2.38 mmol), 2-methyl-5-(4,4,5,5-tetramethyl-1,3,2-dioxaborolan-2-yl)oxazole (648 mg, 3.10 mmol), K$_2$CO$_3$ (989 mg, 7.15 mmol) and Pd(PPh$_3$)$_4$ (138 mg, 0.119 mmol) in dioxane (8 mL) and water (2 mL) was sparged with Ar and heated at 80° C. overnight. Additional 2-methyl-5-(4,4,5,5-tetramethyl-1,3,2- dioxaborolan-2-yl)oxazole (100 mg) and Pd(PPh₃)₄ (50 mg) were added, the mixture heated at 80° C. for 5 h, then cooled to RT and treated with water and EtOAc. The solids were removed via filtration through diatomaceous earth, the layers of the filtrate separated and the organic layer was washed with brine, dried over Na₂SO₄, concentrated to dryness and purified via silica gel chromatography (MeOH/EtOAc) to afford 2-methyl-5-(4-((6-nitropyridin-3-yl)oxy)pyridin-2-yl)oxazole (323 mg, 45%). MS (ESI) m/z: 299.1 (M+H⁺).

A 0° C. mixture of 2-methyl-5-(4-((6-nitropyridin-3-yl) oxy)pyridin-2-yl)oxazole (323 mg, 1.083 mmol) and NH₄Cl (2.317 g, 43.3 mmol) in MeOH (8 mL) and THF (8 mL) was treated portion-wise with zinc dust (708 mg, 10.83 mmol), allowed to warm to RT and stirred overnight. The mixture was diluted with EtOAc, warmed slightly, the solids removed via filtration through diatomaceous earth and washed with EtOAc. The filtrate was concentrated to dryness, treated with EtOAc, heated to reflux, the solids removed via hot filtration and the filtrate concentrated to dryness to afford 5-((2-(2-methyloxazol-5-yl)pyridin-4-yl)oxy)pyridin-2-amine (324 mg, 112%). ¹H NMR (400 MHz, DMSO-d₆): δ 8.43 (d, J=5.7 Hz, 1 H), 7.83 (d, J=2.9 Hz, 1 H), 7.60 (s, 1 H), 7.31 (dd, J=8.9, 3.0 Hz, 1 H), 7.06 (d, J=2.5 Hz, 1 H), 6.83 (dd, J=5.7, 2.5 Hz, 1 H), 6.53 (d, J=8.9 Hz, 1 H), 6.07 (s, 2 H), 2.46 (s, 3 H); MS (ESI) m/z: 269.1 (M+H⁺).

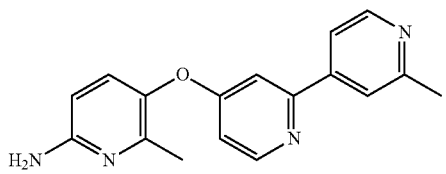 [SMILES: Cc1cc(-c2cc(Oc3ccc(N)nc3C)ccn2)ccn1]

Example A26

A mixture of Example A7 (905 mg, 3.84 mmol), 2-methyl-4-(4,4,5,5-tetramethyl-1,3,2-dioxaborolan-2-yl)pyridine (1.010 g, 4.61 mmol), potassium carbonate (1.592 g, 11.52 mmol) and tetrakis(triphenylphosphine)palladium(0) (222 mg, 0.192 mmol) in dioxane (16 mL) and water (4 mL) was degassed with Ar, sealed and warmed to 85° C. overnight. The mixture was cooled to RT, diluted with EtOAc (40 mL) and water (50 mL), and filtered through diatomaceous earth. The organic phase was separated and washed with brine (50 mL). The organic phase was diluted with methanol (5 mL), treated with SiliaMetS Thiol, (1.42 mmol/g, 4 g, 5.68 mmol), and gently stirred for 3 h. The mixture was filtered, washing the slica gel plug with 3% MeOH/EtOAc (2×10 mL). The filtrates were evaporated at reduced pressure and the residue was purified by silica gel chromatography (0-10% MeOH/EtOAc) to give 6-methyl-5-((2'-methyl-[2,4'-bipyridin]-4-yl) oxy)pyridin-2-amine as a tan solid (806 mg, 71%). ¹H NMR (400 MHz, DMSO-d₆): δ 9.07 (d, J=2.3 Hz, 1 H), 8.48 (d, J=5.7 Hz, 1 H), 8.25 (dd, J=8.1, 2.4 Hz, 1 H), 7.50 (d, J=2.4 Hz, 1 H), 7.33 (d, J=8.2 Hz, 1 H), 7.21 (d, J=8.7 Hz, 1 H), 6.67 (dd, J=5.7, 2.4 Hz, 1 H), 6.35 (d, J=8.7 Hz, 1 H), 5.96 (s, 2 H), 2.50 (s, 3 H), 2.08 (s, 3 H). MS (ESI) m/z: 293.2 (M+H⁺).

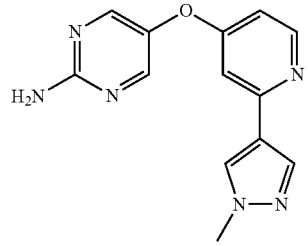 [SMILES: Cn1cc(-c2cc(Oc3cnc(N)nc3)ccn2)cn1]

Example A27

A solution of 2-amino-5-hydroxypyrimidine (1.00 g, 9.00 mmol) in DMA (25 mL) was treated with potassium tert-butoxide (1.24 g, 11.05 mmol). The thick mixture was stirred at room temperature for 1 h. To this was added a solution of 2,4-dichloropyridine (1.21 g, 8.18 mmol) in DMA (10 mL) and the reaction was stirred at RT overnight under Ar. The mixture was diluted with EtOAc (100 mL) and washed with water (100 mL). The organic phase was separated and the aqueous was extracted with EtOAc (100 mL). The combined EtOAc layers were washed with 5% LiCl (100 mL) and brine (100 mL) and then dried over sodium sulfate. The solvents were evaporated at reduced pressure to give 5-((2-chloropyridin-4-yl)oxy)pyrimidin-2-amine as a pale yellow solid (592 mg, 32%). MS (ESI) m/z: 223.0 (M+H⁺).

5-((2-chloropyridin-4-yl)oxy)pyrimidin-2-amine (676 mg, 3.04 mmol), 1-methyl-4-(4,4,5,5-tetramethyl-1,3,2-dioxaborolan-2-yl)-1H-pyrazole (758 mg, 3.64 mmol), potassium carbonate (1.259 g, 9.11 mmol) and tetrakis(triphenylphosphine)palladium(0) (175 mg, 0.152 mmol) were combined in dioxane (12 mL) and water (3 mL). The mixture was degassed with argon, sealed and warmed to 85° C. overnight. The mixture was diluted with EtOAc (75 mL) and water (40 mL) and was filtered to collect an off-white solid. The organic phase was separated, washed with brine (40 mL) and evaporated at reduced pressure to give additional off-white solid. The two crops of solids were combined and triturated with EtOAc (15 mL) with sonication. The solid was collected by filtration, washed with EtOAc (2×5 mL) and dried under vacuum to provide 5-((2-(1-methyl-1H-pyrazol-4-yl)pyridin-4-yl)oxy)pyrimidin-2-amine (455 mg, 55%). ¹H NMR (DMSO-d₆): δ 8.34 (d, J=5.7 Hz, 1 H), 8.26 (s, 1 H), 8.22 (s, 2 H), 7.96 (s, 1 H), 7.19 (d, J=2.4 Hz, 1 H), 6.77 (s, 2 H), 6.67 (dd, J=5.7, 2.5 Hz, 1 H), 3.84 (s, 3 H); MS (ESI) m/z: 269.1 (M+H⁺).

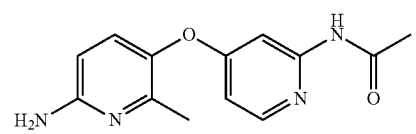 [SMILES: CC(=O)Nc1cc(Oc2ccc(N)nc2C)ccn1]

Example A28

A solution of Example A6 (1.7 g, 6.40 mmol) in dioxane (30 mL) was sparged with Ar, treated with acetamide (1.512 g, 25.6 mmol), Cs₂CO₃ (2.085 g, 6.40 mmol), X-Phos (0.153 g, 0.320 mmol) and Pd₂(dba)₃ (0.293 g, 0.320 mmol) and heated at 80° C. for 20 h. The mixture was cooled to RT, treated with EtOAc, the solids removed via filtration through diatomaceous earth and rinsed well with EtOAc. The filtrate was washed with water, then brine, dried over Na$_2$SO$_4$, concentrated to dryness and purified via silica gel chromatography (EtOAc/DCM) to afford N-(4-((2-methyl-6-nitropyridin-3-yl)oxy)pyridin-2-yl)acetamide (450 mg, 24%) as a light yellow solid. MS (ESI) m/z: 289.1 (M+H$^+$).

A solution of N-(4-((2-methyl-6-nitropyridin-3-yl)oxy)pyridin-2-yl)acetamide (0.44 g, 1.526 mmol) in MeOH (30 mL) was treated with palladium on carbon (50% wet, 0.162 g, 0.153 mmol) and hydrogenated (1 atm) at RT for 24 h. The solids were removed via filtration through diatomaceous earth, washed well with MeOH and the filtrate concentrated to afford N-(4-((6-amino-2-methylpyridin-3-yl)oxy)pyridin-2-yl)acetamide (370 mg, 94%) as a white solid. $^1$H NMR (400 MHz, DMSO-d$_6$): δ 10.46 (s, 1 H), 8.10 (d, J=5.7 Hz, 1 H), 7.53 (d, J=2.3 Hz, 1 H), 7.13 (d, J=8.7 Hz, 1 H), 6.53 (dd, J=5.7, 2.4 Hz, 1 H), 6.32 (d, J=8.7 Hz, 1 H), 5.91 (s, 2 H), 2.02 (s, 3 H), 2.01 (s, 3 H); MS (ESI) m/z: 259.2 (M+H$^+$).

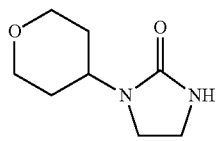 [SMILES: O=C1NCCN1C1CCOCC1]

Example B1

A RB flask was charged with 4-aminotetrahydropyran (9.77 g, 97 mmol) in THF (480 mL) and was cooled in an ice bath. To this stirring solution was added 2-chloroethyl isocyanate (11.19 g, 106 mmol) drop-wise and the reaction was brought to RT and stirred at RT overnight. The reaction mixture was concentrated to dryness and the crude product was washed successively with saturated NH$_4$Cl (60 mL) and saturated NaHCO$_3$ (60 mL). The organic layer was dried over anhydrous Na$_2$SO$_4$ and concentrated to dryness to afford a white solid. Toluene (20 mL) was added and the residue was concentrated to dryness. The process was repeated a second time (to remove any moisture) to afford 1-(2-chloroethyl)-3-(tetrahydro-2H-pyran-4-yl)urea as a white solid. The product was utilized in the next reaction without purification. $^1$H NMR (CDCl$_3$): δ 5.34-4.94 (bs, 1 H), 4.93-4.56 (bs, 1 H), 3.94 (dt, J=11.9, 3.2 Hz, 2 H), 3.84-3.71 (m, 1 H), 3.64-3.59 (m, 2 H), 3.49-3.47 (m, 2 H), 1.95-1.83 (m, 2 H), 1.50-1.34 (m, 2 H); MS (ESI) m/z: 207.1 (M+H$^+$).

A dry RB flask charged with 1-(2-chloroethyl)-3-(tetrahydro-2H-pyran-4-yl)urea (19.96 g, 97 mmol) in THF (480 mL), placed under Ar and stirred for 20 minutes at −20° C. after which 60% Sodium Hydride in mineral oil (9.66 g, 241 mmol) was added portion wise. The reaction was allowed to stir at −20° C. for 1 h and was then allowed to warm to ambient temp overnight. The reaction was cooled in an ice bath and quenched via slow addition of saturated NH$_4$Cl (50 mL). Brine (30 mL) was added and the reaction was allowed to stir for 20 minutes. The organic layer was separated and aqueous layer extracted with EtOAc (2×) and THF (2×). The organic layers were combined, dried over anhydrous Na$_2$SO$_4$ and concentrated to dryness to afford a white gummy solid. The crude product was purified by silica gel chromatography (5% MeOH in CH$_2$Cl$_2$) to afford 1-(tetrahydro-2H-pyran-4-yl)imidazolidin-2-one as a white solid (10.54 g, 64% yield, 2 steps). $^1$H NMR (DMSO-d$_6$): δ 6.24 (s, 1 H), 3.91-3.81 (m, 2 H), 3.73-3.61 (m, 1 H), 3.29-3.23 (m, 2 H), 3.22-3.21 (m, 2 H), 3.19-3.14 (m, 2 H), 1.67-1.53 (m, 2 H), 1.45-1.44 (m, 2 H); MS (ESI) m/z: 171.1 (M+H$^+$).

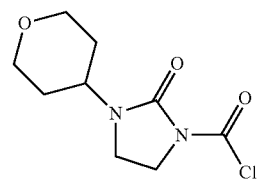 [SMILES: O=C(Cl)N1CCN(C2CCOCC2)C1=O]

Example B2

A 0° C. solution of phosgene (20% in toluene, 0.267 mL, 0.506 mmol) in DCM (5 mL) was treated slowly drop-wise with a solution of Example B1 (0.086 g, 0.505 mmol) and pyridine (0.082 mL, 1.011 mmol) in DCM (3 mL). The mixture was warmed to RT, stirred for 1 hour, then concentrated to dryness to afford 2-oxo-3-(tetrahydro-2H-pyran-4-yl)imidazolidine-1-carbonyl chloride as an off-white solid. The material was carried on to the next step assuming 100% yield (118 mg). MS (ESI) m/z: 304.1 (M+H$^+$) (for material quenched into benzylamine).

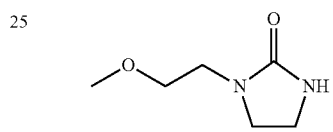

Example B3

A solution of methoxyethylamine (0.40 mL, 4.60 mmol) in THF (15 mL) was treated with 2-chloroethylisocyanate (0.35 mL, 4.10 mmol), stirred at RT for 3 h and concentrated to dryness to afford 1-(2-chloroethyl)-3-(2-methoxyethyl)urea (100% yield assumed) as a white solid. MS (ESI) m/z: 181.1 (M+H$^+$).

A −20° C. solution of 1-(2-chloroethyl)-3-(2-methoxyethyl)urea (0.300 g, 1.661 mmol) in THF (8.3 mL), under Ar, was treated with NaH (60% in mineral oil, 0.166 g, 4.15 mmol) allowed to warm to RT and stirred. The mixture was cooled to 0° C., treated slowly with satd. NH$_4$Cl, then brine, warmed to RT and stirred for 20 min. The layers were separated, the aqueous layer extracted with EtOAc (2×) and the combined organics were dried over Na$_2$SO$_4$, concentrated to dryness and purified via silica gel chromatography (MeOH/DCM) to afford 1-(2-methoxyethyl)imidazolidin-2-one (220 mg, 92%) as a white solid. $^1$H NMR (400 MHz, DMSO-d$_6$): δ 6.26 (s, 1 H), 3.39-3.31 (m, 4 H), 3.22 (s, 3 H), 3.20-3.14 (m, 4 H); MS (ESI) m/z: 145.1 (M+H$^+$).

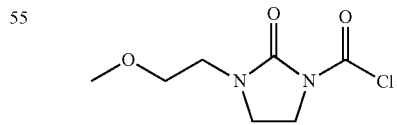

Example B4

A 0° C. solution of phosgene (20% in toluene, 0.642 mL, 6.07 mmol) in DCM (12 mL) was treated drop-wise with a solution of pyridine (0.196 mL, 2.428 mmol) and Example B3 (0.175 g, 1.214 mmol) in DCM (10 mL) allowed to warm to RT and stirred for 1 h. The mixture was concentrated to dryness to afford crude 3-(2-methoxyethyl)-2-oxoimidazolidine-1-carbonyl chloride (100% yield assumed) which was used without further purification. 3-(2-Methoxyethyl)-2-oxoimidazolidine-1-carbonyl chloride was characterized as a benzylamine addition product ($C_{14}H_{19}N_3O_3$). MS (quenched into benzyl amine) (ESI) m/z: 278.2 ($C_{14}H_{19}N_3O_3+H^+$).

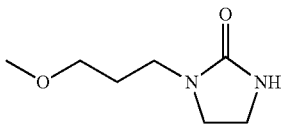

Example B5

A solution of 3-methoxypropylamine (0.45 mL, 4.39 mmol) in THF (15 mL) was treated with 2-chloroethylisocyanate (0.35 mL, 4.10 mmol), stirred at RT for 3 h and concentrated to dryness to afford 1-(2-chloroethyl)-3-(3-methoxypropyl)urea (100% yield assumed) as a white solid. MS (ESI) m/z: 195.1 ($M+H^+$).

A 0° C. solution of 1-(2-chloroethyl)-3-(3-methoxypropyl) urea (0.300 g, 1.541 mmol) in THF (8 mL), under Ar, was treated with NaH (60% in mineral oil, 0.154 g, 3.85 mmol) allowed to warm to RT and stirred. The mixture was cooled to 0° C., treated slowly with satd. NH$_4$Cl, then brine, warmed to RT and stirred for 10 min. The layers were separated, the aqueous layer extracted with EtOAc (2×) and the combined organics were dried over Na$_2$SO$_4$, concentrated to dryness and purified via silica gel chromatography (MeOH/DCM) to afford 1-(3-methoxypropyl)imidazolidin-2-one (214 mg, 88%) as a white solid. $^1$H NMR (400 MHz, DMSO-d$_6$): δ 6.21 (s, 1 H), 3.31-3.24 (m, 4 H), 3.21-3.15 (m, 5 H), 3.06-3.01 (m, 2 H), 1.66-1.58 (m, 2 H); MS (ESI) m/z: 159.1 ($M+H^+$).

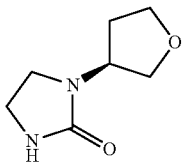 [SMILES: O=C1NCCN1[C@H]1CCOC1]

Example B6

A solution of (S)-(−)-tetrahydro-3-furylamine p-toluenesulfonate salt (0.5 g, 1.928 mmol) in THF (20 mL) was gently agitated with MP-Carbonate Resin (1.825 g, 5.78 mmol, 3.17 mmol/g loading) for 36 h, the resin removed via filtration and the filtrate cooled to 0° C., treated drop-wise with chloroethyl isocyanate (0.224 g, 2.121 mmol), warmed to RT and stirred overnight. The mixture was washed with satd. NH$_4$Cl (1×), satd. NaHCO$_3$ (1×), then brine (1×), dried over MgSO$_4$, concentrated to dryness and purified via silica gel chromatography (MeOH/DCM) to afford (S)-1-(2-chloroethyl)-3-(tetrahydrofuran-3-yl)urea (0.11 g, 30%). $^1$H NMR (400 MHz, DMSO-d$_6$): δ 6.31 (d, J=6.9 Hz, 1 H), 6.01 (t, J=5.9 Hz, 1 H), 4.11-4.08 (m, 1 H), 3.69-3.67 (m, 3 H), 3.55 (t, J=6.2 Hz, 2 H), 3.36 (dd, J=8.8, 3.8 Hz, 1 H), 3.32-3.26 (m, 2 H), 2.03 (dq, J=12.6, 7.6 Hz, 1 H), 1.59-1.61 (m, 1 H); MS (ESI) m/z: 193.1 ($M+H^+$).

A −20° C. solution of (S)-1-(2-chloroethyl)-3-(tetrahydrofuran-3-yl)urea (0.11 g, 0.571 mmol) in THF (6 mL) was treated with NaH (60% in mineral oil, 0.057 g, 1.428 mmol), stirred at −20° C. for 0.5 h, then at RT for 1 h. The mixture was treated with satd. NH$_4$Cl and H$_2$O, extracted with EtOAc (3×) and THF (2×) and the combined organics were washed with brine (1×), dried over MgSO$_4$, concentrated to dryness and purified via silica gel chromatography (MeOH/DCM) to afford (S)-1-(tetrahydrofuran-3-yl)imidazolidin-2-one (26 mg, 29%). $^1$H NMR (400 MHz, DMSO-d$_6$): δ 6.32 (brs, 1 H), 4.36-4.30 (m, 1 H), 3.83-3.77 (m, 1 H), 3.63-3.53 (m, 4 H), 3.31-3.26 (m, 1 H), 3.24-3.21 (m, 2 H); 2.05-1.96 (m, 1 H); 1.84-1.76 (m, 1 H). MS (ESI) m/z: 157.1 ($M+H^+$).

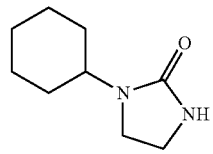 [SMILES: O=C1NCCN1C1CCCCC1]

Example B7

A solution of cyclohexylamine (1.00 g, 10.08 mmol) and 2-chloro ethylisocyanate (1.064 g, 10.08 mmol) in THF (30 mL) was stirred at RT for 4 h, treated with sodium hydride (60% in mineral oil, 0.403 g, 10.08 mmol) and stirred at RT for 16 h. The mixture was poured into satd. NH$_4$Cl, treated with solid NaCl until saturated, extracted with THF (2×) and the combined organics were washed with brine, dried over Na$_2$SO$_4$ and concentrated to dryness. The material was suspended in 30% EtOAc/Hex, stirred and the resulting solid collected via filtration to afford 1-cyclohexylimidazolidin-2-one (650 mg, 38%) as a white solid. $^1$H NMR (400 MHz, DMSO-d$_6$): δ 6.14 (s, 1 H), 3.46-3.37 (m, 1 H), 3.27-3.21 (m, 2 H), 3.19-3.13 (m, 2 H), 1.75-1.68 (m, 2 H), 1.60-1.50 (m, 3 H), 1.37-1.18 (m, 4 H), 1.09-0.98 (m, 1 H).

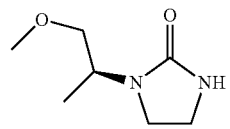

Example B8

A solution of (S)-1-methoxypropan-2-amine (500 mg, 5.61 mmol) in THF (15 mL) was treated with 2-chloroethylisocyanate (592 mg, 5.61 mmol), stirred at RT overnight, then concentrated to dryness. The residue was treated with toluene and concentrated to dryness (twice) to afford (S)-1-(2-chloroethyl)-3-(1-methoxypropan-2-yl)urea (100% yield assumed) as a white solid which was used without further purification. MS (ESI) m/z: 195.1 ($M+H^+$).

A −20° C. solution of (S)-1-(2-chloroethyl)-3-(1-methoxypropan-2-yl)urea (1.092 g, 5.61 mmol) in THF (25 mL) was treated portion-wise with NaH (60% in mineral oil, 505 mg, 12.62 mmol), allowed to warm to RT and stirred overnight. The mixture was treated with EtOAc, water, then 5% citric acid, the layers separated and the organic layer washed with brine, dried over Na$_2$SO$_4$, concentrated to dryness and purified via silica gel chromatography (MeOH/EtOAc) to afford (S)-1-(1-methoxypropan-2-yl)imidazolidin-2-one (95 mg, 11%). MS (ESI) m/z: 159.1 (M+H+).

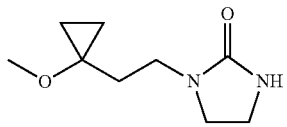

Example B9

A solution of ethyl 3-aminopropanoate hydrochloride (80.0 g, 0.52 mol), benzylbromide (186.7 g, 1.1 mol) and K₂CO₃ (179.4 g, 1.3 mol) in MeCN (1 L) was heated at 40° C. overnight. The mixture was concentrated to dryness, poured into water, extracted with EtOAc (3×) and the combined organics were washed with brine, dried over Na₂SO₄ and purified via silica gel chromatography to give ethyl 3-(dibenzylamino)propanoate (150 g, 97%).

Titanium isopropoxide (860 mg, 3.03 mmol) was added to a solution of ethyl 3-(dibenzylamino)propanoate (9.0 g, 30.3 mmol) in Et2O, cooled to 0° C., treated drop-wise with ethyl magnesium bromide (3M in Et₂O, 30.3 mL) over 1 h, maintaining the temperature at 0~4° C., then allowed to warm to RT and stirred overnight. The mixture was cooled to 0° C., treated with satd. NH₄Cl, stirred at RT for 15 minutes, made basic with satd. NaHCO₃ and extracted with EtOAc (2×). The combined organics were washed with brine, dried over MgSO4, concentrated and purified via silica gel chromatograph to give 1-(2-(dibenzylamino)ethyl)cyclopropanol (7.5 g, 88%) as a pale yellow oil. ¹H NMR (400 MHz, CDCl₃): δ 7.20-7.15 (m, 8 H), 7.12-7.07 (m, 2 H), 3.45 (s, 4 H), 2.61-2.59 (m, 2 H), 1.57 (t, J=5.6 Hz, 2 H), 0.36-0.33 (m, 2 H), 0.30-0.17 (m, 2 H).

A 0° C. solution of 1-(2-(dibenzylamino)ethyl)cyclopropanol (3 g, 10.6 mmol) in THF (50 mL), under N₂, was treated portion-wise with NaH (60%, 0.85 g, 21.3 mmol), stirred at 0° C. for 0.5 h, treated drop-wise with MeI (1.82 g, 12.8 mmol), warmed to RT and stirred for 3 h. The mixture was cooled to 0° C., quenched with satd. NH₄Cl and partially concentrated. The residue was extracted with EtOAc (3×) and the combined organics were washed with brine, dried over Na₂SO₄, concentrated and purified via silica gel chromatography to afford N,N-dibenzyl-2-(1-methoxycyclopropyl)ethanamine (1.2 g, 38%). ¹H NMR (400 MHz, CDCl₃): δ 7.39-7.21 (m, 10 H), 3.60 (s, 4 H), 3.12 (s, 3 H), 2.65 (t, J=8 Hz, 2 H), 1.75 (t, J=8 Hz, 2 H), 0.68-0.65 (m, 2 H), 0.34-0.31 (m, 2 H).

A solution of N,N-dibenzyl-2-(1-methoxycyclopropyl) ethanamine (0.750 g, 2.54 mmol) in EtOH (50 mL) was treated with 20% palladium hydroxide (50 wt % with water, 0.357 g, 0.254 mmol) and hydrogenated (40 psi) for 4 h. The solids were removed via filtration through diatomaceous earth, rinsed well with MeOH and the filtrate carefully concentrated to near-dryness to afford crude 2-(1-methoxycyclopropyl)ethanamine (361 mg, 95% yield at 77% purity) as a yellow oil which was used without further purification. ¹H NMR (400 MHz, DMSO-d₆): δ 5.41 (s, 2 H), 3.13 (s, 3 H), 2.64 (t, J=7.3 Hz, 2 H), 1.59 (t, J=7.3 Hz, 2 H), 0.62-0.57 (m, 2 H), 0.36 (m, 2 H).

A 0° C. solution of 2-(1-methoxycyclopropyl)ethanamine (0.361 g, 2.413 mmol) in THF (15 mL) was treated drop-wise with 2-chloroethyl isocyanate (0.226 mL, 2.65 mmol), allowed to warm to RT, stirred overnight, then concentrated to dryness. The residue was treated with toluene and concentrated to dryness (twice) to afford 1-(2-chloroethyl)-3-(2-(1-methoxycyclopropyl)ethyl)urea (429 mg, 81%) as a yellow oil. MS (ESI) m/z: 221.1 (M+H+).

A −20° C. solution of 1-(2-chloroethyl)-3-(2-(1-methoxycyclopropyl)ethyl)urea (0.429 g, 1.944 mmol) in THF (10 mL), under argon, was treated with NaH (60% in mineral oil, 0.194 g, 4.86 mmol), and the mixture allowed to warm to RT as the cooling bath expired. The mixture was cooled to 0° C., quenched with satd. NH₄Cl, warmed to RT, treated with brine, extracted with EtOAc (2×) and the combined organics were dried over MgSO₄, concentrated to dryness and purified via silica gel chromatography (MeOH/DCM) to afford 1-(2-(1-methoxycyclopropyl)ethyl)imidazolidin-2-one (196 mg, 55%) as an off-white solid. ¹H NMR (400 MHz, DMSO-d₆): δ 6.22 (s, 1 H), 3.32-3.27 (m, 2 H), 3.19-3.17 (m, 2 H), 3.14 (s, 3 H), 3.12-3.11 (m, 2 H), 1.67-1.65 (m, 2 H), 0.63-0.62 (m, 2 H), 0.39-0.38 (m, 2 H); MS (ESI) m/z: 185.1 (M+H+).

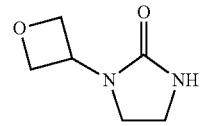

Example B10

A 0° C. solution of 3-oxetanamine (0.200 g, 2.74 mmol) in THF (15 mL) was treated drop-wise with 2-chloroethyl isocyanate (0.257 mL, 3.01 mmol), allowed to warm to RT as the cooling bath expired, then concentrated to dryness. The residue was treated with toluene and concentrated to dryness (twice) to afford a white solid. The solid was dissolved in THF (15 mL), cooled to −20° C., under Ar, treated with NaH (60% in mineral oil, 0.274 g, 6.84 mmol), allowed to warm to RT and stirred overnight. The mixture was cooled to 0° C., quenched with satd. NH₄Cl, warmed to RT, treated with brine and extracted with EtOAc (2×). The combined organics were dried over MgSO₄ and concentrated to dryness. The aqueous layer was treated with solid NaCl until saturated, extracted with 1:1 EtOAc/THF (4×), then frozen and lyophilized. The lyophilized solid was stirred with EtOH for 1 h, the liquid decanted and the process repeated. The EtOH extracts were combined with the EtOAc/THF extracts, concentrated to dryness, then treated with 10% MeOH/DCM and the solids removed via filtration. The filtrate was combined with the initial EtOAc extracts and purified via silica gel chromatography (MeOH/DCM) to afford 1-(oxetan-3-yl)imidazolidin-2-one (270 mg, 69%) as a white solid. ¹H NMR (400 MHz, DMSO-d₆): δ 6.52 (s, 1 H), 4.86 (m, 1 H), 4.71 (t, J=6.6 Hz, 2 H), 4.62 (t, J=7.2 Hz, 2 H), 3.58 (m, 2 H), 3.29 (m, 2 H); MS (ESI) m/z: 143.1 (M+H+).

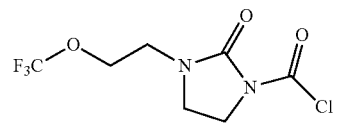 [SMILES: O=C(Cl)N1CCN(CCOC(F)(F)F)C1=O]

Example B11

A 0° C. suspension of 2-(trifluoromethoxy)ethylamine hydrochloride (0.308 g, 1.861 mmol) in THF (10 mL) was treated with NaH (60% in mineral oil, 0.082 g, 2.047 mmol), stirred at 0° C. for 0.5 h, treated drop-wise with 2-chloroethyl isocyanate (0.175 mL, 2.047 mmol), allowed to warm to RT and stirred overnight. The mixture was treated with EtOAc, the solids removed via filtration and the filtrate concentrated to dryness to afford 1-(2-chloroethyl)-3-(2-(trifluoromethoxy)ethyl)urea (610 mg, 140%) containing EtOAc. $^1$H NMR (400 MHz, DMSO-$d_6$): δ 6.29 (br s, 2 H), 4.04-3.97 (m, 2 H), 3.55 (t, J=6.2 Hz, 2 H), 3.33-3.24 (m, 4 H).

A −20° C. solution of 1-(2-chloroethyl)-3-(2-(trifluoromethoxy)ethyl)urea (0.436 g, 1.858 mmol) in THF (20 mL) was treated with NaH (60% in mineral oil, 0.082 g, 2.044 mmol), warmed to RT and stirred overnight. The mixture was cooled to −20° C., treated with additional NaH (60% in mineral oil, 0.082 g, 2.044 mmol) warmed to RT, stirred for 6 h, then quenched with satd. NH$_4$Cl. The mixture was extracted with EtOAc which was dried over MgSO$_4$, concentrated to dryness and purified via silica gel chromatography (EtOAc/Hex) to afford 1-(2-(trifluoromethoxy)ethyl)imidazolidin-2-one (156 mg, 42%). $^1$H NMR (400 MHz, DMSO-$d_6$): δ 6.41 (s, 1 H), 4.13 (t, J=5.3 Hz, 2 H), 3.35-3.34 (m, 4 H), 3.22-3.20 (m, 2H); MS (ESI) m/z: 199.1 (M+H$^+$).

A 0° C. solution of phosgene (20 wt % in toluene, 0.497 mL, 0.945 mmol) in DCM (4 mL) was treated slowly with a solution of 1-(2-(trifluoromethoxy)ethyl)imidazolidin-2-one (0.156 g, 0.787 mmol) and pyridine (0.127 mL, 1.575 mmol) in DCM (4 mL), stirred for 1 h at 0° C., then concentrated to dryness to afford 2-oxo-3-(2-(trifluoromethoxy)ethyl)imidazolidine-1-carbonyl chloride (100% yield assumed). MS [quenched in MeOH] (ESI) m/z: 257.1 (M+H$^+$).

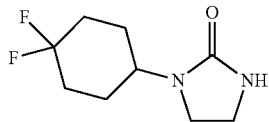 [SMILES: O=C1NCCN1C1CCC(F)(F)CC1]

Example B12

A solution of 4,4-difluorocyclohexanamine hydrochloride (0.800 g, 4.66 mmol) in THF (20 mL) was treated with Na$_2$CO$_3$ (0.800 g, 7.55 mmol) followed by 1-chloro-2-isocyanatoethane (0.800 g, 7.58 mmol) and stirred at RT for 2 h. The mixture was cooled to 0° C., treated with NaH (60% in mineral oil, 0.300 g, 7.50 mmol), warmed to RT and stirred for 4 h. The mixture was poured into satd. NH$_4$Cl solution, the layers separated and the aqueous layer extracted with DCM (3×). The combined organics were washed with brine, dried over Na$_2$SO$_4$ and concentrated to dryness to afford 1-(4,4-difluorocyclohexyl)imidazolidin-2-one (624 mg, 66%) as a white solid. MS (ESI) m/z: 205.1 (M+H$^+$).

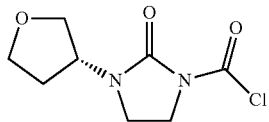 [SMILES: O=C(Cl)N1CCN([C@@H]2CCOC2)C1=O]

Example B13

A 0° C. suspension of (R)-(+)-tetrahydro-3-furylamine p-toluenesulfonate salt (1.00 g, 3.86 mmol) in THF (40 mL) was treated with NaH (60% in mineral oil, 0.170 g, 4.24 mmol), stirred at 0° C. for 1.5 h, treated with 2-chloroethyl isocyanate (0.362 mL, 4.24 mmol) and stirred at RT overnight as the cooling bath expired. The mixture was treated with satd. NH$_4$Cl and water, extracted with EtOAc (2×) and the combined organics were washed with brine (2×), dried over Na$_2$SO$_4$ and concentrated to dryness. The residue was treated with 1:1 EtOAc/Hex and the resulting solid collected via filtration to afford (R)-1-(2-chloroethyl)-3-(tetrahydrofuran-3-yl)urea (522 mg, 70%). MS (ESI) m/z: 193.1 (M+H$^+$).

A −20° C. solution of (R)-1-(2-chloroethyl)-3-(tetrahydrofuran-3-yl)urea (0.522 g, 2.71 mmol) in THF (30 mL) was treated with NaH (60% in mineral oil, 0.130 g, 3.25 mmol) and the mixture stirred at RT overnight as the cooling bath expired. The mixture was treated with satd. NH$_4$Cl, dried over MgSO$_4$, concentrated to dryness and purified via silica gel chromatography (MeOH/DCM) to afford (R)-1-(tetrahydrofuran-3-yl)imidazolidin-2-one (280 mg, 66%). MS (ESI) m/z: 157.1 (M+H$^+$).

A 0° C. solution of phosgene (20% in toluene, 1.132 mL, 2.151 mmol) in DCM (9 mL) was treated slowly with a solution of (R)-1-(tetrahydrofuran-3-yl)imidazolidin-2-one (0.28 g, 1.793 mmol) and pyridine (0.290 mL, 3.59 mmol) in DCM (9 mL) and stirred at 0° C. for 45 min. The mixture was concentrated to dryness to afford crude (R)-2-oxo-3-(tetrahydrofuran-3-yl)imidazolidine-1-carbonyl chloride (100% yield assumed) which was used without further purification.

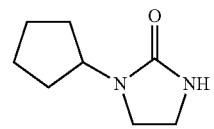 [SMILES: O=C1NCCN1C1CCCC1]

Example B14

A 0° C. solution of cyclopentylamine (4.63 mL, 47.0 mmol) in THF (235 mL) was treated drop-wise with 2-chloroethyl isocyanate (4.41 mL, 51.7 mmol) which was allowed to warm to RT, then concentrated to dryness. The solid was suspended in toluene and concentrated again to dryness to afford 1-(2-chloroethyl)-3-cyclopentylurea (8.95 g, 100%) as an off-white solid. $^1$H NMR (400 MHz, DMSO-$d_6$): δ 6.01 (d, J=7.3 Hz, 1 H), 5.91 (t, J=5.8 Hz, 1 H), 3.85-3.76 (m, 1 H), 3.54 (t, J=6.2 Hz, 2 H), 3.27 (q, J=6.1 Hz, 2 H), 1.78-1.69 (m, 2 H), 1.62-1.53 (m, 2 H), 1.51-1.42 (m, 2 H), 1.30-1.20 (m, 2 H); MS (ESI) m/z: 191.1 (M+H$^+$).

A −20° C. solution of 1-(2-chloroethyl)-3-cyclopentylurea (8.5 g, 44.6 mmol) in THF (446 mL), under Ar, was treated with NaH (60% in mineral oil, 4.46 g, 111 mmol), stirred at −10° C. for 1 h, 0° C. for 1 h, then RT for 3 h. The mixture was cooled to 0° C., treated with 50% satd. NH$_4$Cl, the layers separated and the aqueous layer extracted with EtOAc (3×). The combined organics were dried over Na$_2$SO$_4$ and concentrated to dryness. The material was suspended in Et$_2$O, the solids removed via filtration and the filtrate concentrated to dryness. The resulting material was dissolved in DCM, treated drop-wise with hexane until solids formed and the solids were collected via filtration and dried to afford 1-cyclopentylimidazolidin-2-one (4.3 g, 63%) as a white solid. $^1$H NMR (400 MHz, DMSO-$d_6$): δ 6.16 (s, 1 H), 4.07-3.98 (m, 1 H), 3.28-3.22 (m, 2 H), 3.19-3.14 (m, 2 H), 1.66-1.55 (m, 4 H), 1.52-1.41 (m, 4 H); MS (ESI) m/z: 155.1 (M+H$^+$).

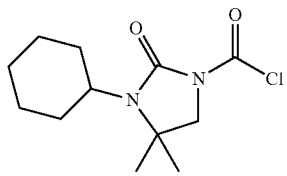 [SMILES: CC1(C)CN(C(=O)Cl)C(=O)N1C1CCCCC1]

Example B15

A solution of 2-methylallylamine (0.156 g, 2.197 mmol) in dioxane (5 mL) was treated with DBU (0.030 mL, 0.200 mmol) and cyclohexyl isocyanate (0.25 g, 1.997 mmol) and heated at 60° C. overnight. The mixture was cooled to RT, treated with water, extracted with EtOAc (2×) and the combined organics were washed with brine, dried over $Na_2SO_4$ and concentrated to dryness to afford 1-cyclohexyl-3-(2-methylallyl)urea (340 mg, 87%). $^1$H NMR (400 MHz, DMSO-$d_6$): δ 5.80 (m, 1 H), 5.72 (d, J=8.0 Hz, 1 H), 4.72 (m, 1 H), 4.68 (m, 1 H), 3.50 (d, J=5.3 Hz, 2 H), 3.30 (m, 1 H), 1.70 (m, 2 H), 1.61 (s, 3 H), 1.60 (m, 1 H), 1.48 (m, 1 H), 1.27 (m, 2 H), 1.13 (m, 4 H); MS (ESI) m/z: 197.2 (M+H$^+$).

A solution of 1-cyclohexyl-3-(2-methylallyl)urea (0.34 g, 1.732 mmol) in TFA (3 mL) was stirred at RT overnight, then concentrated to dryness. The residue treated was treated with satd. $NaHCO_3$, extracted with EtOAc (2×) and the combined organics were washed with brine, dried over $Na_2SO_4$ and concentrated to dryness to afford crude 1-cyclohexyl-5,5-dimethylimidazolidin-2-one (100% yield assumed) which was used without further purification. MS (ESI) m/z: 197.2 (M+H$^+$).

A 0° C. solution of phosgene (15% in toluene, 1.854 mL, 2.60 mmol) in DCM (10 mL) was treated drop-wise with a solution of 1-cyclohexyl-5,5-dimethylimidazolidin-2-one (0.34 g, 1.732 mmol) and pyridine (0.28 mL) in DCM (5 mL), stirred at 0° C. for 0.5 h, then concentrated to dryness to afford crude 3-cyclohexyl-4,4-dimethyl-2-oxoimidazolidine-1-carbonyl chloride (0.45 g, 100%) which was used without further purification.

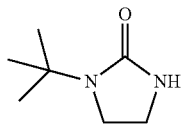

Example B16

A solution of t-butylamine (6.00 g, 82 mmol) in MeCN (120 mL) was treated with 2-chloroethylisocyanate (9.00 g, 85 mmol), stirred at RT for 1 h, and the resulting solid was collected via filtration to afford 1-(tert-butyl)-3-(2-chloroethyl)urea (12.2 g, 83%) as a white solid. $^1$H NMR (400 MHz, DMSO-$d_6$): δ 5.89 (t, J=5.9 Hz, 1 H), 5.82 (s, 1 H), 3.53 (t, J=6.2 Hz, 2 H), 3.24 (q, J=6.1 Hz, 2 H), 1.19 (s, 9 H); MS (ESI) m/z: 179.1 (M+H$^+$).

A 0° C. solution of 1-(tert-butyl)-3-(2-chloroethyl)urea (2.00 g, 11.19 mmol) in THF (20 mL) was treated with NaH (60% in mineral oil, 0.800 g, 33.3 mmol), stirred at RT for 1 h, then heated at 65° C. overnight. The mixture was cooled to RT, concentrated to dryness, treated with satd. $NH_4Cl$, extracted with EtOAc (3×) and the combined organics were dried over $Na_2SO_4$ and concentrated to dryness to afford 1-(tert-butyl)imidazolidin-2-one (1.19 g, 75%). MS (ESI) m/z: 143.1 (M+H$^+$).

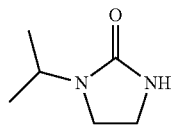

Example B17

A solution of isopropylamine (3.00 g, 50.8 mmol) in MeCN (30 mL) was treated with 2-chloroethylisocyanate (6.00 g, 56.9 mmol), stirred at RT for 1 h and the resulting solid collected via filtration to afford 1-(2-chloroethyl)-3-isopropylurea (6.12 g, 73%) as a white solid. $^1$H NMR (400 MHz, DMSO-$d_6$): δ 5.96 (t, J=5.9 Hz, 1 H), 5.87 (d, J=7.7 Hz, 1 H), 3.62 (m, 1 H), 3.53 (t, J=6.3 Hz, 2 H), 3.25 (m, 2 H), 0.99 (d, J=6.5 Hz, 6 H); MS (ESI) m/z: 165.1 (M+H$^+$).

A 0° C. suspension of 1-(2-chloroethyl)-3-isopropylurea (6.00 g, 36.4 mmol) in THF (60 mL) was treated with NaH (60% in mineral oil, 2.50 g, 104 mmol) and stirred at RT overnight. The mixture was concentrated to dryness, treated with satd. $NH_4Cl$, extracted with EtOAc (3×) and the combined organics were dried over $Na_2SO_4$ and concentrated to dryness to afford 1-isopropylimidazolidin-2-one (3.21 g, 69%) as a waxy solid. MS (ESI) m/z: 129.1 (M+H$^+$).

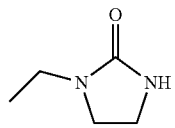

Example B18

A mixture of ethylamine (2.0M in THF, 2.369 mL, 4.74 mmol) and chloroethylisocyanate (0.50 g, 4.74 mmol) was stirred at RT for 2 h, concentrated to dryness and treated with MeCN. The solid was collected via filtration and dried to afford 1-(2-chloroethyl)-3-ethylurea (460 mg, 65%). $^1$H NMR (400 MHz, DMSO-$d_6$): δ 6.05 (s, 1 H), 5.96 (s, 1 H), 3.54 (t, J=6.3 Hz, 2 H), 3.30-3.23 (m, 2 H), 3.02-2.93 (m, 2 H), 0.96 (t, J=7.2 Hz, 3 H); MS (ESI) m/z: 151.1 (M+H$^+$).

A 5° C. solution of 1-(2-chloroethyl)-3-ethylurea (0.46 g, 3.05 mmol) in THF (20 mL), under Ar, was treated with NaH (60% in mineral oil, 0.134 g, 3.36 mmol), warmed to RT and stirred overnight. The mixture was treated with satd. $NH_4Cl$, extracted with EtOAc (2×) and the combined organics were washed with brine, dried over $Na_2SO_4$ and concentrated to dryness to afford crude 1-ethylimidazolidin-2-one (190 mg, 55%) which was used without further purification. MS (ESI) m/z: 115.1 (M+H$^+$).

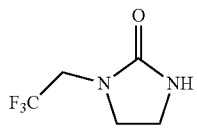 [SMILES: O=C1NCCN1CC(F)(F)F]

Example B19

A solution of 2,2,2-trifluoroethanamine (0.469 g, 4.74 mmol) and chloroethylisocyanate (0.50 g, 4.74 mmol) in THF (10 mL) was stirred at RT for 2 h, then concentrated to dryness. The residue was treated with DCM, concentrated to dryness and dried to afford 1-(2-chloroethyl)-3-(2,2,2-trifluoroethyl)urea (910 mg, 94%). $^1$H NMR (400 MHz, DMSO-$d_6$): δ 6.67 (t, J=6.5 Hz, 1 H), 6.41 (m, 1 H), 3.80 (m, 2 H), 3.57 (t, J=6.2 Hz, 2 H), 3.32 (m, 2 H); MS (ESI) m/z: 205.0 (M+H$^+$).

A 5° C. solution of 1-(2-chloroethyl)-3-(2,2,2-trifluoroethyl)urea (0.91 g, 4.45 mmol) in THF (20 mL), under Ar, was treated with NaH (60% in mineral oil, 0.196 g, 4.89 mmol), warmed to RT and stirred for 5 h. The mixture was treated with satd. NH$_4$Cl, extracted with EtOAc (3×) and the combined organics were washed with brine, dried over Na$_2$SO$_4$ and concentrated to dryness to afford 1-(2,2,2-trifluoroethyl)imidazolidin-2-one (730 mg, 98%). $^1$H NMR (400 MHz, DMSO-$d_6$): δ 6.76 (s, 1 H), 3.81 (q, J=9.9 Hz, 2 H), 3.43 (m, 2 H), 3.28 (m, 2 H); MS (ESI) m/z: 169.0 (M+H$^+$).

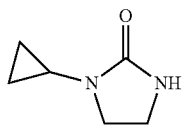

Example B20

A solution of cyclopropanamine (0.541 g, 9.48 mmol) in THF (10 mL) was treated with chloroethylisocyanate (1.0 g, 9.48 mmol), stirred at RT for 2 h, then concentrated to dryness and treated with MeCN. The resulting solid was collected via filtration and dried to afford 1-(2-chloroethyl)-3-cyclopropylurea (1.31 g, 85%). $^1$H NMR (400 MHz, DMSO-$d_6$): δ 6.28 (s, 1 H), 6.12 (br s, 1 H), 3.55 (t, J=6.4 Hz, 2 H), 3.30 (m, 2 H), 2.36 (m, 1 H), 0.55 (m, 2 H), 0.31 (m, 2 H); MS (ESI) m/z: 162.9 (M+H$^+$).

A 0° C. solution of 1-(2-chloroethyl)-3-cyclopropylurea (1.31 g, 8.06 mmol) in THF (40 mL) was treated with NaH (60% in mineral oil, 0.387 g, 9.67 mmol), stirred for 10 minutes, then warmed to RT and stirred for 6 h. The mixture was treated with satd. NH$_4$Cl, the solids removed via filtration and washed with EtOAc. The filtrate was washed with brine, dried over Na$_2$SO$_4$ and concentrated to dryness to afford crude 1-cyclopropylimidazolidin-2-one (760 mg, 75%) which was used without further purification.

$^1$H NMR (400 MHz, DMSO-$d_6$): δ 6.27 (s, 1 H), 3.25 (m, 2 H), 3.14 (m, 2 H), 2.29 (m, 1 H), 0.53 (m, 4 H).

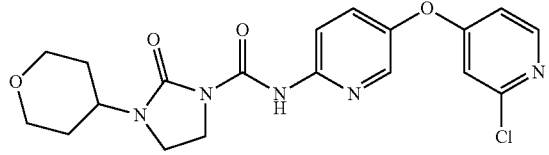 [SMILES: O=C(Nc1ccc(Oc2ccnc(Cl)c2)cn1)N1CCN(C2CCOCC2)C1=O]

Example C1

A 0° C. mixture of Example A5 (1 g, 4.51 mmol) and pyridine (1.1 mL, 13.6 mmol) in DCM (25 mL) was treated with a solution of Example B2 (1.680 g, 7.22 mmol) in DCM (8 mL), warmed to RT and stirred 45 min. The mixture was concentrated to dryness, the residue treated with DCM and Et2O, sonicated and the resulting solid collected via filtration. The solid was dissolved in DCM, washed with water, the aqueous layer back-extracted with DCM (3×) and the combined organics were dried over Na$_2$SO$_4$ and concentrated to dryness to afford N-(5-((2-chloropyridin-4-yl)oxy)pyridin-2-yl)-2-oxo-3-(tetrahydro-2H-pyran-4-yl)imidazolidine-1-carboxamide (2.24 g, 119%) which was used without further purification. MS (ESI) m/z: 418.1 (M+H$^+$).

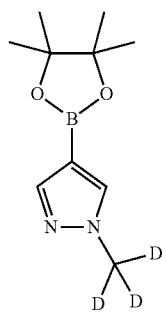 [SMILES: [2H]C([2H])([2H])n1cc(B2OC(C)(C)C(C)(C)O2)cn1]

Example C2

A mixture of 4-(4,4,5,5-tetramethyl-1,3,2-dioxaborolan-2-yl)-1H-pyrazole (1.5 g, 7.73 mmol) K$_2$CO$_3$ (1.068 g, 7.73 mmol) and methyl iodide-$d_3$ (2.241 g, 15.46 mmol) in MeCN (15.5 mL) was heated at 60° C. overnight. The solids were removed via filtration, washed with acetone and the filtrate concentrated to dryness to afford crude 4-(4,4,5,5-tetramethyl-1,3,2-dioxaborolan-2-yl)-1-(trideuteromethyl)-1H-pyrazole (877 mg, 54%) which was used without further purification. MS (ESI) m/z: 212.2 (M+H$^+$).

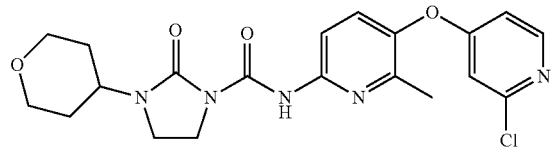 [SMILES: Cc1nc(NC(=O)N2CCN(C3CCOCC3)C2=O)ccc1Oc1ccnc(Cl)c1]

Example C3

Phosgene (20% in toluene, 2.62 g, 5.3 mmol) was treated with a solution of Example B1 (0.27 g, 1.59 mmol) and pyridine (0.43 mL, 5.3 mmol) in DCM (5 mL), stirred for 15 min, then concentrated to dryness. The residue was dissolved in DCM (5 mL), treated with a solution of Example A7 (0.25 g, 1.06 mmol) and TEA (0.74 mL, 5.3 mmol) in DCM (5 mL) and stirred at RT for 1 h. The mixture was treated with satd. NaHCO$_3$, extracted with EtOAc (2×) and the combined organics were washed with brine, dried over Na$_2$SO$_4$, concentrated to dryness and purified via silica gel chromatography (EtOAc/Hex) to afford N-(5-((2-chloropyridin-4-yl)oxy)-6-methylpyridin-2-yl)-2-oxo-3-(tetrahydro-2H-pyran-4-yl)imidazolidine-1-carboxamide (0.24 g, 52%). $^1$H NMR (400 MHz, DMSO-$d_6$): δ 10.91 (s, 1 H), 8.27 (d, J=5.8 Hz, 1 H), 7.90 (d, J=8.8 Hz, 1 H), 7.65 (d, J=8.8 Hz, 1 H), 7.02 (d, J=2.3 Hz, 1 H), 6.92 (dd, J=5.8, 2.3 Hz, 1 H), 3.94-3.84 (m, 5

H), 3.48-3.35 (m, 4 H), 2.21 (s, 3 H), 1.74-1.66 (m, 2 H), 1.60 (d, J=12.5 Hz, 2 H); MS (ESI) m/z: 432.1 (M+H⁺).

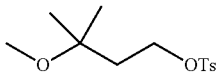 [SMILES: COC(C)(C)CCOS(=O)(=O)c1ccc(C)cc1]

Example C4

A solution of 3-methoxy-3-methylbutan-1-ol (2.50 g, 21.16 mmol) in DCM (30 mL) was treated with p-toluene sulfonyl chloride (5.00 g, 26.2 mmol) followed by TEA (4.28 g, 42.3 mmol) and stirred at RT for 3 h. The mixture was washed with satd. NaHCO$_3$, then brine, dried over Na$_2$SO$_4$ and concentrated to dryness to afford 3-methoxy-3-methylbutyl 4-methylbenzenesulfonate (2.84 g, 49%). $^1$H NMR (400 MHz, DMSO-d$_6$): δ 7.76 (d, J=8.2 Hz, 2 H), 7.45 (d, J=8.1 Hz, 2 H), 4.03 (t, J=7.2 Hz, 2 H), 2.96 (s, 3 H), 2.38 (s, 3 H), 1.75 (t, J=7.2 Hz, 2 H), 1.01 (s, 6 H); MS (ESI) m/z: 295.0 (M+Na⁺).

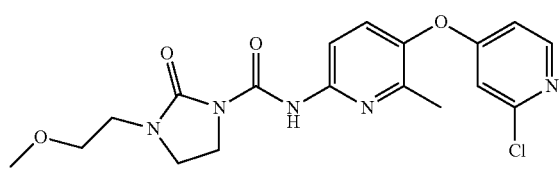 [SMILES: COCCN1CCN(C(=O)Nc2ccc(Oc3ccnc(Cl)c3)c(C)n2)C1=O]

Example C5

A 0° C. mixture of Example A7 (0.350 g, 1.485 mmol) and pyridine (0.251 mL, 3.12 mmol) in DCM (10 mL) was treated with a solution of Example B4 (0.368 g, 1.782 mmol) in DCM (5 mL) and stirred at RT overnight. The mixture was treated with satd. NaHCO$_3$, extracted with DCM (2×) and the combined organics were dried over Na$_2$SO$_4$, concentrated to dryness and purified twice via silica gel chromatography (MeOH/DCM) to afford N-(5-((2-chloropyridin-4-yl)oxy)-6-methylpyridin-2-yl)-3-(2-methoxyethyl)-2-oxoimidazolidine-1-carboxamide (487 mg, 81%) as a yellow oil. MS (ESI) m/z: 406.1 (M+H⁺).

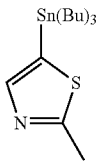

Example C6

A −78° C. solution of 2-methylthiazole (2 g, 20.17 mmol) in THF (50 mL) was treated drop-wise with n-butyllithium (2.5 M in Hex, 10.49 mL, 26.2 mmol), stirred for 1 h, treated drop-wise with a solution of tributyltin chloride (7.11 mL, 26.2 mmol) in THF (25 mL) and stirred for an additional 1 h at −78° C. The mixture was allowed to warm to RT, stirred for 1 h, treated slowly with ice-cold satd. NaHCO$_3$ (20 mL) and quickly extracted with Et$_2$O (3×). The combined organics were washed with brine, dried over Na$_2$SO$_4$, concentrated to dryness and purified via silica gel chromatography (EtOAc/Hex) to afford 2-methyl-5-(tributylstannyl)thiazole (6.67 g, 85%). $^1$H NMR (400 MHz, DMSO-d$_6$): δ 7.55 (s, 1 H), 2.67 (s, 3 H), 1.54-1.45 (m, 6 H), 1.30-1.23 (m, 6 H), 1.09-1.04 (m, 6 H), 0.83 (t, J=7.3 Hz, 9 H).

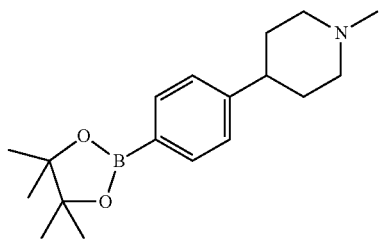

Example C7

A mixture of 4-(4-bromo-phenyl)-1-methyl-piperidine (1.0 g, 3.93 mmol), bis(pinacolato)diboron (1.499 g, 5.90 mmol), K$_2$CO$_3$ (1.158 g, 11.80 mmol), dppf (0.218 g, 0.393 mmol) and Pd$_2$(dba)$_3$ (0.180 g, 0.197 mmol) in dioxane (10 mL) was sparged with Ar and heated at 85° C. overnight. The mixture was treated with additional bis(pinacolato)diboron (0.5 g), dppf (0.050 g) and Pd$_2$(dba)$_3$ (0.04 g), sparged with Ar and heated at 105° C. for 5 h. The mixture was cooled to RT, diluted with EtOAc and the solids removed via filtration through diatomaceous earth, washed with EtOAc and the filtrate concentrated to dryness to afford 1-methyl-4-(4-(4,4,5,5-tetramethyl-1,3,2-dioxaborolan-2-yl)phenyl)piperidine (100% yield assumed) which was used without further purification. MS (ESI) m/z: 302.2 (M+H⁺).

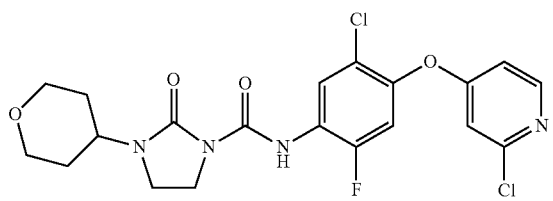 [SMILES: O=C(Nc1cc(Cl)c(Oc2ccnc(Cl)c2)cc1F)N1CCN(C2CCOCC2)C1=O]

Example C8

A 0° C. suspension of Example A21 (0.145 g, 0.533 mmol) and TEA (0.223 mL, 1.598 mmol) in DCM (2.5 mL) was treated with a thin suspension of crude Example B2 (0.198 g, 0.852 mmol) in DCM (2.5 mL), warmed to RT and stirred for 0.5 h. The mixture was washed with water (3×), dried over MgSO$_4$, concentrated to dryness and purified via silica gel chromatography (EtOAc/Hex) to afford N-(5-chloro-4-((2-chloropyridin-4-yl)oxy)-2-fluorophenyl)-2-oxo-3-(tetrahydro-2H-pyran-4-yl)imidazolidine-1-carboxamide (202 mg, 81%) as a pale pink solid. $^1$H NMR (400 MHz, DMSO-d$_6$): δ 10.93 (d, J=2.7 Hz, 1 H), 8.40 (d, J=8.0 Hz, 1 H), 8.30 (d, J=5.8 Hz, 1 H), 7.64 (d, J=11.2 Hz, 1 H), 7.09 (d, J=2.3 Hz, 1 H), 6.97 (dd, J=5.8, 2.3 Hz, 1 H), 3.91-3.88 (m, 3 H), 3.80 (m, 2 H), 3.47 (t, J=8.2 Hz, 2 H), 3.37 (t, J=11.6 Hz, 2 H), 1.71 (m, 2 H), 1.59 (m, 2 H); MS (ESI) m/z: 469.1 (M+H⁺).

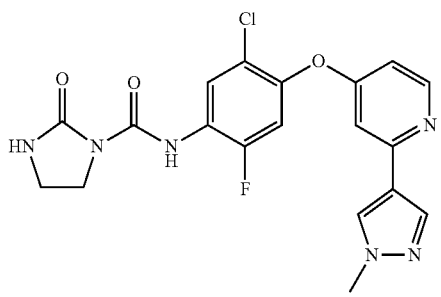 [SMILES: Cn1cc(-c2cc(Oc3cc(F)c(NC(=O)N4CCNC4=O)cc3Cl)ccn2)cn1]

Example C9

A 0° C. solution of triphosgene (0.330 g, 1.112 mmol) in MeCN (5 mL) was treated with a solution of imidazolidin-2-one (0.200 g, 2.323 mmol) MeCN (5 mL), stirred at RT for 10 min, added to a suspension of Example A22 (0.400 g, 1.255 mmol) in MeCN (5 mL) and heated at 50° C. for 1 h. The solids were collected via filtration to afford N-(5-chloro-2-fluoro-4-((2-(1-methyl-1H-pyrazol-4-yl)pyridin-4-yl)oxy)phenyl)-2-oxoimidazolidine-1-carboxamide (424 mg, 78%). $^1$H NMR (400 MHz, DMSO-$d_6$): δ 11.00 (d, J=2.7 Hz, 1 H), 8.63 (s, 1 H), 8.48 (m, 2 H), 8.32 (s, 1 H), 8.04 (s, 1 H), 7.68 (d, J=11.1 Hz, 1 H), 7.59 (s, 1 H), 7.06 (br s, 1 H), 3.90 (m, 5 H), 3.40 (m, 2 H); MS (ESI) m/z: (M+H$^+$): 431.1.

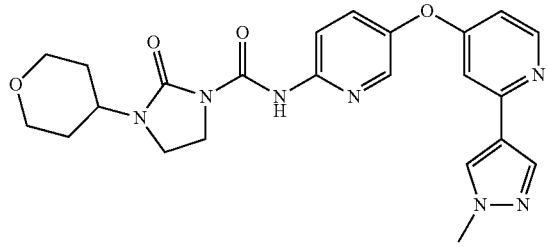 [SMILES: Cn1cc(-c2cc(Oc3ccc(NC(=O)N4CCN(C5CCOCC5)C4=O)nc3)ccn2)cn1]

Example 1

A 0° C. solution of Example A2 (6.4 g, 23.94 mmol) and pyridine (6 mL, 74.2 mmol) in DCM (150 mL) was treated with a solution of Example B2 (8.36 g, 35.9 mmol) in DCM (10 mL), stirred at 0° C. for 5 min, warmed to RT and stirred for 1.5 h. The mixture was diluted with water, stirred for 15 min, and the layers separated. The organic layer was washed with water and the combined aqueous layers were extracted with DCM (4×). The combined organics were dried over Na2SO4, concentrated to dryness, treated with MeOH and concentrated again to dryness. The residue was dissolved in DCM, sonicated, treated with MTBE, sonicated and the resulting solid collected via filtration. The solid was treated with Et$_2$O, sonicated and again collected via filtration to afford N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide (8.93 g, 80%). $^1$H NMR (400 MHz, DMSO-$d_6$): δ 10.96 (s, 1 H), 8.36 (d, J=5.7 Hz, 1 H), 8.25 (s, 1 H), 8.23 (d, J=2.9 Hz, 1 H), 8.07 (dd, J=9.0, 0.7 Hz, 1 H), 7.96 (d, J=0.7 Hz, 1 H), 7.72 (dd, J=9.0, 2.9 Hz, 1 H), 7.22 (d, J=2.4 Hz, 1 H), 6.69 (dd, J=5.7, 2.5 Hz, 1 H), 3.93-3.87 (m, 3 H), 3.84 (s, 3 H), 3.83-3.77 (m, 2 H), 3.49-3.43 (m, 2 H) 3.42-3.34 (m, 2 H), 1.78-1.64 (m, 2 H), 1.59 (m, 2 H); MS (ESI) m/z: 464.2 (M+H$^+$).

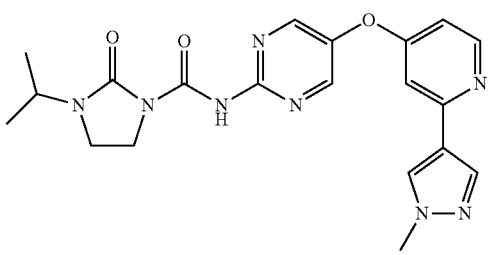 [SMILES: CC(C)N1CCN(C(=O)Nc2ncc(Oc3ccnc(-c4cnn(C)c4)c3)cn2)C1=O]

Example 2

A solution of phosgene (15% in toluene, 1.77 mL, 2.52 mmol) was cooled to 0° C. To this was added, drop-wise over 15 min, a solution of pyridine (0.226 mL, 2.80 mmol) and Example B17 (158 mg, 1.23 mmol) in DCM (2 mL). The reaction mixture was stirred for 1 h at RT and was evaporated at reduced pressure to near dryness. This residue was then treated with DCM (2 mL) and added drop-wise to a 0° C. mixture (not a solution) of Example A27 (150 mg, 0.559 mmol) and pyridine (0.22 mL, 2.80 mmol) in DCM (2 mL). The reaction mixture was stirred at 0° C. for 15 min, then at RT for 20 h. The mixture was treated with half-saturated sodium bicarbonate (15 mL) and EtOAc (25 mL) and warmed gently to dissolve most solids. The mixture was filtered and the organic phase of the filtrate was washed with brine (25 mL), dried over sodium sulfate and evaporated at reduced pressure. Purification by reverse phase silica gel chromatography (5-45% MeCN/water (0.1% TFA)) provided 3-isopropyl-N-(5-((2-(1-methyl-1H-pyrazol-4-yl)pyridin-4-yl)oxy)pyrimidin-2-yl)-2-oxoimidazolidine-1-carboxamide (56 mg, 21%). $^1$H NMR (400 MHz, DMSO-$d_6$): δ 11.30 (s, 1 H), 8.66 (s, 2 H), 8.39 (d, J=5.7 Hz, 1 H), 8.27 (s, 1 H), 7.98 (s, 1 H), 7.28 (d, J=2.5 Hz, 1 H), 6.81 (dd, J=5.7, 2.5 Hz, 1 H), 4.03-4.02 (m, 1 H), 3.84 (s, 3 H), 3.79 (t, J=8.2 Hz, 2 H), 3.41 (t, J=8.2 Hz, 2 H), 1.13 (d, J=6.7 Hz, 6 H); MS (ESI) m/z: 423.2 (M+H$^+$).

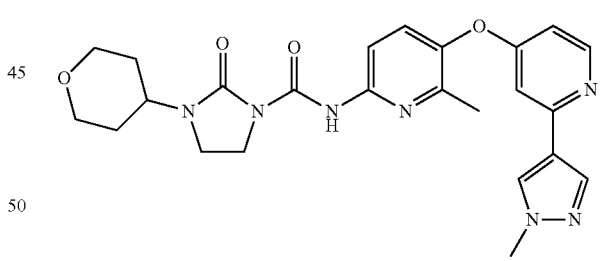

Example 3

A solution of Example B1 (0.1 g, 0.6 mmol) and pyridine (0.07 g, 0.9 mmol) in DCM (3 mL) was added to phosgene (20% in toluene, 0.75 g, 1.51 mmol), under Ar, stirred for 15 min, then concentrated to dryness. The residue was dissolved in DCM (5 mL), treated with a solution of Example A4 (0.085 g, 0.3 mmol) and TEA (0.2 mL, 1.5 mmol) in DCM (3 mL) and stirred at RT for 0.5 h. The mixture was treated with satd. NaHCO$_3$, extracted with EtOAc (2×) and the combined organics were washed with brine, dried over Na$_2$SO$_4$, concentrated to dryness and purified via silica gel chromatography (MeOH/DCM) to afford N-(6-methyl-5-((2-(1-methyl- 1H-pyrazol-4-yl)pyridin-4-yl)oxy)pyridin-2-yl)-2-oxo-3-(tetrahydro-2H-pyran-4-yl)imidazolidine-1-carboxamide (110 mg, 76%). ¹H NMR (400 MHz, DMSO-d₆): δ 10.89 (s, 1 H), 8.35-8.32 (m, 1 H), 8.25 (s, 1 H), 7.95 (s, 1 H), 7.89 (d, J=8.8 Hz, 1 H), 7.61 (d, J=8.8 Hz, 1 H), 7.16 (d, J=2.4 Hz, 1 H), 6.59 (dd, J=5.7, 2.5 Hz, 1 H), 3.90-3.75 (m, 8 H), 3.44-3.40 (m, 4 H), 2.24 (s, 3 H), 1.72 (m, 2 H), 1.60 (dd, J=12.4, 4.0 Hz, 2 H); MS (ESI) m/z: 478.2 (M+H⁺).

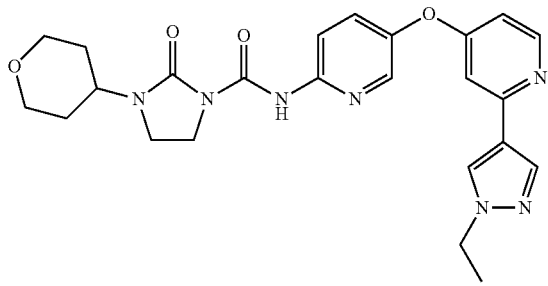 [SMILES: CCn1cc(-c2cc(Oc3ccc(NC(=O)N4CCN(C5CCOCC5)C4=O)nc3)ccn2)cn1]

Example 4

A mixture of Example C1 (0.15 g, 0.40 mmol), 1-ethyl-4-(4,4,5,5-tetramethyl-1,3,2-dioxaborolan-2-yl)-1H-pyrazole (0.088 g, 0.40 mmol), and K₂CO₃ (0.2 g, 1.44 mmol) in 4:1 dioxane/water (5 mL) was sparged with Ar, treated with Pd(PPh₃)₄ (0.040 g, 0.036 mmol), sparged again with Ar and heated at 80° C. overnight. The mixture was cooled to RT, treated with brine, extracted with EtOAc (2×) and the combined organics were dried over Na₂SO₄, concentrated to dryness and purified via silica gel chromatography (MeOH/DCM). The material was treated with Et₂O, allowed to stand at RT and the resulting solid collected via filtration to afford N-(5-((2-(1-ethyl-1H-pyrazol-4-yl)pyridin-4-yl)oxy)pyridin-2-yl)-2-oxo-3-(tetrahydro-2H-pyran-4-yl)imidazolidine-1-carboxamide (137 mg, 80%). ¹H NMR (400 MHz, DMSO-d₆): δ 10.96 (s, 1 H), 8.37 (d, J=5.7 Hz, 1 H), 8.30 (s, 1 H), 8.23 (d, J=2.9 Hz, 1 H), 8.07 (d, J=9.0 Hz, 1 H), 7.97 (s, 1 H), 7.71 (dd, J=9.0, 2.9 Hz, 1 H), 7.24 (d, J=2.4 Hz, 1 H), 6.69 (dd, J=5.7, 2.4 Hz, 1 H), 4.13 (q, J=7.3 Hz, 2 H), 3.86 (m, 5 H), 3.40 (m, 4 H), 1.71 (m, 2 H), 1.59 (m, 2 H), 1.37 (t, J=7.3 Hz, 3 H); MS (ESI) m/z: 478.2 (M+H⁺).

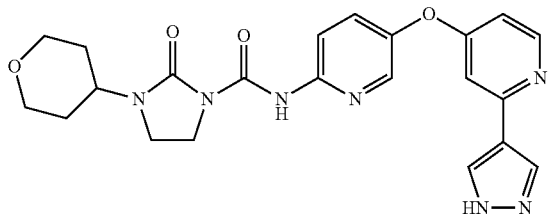 [SMILES: O=C(Nc1ccc(Oc2ccnc(-c3cn[nH]c3)c2)cn1)N1CCN(C2CCOCC2)C1=O]

Example 5

A mixture of Example C1 (0.15 g, 0.359 mmol), 4-(4,4,5,5-tetramethyl-1,3,2-dioxaborolan-2-yl)-1H-pyrazole (0.077 g, 0.395 mmol), and K₂CO₃ (0.198 g, 1.436 mmol) in 4:1 dioxane/water (5 mL) was sparged with Ar, treated with Pd(PPh₃)₄ (0.041 g, 0.036 mmol), sparged again with Ar and heated at 80° C. overnight. The mixture was cooled to RT, treated with brine, extracted with EtOAc (2×) and the combined organics were dried over Na₂SO₄, concentrated to dryness and purified via silica gel chromatography (MeOH/DCM). The material was treated with Et₂O, allowed to stand at RT and the resulting solid collected via filtration to afford N-(5-((2-(1H-pyrazol-4-yl)pyridin-4-yl)oxy)pyridin-2-yl)-2-oxo-3-(tetrahydro-2H-pyran-4-yl)imidazolidine-1-carboxamide (80 mg, 48%). ¹H NMR (400 MHz, DMSO-d₆): δ 13.04 (s, 1 H), 10.96 (s, 1 H), 8.37 (d, J=5.7 Hz, 1 H), 8.32 (s, 1 H), 8.23 (d, J=2.9 Hz, 1 H), 8.07 (d, J=9.0 Hz, 1 H), 8.02 (s, 1 H), 7.71 (dd, J=9.0, 2.9 Hz, 1 H), 7.32 (d, J=2.4 Hz, 1 H), 6.67 (dd, J=5.7, 2.4 Hz, 1 H), 3.91-3.80 (m, 5 H), 3.40 (m, 4 H), 1.71 (m, 2 H), 1.59 (m, 2 H); MS (ESI) m/z: 450.2 (M+H⁺).

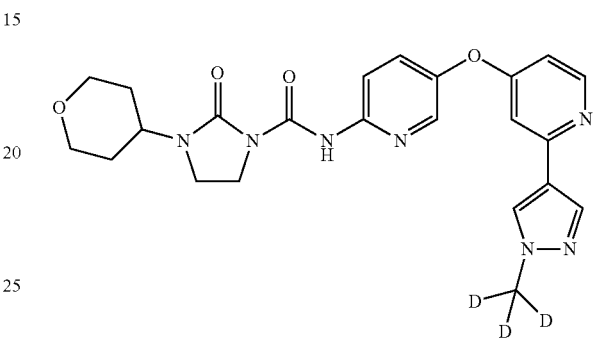

Example 6

A suspension of Example C1 (0.350 g, 0.838 mmol), Example C2 (0.212 g, 1.005 mmol) and K₂CO₃ (0.463 g, 3.35 mmol) in dioxane (6.7 mL) and water (1.7 mL) was sparged with Ar for 0.5 h, treated with Pd(PPh₃)₄ (0.145 g, 0.126 mmol), sparged again with Ar and heated at 80° C. overnight. Reaction mixture had concentrated to dryness; it was cooled to RT, re-suspended in dioxane (6.7 mL) and water (1.7 mL), sparged with Ar, treated with Pd(PPh₃)₄ (0.050 g, 0.043 mmol), sparged again with Ar and heated at 80° C. for 24 h. The mixture was cooled to RT, treated with satd. NaHCO₃, extracted with EtOAc (3×) and the combined organics were dried over Na₂SO₄, concentrated to dryness and purified twice via silica gel chromatography (MeOH/DCM) to afford 2-oxo-3-(tetrahydro-2H-pyran-4-yl)-N-(5-((2-(1-(trideuteromethyl)-1H-pyrazol-4-yl)pyridin-4-yl)oxy)pyridin-2-yl)imidazolidine-1-carboxamide (41 mg, 10.5%) as a beige solid. ¹H NMR (400 MHz, DMSO-d₆): δ 10.96 (s, 1 H), 8.37 (d, J=5.7 Hz, 1 H), 8.25 (d, J=0.8 Hz, 1 H), 8.23 (dd, J=2.9, 0.7 Hz, 1 H), 8.07 (dd, J=9.0, 0.7 Hz, 1 H), 7.96 (d, J=0.8 Hz, 1 H), 7.72 (dd, J=9.0, 2.9 Hz, 1 H), 7.22 (d, J=2.4 Hz, 1 H), 6.69 (dd, J=5.7, 2.4 Hz, 1 H), 3.93-3.77 (m, 5 H), 3.49-3.35 (m, 4 H), 1.77-1.65 (m, 2 H), 1.63-1.56 (m, 2 H); MS (ESI) m/z: 467.2 (M+H⁺).

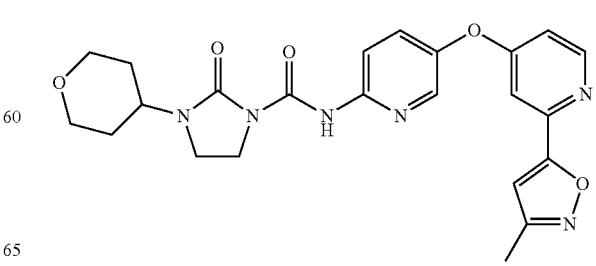

Example 7

A solution of Example A5 (0.60 g, 2.70 mmol) in THF (10 mL) was treated with di-tert-butyl dicarbonate (0.65 g, 3.0 mmol) and DMAP (0.066 g, 0.54 mmol) and stirred at RT overnight. The mixture was diluted with 30% EtOAc/Hex, stirred for 10 and the solid collected via filtration and dried. The filtrate was concentrated to dryness, purified via silica gel chromatography (EtOAc/Hex) and combined with the above-isolated solid to afford tert-butyl (5-((2-chloropyridin-4-yl)oxy)pyridin-2-yl)carbamate (703 mg, 81% yield). MS (ESI) m/z: 322.1 (M+H$^+$).

A solution of tert-butyl (5-((2-chloropyridin-4-yl)oxy)pyridin-2-yl)carbamate (0.70 g, 2.18 mmol) in DMF (5 mL) was sparged with Ar, treated with ethynyltrimethylsilane (0.64 g, 6.55 mmol), TEA (1 mL), copper(I)iodide (0.042 g, 0.22 mmol) and trans dichlorobis(triphenylphosphine)palladium (0) (0.15 g, 0.22 mmol) and heated at 75° C., under Ar, overnight. The mixture was cooled to RT, diluted with EtOAc, the solids removed via filtration through diatomaceous earth and washed with EtOAc and water. The layers of the filtrate were separated, the aqueous layer extracted with EtOAc (2×) and the combined organics were washed with brine, dried over Na$_2$SO$_4$ and concentrated to dryness. The material was dissolved in MeOH (20 mL), treated with K$_2$CO$_3$ (0.7 g), stirred at RT for 2 h, then concentrated to dryness. The residue was treated with EtOAc, sonicated, the solids removed via filtration through diatomaceous earth, washed with EtOAc and the filtrate concentrated to dryness and purified via silica gel chromatography (EtOAc/Hex) to afford tert-butyl (5-((2-ethynylpyridin-4-yl)oxy)pyridin-2-yl)carbamate (0.29 g, 43%). $^1$H NMR (400 MHz, DMSO-d$_6$): δ 9.96 (s, 1 H), 8.41 (d, J=5.6 Hz, 1 H), 8.18 (d, J=2.8 Hz, 1 H), 7.88 (d, J=9.2 Hz, 1 H), 7.66 (m, 1 H), 7.07 (d, J=2.4 Hz, 1 H), 6.95 (m, 1 H), 4.34 (s, 1 H), 1.46 (s, 9 H); MS (ESI) m/z: 312.1 (M+H$^+$).

A solution of NCS (0.36 g, 2.70 mmol) in DMF (2 mL) was treated with acetaldoxime (0.16 g, 2.70 mmol), stirred at RT for 0.5 h, added to a solution of tert-butyl (5-((2-ethynylpyridin-4-yl)oxy)pyridin-2-yl)carbamate (0.28 g, 0.90 mmol) and TEA (2 mL) in DMF (2 mL) and heated at 60° C. for 2 h. The mixture was treated with water, extracted with EtOAc (3×) and the combined organics were washed with brine, dried over Na$_2$SO$_4$, concentrated to dryness and purified via silica gel chromatography (MeOH/DCM) to afford tert-butyl (5-((2-(3-methylisoxazol-5-yl)pyridin-4-yl)oxy)pyridin-2-yl)carbamate (250 mg, 75%). MS (ESI) m/z: 369.1 (M+H$^+$).

A solution of tert-butyl (5-((2-(3-methylisoxazol-5-yl)pyridin-4-yl)oxy)pyridin-2-yl)carbamate (0.30 g, 0.84 mmol) in THF (5 mL) was treated with HCl (3 M, 2.8 mL, 8.4 mmol), heated at 55° C. for 4 h, then cooled to RT and concentrated to dryness. The residue was treated with NaHCO3, EtOAc and water, the layers separated and the aqueous layer extracted with EtOAc (2×). The combined organics were washed with brine, dried over Na$_2$SO$_4$ and concentrated to dryness to afford 5-((2-(3-methylisoxazol-5-yl)pyridin-4-yl)oxy)pyridin-2-amine (0.24 g, 106%). $^1$H NMR (400 MHz, DMSO-d$_6$): δ 8.52 (d, J=5.6 Hz, 1 H), 7.84 (br s, 1 H), 7.32 (m, 2 H), 6.95 (m, 2 H), 6.53 (d, J=9.2 Hz, 1 H), 6.07 (br s, 2 H), 2.28 (s, 3 H); MS (ESI) m/z: 269.1 (M+H$^+$).

A 0° C. mixture of 5-((2-(3-methylisoxazol-5-yl)pyridin-4-yl)oxy)pyridin-2-amine (0.052 g, 0.194 mmol) and TEA (0.059 g, 0.582 mmol) in DCM (3 mL) was treated with a suspension of crude Example B2 (0.090 g, 0.388 mmol) in DCM (2 mL), warmed to RT and stirred. The mixture was re-cooled to 0° C., treated with additional Example B2 (68 mg), warmed to RT and stirred overnight. The mixture was concentrated to dryness, purified via silica gel chromatography (MeOH/DCM), treated with Et$_2$O, and the resulting solid collected via filtration to afford N-(5-((2-(3-methylisoxazol-5-yl)pyridin-4-yl)oxy)pyridin-2-yl)-2-oxo-3-(tetrahydro-2H-pyran-4-yl)imidazolidine-1-carboxamide (45 mg, 49%). $^1$H NMR (400 MHz, DMSO-d$_6$): δ 10.99 (s, 1 H), 8.57 (d, J=5.7 Hz, 1 H), 8.28 (dd, J=2.9, 0.7 Hz, 1 H), 8.09 (m, 1 H), 7.78 (dd, J=9.0, 2.9 Hz, 1 H), 7.41 (d, J=2.5 Hz, 1 H), 7.04 (dd, J=5.7, 2.5 Hz, 1 H), 6.98 (s, 1 H), 3.94-3.86 (m, 3 H), 3.83-3.80 (m, 2 H), 3.50-3.35 (m, 4 H), 2.28 (s, 3 H), 1.78-1.65 (m, 2 H), 1.64-1.55 (m, 2 H); MS (ESI) m/z: 465.2 (M+H$^+$).

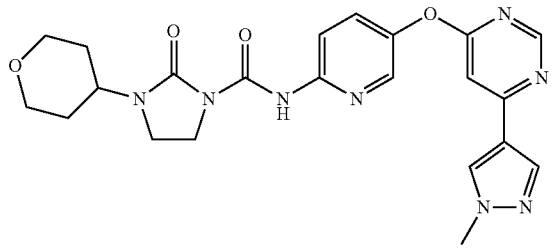 [SMILES: Cn1cc(-c2cc(Oc3ccc(NC(=O)N4CCN(C5CCOCC5)C4=O)nc3)ncn2)cn1]

Example 8

A −10° C. suspension of NaH (60% in mineral oil, 0.73 g, 18.2 mmol) in DMA (15 mL) was treated with 6-aminopyridin-3-ol (1.0 g, 9.1 mmol), stirred for 0.5 h, treated drop-wise with a solution of 4,6-dichloropyrimidine (2.03 g, 13.6 mmol) in DMA (10 mL), warmed to RT and stirred for 2 h. The mixture was treated with water, extracted with DCM (3×) and the combined organics were washed with 5% LiCl, then brine, dried over Na$_2$SO$_4$, concentrated to dryness and purified via silica gel chromatography (EtOAc) to afford 5-((6-chloropyrimidin-4-yl)oxy)pyridin-2-amine (1.0 g, 50%). $^1$H NMR (400 MHz, DMSO-d$_6$): δ 8.62 (d, 1 H), 7.79 (d, 1 H), 7.33-7.26 (m, 2 H), 6.48 (d, 1 H), 6.00 (s, 2 H); MS (ESI) m/z: 223.0 (M+H$^+$).

A mixture of 5-((6-chloropyrimidin-4-yl)oxy)pyridin-2-amine (0.50 g, 2.25 mmol), 1-methyl-4-(4,4,5,5-tetramethyl-1,3,2-dioxaborolan-2-yl)-1H-pyrazole (0.47 g, 2.25 mmol), and Cs$_2$CO$_3$ (1.46 g, 4.49 mmol) in 5:1 dioxane/water (6 mL) was sparged with Ar, treated with Pd(PPh$_3$)$_4$ (0.26 g, 0.23 mmol), sparged again with Ar and heated at 90° C. overnight. The mixture was cooled to RT, the solids removed via filtration, washed with dioxane and the filtrate concentrated to dryness. The residue was treated with water, extracted with EtOAc, washed with brine, dried over Na$_2$SO$_4$, and concentrated to dryness. The material was treated with EtOAc and the resulting solid collected via filtration to afford 5-((6-(1-methyl-1H-pyrazol-4-yl)pyrimidin-4-yl)oxy)pyridin-2-amine (0.41 g, 68%). $^1$H NMR (400 MHz, DMSO-d$_6$): δ 8.60 (d, 1 H), 8.44 (s, 1 H), 8.12 (s, 1 H), 7.78 (d, 1 H), 7.28 (m, 2 H), 6.48 (d, 1 H), 5.94 (s, 2 H), 3.88 (s, 3 H); MS (ESI) m/z: 269.1 (M+H$^+$).

A 0° C. solution of Example B2 (0.14 g, 0.60 mmol) in DCM (3 mL) was treated drop-wise with a solution of 5-((6-(1-methyl-1H-pyrazol-4-yl)pyrimidin-4-yl)oxy)pyridin-2-amine (0.08 g, 0.30 mmol) and TEA (0.1 mL, 0.9 mmol) in DCM (2 mL), warmed to RT and stirred for 2 h. The mixture was concentrated to dryness, purified via silica gel chromatography (MeOH/DCM), treated with Et$_2$O and the resulting solid collected via filtration to afford N-(5-((6-(1-methyl-1H-pyrazol-4-yl)pyrimidin-4-yl)oxy)pyridin-2-yl)-2-oxo-3-(tetrahydro-2H-pyran-4-yl)imidazolidine-1-carboxamide (93 mg, 67%). $^1$H NMR (400 MHz, DMSO-d$_6$): δ 10.94 (s, 1 H), 8.62 (d, J=1.1 Hz, 1 H), 8.46 (s, 1 H), 8.22 (m, 1 H), 8.16 (d, J=0.7 Hz, 1 H), 8.04 (d, J=9.0 Hz, 1 H), 7.74 (dd, J=9.0, 2.9 Hz, 1 H), 7.42 (d, J=1.1 Hz, 1 H), 3.89 (s, 3 H), 4.00-3.70 (m, 5 H), 3.42-3.39 (m, 4 H), 1.76-1.65 (m, 2 H), 1.59 (m, 2 H); MS (ESI) m/z: 465.2 (M+H+).

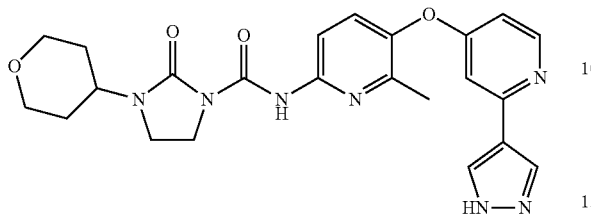

Example 9

A solution of Example C3 (0.12 g, 0.28 mmol) in dioxane (4 mL) was sparged with Ar, treated with 4-(4,4,5,5-tetramethyl-1,3,2-dioxaborolan-2-yl)-1H-pyrazole (0.08 g, 0.42 mmol), a solution of K₂CO₃ (0.077 g, 0.55 mmol) in water (1 mL) and Pd(PPh₃)₄ (0.032 g, 0.03 mmol) and heated at 90° C. overnight. The mixture was cooled to RT, diluted with water, extracted with EtOAc (2×) and the combined organics were washed with brine, dried over Na₂SO₄, concentrated to dryness and purified via silica gel chromatography (MeOH/DCM) to afford N-(5-((2-(1H-pyrazol-4-yl)pyridin-4-yl)oxy)-6-methylpyridin-2-yl)-2-oxo-3-(tetrahydro-2H-pyran-4-yl)imidazolidine-1-carboxamide (72 mg, 56%). ¹H NMR (400 MHz, DMSO-d₆): δ 13.05 (br s, 1 H), 10.89 (s, 1 H), 8.35 (d, J=5.7 Hz, 1 H), 8.31 (brs, 1 H), 8.03 (s, 1 H), 7.89 (d, J=8.8 Hz, 1 H), 7.61 (d, J=8.8 Hz, 1 H), 7.28 (d, J=2.4 Hz, 1 H), 6.56 (dd, J=5.7, 2.4 Hz, 1 H), 3.95-3.77 (m, 5 H), 3.43-3.39 (m, 4 H), 2.24 (s, 3 H), 1.71-1.70 (m, 2 H), 1.60 (d, J=12.4 Hz, 2 H); MS (ESI) m/z: 464.2 (M+H+).

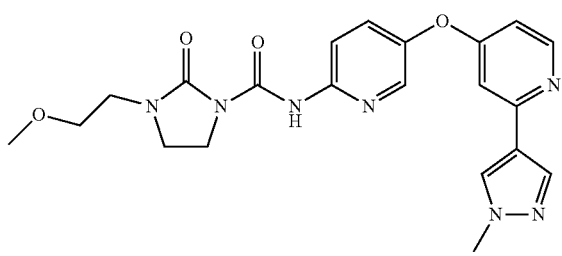 [SMILES: COCCN1CCN(C(=O)Nc2ccc(Oc3ccnc(-c4cnn(C)c4)c3)cn2)C1=O]

Example 10

A 0° C. mixture of Example A2 (0.150 g, 0.561 mmol) and pyridine (0.15 mL, 1.862 mmol) in DCM (5 mL) was treated with a solution of Example B4 (0.232 g, 1.122 mmol) in THF (5 mL), warmed to RT and stirred overnight. The mixture was concentrated to dryness, purified via silica gel chromatography (MeOH/DCM) and the resulting material was treated with Et₂O and the solid collected via filtration to afford 3-(2-methoxyethyl)-N-(5-((2-(1-methyl-11H-pyrazol-4-yl)pyridin-4-yl)oxy)pyridin-2-yl)-2-oxoimidazolidine-1-carboxamide (151 mg, 62%) as a white solid. ¹H NMR (400 MHz, DMSO-d₆): δ 10.95 (s, 1 H), 8.36 (d, J=5.7 Hz, 1 H), 8.25 (s, 1 H), 8.23 (d, J=2.9 Hz, 1 H), 8.07 (d, J=9.0 Hz, 1 H), 7.96 (s, 1 H), 7.72 (dd, J=9.0, 2.9 Hz, 1 H), 7.22 (d, J=2.4 Hz, 1 H), 6.69 (dd, J=5.7, 2.4 Hz, 1 H), 3.84 (s, 3 H), 3.83-3.80 (m, 2 H), 3.53-3.46 (m, 4 H), 3.41-3.36 (m, 2 H), 3.26 (s, 3 H); MS (ESI) m/z: 438.1 (M+H+).

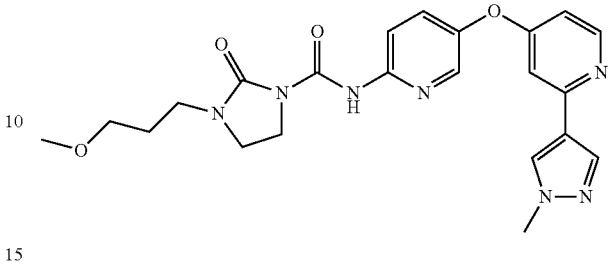

Example 11

A 0° C. solution of phosgene (20% in toluene, 0.7 mL, 6.62 mmol) in DCM (13 mL) was treated drop-wise with a solution of pyridine (0.25 mL, 3.09 mmol) and Example B5 (0.203 g, 1.283 mmol) in DCM (10 mL) allowed to warm to RT and stirred for 0.5 h. The mixture was concentrated to dryness to afford crude 3-(3-methoxypropyl)-2-oxoimidazolidine-1-carbonyl chloride (100% yield assumed) which was used without further purification. MS (quenched into benzyl amine) (ESI) m/z: 292.1 (M+72+H+).

A 0° C. mixture of Example A2 (0.160 g, 0.599 mmol) and pyridine (0.15 mL, 1.862 mmol) in DCM (5 mL) was treated with a solution of 3-(3-methoxypropyl)-2-oxoimidazolidine-1-carbonyl chloride (0.264 g, 1.197 mmol) in THF (5 mL), warmed to RT and stirred overnight. The mixture was treated with water, stirred for 10 min, the layers separated and the aqueous layer extracted with DCM (2×). The combined organics were dried over Na₂SO₄, concentrated to dryness, purified via silica gel chromatography (MeOH/DCM) and the resulting material was treated with Et₂O and the solid collected via filtration to afford 3-(3-methoxypropyl)-N-(5-((2-(1-methyl-1H-pyrazol-4-yl)pyridin-4-yl)oxy)pyridin-2-yl)-2-oxoimidazolidine-1-carboxamide (155 mg, 57%) as a white solid. ¹H NMR (400 MHz, DMSO-d₆): δ 10.97 (s, 1 H), 8.36 (d, J=5.7 Hz, 1 H), 8.25 (s, 1 H), 8.22 (d, J=2.9 Hz, 1 H), 8.07 (d, J=9.0 Hz, 1 H), 7.96 (s, 1 H), 7.72 (dd, J=9.0, 2.9 Hz, 1 H), 7.22 (d, J=2.4 Hz, 1 H), 6.69 (dd, J=5.7, 2.4 Hz, 1 H), 3.84 (s, 3 H), 3.81-3.79 (m, 2 H), 3.46 (m, 2 H), 3.34 (m, 2 H), 3.27 (m, 2 H), 3.22 (s, 3 H), 1.77-1.69 (m, 2 H); MS (ESI) m/z: 452.2 (M+H+).

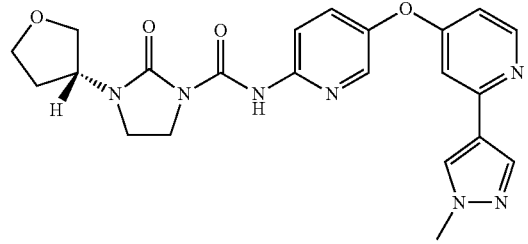 [SMILES: Cn1cc(-c2cc(Oc3ccc(NC(=O)N4CCN([C@@H]5CCOC5)C4=O)nc3)ccn2)cn1]

Example 12

A 0° C. solution of phosgene (20% in toluene, 0.092 mL, 0.174 mmol) in DCM (2 mL) was treated slowly with a solution of Example B6 (26 mg, 0.166 mmol) and pyridine (0.027 mL, 0.331 mmol) in DCM (2 mL), stirred at 0° C. for 0.5 h, then concentrated to dryness. The residue was dissolved in DCM (2 mL), treated with pyridine (0.0400 mL, 0.495 mmol), cooled to 0° C., treated slowly with a solution of Example A2 (36 mg, 0.165 mmol) in DCM (2 mL), warmed to RT and stirred for 1.5 h. The mixture was diluted with water, extracted with DCM and the organic layer was washed with water, then brine, dried over $Na_2SO_4$, concentrated to dryness and purified via silica gel chromatography (MeOH/DCM) to afford (S)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide (33 mg, 45%). $^1$H NMR (400 MHz, DMSO-$d_6$): δ 10.95 (s, 1 H), 8.38 (d, J=5.8 Hz, 1 H), 8.27 (s, 1 H), 8.23 (d, J=2.9 Hz, 1 H), 8.07 (d, J=9.0 Hz, 1 H), 7.97 (s, 1 H), 7.72 (dd, J=9.0, 2.9 Hz, 1 H), 7.25 (s, 1 H), 6.71 (d, J=5.5 Hz, 1 H), 4.57-4.49 (m, 1 H), 3.91-3.86 (m, 1 H), 3.84 (s, 3 H), 3.83-3.76 (m, 3 H), 3.70-3.57 (m, 2 H), 3.51-3.43 (m, 2 H), 2.19-2.09 (m, 1 H), 2.02-1.91 (m, 1 H); MS (ESI) m/z: 450.1 (M+H$^+$).

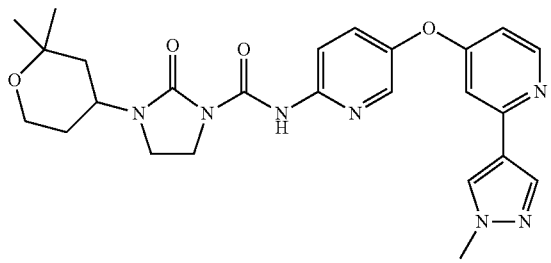 [SMILES: Cn1cc(-c2cc(Oc3ccc(NC(=O)N4CCN(C5CCOC(C)(C)C5)C4=O)nc3)ccn2)cn1]

Example 13

A 0° C. suspension of 2,2-dimethyltetrahydro-2H-pyran-4-amine (0.806 g, 6.24 mmol) in THF (30 mL) was treated drop-wise with 2-chloroethyl isocyanate (0.585 mL, 6.86 mmol), allowed to warm to RT as the cooling bath expired and stirred overnight. The mixture was treated with additional 2-chloroethyl isocyanate (160 μL) and stirred at RT for an additional 24 hours, then concentrated to dryness, the residue dissolved in EtOAc and washed with saturated $NH_4Cl$ (1×), $NaHCO_3$ (1×) and brine (1×), dried over $MgSO_4$ and concentrated to dryness to afford 1-(2-chloroethyl)-3-(2,2-dimethyltetrahydro-2H-pyran-4-yl)urea (700 mg, 48%) as a yellow oil. MS (ESI) m/z: 235.1 (M+H$^+$).

A −20° C. solution of 1-(2-chloroethyl)-3-(2,2-dimethyltetrahydro-2H-pyran-4-yl)urea (0.700 g, 2.98 mmol) in THF (15 mL), under Ar, was treated with NaH (60% in mineral oil, 0.298 g, 7.46 mmol), allowed to warm to RT as the cooling bath expired and stirred overnight. The mixture was cooled to 0° C., quenched with saturated $NH_4Cl$, warmed to RT, treatd with brine, extracted with EtOAc (2×) and the combined organics were dried over $MgSO_4$, concentrated to dryness and purified via silica gel chromatography (MeOH/DCM) to afford 1-(2,2-dimethyltetrahydro-2H-pyran-4-yl)imidazolidin-2-one as a white solid (155 mg, 26%). $^1$H NMR (400 MHz, DMSO-$d_6$): δ 6.24 (s, 1 H), 3.85 (m, 1 H), 3.67-3.54 (m, 2 H), 3.26-3.13 (m, 4 H), 1.53-1.37 (m, 4 H), 1.14 (d, J=10.2 Hz, 6 H); MS (ESI) m/z: 199.2 (M+H$^+$).

A 0° C. solution of phosgene (20% in toluene, 0.361 mL, 0.676 mmol) in DCM (2 mL), under Ar, was treated slowly drop-wise with a solution of 1-(2,2-dimethyltetrahydro-2H-pyran-4-yl)imidazolidin-2-one (0.067 g, 0.338 mmol) and pyridine (0.055 mL, 0.676 mmol) in DCM (1 mL). The mixture was warmed to RT and concentrated to dryness to afford 3-(2,2-dimethyltetrahydro-2H-pyran-4-yl)-2-oxoimidazolidine-1-carbonyl chloride as a yellow solid which was carried on to the next step assuming 100% yield (88 mg).

A 0° C. solution of Example A2 (0.060 g, 0.224 mmol) and TEA (0.094 mL, 0.673 mmol) in DCM (1 mL) was treated with a solution of crude 3-(2,2-dimethyltetrahydro-2H-pyran-4-yl)-2-oxoimidazolidine-1-carbonyl chloride (0.088 g, 0.337 mmol) in DCM (1 mL). The mixture was warmed to RT, stirred for 0.5 h, then concentrated to dryness and purified via silica gel chromatography (MeOH/DCM) to afford 3-(2,2-dimethyltetrahydro-2H-pyran-4-yl)-N-(5-((2-(1-methyl-1H-pyrazol-4-yl)pyridin-4-yl)oxy)pyridin-2-yl)-2-oxoimidazolidine-1-carboxamide as an off-white solid (74 mg, 67%). $^1$H NMR (400 MHz, DMSO-$d_6$): δ 10.96 (s, 1 H), 8.36 (d, J=5.7 Hz, 1 H), 8.25 (s, 1 H), 8.21 (m, 1 H), 8.05 (m, 1 H), 7.96 (d, J=0.7 Hz, 1 H), 7.72 (dd, J=9.0, 2.9 Hz, 1 H), 7.23 (d, J=2.4 Hz, 1 H), 6.68 (dd, J=5.7, 2.4 Hz, 1 H), 4.04 (m, 1 H), 3.84 (s, 3 H), 3.84-3.75 (m, 2 H), 3.70-3.59 (m, 2 H), 3.46-3.39 (m, 2 H), 1.60-1.47 (m, 4 H), 1.18 (d, J=15.1 Hz, 6 H); MS (ESI) m/z: 492.2 (M+H$^+$).

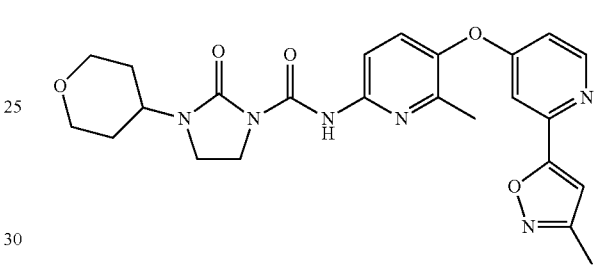

Example 14

A solution of Example A3 (0.35 g, 1.260 mmol) in DMF (5 mL) was sparged with argon, treated with TEA (1 mL) trimethylsilylacetylene (0.531 mL, 3.78 mmol), copper(I) iodide (0.024 g, 0.126 mmol) and trans-dichlorobis(triphenylphosphine)palladium(0) (0.088 g, 0.126 mmol) and heated at 75° C. under argon for 16 h. The mixture was cooled to RT, treated with EtOAc, solids removed via filtration through diatomaceous earth, rinsed well with EtOAc and $H_2O$ and the layers of the filtrate separated. The aqueous layer was extracted with EtOAc (1×) and the combined organics were washed with brine, dried over $Na_2SO_4$ and concentrated to dryness. The resulting material was dissolved in MeOH (20 mL), treated with $K_2CO_3$ (300 mg) and stirred at RT for 1 h. The mixture was concentrated to dryness, treated with EtOAc, sonicated, the solids removed via filtration through diatomaceous earth, rinsed well with EtOAc and the filtrate concentrated to dryness and purified via silica gel chromatography (EtOAc/Hex) to afford N-(5-((2-ethynylpyridin-4-yl)oxy)-6-methylpyridin-2-yl)acetamide (102 mg, 30%) as a light red solid. $^1$H NMR (400 MHz, DMSO-$d_6$): δ 10.62 (s, 1 H); 8.40 (d, J=5.8 Hz, 1 H); 8.01 (d, J=8.8 Hz, 1 H); 7.60 (d, J=6.0 Hz, 1 H); 7.04 (d, J=2.5 Hz, 1 H); 6.89 (dd, J=5.8, 2.6 Hz, 1 H); 4.34 (s, 1 H); 2.22 (s, 3 H); 2.07 (s, 3 H); MS (ESI) m/z: 268.1 (M+H$^+$).

A solution of N-chlorosuccinimide (0.153 g, 1.145 mmol) in DMF (1 mL) was treated with acetaldoxime (0.068 g, 1.145 mmol), stirred at RT for 30 min, then added to a solution of N-(5-((2-ethynylpyridin-4-yl)oxy)-6-methylpyridin-2-yl)acetamide (0.102 g, 0.382 mmol) and TEA (0.5 mL) in DMF (1 mL) and heated at 60° C. for 1 h. The mixture was cooled to RT, treated with $H_2O$, extracted with EtOAc (2×) and the combined organics were washed with $H_2O$, then brine, dried over $Na_2SO_4$, concentrated to dryness and purified via silica gel chromatography (MeOH/DCM) to afford N-(6-methyl-5-((2-(3-methylisoxazol-5-yl)pyridin-4-yl)oxy)pyridin-2-yl)acetamide (110 mg, 89%) as a white solid. $^1$H NMR (400 MHz, DMSO-d$_6$): δ 10.64 (s, 1 H), 8.55 (d, J=5.7 Hz, 1 H), 8.03 (d, J=8.8 Hz, 1 H), 7.64 (d, J=8.8 Hz, 1 H), 7.35 (d, J=2.5 Hz, 1 H), 6.96 (m, 2 H), 2.28 (s, 3 H), 2.25 (s, 3 H), 2.08 (s, 3 H); MS (ESI) m/z: 325.1 (M+H$^+$).

A mixture of N-(6-methyl-5-((2-(3-methylisoxazol-5-yl)pyridin-4-yl)oxy)pyridin-2-yl)acetamide (0.11 g, 0.339 mmol) and 2M HCl (1.696 mL, 3.39 mmol) in THF (3 mL) was heated at 60° C. for 4 h. The mixture was cooled to RT, treated with EtOAc and H$_2$O, neutralized with NaHCO$_3$, the layers separated and the aqueous layer extracted with EtOAc (1×). The combined organics were washed with brine, dried over Na$_2$SO$_4$ and concentrated to dryness to afford 6-methyl-5-((2-(3-methylisoxazol-5-yl)pyridin-4-yl)oxy)pyridin-2-amine (90 mg, 94%) as a white solid. $^1$H NMR (400 MHz, DMSO-d$_6$): δ 8.51 (d, J=5.7 Hz, 1 H); 7.26 (d, J=2.5 Hz, 1 H); 7.22 (d, J=8.7 Hz, 1 H); 6.95 (s, 1 H); 6.89 (dd, J=5.7, 2.5 Hz, 1 H); 6.36 (d, J=8.7 Hz, 1 H); 6.00 (s, 2 H); 2.28 (s, 3 H); 2.06 (s, 3 H); MS (ESI) m/z: 283.1 (M+H$^+$).

Phosgene (20% in toluene, 0.613 g, 1.24 mmol) was treated with a solution of Example B1 (0.063 g, 0.37 mmol) and pyridine (0.1 mL, 1.24 mmol) in DCM (2 mL), stirred for 15 min, then concentrated to dryness. The residue was dissolved in DCM (2 mL), treated with a solution of 6-methyl-5-((2-(3-methylisoxazol-5-yl)pyridin-4-yl)oxy)pyridin-2-amine (0.07 g, 0.25 mmol) and TEA (0.17 mL, 1.24 mmol) in DCM (2 mL) and stirred at RT for 1 h. The mixture was treated with satd. NaHCO$_3$, extracted with EtOAc (2×) and the combined organics were washed with brine, dried over Na$_2$SO$_4$, concentrated to dryness and purified via silica gel chromatography (MeOH/DCM) to afford N-(6-methyl-5-((2-(3-methylisoxazol-5-yl)pyridin-4-yl)oxy)pyridin-2-yl)-2-oxo-3-(tetrahydro-2H-pyran-4-yl)imidazolidine-1-carboxamide (75 mg, 63%). $^1$H NMR (400 MHz, DMSO-d$_6$): δ 10.92 (s, 1 H), 8.55 (d, J=5.7 Hz, 1 H), 7.92 (d, J=8.8 Hz, 1 H), 7.67 (d, J=8.8 Hz, 1 H), 7.34 (d, J=2.5 Hz, 1 H), 6.98 (s, 1 H), 6.96 (dd, J=5.7, 2.5 Hz, 1 H), 3.95-3.77 (m, 5 H), 3.48-3.35 (m, 4 H), 2.28 (s, 3 H), 2.24 (s, 3 H), 1.71-1.70 (m, 2 H), 1.60 (d, J=12.5 Hz, 2 H); MS (ESI) m/z: 479.2 (M+H$^+$).

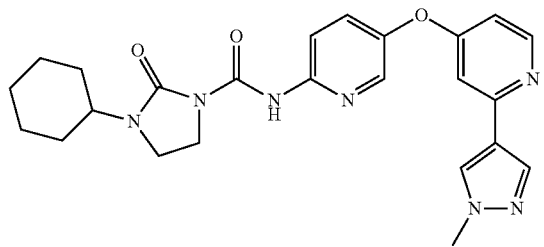 [SMILES: Cn1cc(-c2cc(Oc3ccc(NC(=O)N4CCN(C5CCCCC5)C4=O)nc3)ccn2)cn1]

Example 15

A solution of Example B7 (0.085 g, 0.505 mmol) and pyridine (0.133 g, 1.684 mmol) in DCM (2 mL) was added to phosgene (20% in toluene, 0.833 g, 1.684 mmol), under Ar, stirred for 15 min, then concentrated to dryness. The residue was dissolved in DCM (2 mL), treated with a solution of Example A2 (0.09 g, 0.337 mmol) and TEA (0.102 g, 1.010 mmol) in DCM (2 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM) to afford 3-cyclohexyl-N-(5-((2-(1-methyl-1H-pyrazol-4-yl)pyridin-4-yl)oxy)pyridin-2-yl)-2-oxoimidazolidine-1-carboxamide (100 mg, 64%) as a white solid. $^1$H NMR (400 MHz, DMSO-d$_6$): δ 10.99 (s, 1 H), 8.37 (d, J=5.7 Hz, 1 H), 8.26 (s, 1 H), 8.23 (d, J=2.9 Hz, 1 H), 8.07 (d, J=9.0 Hz, 1 H), 7.96 (s, 1 H), 7.71 (dd, J=9.0, 2.9 Hz, 1 H), 7.23 (d, J=2.4 Hz, 1 H), 6.70 (dd, J=5.7, 2.4 Hz, 1 H), 3.84 (s, 3 H), 3.79 (m, 2 H), 3.61 (m, 1 H), 3.43 (m, 2 H), 1.67 (m, 5 H), 1.35 (m, 4 H), 1.08 (m, 1 H); MS (ESI) m/z: 462.2 (M+H$^+$).

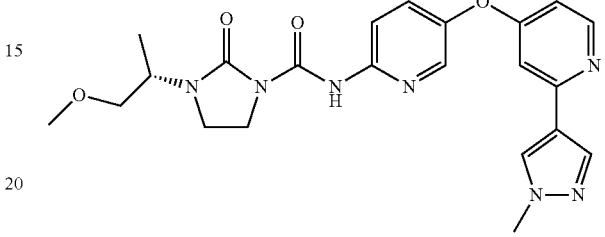

Example 16

A solution of Example B8 (95 mg, 0.601 mmol) and pyridine (71 mg, 0.901 mmol) in DCM (4 mL) was added phosgene (20% in toluene, 743 mg, 1.501 mmol), under Ar, stirred for 15 minutes, then concentrated to dryness. The residue was treated with a solution of Example A2 (80 mg, 0.300 mmol) and TEA (152 mg, 1.501 mmol) in DCM (4 mL) and stirred at RT for 0.5 h. The mixture was treated with water, extracted with EtOAc (2×) and the combined organics were washed with brine, dried over Na$_2$SO$_4$, concentrated to dryness and purified via silica gel chromatography (MeOH/DCM) to afford (S)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide (79 mg, 58%) as a white solid. $^1$H NMR (400 MHz, DMSO-d$_6$): δ 10.98 (s, 1 H), 8.37 (d, J=5.7 Hz, 1 H), 8.25 (s, 1 H), 8.22-8.21 (m, 1 H), 8.06-8.05 (m, 1 H), 7.96 (d, J=0.7 Hz, 1 H), 7.72 (dd, J=9.0, 2.9 Hz, 1 H), 7.22 (d, J=2.4 Hz, 1 H), 6.69 (dd, J=5.7, 2.4 Hz, 1 H), 4.11-4.08 (m, 1 H), 3.84 (s, 3 H), 3.83-3.77 (m, 2 H), 3.50-3.33 (m, 4 H), 3.26 (s, 3 H), 1.09 (d, J=6.9 Hz, 3 H); MS (ESI) m/z: 452.2 (M+H$^+$).

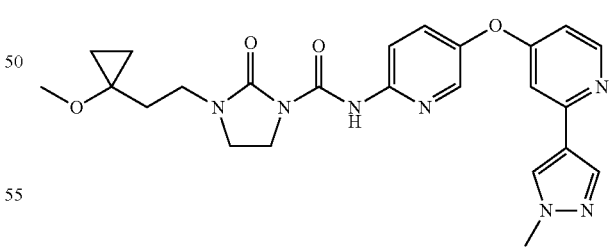

Example 17

A 0° C. solution of phosgene (20% in toluene, 0.711 mL, 0.980 mmol) in DCM (6 mL) was treated slowly drop-wise with a solution of Example B9 (0.129 g, 0.700 mmol) and pyridine (0.113 mL, 1.400 mmol) in DCM (2 mL), warmed to RT, stirred for 0.5 h, then concentrated to dryness. The residue was dissolved in DCM (2 mL), added to a 0° C. solution of Example A2 (0.058 g, 0.218 mmol) and TEA (0.091 mL, 0.654 mmol) in DCM (1 mL), warmed to RT and stirred for 0.5 h. The mixture was treated with water, stirred for 15 min and the layers separated. The organic layer was washed with additional water (2×), dried over MgSO$_4$, concentrated to dryness and purified via silica gel chromatography (MeOH/DCM) to afford 3-(2-(1-methoxycyclopropyl)ethyl)-N-(5-((2-(1-methyl-1H-pyrazol-4-yl)pyridin-4-yl)oxy)pyridin-2-yl)-2-oxoimidazolidine-1-carboxamide (25 mg, 24%) as a white solid. $^1$H NMR (400 MHz, DMSO-d$_6$): δ 10.99 (s, 1 H), 8.37 (d, J=5.7 Hz, 1 H), 8.25 (s, 1 H), 8.22 (d, J=2.9 Hz, 1 H), 8.07 (d, J=9.0 Hz, 1 H), 7.96 (d, J=0.7 Hz, 1 H), 7.72 (dd, J=9.0, 2.9 Hz, 1 H), 7.22 (d, J=2.4 Hz, 1 H), 6.69 (dd, J=5.7, 2.4 Hz, 1 H), 3.84 (s, 3 H), 3.80 (m, 2 H), 3.50 (m, 2 H), 3.34 (m, 2 H), 3.17 (s, 3 H), 1.77 (t, J=7.4 Hz, 2 H), 0.67 (m, 2 H), 0.42 (m, 2 H); MS (ESI) m/z: 478.2 (M+H$^+$).

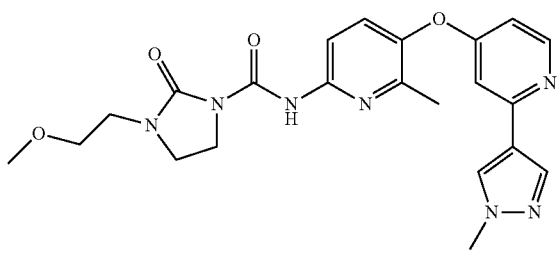 [SMILES: COCCN1CCN(C(=O)Nc2ccc(Oc3ccnc(-c4cnn(C)c4)c3)c(C)n2)C1=O]

Example 18

A 0° C. solution of phosgene (15% in toluene, 30 mL, 42.5 mmol) in DCM (25 mL) was treated drop-wise with a solution of pyridine (5 mL) and Example B3 (3.07 g, 21.33 mmol) in DCM (25 mL), stirred at RT for 1 h, then concentrated to dryness. The residue was dissolved in DCM (25 mL), added to a 0° C. solution of Example A4 (3.0 g, 10.66 mmol) and pyridine (5 mL) in DCM (25 mL), warmed to RT and stirred overnight. The mixture was treated with satd. NaHCO$_3$, stirred for 0.5 h, the layers separated and the aqueous layer extracted with additional DCM (2×). The combined organics were washed with brine, dried over Na$_2$SO$_4$, concentrated to dryness and purified via silica gel chromatography (MeOH/DCM). The material was treated with EtOAc, sonicated and the resulting solid was collected via filtration to afford 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide (3.05 g, 63%) as a white solid. $^1$H NMR (400 MHz, DMSO-d$_6$): δ 10.88 (s, 1 H), 8.34 (d, J=5.7 Hz, 1 H), 8.25 (s, 1 H), 7.95 (s, 1 H), 7.90 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 3.84 (s, 3 H), 3.81-3.79 (m, 2 H), 3.51-3.49 (m, 4 H), 3.41-3.37 (m, 2 H), 3.26 (s, 3 H), 2.24 (s, 3 H); MS (ESI) m/z: 452.2 (M+H$^+$).

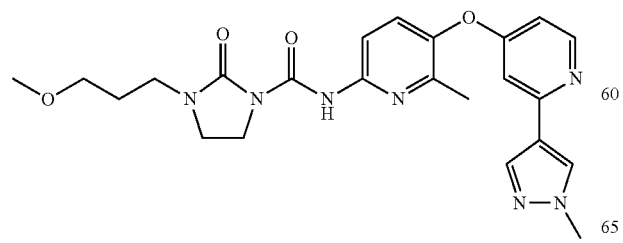

Example 19

A solution of Example B5 (0.081 g, 0.512 mmol) and pyridine (0.129 mL, 1.600 mmol) in DCM (2 mL) was added to phosgene (20% in toluene, 0.791 g, 1.60 mmol), under Ar, stirred for 15 minutes, then concentrated to dryness. The residue was dissolved in DCM (2 mL), treated with a solution of Example A4 (0.09 g, 0.320 mmol) and TEA (0.134 mL, 0.960 mmol) in DCM (2 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM) to afford 3-(3-methoxypropyl)-N-(6-methyl-5-((2-(1-methyl-1H-pyrazol-4-yl)pyridin-4-yl)oxy)pyridin-2-yl)-2-oxoimidazolidine-1-carboxamide (86 mg, 58%) as a white solid. $^1$H NMR (400 MHz, DMSO-d$_6$): δ 10.90 (s, 1 H), 8.35 (d, J=5.7 Hz, 1 H), 8.26 (s, 1 H), 7.96 (s, 1 H), 7.90 (d, J=8.8 Hz, 1 H), 7.61 (d, J=8.8 Hz, 1 H), 7.17 (d, J=2.4 Hz, 1 H), 6.61 (dd, J=5.7, 2.4 Hz, 1 H), 3.84 (s, 3 H), 3.81-3.79 (m, 2 H), 3.49-3.43 (m, 2 H), 3.37-3.33 (m, 2 H), 3.29-3.24 (m, 2 H), 3.23 (s, 3 H), 2.24 (s, 3 H), 1.78-1.70 (m, 2 H); MS (ESI) m/z: 466.2 (M+H$^+$).

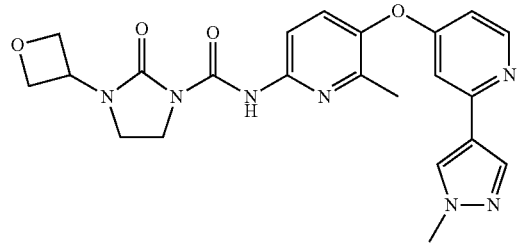 [SMILES: Cc1nc(NC(=O)N2CCN(C3COC3)C2=O)ccc1Oc1ccnc(-c2cnn(C)c2)c1]

Example 20

A 0° C. solution of phosgene (20% in toluene, 0.853 mL, 1.177 mmol) in DCM (6 mL) was treated slowly drop-wise with a solution of Example B10 (0.119 g, 0.841 mmol) and pyridine (0.136 mL, 1.681 mmol) in DCM (2 mL), warmed to RT, stirred for 0.5 h, then concentrated to dryness. The residue was dissolved in DCM (2 mL), added to a 0° C. solution of Example A4 (0.074 g, 0.263 mmol) and TEA (0.110 mL, 0.788 mmol) in DCM (1 mL), warmed to RT and stirred overnight. The mixture was diluted with DCM, washed with water (3×), dried over MgSO$_4$, concentrated to dryness and purified via silica gel chromatography (MeOH/DCM) to afford N-(6-methyl-5-((2-(1-methyl-1H-pyrazol-4-yl)pyridin-4-yl)oxy)pyridin-2-yl)-3-(oxetan-3-yl)-2-oxoimidazolidine-1-carboxamide (39 mg, 33%) as a white solid. $^1$H NMR (400 MHz, DMSO-d$_6$): δ 10.78 (s, 1 H), 8.34 (d, J=5.7 Hz, 1 H), 8.24 (s, 1 H), 7.95 (d, J=0.7 Hz, 1 H), 7.89 (d, J=8.8 Hz, 1 H), 7.61 (d, J=8.8 Hz, 1 H), 7.16 (d, J=2.4 Hz, 1 H), 6.59 (dd, J=5.7, 2.4 Hz, 1 H), 5.02 (m, 1 H), 4.77 (t, J=6.6 Hz, 2 H), 4.69 (t, J=7.3 Hz, 2 H), 3.84 (m, 5 H), 3.73 (m, 2 H), 2.24 (s, 3 H); MS (ESI) m/z: 450.2 (M+H$^+$).

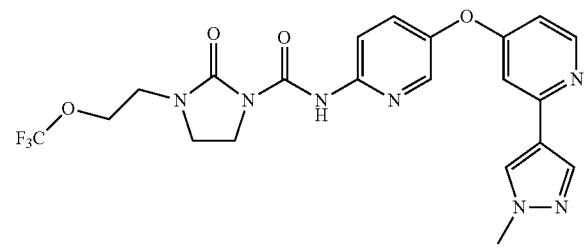 [SMILES: Cn1cc(-c2cc(Oc3ccc(NC(=O)N4CCN(CCOC(F)(F)F)C4=O)nc3)ccn2)cn1]

Example 21

A solution of Example B11 (0.1025 g, 0.393 mmol) in DCM (4 mL) was treated with a solution of Example A2 (0.105 g, 0.393 mmol) and TEA (0.082 mL, 0.590 mmol) in DCM (4 mL), stirred at RT for 1 h, diluted with DCM, washed with water (2×), then brine (1×), dried over MgSO$_4$ and concentrated to dryness. The material was purified via silica gel chromatography (MeOH/EtOAc) to afford N-(5-((2-(1-methyl-1H-pyrazol-4-yl)pyridin-4-yl)oxy)pyridin-2-yl)-2-oxo-3-(2-(trifluoromethoxy)ethyl)imidazolidine-1-carboxamide (93 mg, 48%) as a white solid. $^1$H NMR (400 MHz, DMSO-d$_6$): δ 10.89 (s, 1 H), 8.37 (d, J=5.7 Hz, 1 H), 8.26 (s, 1 H), 8.23 (d, J=2.9 Hz, 1 H), 8.07 (d, J=9.0 Hz, 1 H), 7.96 (s, 1 H), 7.73 (dd, J=9.0, 2.9 Hz, 1 H), 7.23 (d, J=2.4 Hz, 1 H), 6.70 (dd, J=5.7, 2.4 Hz, 1 H), 4.25 (t, J=5.1 Hz, 2 H), 3.84-3.82 (m, 5 H), 3.54-3.53 (m, 4 H); MS (ESI) m/z: 492.1 (M+H$^+$).

Example 22

A solution of Example B7 (0.086 g, 0.514 mmol) and pyridine (0.122 mL, 1.511 mmol) in DCM (2 mL) was added to phosgene (20% in toluene, 0.747 g, 1.511 mmol), under Ar, stirred for 15 min, then concentrated to dryness. The residue was dissolved in DCM (2 mL), treated with a solution of Example A4 (0.085 g, 0.302 mmol) and TEA (0.126 mL, 0.906 mmol) in DCM (2 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM) to afford 3-cyclohexyl-N-(6-methyl-5-((2-(1-methyl-1H-pyrazol-4-yl)pyridin-4-yl)oxy)pyridin-2-yl)-2-oxoimidazolidine-1-carboxamide (110 mg, 79%) as a white solid. $^1$H NMR (400 MHz, DMSO-d$_6$): δ 10.92 (s, 1 H), 8.34 (d, J=5.7 Hz, 1 H), 8.24 (s, 1 H), 7.95 (s, 1 H), 7.89 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 3.84 (s, 3 H), 3.80-3.78 (m, 2 H), 3.60-3.58 (m, 1 H), 3.50-3.52 (m, 2 H), 2.24 (s, 3 H), 1.70-1.66 (m, 5 H), 1.39-1.38 (m, 4 H), 1.11-1.08 (m, 1 H); MS (ESI) m/z: 476.2 (M+H$^+$).

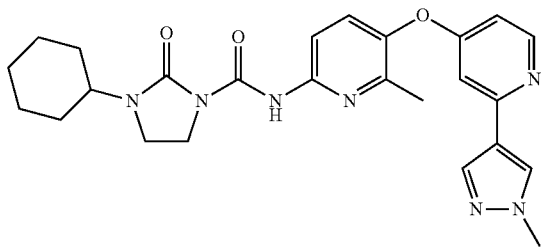 [SMILES: Cc1nc(NC(=O)N2CCN(C3CCCCC3)C2=O)ccc1Oc1ccnc(-c2cnn(C)c2)c1]

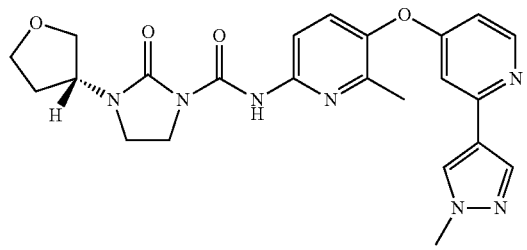 [SMILES: Cc1nc(NC(=O)N2CCN([C@@H]3CCOC3)C2=O)ccc1Oc1ccnc(-c2cnn(C)c2)c1]

Example 23

A 0° C. solution of phosgene (20% in toluene, 0.445 mL, 0.845 mmol) in DCM (4 mL) was treated slowly with a solution of Example B6 (0.110 g, 0.704 mmol) and pyridine (0.114 mL, 1.409 mmol) in DCM (4 mL), stirred at 0° C. 1 h, then concentrated to dryness. The residue was dissolved in DCM (4 mL), treated with a solution of Example A4 (0.149 g, 0.528 mmol) and TEA (0.147 mL, 1.056 mmol) in DCM (4 mL) and stirred at RT for 1.5 h. The mixture was diluted with DCM, washed with water (2×), the combined aqueous washes were back-extracted with DCM (1×) and the combined organics were washed with brine (2×), dried over MgSO$_4$, concentrated to dryness and purified via silica gel chromatography (MeOH/DCM) to afford (S)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide (139 mg, 43%) as a white solid. $^1$H NMR (400 MHz, DMSO-d$_6$): δ 10.87 (s, 1H), 8.35 (d, J=5.7 Hz, 1 H), 8.25 (s, 1 H), 7.96 (s, 1 H), 7.89 (d, J=8.8 Hz, 1 H), 7.61 (d, J=8.8 Hz, 1 H), 7.17 (d, J=2.4 Hz, 1 H), 6.59 (dd, J=5.7, 2.4 Hz, 1 H), 4.51-4.50 (m, 1 H), 3.91-3.86 (m, 1 H), 3.84 (s, 3 H), 3.82-3.75 (m, 3 H), 3.70-3.60 (m, 2 H), 3.47 (t, J=8.2 Hz, 2 H), 2.24 (s, 3 H), 2.20-2.10 (m, 1 H), 2.01-1.91 (m, 1 H); MS (ESI) m/z: 464.2 (M+H$^+$).

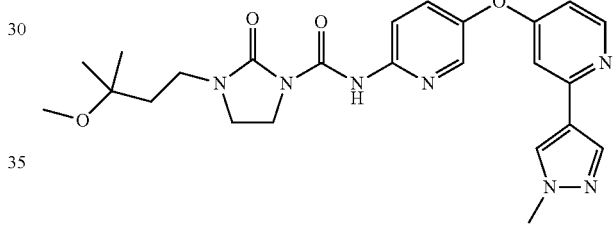

Example 24

A 0° C. solution of triphosgene (0.500 g, 1.685 mmol) in MeCN (10 mL) was treated with a solution of imidazolidin-2-one (0.800 g, 9.29 mmol) in MeCN (10 mL), stirred at RT for 0.5 h, added to a suspension of Example A2 (0.800 g, 2.99 mmol) in MeCN (10 mL) and stirred at RT for 4 h. The solids were collected via filtration to afford N-(5-((2-(1-methyl-1H-pyrazol-4-yl)pyridin-4-yl)oxy)pyridin-2-yl)-2-oxoimidazolidine-1-carboxamide (862 mg, 76%) as an off-white solid. MS (ESI) m/z: 380.1 (M+H$^+$).

A 0° C. solution of N-(5-(((2-(1-methyl-1H-pyrazol-4-yl)pyridin-4-yl)oxy)pyridin-2-yl)-2-oxoimidazolidine-1-carboxamide (0.350 g, 0.923 mmol) in DMF (5 mL) was treated with NaH (60% in mineral oil, 0.100 g, 2.50 mmol), stirred at RT for 0.5 h, treated with Example C4 (0.500 g, 1.836 mmol) and stirred at RT overnight. The mixture was treated with water, extracted with EtOAc (3×) and the combined organics were dried over Na$_2$SO$_4$, concentrated to dryness and purified via silica gel chromatography (MeOH/DCM) to afford 3-(3-methoxy-3-methylbutyl)-N-(5-((2-(1-methyl-1H-pyrazol-4-yl)pyridin-4-yl)oxy)pyridin-2-yl)-2-oxoimidazolidine-1-carboxamide (138 mg, 28%) as a white solid. $^1$H NMR (400 MHz, DMSO-d$_6$): δ 10.98 (s, 1 H), 8.36 (d, J=5.7 Hz, 1 H), 8.25 (s, 1 H), 8.22 (d, J=2.9 Hz, 1 H), 8.06 (d, J=9.0 Hz, 1 H), 7.96 (s, 1 H), 7.71 (dd, J=9.0, 2.9 Hz, 1 H), 7.22 (d, J=2.4 Hz, 1 H), 6.69 (dd, J=5.7, 2.4 Hz, 1 H), 3.84 (s, 3 H), 3.80 (m, 2 H), 3.47 (t, J=8.2 Hz, 2 H), 3.25 (m, 2 H), 3.09 (s, 3 H), 1.71 (m, 2 H), 1.11 (s, 6 H); MS (ESI) m/z: 480.2 (M+H⁺).

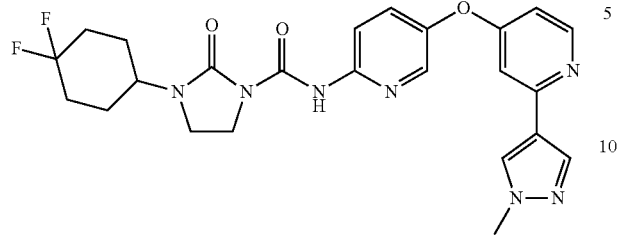

Example 25

A 0° C. solution of phosgene (20% in toluene, 2.00 mL, 3.78 mmol) was treated with a solution of Example B12 (0.200 g, 0.979 mmol) and pyridine (0.150 g, 1.896 mmol) in DCM (10 mL), stirred at RT for 0.5 h, then concentrated to dryness. The residue was treated with a solution of Example A2 (0.150 g, 0.561 mmol) and pyridine (0.150 g, 1.896 mmol) in DCM (10 mL) and stirred at RT for 1 h. The mixture was concentrated to dryness and purified via silica gel chromatography (EtOAc/DCM) to afford 3-(4,4-difluorocyclohexyl)-N-(5-((2-(1-methyl-1H-pyrazol-4-yl)pyridin-4-yl)oxy)pyridin-2-yl)-2-oxoimidazolidine-1-carboxamide (90 mg, 32%) as a white solid. ¹H NMR (400 MHz, DMSO-d₆): δ 10.95 (s, 1 H), 8.36 (d, J=5.7 Hz, 1 H), 8.25 (s, 1 H), 8.23 (d, J=2.9 Hz, 1 H), 8.07 (d, J=9.0 Hz, 1 H), 7.96 (s, 1 H), 7.72 (dd, J=9.0, 2.9 Hz, 1 H), 7.22 (d, J=2.4 Hz, 1 H), 6.68 (dd, J=5.7, 2.4 Hz, 1 H), 3.85 (m, 6 H), 3.45 (t, J=8.2 Hz, 2 H), 2.13 (m, 4 H), 1.73 (m, 4 H); MS (ESI) m/z: 498.2 (M+H⁺).

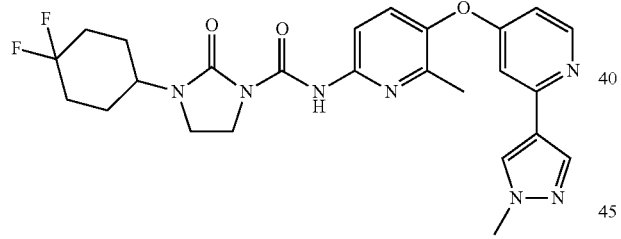

Example 26

A 0° C. solution of phosgene (20% in toluene, 1.50 mL, 2.84 mmol) was treated with a solution of Example B12 (0.200 g, 0.979 mmol) and pyridine (0.150 g, 1.896 mmol) in DCM (10 mL), stirred at RT for 0.5 h, then concentrated to dryness. The residue was treated with a solution of Example A4 (0.150 g, 0.533 mmol) and pyridine (0.150 g, 1.896 mmol) in DCM (10 mL) and stirred at RT for 2 h. The mixture was concentrated to dryness and purified via silica gel chromatography (EtOAc/DCM) to afford 3-(4,4-difluorocyclohexyl)-N-(6-methyl-5-((2-(1-methyl-1H-pyrazol-4-yl)pyridin-4-yl)oxy)pyridin-2-yl)-2-oxoimidazolidine-1-carboxamide (116 mg, 42%) as a white solid. ¹H NMR (400 MHz, DMSO-d₆): δ 10.88 (s, 1 H), 8.34 (d, J=5.7 Hz, 1 H), 8.25 (s, 1 H), 7.95 (s, 1 H), 7.89 (d, J=8.8 Hz, 1 H), 7.61 (d, J=8.8 Hz, 1 H), 7.17 (d, J=2.4 Hz, 1 H), 6.59 (dd, J=5.7, 2.4 Hz, 1 H), 3.84 (m, 6 H), 3.45 (t, J=8.2 Hz, 2 H), 2.24 (s, 3 H), 2.06 (m, 4 H), 1.76 (s, 4 H); MS (ESI) m/z: 512.2 (M+H⁺).

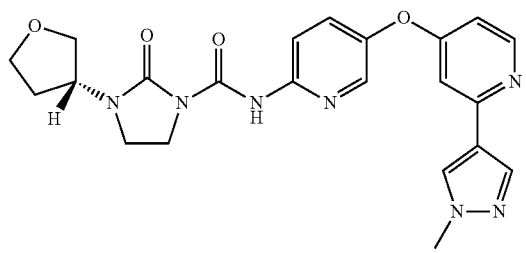 [SMILES: Cn1cc(-c2cc(Oc3ccc(NC(=O)N4CCN([C@@H]5CCOC5)C4=O)nc3)ccn2)cn1]

Example 27

A solution of Example B13 (0.196 g, 0.896 mmol) in DCM (4 mL) was treated with a solution of Example A2 (0.160 g, 0.598 mmol) and TEA (0.250 mL, 1.793 mmol) in DCM (4 mL) and stirred at RT for 1.5 h. The mixture was treated with water, extracted with DCM (2×) and the combined organics were washed with brine (2×), dried over MgSO₄, concentrated to dryness and purified via silica gel chromatography (MeOH/DCM) to afford (R)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide (150 mg, 56%) as a white solid. ¹H NMR (400 MHz, DMSO-d₆): δ 10.94 (s, 1 H), 8.37 (d, J=5.7 Hz, 1 H), 8.26 (s, 1 H), 8.23 (d, J=2.9 Hz, 1 H), 8.07 (d, J=9.0 Hz, 1 H), 7.96 (s, 1 H), 7.72 (dd, J=9.0, 2.9 Hz, 1 H), 7.23 (d, J=2.4 Hz, 1 H), 6.69 (dd, J=5.7, 2.4 Hz, 1 H), 4.54-4.52 (m, 1 H), 3.88-3.87 (m, 1 H), 3.84 (s, 3 H), 3.80-3.78 (m, 3 H), 3.64-3.63 (m, 2 H), 3.47 (t, J=8.2 Hz, 2 H), 2.15-2.14 (m, 1 H), 1.97-1.94 (m, 1 H); MS (ESI) m/z: 450.1 (M+H⁺).

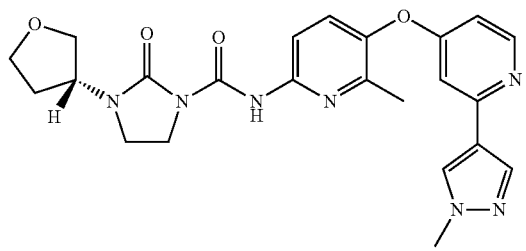 [SMILES: Cc1nc(NC(=O)N2CCN([C@@H]3CCOC3)C2=O)ccc1Oc1ccnc(-c2cnn(C)c2)c1]

Example 28

A solution of Example B13 (0.196 g, 0.896 mmol) in DCM (4 mL) was treated with a solution of Example A4 (0.168 g, 0.598 mmol) and TEA (0.249 mL, 1.793 mmol) in DCM (4 mL) and stirred at RT for 1.5 h. The mixture was treated with water, extracted with DCM (2×) and the combined organics were washed with brine (2×), dried over MgSO₄, concentrated to dryness and purified via silica gel chromatography (MeOH/DCM) to afford (R)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide (208 mg, 75%) as a white solid. ¹H NMR (400 MHz, DMSO-d₆): δ 10.87 (s, 1 H), 8.35 (d, J=5.7 Hz, 1 H), 8.25 (s, 1 H), 7.96 (s, 1 H), 7.89 (d, J=8.8 Hz, 1 H), 7.61 (d, J=8.8 Hz, 1 H), 7.17 (d, J=2.4 Hz, 1 H), 6.59 (dd, J=5.7, 2.4 Hz, 1 H), 4.54-4.48 (m, 1 H), 3.88-3.87 (m, 1 H), 3.84 (s, 3 H), 3.80-3.78 (m, 3 H), 3.66-3.65 (m, 2 H), 3.47 (t, J=8.2 Hz, 2 H), 2.24 (s, 3 H), 2.15-2.13 (m, 1 H), 1.98-1.95 (m, 1 H); MS (ESI) m/z: 464.2 (M+H⁺).

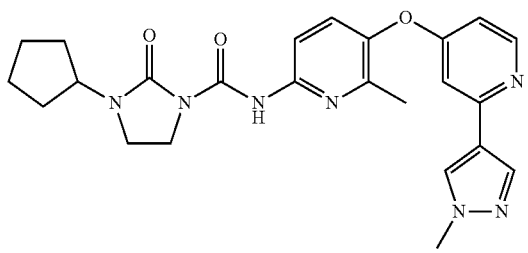 [SMILES: Cc1nc(NC(=O)N2CCN(C3CCCC3)C2=O)ccc1Oc1ccnc(-c2cnn(C)c2)c1]

Example 29

A 0° C. solution of Example B14 (0.159 g, 1.031 mmol) and pyridine (0.272 mL, 3.37 mmol) in DCM (5 mL) was treated drop-wise with phosgene (20% in toluene, 1.579 mL, 2.99 mmol), warmed to RT, added to a solution of Example A4 (0.158 g, 0.561 mmol) and pyridine (0.136 mL, 1.684 mmol) in DCM (5 mL) and stirred at RT for 2 h. The mixture was treated with satd. NaHCO$_3$, extracted with DCM (3×) and the combined organics were dried over Na$_2$SO$_4$, concentrated to dryness and purified via silica gel chromatography (MeOH/DCM) to afford 3-cyclopentyl-N-(6-methyl-5-((2-(1-methyl-1H-pyrazol-4-yl)pyridin-4-yl)oxy)pyridin-2-yl)-2-oxoimidazolidine-1-carboxamide (181 mg, 70%) as a white solid. $^1$H NMR (400 MHz, DMSO-d$_6$): δ 10.92 (s, 1 H), 8.34 (d, J=5.7 Hz, 1 H), 8.25 (s, 1 H), 7.95 (s, 1 H), 7.89 (d, J=8.8 Hz, 1 H), 7.60 (d, J=8.8 Hz, 1 H), 7.16 (d, J=2.4 Hz, 1 H), 6.59 (dd, J=5.7, 2.5 Hz, 1 H), 4.22-4.13 (m, 1 H), 3.84 (s, 3 H), 3.79 (m, 2 H), 3.44 (m, 2 H), 2.24 (s, 3 H), 1.81-1.72 (m, 2 H), 1.69-1.51 (m, 6 H); MS (ESI) m/z: 462.2 (M+H$^+$).

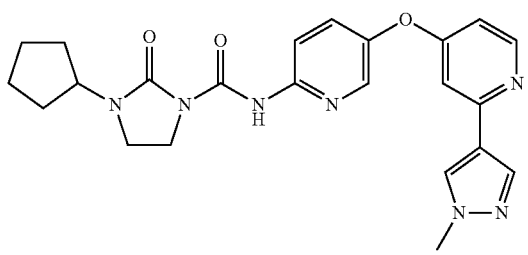 [SMILES: Cn1cc(-c2cc(Oc3ccc(NC(=O)N4CCN(C5CCCC5)C4=O)nc3)ccn2)cn1]

Example 30

A 0° C. solution of Example B14 (0.159 g, 1.031 mmol) and pyridine (0.272 mL, 3.37 mmol) in DCM (5 mL) was treated drop-wise with phosgene (20% in toluene, 1.579 mL, 2.99 mmol), warmed to RT, added to a solution of Example A2 (0.15 g, 0.561 mmol) and pyridine (0.136 mL, 1.684 mmol) in DCM (5 mL) and stirred at RT for 2 h. The mixture was treated with satd. NaHCO$_3$, extracted with DCM (3×) and the combined organics were dried over Na$_2$SO$_4$, concentrated to dryness and purified via silica gel chromatography (MeOH/DCM) to afford 3-cyclopentyl-N-(5-((2-(1-methyl-1H-pyrazol-4-yl)pyridin-4-yl)oxy)pyridin-2-yl)-2-oxoimidazolidine-1-carboxamide (72 mg, 29%) as a white solid. $^1$H NMR (400 MHz, DMSO-d$_6$): δ 11.00 (s, 1 H), 8.36 (d, J=5.7 Hz, 1 H), 8.25 (s, 1 H), 8.22 (d, J=2.9 Hz, 1 H), 8.07 (d, J=9.0 Hz, 1 H), 7.96 (s, 1 H), 7.71 (dd, J=9.0, 2.9 Hz, 1 H), 7.22 (d, J=2.4 Hz, 1 H), 6.69 (dd, J=5.7, 2.4 Hz, 1 H), 4.20 (m, 1 H), 3.84 (s, 3 H), 3.80-3.79 (m, 2 H), 3.45-3.44 (m, 2 H), 1.80-1.72 (m, 2 H), 1.69-1.51 (m, 6 H); MS (ESI) m/z: 448.2 (M+H$^+$).

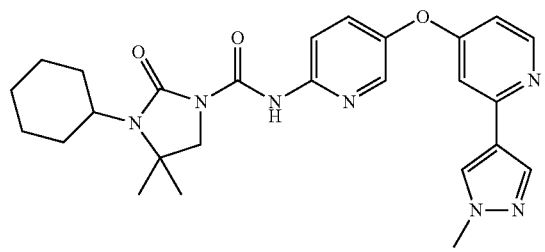 [SMILES: Cn1cc(-c2cc(Oc3ccc(NC(=O)N4CC(C)(C)N(C5CCCCC5)C4=O)nc3)ccn2)cn1]

Example 31

A 0° C. solution of Example A2 (0.114 g, 0.425 mmol) and TEA (0.1 mL) in DCM (5 mL) was treated with a solution of Example B15 (0.22 g, 0.850 mmol) in DCM (5 mL), stirred at 0° C. for 0.5 h, then warmed to RT and stirred overnight. The mixture was treated with water, extracted with EtOAc and the organic layer was washed with brine, dried over Na$_2$SO$_4$, concentrated to dryness and purified via silica gel chromatography (EtOAc/Hex) to afford 3-cyclohexyl-4,4-dimethyl-N-(5-((2-(1-methyl-1H-pyrazol-4-yl)pyridin-4-yl)oxy)pyridin-2-yl)-2-oxoimidazolidine-1-carboxamide (22 mg, 9.5%). $^1$H NMR (400 MHz, DMSO-d$_6$): δ 12.67 (s, 1 H), 8.35 (d, J=5.7 Hz, 1 H), 8.23 (m, 2 H), 8.07 (d, J=9.0 Hz, 1 H), 7.94 (s, 1 H), 7.69 (dd, J=9.0, 2.9 Hz, 1 H), 7.20 (d, J=2.5 Hz, 1 H), 6.68 (dd, J=5.7, 2.4 Hz, 1 H), 3.83 (s, 3 H), 3.73 (s, 2 H), 3.40 (s, 1 H), 1.70 (m, 4 H), 1.43 (s, 6 H), 1.25 (m, 6 H); MS (ESI) m/z: 490.2 (M+H$^+$).

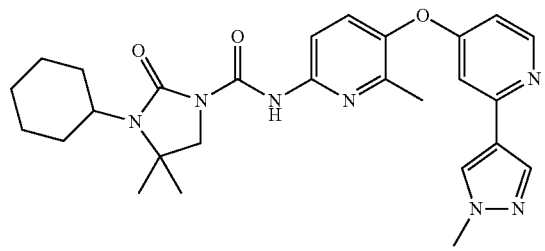 [SMILES: Cc1nc(NC(=O)N2CC(C)(C)N(C3CCCCC3)C2=O)ccc1Oc1ccnc(-c2cnn(C)c2)c1]

Example 32

A 0° C. solution of Example A4 (0.024 g, 0.085 mmol) and TEA (0.1 mL) in DCM (5 mL) was treated with a solution of Example B15 (0.044 g, 0.171 mmol) in DCM (5 mL), stirred at 0° C. for 0.5 h, then warmed to RT and stirred overnight. The mixture was treated with water, extracted with EtOAc and the organic layer was washed with brine, dried over Na$_2$SO$_4$, concentrated to dryness and purified via silica gel chromatography (EtOAc/Hex) to afford 3-cyclohexyl-4,4-dimethyl-N-(6-methyl-5-((2-(1-methyl-1H-pyrazol-4-yl)pyridin-4-yl)oxy)pyridin-2-yl)-2-oxoimidazolidine-1-carboxamide (16 mg, 33%). $^1$H NMR (400 MHz, DMSO-d$_6$): δ 12.68 (s, 1 H), 8.33 (d, J=5.7 Hz, 1 H), 8.23 (s, 1 H), 7.94 (s, 1 H), 7.88 (d, J=8.8 Hz, 1 H), 7.58 (d, J=8.8 Hz, 1 H), 7.14 (d, J=2.4 Hz, 1 H), 6.59 (dd, J=5.7, 2.5 Hz, 1 H), 3.83 (s, 3 H), 3.73 (s, 2 H), 3.47 (m, 1 H), 2.22 (s, 3 H), 1.72 (m, 4 H), 1.42 (s, 6 H), 1.31 (s, 6 H); MS (ESI) m/z: 504.2 (M+H$^+$).

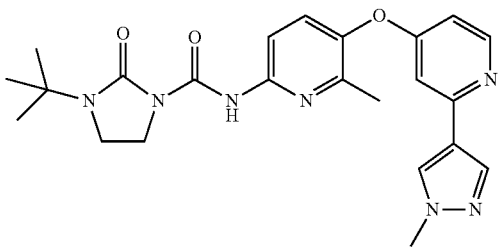 [SMILES: Cc1nc(NC(=O)N2CCN(C(C)(C)C)C2=O)ccc1Oc1ccnc(-c2cnn(C)c2)c1]

Example 33

A solution of triphosgene (0.200 g, 0.674 mmol) in DCM (5 mL) was treated with a solution of Example B16 (0.500 g, 3.52 mmol) and pyridine (0.100 g, 1.264 mmol) in DCM (5 mL), stirred at RT for 0.5 h, then concentrated to dryness. The residue was treated with a solution of Example A4 (0.150 g, 0.533 mmol) and pyridine (0.100 g, 1.264 mmol) in DCM (5 mL) and stirred at RT for 2 h. The mixture was concentrated to dryness and purified via silica gel chromatography (MeOH/DCM) to afford 3-(tert-butyl)-N-(6-methyl-5-((2-(1-methyl-1H-pyrazol-4-yl)pyridin-4-yl)oxy)pyridin-2-yl)-2-oxoimidazolidine-1-carboxamide (55 mg, 22%) as an off-white solid. $^1$H NMR (400 MHz, DMSO-$d_6$): δ 10.97 (s, 1 H), 8.34 (d, J=5.7 Hz, 1 H), 8.24 (s, 1 H), 7.95 (s, 1 H), 7.88 (d, J=8.8 Hz, 1 H), 7.59 (d, J=8.8 Hz, 1 H), 7.16 (d, J=2.4 Hz, 1 H), 6.58 (dd, J=5.7, 2.4 Hz, 1 H), 3.83 (s, 3 H), 3.70 (t, J=8.2 Hz, 2 H), 3.50 (t, J=8.2 Hz, 2 H), 2.23 (s, 3 H), 1.35 (s, 9 H); MS (ESI) m/z: 450.2 (M+H$^+$).

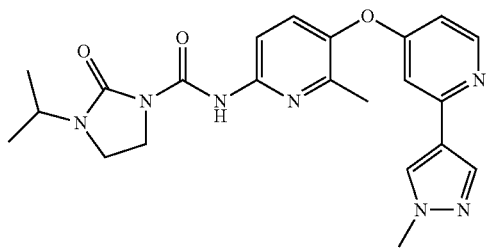

Example 35

A solution of triphosgene (0.200 g, 0.674 mmol) in DCM (5 mL) was treated with a solution of Example B17 (0.250 g, 1.950 mmol) and pyridine (0.100 g, 1.264 mmol) in DCM (5 mL), stirred at RT for 0.5 h, then concentrated to dryness. The residue was treated with a solution of Example A4 (0.150 g, 0.533 mmol) and pyridine (0.100 g, 1.264 mmol) in DCM (5 mL) and stirred at RT for 2 h. The mixture was concentrated to dryness and purified via silica gel chromatography (MeOH/DCM) to afford 3-isopropyl-N-(6-methyl-5-((2-(1-methyl-1H-pyrazol-4-yl)pyridin-4-yl)oxy)pyridin-2-yl)-2-oxoimidazolidine-1-carboxamide (178 mg, 77%) as a white solid. $^1$H NMR (400 MHz, DMSO-$d_6$): δ 10.91 (s, 1 H), 8.33 (d, J=5.7 Hz, 1 H), 8.24 (s, 1 H), 7.94 (s, 1 H), 7.88 (d, J=8.8 Hz, 1 H), 7.59 (d, J=8.8 Hz, 1 H), 7.15 (d, J=2.4 Hz, 1 H), 6.57 (dd, J=5.7, 2.4 Hz, 1 H), 4.00 (m, 1 H), 3.83 (s, 3 H), 3.78 (m, 2 H), 3.40 (t, J=8.2 Hz, 2 H), 2.22 (s, 3 H), 1.12 (d, J=6.8 Hz, 6 H); MS (ESI) m/z: 436.2 (M+H$^+$).

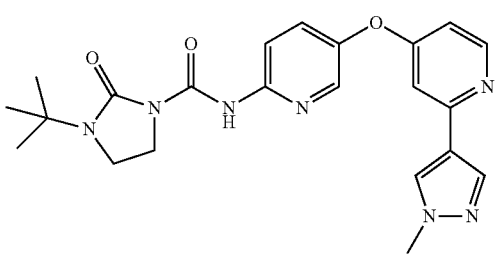 [SMILES: Cn1cc(-c2cc(Oc3ccc(NC(=O)N4CCN(C(C)(C)C)C4=O)nc3)ccn2)cn1]

Example 34

A solution of triphosgene (0.200 g, 0.674 mmol) in DCM (5 mL) was treated with a solution of Example B16 (0.500 g, 3.52 mmol) and pyridine (0.100 g, 1.264 mmol) in DCM (5 mL), stirred at RT for 0.5 h, then concentrated to dryness. The residue was treated with a solution of Example A2 (0.150 g, 0.561 mmol) and pyridine (0.100 g, 1.264 mmol) in DCM (5 mL) and stirred at RT for 2 h. The mixture was concentrated to dryness and purified via silica gel chromatography (MeOH/DCM) to afford 3-(tert-butyl)-N-(5-((2-(1-methyl-1H-pyrazol-4-yl)pyridin-4-yl)oxy)pyridin-2-yl)-2-oxoimidazolidine-1-carboxamide (112 mg, 45%) as an off-white solid. $^1$H NMR (400 MHz, DMSO-$d_6$): δ 11.04 (s, 1 H), 8.35 (d, J=5.7 Hz, 1 H), 8.24 (s, 1 H), 8.20 (d, J=2.9 Hz, 1 H), 8.05 (d, J=9.0 Hz, 1 H), 7.94 (s, 1 H), 7.70 (dd, J=9.0, 2.9 Hz, 1 H), 7.21 (d, J=2.4 Hz, 1 H), 6.67 (dd, J=5.7, 2.4 Hz, 1 H), 3.83 (s, 3 H), 3.70 (t, J=8.2 Hz, 2 H), 3.50 (t, J=8.2 Hz, 2 H), 1.35 (s, 9 H); MS (ESI) m/z: 436.2 (M+H$^+$).

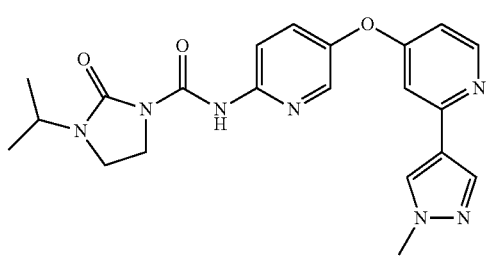 [SMILES: CC(C)N1CCN(C(=O)Nc2ccc(Oc3ccnc(-c4cnn(C)c4)c3)cn2)C1=O]

Example 36

A solution of triphosgene (0.200 g, 0.674 mmol) in DCM (5 mL) was treated with a solution of Example B17 (0.250 g, 1.950 mmol) and pyridine (0.100 g, 1.264 mmol) in DCM (5 mL), stirred at RT for 0.5 h, then concentrated to dryness. The residue was treated with a solution of Example A2 (0.150 g, 0.561 mmol) and pyridine (0.100 g, 1.264 mmol) in DCM (5 mL) and stirred at RT for 2 h. The mixture was concentrated to dryness and purified via silica gel chromatography (MeOH/DCM) to afford 3-isopropyl-N-(5-((2-(1-methyl-1H-pyrazol-4-yl)pyridin-4-yl)oxy)pyridin-2-yl)-2-oxoimidazolidine-1-carboxamide (180 mg, 76%) as a white solid. $^1$H NMR (400 MHz, DMSO-$d_6$): δ 10.98 (s, 1 H), 8.35 (d, J=5.7 Hz, 1 H), 8.24 (s, 1 H), 8.21 (d, J=2.9 Hz, 1 H), 8.05 (d, J=9.0 Hz, 1 H), 7.94 (s, 1 H), 7.70 (dd, J=9.0, 2.9 Hz, 1 H), 7.21 (d, J=2.4 Hz, 1 H), 6.67 (dd, J=5.7, 2.4 Hz, 1 H), 4.02 (m, 1 H), 3.83 (s, 3 H), 3.79 (m, 2 H), 3.43 (t, J=8.2 Hz, 2 H), 1.12 (d, J=6.8 Hz, 6 H); MS (ESI) m/z: 422.2 (M+H$^+$).

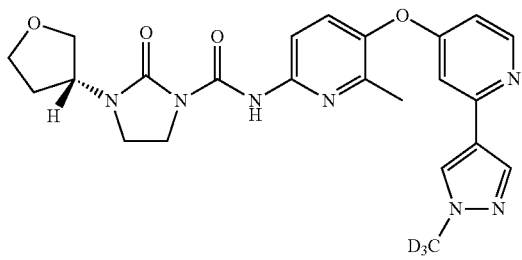 [SMILES: [2H]C([2H])([2H])n1cc(-c2cc(Oc3ccc(NC(=O)N4CCN([C@@H]5CCOC5)C4=O)nc3C)ccn2)cn1]

Example 37

A suspension of Example A6 (0.744 g, 2.80 mmol), Example C2 (0.65 g, 3.08 mmol), and Cs$_2$CO$_3$ (2.74 g, 8.40 mmol) in DMF (7.5 mL) was sparged with Ar, treated with Pd(PPh$_3$)$_4$ (0.323 g, 0.280 mmol) sparged again with Ar and heated at 90° C. overnight. The mixture was cooled to RT, treated with EtOAc and the solids removed via filtration through diatomaceous earth. The filtrate was concentrated to dryness and purified via silica gel chromatography (MeOH/DCM) to afford 2-methyl-6-nitro-3-((2-(1-(trideuteromethyl)-1H-pyrazol-4-yl)pyridin-4-yl)oxy)pyridine (880 mg, 100%) as a brown solid. $^1$H NMR (400 MHz, DMSO-d$_6$): δ 8.45 (d, J=5.6 Hz, 1 H), 8.26 (d, J=0.7 Hz, 1 H), 8.22 (d, J=8.7 Hz, 1 H), 7.98 (d, J=0.7 Hz, 1 H), 7.82 (d, J=8.7 Hz, 1 H), 7.35 (d, J=2.4 Hz, 1 H), 6.88 (dd, J=5.6, 2.4 Hz, 1 H), 2.49 (s, 3 H); MS (ESI) m/z: 315.1 (M+H$^+$).

A solution of 2-methyl-6-nitro-3-((2-(1-(trideuteromethyl)-1H-pyrazol-4-yl)pyridin-4-yl)oxy)pyridine (1.6 g, 5.09 mmol) in MeOH (20 mL) and THF (20 mL) was treated with NH$_4$Cl (4.27 g, 80 mmol), then portion-wise with zinc powder (2.134 g, 32.6 mmol) and stirred at RT for 0.5 h. The mixture was diluted with EtOAc, the solids removed via filtration through diatomaceous earth and the filtrate concentrated to dryness. The residue was dissolved in hot EtOAc, cooled to RT and the resulting solid collected via filtration to afford 6-methyl-5-((2-(1-(trideuteromethyl)-1H-pyrazol-4-yl)pyridin-4-yl)oxy)pyridin-2-amine (1.25 g, 86%) as a pink solid. $^1$H NMR (400 MHz, DMSO-d$_6$): δ 8.77 (dd, J=5.7, 0.5 Hz, 1 H), 8.54 (d, J=0.7 Hz, 1 H), 8.36 (d, J=0.7 Hz, 1 H), 7.52 (d, J=8.6 Hz, 1 H), 7.51-7.50 (m, 1 H), 6.98 (dd, J=5.7, 2.4 Hz, 1 H), 6.92 (dd, J=8.6, 0.7 Hz, 1 H), 5.84 (s, 2 H), 2.57 (s, 3H); MS (ESI) m/z: 285.1 (M+H$^+$).

A solution of Example B13 (0.208 g, 0.950 mmol) in DCM (4 mL) was treated with a solution of 6-methyl-5-((2-(1-(trideuteromethyl)-1H-pyrazol-4-yl)pyridin-4-yl)oxy)pyridin-2-amine (0.15 g, 0.528 mmol) and TEA (0.219 mL, 1.583 mmol) in DCM (4 mL) and stirred at RT for 1.5 h. The mixture was treated with brine, extracted with EtOAc (3×) and the combined organics were dried over Na$_2$SO$_4$, concentrated to dryness and purified via silica gel chromatography (EtOAc/DCM). The material was treated with MeCN and Et$_2$O, sonicated and the resulting solid collected via filtration to afford (R)—N-(6-methyl-5-((2-(1-(trideuteromethyl)-1H-pyrazol-4-yl)pyridin-4-yl)oxy)pyridin-2-yl)-2-oxo-3-(tetrahydrofuran-3-yl)imidazolidine-1-carboxamide (120 mg, 49%). $^1$H NMR (400 MHz, DMSO-d$_6$): δ 10.87 (s, 1 H), 8.34 (d, J=5.7 Hz, 1 H), 8.24 (d, J=0.7 Hz, 1 H), 7.95 (d, J=0.7 Hz, 1 H), 7.89 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 4.45 (m, 1 H), 3.87 (d, J=6.3 Hz, 1 H), 3.79 (m, 3 H), 3.65 (m, 2 H), 3.47 (m, 2 H), 2.24 (s, 3 H), 2.14 (m, 1 H), 1.96 (m, 1H); MS (ESI) m/z: 467.2 (M+H$^+$).

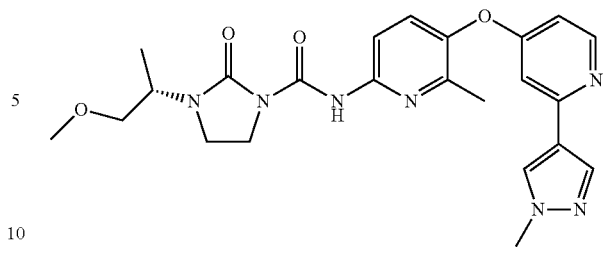

Example 38

A solution of Example B8 (180 mg, 1.138 mmol) and pyridine (225 mg, 2.84 mmol) in DCM (6 mL) was added to phosgene (15% in toluene, 1.876 mg, 2.84 mmol) under Ar, stirred for 15 min, then concentrated to dryness. The residue was dissolved in DCM (2 mL), treated with a solution of Example A4 (160 mg, 0.569 mmol) and TEA (288 mg, 2.84 mmol) in DCM (4 mL) and stirred at RT for 2 h. The mixture was treated with water, extracted with EtOAc (2×) and the combined organics were washed with brine, dried over Na$_2$SO$_4$, concentrated to dryness and purified via reverse-phase chromatography (MeCN/H$_2$O with 0.1% TFA). The organics were removed under reduced pressure, the aqueous residue neutralized with satd. NaHCO$_3$ and extracted with EtOAc (2×). The combined organics were dried over Na$_2$SO$_4$, concentrated to dryness and re-purified via silica gel chromatography (MeOH/DCM) to afford (S)-3-(1-methoxypropan-2-yl)-N-(6-methyl-5-((2-(1-methyl-1H-pyrazol-4-yl)pyridin-4-yl)oxy)pyridin-2-yl)-2-oxoimidazolidine-1-carboxamide (49 mg, 18%). $^1$H NMR (400 MHz, DMSO-d$_6$): δ 10.91 (s, 1 H), 8.34 (d, J=5.7 Hz, 1 H), 8.25 (s, 1H), 7.95 (s, 1 H), 7.89 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 4.10-4.07 (m, 1 H), 3.84 (s, 3 H), 3.80 (m, 2 H), 3.48-3.32 (m, 4 H), 3.26 (s, 3 H), 2.24 (s, 3 H), 1.09 (d, J=6.9 Hz, 3H); MS (ESI) m/z: 466.2 (M+H$^+$).

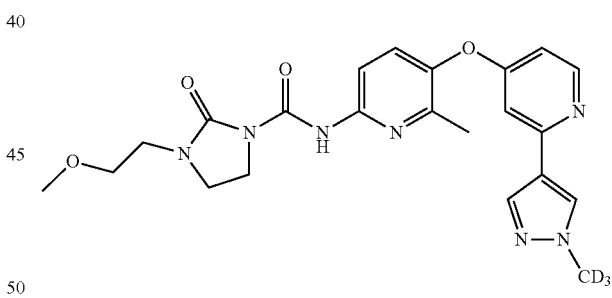

Example 39

A mixture of Example C5 (0.200 g, 0.493 mmol), Example C2 (0.114 g, 0.542 mmol) and K$_2$CO$_3$ (0.272 g, 1.971 mmol) in dioxane (8 mL) and water (2 mL) was sparged with Ar, treated with Pd(PPh$_3$)$_4$ (0.085 g, 0.074 mmol), sparged again with Ar and heated at 90° C. overnight. The mixture was cooled to RT, treated with satd. NaHCO$_3$, extracted with EtOAc (3×) and the combined organics were dried over Na$_2$SO$_4$, concentrated to dryness and purified via silica gel chromatography (MeOH/DCM) to afford 3-(2-methoxyethyl)-N-(6-methyl-5-((2-(1-(trideuteromethyl)-1H-pyrazol-4-yl)pyridin-4-yl)oxy)pyridin-2-yl)-2-oxoimidazolidine-1-carboxamide (130 mg, 58%) as a white solid. $^1$H NMR (400 MHz, DMSO-d$_6$): δ 10.88 (s, 1 H), 8.34 (d, J=5.7

Hz, 1 H), 8.24 (s, 1 H), 7.95 (s, 1 H), 7.90 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 3.80 (m, 2 H), 3.54-3.46 (m, 4 H), 3.38 (m, 2 H), 3.26 (s, 3 H), 2.24 (s, 3H); MS (ESI) m/z: 455.2 (M+H+).

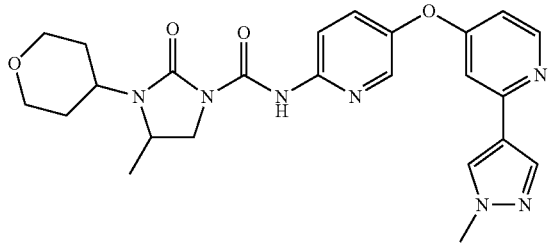 [SMILES: CC1CN(C(=O)Nc2ccc(Oc3ccnc(-c4cnn(C)c4)c3)cn2)C(=O)N1C1CCOCC1]

Example 40

A biphasic mixture of 4-aminotetrahydropyran hydrochloride (1.0 g, 7.27 mmol) in EtOAc (20 mL) and satd. NaHCO₃ (20 mL) was treated with isopropenyl chloroformate (0.874 mL, 7.99 mmol), stirred at RT for 2 h and the layers separated. The aqueous layer was extracted with EtOAc (1×) and the combined organics were washed with brine, dried over Na₂SO₄ and concentrated to dryness to afford prop-1-en-2-yl(tetrahydro-2H-pyran-4-yl)carbamate (1.2 g, 89%). ¹H NMR (400 MHz, DMSO-d₆): δ 7.48 (d, J=7.7 Hz, 1 H), 4.57 (d, J=7.9 Hz, 2 H), 3.80-3.78 (m, 2 H), 3.51-3.40 (m, 1 H), 3.33-3.25 (m, 2H), 1.83 (s, 3 H), 1.69 (m, 2 H), 1.43-1.32 (m, 2H).

A solution of prop-1-en-2-yl(tetrahydro-2H-pyran-4-yl)carbamate (0.50 g, 2.70 mmol) in dioxane (20 mL) was treated with DBU (0.1 mL) and propargylamine (0.149 g, 2.70 mmol) and heated at 90° C. overnight. The mixture was cooled to RT, treated with brine and extracted with EtOAc (3×). The combined organics were dried over Na₂SO₄, concentrated to dryness, treated with Et₂O and the resulting solid collected via filtration to afford 1-(prop-2-yn-1-yl)-3-(tetrahydro-2H-pyran-4-yl)urea (400 mg, 81%). ¹H NMR (400 MHz, DMSO-d₆): δ 6.00 (m, 1 H), 5.99 (m, 1 H), 3.76 (m, 2 H), 3.75 (m, 2 H), 3.56 (m, 1 H), 3.30 (m, 2 H), 3.02 (t, J=2.5 Hz, 1 H), 1.68 (m, 2 H), 1.29 (m, 2H); MS (ESI) m/z: 183.1 (M+H+).

A 5° C. solution of 1-(prop-2-yn-1-yl)-3-(tetrahydro-2H-pyran-4-yl)urea (0.40 g, 2.195 mmol) in THF (20 mL) under Ar, was treated with NaH (60% in mineral oil, 0.097 g, 2.415 mmol), warmed to RT and stirred overnight. The mixture was treated with satd. NH₄Cl, extracted with EtOAc (2×) and the combined organics were washed with 5% LiCl, then brine and dried over Na₂SO₄. The solution was treated with Pd on C (260 mg) and hydrogenated (30 psi) for 5 h. The mixture was filtered, treated with fresh Pd on C (260 mg) and hydrogenated (44 psi) overnight. The solids were removed via filtration through diatomaceous earth, washed with EtOAc and the filtrate concentrated to dryness to afford crude 5-methyl-1-(tetrahydro-2H-pyran-4-yl)imidazolidin-2-one (190 mg, 47%) which was used without further purification. MS (ESI) m/z: 185.1 (M+H+).

A 0° C. solution of phosgene (15% in toluene, 2 mL, 2.84 mmol) in DCM (5 mL) was treated drop-wise with a solution of pyridine (0.1 mL, 1.236 mmol) and 5-methyl-1-(tetrahydro-2H-pyran-4-yl)imidazolidin-2-one (0.103 g, 0.561 mmol) in DCM (5 mL), stirred at RT for 1 h, then concentrated to dryness. The residue was dissolved in DCM (5 mL), cooled to 0° C., treated with a solution of Example A2 (0.10 g, 0.374 mmol) and pyridine (0.1 mL) in DCM (5 mL), warmed to RT and stirred overnight. The solids were removed via filtration, washed with DCM and the filtrate concentrated to dryness and purified via silica gel chromatography (MeOH/DCM) to afford 4-methyl-N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide (16 mg, 9%). ¹H NMR (400 MHz, DMSO-d₆): δ 10.96 (s, 1 H), 8.36 (d, J=5.7 Hz, 1 H), 8.25 (s, 1 H), 8.23 (d, J=2.9 Hz, 1 H), 8.06 (d, J=9.0 Hz, 1 H), 7.95 (s, 1 H), 7.71 (dd, J=9.0, 2.9 Hz, 1 H), 7.22 (d, J=2.4 Hz, 1 H), 6.68 (dd, J=5.7, 2.4 Hz, 1 H), 3.90 (m, 4H), 3.87 (m, 1 H), 3.84 (s, 3 H), 3.66 (m, 1 H), 3.39 (m, 1 H), 3.34 (m, 1 H), 2.05 (m, 1 H), 1.90 (m, 1 H), 1.70 (m, 1 H), 1.68 (m, 1 H), 1.28 (d, J=5.4 Hz, 3H); MS (ESI) m/z: 478.2 (M+H+).

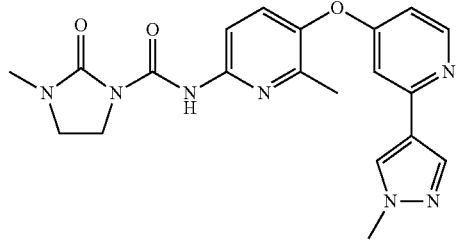 [SMILES: Cc1nc(NC(=O)N2CCN(C)C2=O)ccc1Oc1ccnc(-c2cnn(C)c2)c1]

Example 41

A 0° C. solution of phosgene (15% in toluene, 2 mL, 2.84 mmol) in DCM (5 mL) was treated drop-wise with a solution of pyridine (0.1 mL, 1.236 mmol) and 1-methylimidazolidin-2-one (0.053 g, 0.533 mmol) in DCM (5 mL), stirred at RT for 1 h, then concentrated to dryness. The residue was dissolved in DCM (5 mL), cooled to 0° C., treated with a solution of Example A4 (0.10 g, 0.355 mmol) and pyridine (0.1 mL) in DCM (5 mL), warmed to RT and stirred overnight. The solids were removed via filtration, washed with DCM and the filtrate concentrated to dryness. The residue was treated with EtOAc, the solid collected via filtration and purified via reverse-phase chromatography (MeCN/H₂O with 0.1% TFA). The combined fractions were treated with satd. NaHCO₃, extracted with EtOAc and the organic layer dried over Na₂SO₄ and concentrated to dryness to afford 3-methyl-N-(6-methyl-5-((2-(1-methyl-1H-pyrazol-4-yl)pyridin-4-yl)oxy)pyridin-2-yl)-2-oxoimidazolidine-1-carboxamide (66 mg, 46%). ¹H NMR (400 MHz, DMSO-d₆): δ 10.89 (s, 1 H), 8.34 (d, J=5.7 Hz, 1 H), 8.25 (s, 1 H), 7.95 (s, 1 H), 7.90 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 3.84 (s, 3 H), 3.79 (m, 2 H), 3.44 (m, 2 H), 2.80 (s, 3 H), 2.24 (s, 3H); MS (ESI) m/z: 408.2 (M+H+).

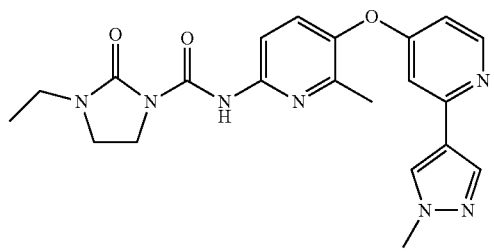 [SMILES: CCN1CCN(C(=O)Nc2ccc(Oc3ccnc(-c4cnn(C)c4)c3)c(C)n2)C1=O]

Example 42

A 0° C. solution of phosgene (15% in toluene, 18.3 mL, 25.6 mmol) in DCM (30 mL) was treated drop-wise with a solution of pyridine (2.1 mL, 26.1 mmol) and Example B18 (2.0 g, 17.5 mmol) in DCM (5 mL), stirred at RT overnight, then concentrated to dryness. The residue was dissolved in DCM (10 mL) and the resultant mixture was added to a stirring solution of Example A4 (4.8 g, 17.1 mmol) and pyridine (2.1 mL, 26.1 mmol) in THF (50 mL). The reaction mixture was stirred overnight at RT. The mixture was concentrated to dryness and the residue was partitioned with EtOAc and with satd. NaHCO$_3$. The aqueous portion was extracted with EtOAc (3×) and the combined organics were dried over Na$_2$SO$_4$ and concentrated in vacuo. The residue was twice purified by silica gel chromatography (6% MeOH/DCM) to afford a yellow oil. The oil was treated with Et$_2$O and the mixture was sonicated for ~30 min. The resulting white solid was collected by filtration, washed with Et$_2$O and dried under vacuum to provide 3-ethyl-N-(6-methyl-5-((2-(1-methyl-1H-pyrazol-4-yl)pyridin-4-yl)oxy)pyridin-2-yl)-2-oxoimidazolidine-1-carboxamide (4.00 g, 55%). $^1$H NMR (400 MHz, DMSO-d$_6$): δ 10.90 (s, 1 H), 8.34 (d, J=5.7 Hz, 1 H), 8.25 (s, 1H), 7.95 (d, J=0.7 Hz, 1 H), 7.90 (d, J=8.8 Hz, 1 H), 7.60 (d, J=8.8 Hz, 1 H), 7.16 (d, J=2.4 Hz, 1 H), 6.59 (dd, J=5.7, 2.4 Hz, 1 H), 3.84 (s, 3 H), 3.80 (m, 2 H), 3.46 (m, 2 H), 3.25 (q, J=7.2 Hz, 2 H), 2.24 (s, 3 H), 1.09 (t, J=7.2 Hz, 3H); MS (ESI) m/z: 422.2 (M+H$^+$).

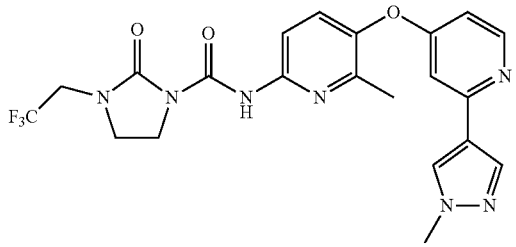 [SMILES: Cc1nc(NC(=O)N2CCN(CC(F)(F)F)C2=O)ccc1Oc1ccnc(-c2cnn(C)c2)c1]

Example 43

A 0° C. solution of phosgene (15% in toluene, 2.5 mL, 3.54 mmol) in DCM (5 mL) was treated drop-wise with a solution of pyridine (0.1 mL, 1.236 mmol) and Example B19 (0.090 g, 0.533 mmol) in DCM (5 mL), stirred at RT for 1 h, then concentrated to dryness. The residue was dissolved in DCM (5 mL), cooled to 0° C., treated with a solution of Example A4 (0.10 g, 0.355 mmol) and pyridine (0.1 mL) in DCM (5 mL), warmed to RT and stirred for 4 h. The solids were removed via filtration, washed with DCM and the filtrate concentrated to dryness. The residue was treated with EtOAc, the solid collected via filtration and purified via reverse-phase chromatography (MeCN/H$_2$O with 0.1% TFA). The combined fractions were treated with satd. NaHCO$_3$, extracted with EtOAc and the organic layer dried over Na$_2$SO$_4$ and concentrated to dryness to afford N-(6-methyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide (75 mg, 44%). $^1$H NMR (400 MHz, DMSO-d$_6$): δ 10.69 (s, 1 H), 8.35 (d, J=5.7 Hz, 1 H), 8.25 (s, 1 H), 7.95 (d, J=0.7 Hz, 1 H), 7.90 (d, J=8.8 Hz, 1 H), 7.63 (d, J=8.8 Hz, 1 H), 7.17 (d, J=2.4 Hz, 1 H), 6.60 (dd, J=5.7, 2.4 Hz, 1 H), 4.11 (q, J=9.6 Hz, 2 H), 3.90 (m, 2 H), 3.84 (s, 3 H), 3.59 (m, 2 H), 2.25 (s, 3H); MS (ESI) m/z: 476.1 (M+H$^+$).

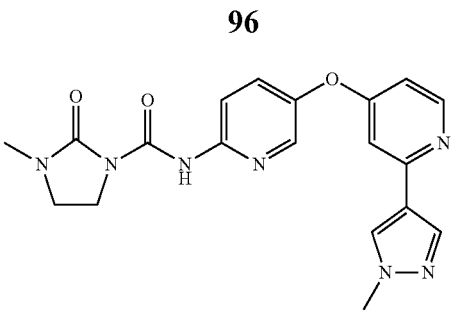

Example 44

A 0° C. solution of phosgene (15% in toluene, 2 mL, 2.84 mmol) in DCM (5 mL) was treated drop-wise with a solution of pyridine (0.1 mL, 1.236 mmol) and 1-methylimidazolidin-2-one (0.056 g, 0.561 mmol) in DCM (5 mL), stirred at RT for 2 h, then concentrated to dryness. The residue was dissolved in DCM (5 mL), cooled to 0° C., treated with a solution of Example A2 (0.10 g, 0.374 mmol) and pyridine (0.1 mL) in DCM (5 mL), warmed to RT and stirred for 4 h. The solids were removed via filtration, washed with DCM and the filtrate concentrated to dryness. The residue was treated with EtOAc/DCM/MeCN, allowed to stand overnight and the resulting solid collected via filtration to afford 3-methyl-N-(5-((2-(1-methyl-1H-pyrazol-4-yl)pyridin-4-yl)oxy)pyridin-2-yl)-2-oxoimidazolidine-1-carboxamide (80 mg, 52%). $^1$H NMR (400 MHz, DMSO-d$_6$): δ 11.04 (s, 1 H), 8.66 (s, 1 H), 8.52 (d, J=6.7 Hz, 1 H), 8.35 (s, 1 H), 8.32 (m, 1 H), 8.12 (d, J=9.1 Hz, 1 H), 7.83 (dd, J=9.1, 2.9 Hz, 1 H), 7.64 (s, 1 H), 7.13 (m, 1 H), 3.90 (s, 3 H), 3.80 (m, 2 H), 3.45 (m, 2 H), 2.80 (s, 3H); MS (ESI) m/z: 394.2 (M+H$^+$).

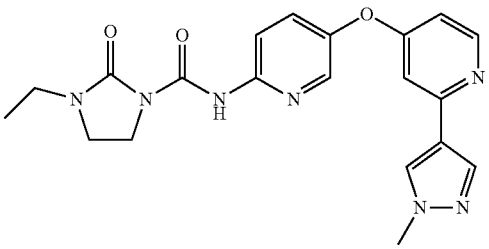 [SMILES: CCN1CCN(C(=O)Nc2ccc(Oc3ccnc(-c4cnn(C)c4)c3)cn2)C1=O]

Example 45

A 0° C. solution of phosgene (15% in toluene, 2 mL, 2.84 mmol) in DCM (5 mL) was treated drop-wise with a solution of pyridine (0.1 mL, 1.236 mmol) and Example B18 (0.085 g, 0.748 mmol) in DCM (5 mL), stirred at RT for 2 h, then concentrated to dryness. The residue was dissolved in DCM (5 mL), cooled to 0° C., treated with a solution of Example A2 (0.10 g, 0.374 mmol) and pyridine (0.1 mL) in DCM (5 mL), warmed to RT and stirred for 4 h. The solids were removed via filtration, washed with DCM and the filtrate concentrated to dryness. The residue was treated with EtOAc/DCM/MeCN, allowed to stand for 3 days and the resulting solid collected via filtration to afford 3-ethyl-N-(5-((2-(1-methyl-1H-pyrazol-4-yl)pyridin-4-yl)oxy)pyridin-2-yl)-2-oxoimidazolidine-1-carboxamide (65 mg, 42%). $^1$H NMR (400 MHz, DMSO-d$_6$): δ 11.05 (s, 1 H), 8.62 (s, 1 H), 8.52 (d, J=6.6 Hz, 1H), 8.32 (m, 1 H), 8.30 (s, 1 H), 8.12 (d, J=9.1 Hz, 1 H), 7.82 (dd, J=9.1, 2.9 Hz, 1 H), 7.62 (s, 1 H), 7.11 (s, 1 H), 3.90 (s, 3 H), 3.81 (m, 2 H), 3.46 (m, 2 H), 3.26 (q, J=7.2 Hz, 2 H), 1.09 (t, J=7.2 Hz, 3H); MS (ESI) m/z: 408.2 (M+H⁺).

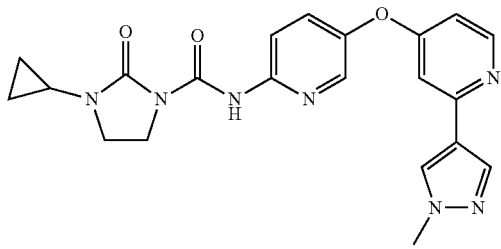 [SMILES: Cn1cc(-c2cc(Oc3ccc(NC(=O)N4CCN(C5CC5)C4=O)nc3)ccn2)cn1]

Example 46

A 0° C. solution of phosgene (15% in toluene, 2 mL, 2.84 mmol) in DCM (5 mL) was treated drop-wise with a solution of pyridine (0.1 mL, 1.236 mmol) and Example B20 (0.071 g, 0.748 mmol) in DCM (5 mL), stirred at RT for 1 h, then concentrated to dryness. The residue was dissolved in DCM (5 mL), cooled to 0° C., treated with a solution of Example A2 (0.10 g, 0.374 mmol) and pyridine (0.1 mL) in DCM (5 mL), warmed to RT and stirred overnight. The mixture was treated with brine, extracted with EtOAc and the organic layer was dried over Na₂SO₄, concentrated to dryness and purified via reverse-phase chromatography (MeCN/H₂O with 0.1% TFA). The combined fractions were treated with satd. NaHCO₃, extracted with EtOAc and the organic layer was dried over Na₂SO₄ and concentrated to dryness to afford 3-cyclopropyl-N-(5-((2-(1-methyl-1H-pyrazol-4-yl)pyridin-4-yl)oxy)pyridin-2-yl)-2-oxoimidazolidine-1-carboxamide (107 mg, 67%). ¹H NMR (400 MHz, DMSO-d₆): δ 10.96 (s, 1 H), 8.37 (d, J=5.7 Hz, 1 H), 8.26 (s, 1 H), 8.23 (d, J=2.9 Hz, 1 H), 8.07 (d, J=9.0 Hz, 1 H), 7.96 (s, 1 H), 7.72 (dd, J=9.0, 2.9 Hz, 1 H), 7.23 (d, J=2.4 Hz, 1 H), 6.69 (dd, J=5.7, 2.4 Hz, 1 H), 3.85 (s, 3 H), 3.75 (m, 2 H), 3.41 (m, 2 H), 2.60 (s, 1 H), 0.70 (d, J=5.4 Hz, 4H); MS (ESI) m/z: 420.2 (M+H⁺).

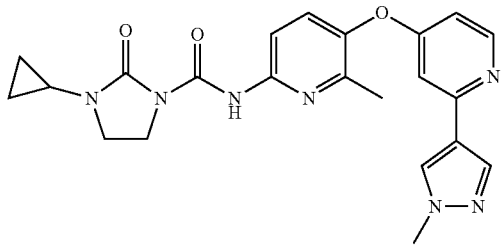 [SMILES: Cc1nc(NC(=O)N2CCN(C3CC3)C2=O)ccc1Oc1ccnc(-c2cnn(C)c2)c1]

Example 47

A 0° C. solution of phosgene (15% in toluene, 2 mL, 2.84 mmol) in DCM (5 mL) was treated drop-wise with a solution of pyridine (0.1 mL, 1.236 mmol) and Example B20 (0.067 g, 0.533 mmol) in DCM (5 mL), stirred at RT for 1 h, then concentrated to dryness. The residue was dissolved in DCM (5 mL), cooled to 0° C., treated with a solution of Example A4 (0.10 g, 0.355 mmol) and pyridine (0.1 mL) in DCM (5 mL), warmed to RT and stirred overnight. The mixture was treated with brine, extracted with EtOAc and the organic layer was dried over Na₂SO₄, concentrated to dryness and purified via reverse-phase chromatography (MeCN/H₂O with 0.1% TFA). The combined fractions were treated with satd. NaHCO₃, extracted with EtOAc and the organic layer was dried over Na₂SO₄ and concentrated to dryness to afford 3-cyclopropyl-N-(6-methyl-5-((2-(1-methyl-1H-pyrazol-4-yl)pyridin-4-yl)oxy)pyridin-2-yl)-2-oxoimidazolidine-1-carboxamide (72 mg, 46%). ¹H NMR (400 MHz, DMSO-d₆): δ 10.90 (s, 1 H), 8.35 (d, J=5.7 Hz, 1 H), 8.26 (s, 1 H), 7.96 (d, J=0.7 Hz, 1 H), 7.89 (d, J=8.8 Hz, 1 H), 7.61 (d, J=8.8 Hz, 1 H), 7.17 (d, J=2.4 Hz, 1H), 6.60 (dd, J=5.7, 2.4 Hz, 1 H), 3.84 (s, 3 H), 3.75 (m, 2 H), 3.42 (m, 2 H), 2.59 (m, 1 H), 2.25 (s, 3 H), 0.71 (d, J=5.4 Hz, 4H); MS (ESI) m/z: 434.2 (M+H⁺).

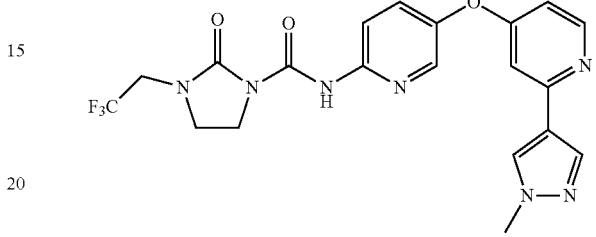

Example 48

A 0° C. solution of phosgene (15% in toluene, 2.5 mL, 3.54 mmol) in DCM (5 mL) was treated drop-wise with a solution of pyridine (0.1 mL, 1.236 mmol) and Example B19 (0.094 g, 0.561 mmol) in DCM (5 mL), stirred at RT for 1 h, then concentrated to dryness. The residue was dissolved in DCM (5 mL), cooled to 0° C., treated with a solution of Example A2 (0.10 g, 0.374 mmol) and pyridine (0.1 mL) in DCM (5 mL), warmed to RT and stirred overnight. The mixture was concentrated to dryness, treated with Et₂O/DCM and sonicated. The resulting solid was collected via filtration to afford N-(5-((2-(1-methyl-1H-pyrazol-4-yl)pyridin-4-yl)oxy)pyridin-2-yl)-2-oxo-3-(2,2,2-trifluoroethyl)imidazolidine-1-carboxamide (95 mg, 55%). ¹H NMR (400 MHz, DMSO-d₆): δ 10.76 (s, 1 H), 8.38 (d, J=5.7 Hz, 1 H), 8.27 (s, 1 H), 8.25 (d, J=2.9 Hz, 1 H), 8.08 (d, J=9.0 Hz, 1 H), 7.97 (s, 1 H), 7.75 (dd, J=9.0, 2.9 Hz, 1 H), 7.24 (d, J=2.4 Hz, 1 H), 6.71 (dd, J=5.7, 2.4 Hz, 1 H), 4.12 (q, J=9.6 Hz, 2 H), 3.88 (m, 2 H), 3.85 (s, 3 H), 3.60 (m, 2H); MS (ESI) m/z: 462.2 (M+H⁺).

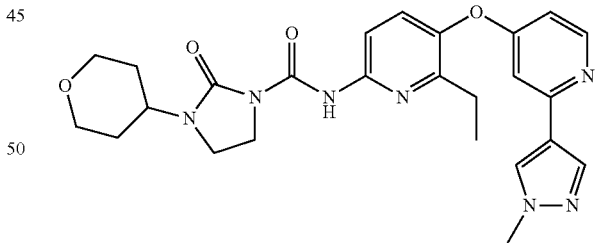

Example 49

A solution of phosgene (15% in toluene, 1.440 g, 2.184 mmol) under Ar, was treated with a solution of Example B1 (0.149 g, 0.874 mmol) and pyridine (0.104 g, 1.310 mmol) in DCM (4 mL), stirred for 15 min, then concentrated to dryness. The residue was treated with a solution of Example A9 (0.129 g, 0.437 mmol) and TEA (0.221 g, 2.184 mmol) in DCM (4 mL), stirred for 0.5 h, then treated with water and EtOAc. The layers were separated, the aqueous layer extracted with additional EtOAc (1×) and the combined organics were washed with brine, dried over Na₂SO₄, concentrated to dryness and purified via reverse-phase chromatography (MeCN/H₂O with 0.1% TFA). The organics were removed under reduced pressure and the aqueous residue was neutralized with satd. NaHCO₃ and extracted with EtOAc (2×). The combined organics were washed with brine, dried over Na₂SO₄ and concentrated to dryness to afford N-(6-ethyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide (130 mg, 60%). ¹H NMR (400 MHz, DMSO-d₆): δ 10.91 (s, 1 H), 8.33 (d, J=5.7 Hz, 1 H), 8.24 (s, 1 H), 7.94 (d, J=0.7 Hz, 1 H), 7.89 (d, J=8.8 Hz, 1 H), 7.59 (d, J=8.8 Hz, 1 H), 7.17 (d, J=2.4 Hz, 1 H), 6.58 (dd, J=5.7, 2.4 Hz, 1 H), 3.90-3.87 (m, 3 H), 3.83 (s, 3 H), 3.81-3.79 (m, 2 H), 3.45 (t, J=8.3 Hz, 2 H), 3.37 (dd, J=12.4, 10.5 Hz, 2 H), 2.56 (q, J=7.5 Hz, 2 H), 1.71 (qd, J=12.2, 4.5 Hz, 2 H), 1.62-1.58 (m, 2 H), 1.10 (t, J=7.5 Hz, 3H); MS (ESI) m/z: 492.3 (M+H⁺).

Example 51

A mixture of Example C1 (0.250 g, 0.598 mmol), K₂CO₃ (0.165 g, 1.197 mmol) and 2-methyl-4-(4,4,5,5-tetramethyl-1,3,2-dioxaborolan-2-yl)pyridine (0.157 g, 0.718 mmol) in dioxane (8 mL) and water (2 mL) was sparged with Ar, treated with Pd(PPh₃)₄ (0.069 g, 0.060 mmol), sparged again with Ar and heated at 95° C. for 36 h. The mixture was cooled to RT, treated with satd. NaHCO₃ and extracted with EtOAc (4×). The combined organics were dried over Na₂SO₄, concentrated to dryness and purified via silica gel chromatography (MeOH/DCM) to afford N-(5-((2'-methyl-[2,4'-bipyridin]-4-yl)oxy)pyridin-2-yl)-2-oxo-3-(tetrahydro-2H-pyran-4-yl)imidazolidine-1-carboxamide (56 mg, 20%). ¹H NMR (400 MHz, DMSO-d₆): δ 10.98 (s, 1 H), 8.59 (d, J=5.6 Hz, 1 H), 8.52 (d, J=5.2 Hz, 1H), 8.27 (d, J=3.0 Hz, 1 H), 8.08 (d, J=9.1 Hz, 1 H), 7.89 (s, 1 H), 7.81-7.74 (m, 2 H), 7.70 (d, J=2.4 Hz, 1 H), 6.97 (dd, J=5.6, 2.4 Hz, 1 H), 3.93-3.78 (m, 5 H), 3.49-3.35 (m, 4 H), 2.52 (s, 3 H), 1.77-1.65 (m, 2 H), 1.62-1.56 (m, 2H); MS (ESI) m/z: 475.2 (M+H⁺).

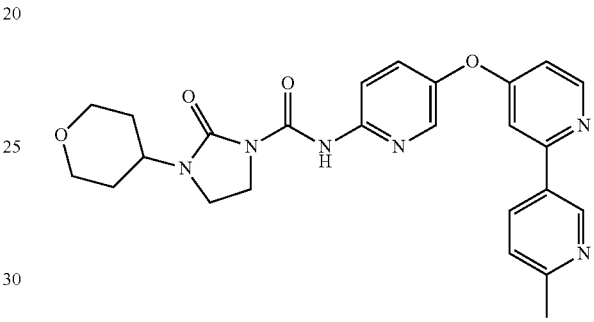

Example 52

A mixture of Example C1 (0.200 g, 0.479 mmol), K₂CO₃ (0.132 g, 0.957 mmol) and 2-methyl-5-(4,4,5,5-tetramethyl-1,3,2-dioxaborolan-2-yl)pyridine (0.126 g, 0.574 mmol) in dioxane (8 mL) and water (2 mL) was sparged with Ar, treated with Pd(PPh₃)₄ (0.055 g, 0.048 mmol), sparged again with Ar and heated at 95° C. overnight. The mixture was cooled to RT, treated with satd. NaHCO₃ and extracted with EtOAc (4×). The combined organics were dried over Na₂SO₄, concentrated to dryness, suspended in MeCN and sonicated. The resulting solid was collected via filtration and dried to afford N-(5-((6'-methyl-[2,3'-bipyridin]-4-yl)oxy)pyridin-2-yl)-2-oxo-3-(tetrahydro-2H-pyran-4-yl)imidazolidine-1-carboxamide (118 mg, 52%). ¹H NMR (400 MHz, DMSO-d₆): δ 10.97 (s, 1 H), 9.09 (d, J=2.3 Hz, 1 H), 8.54 (d, J=5.7 Hz, 1 H), 8.29-8.24 (m, 2 H), 8.07 (d, J=9.0 Hz, 1 H), 7.75 (dd, J=9.0, 2.9 Hz, 1 H), 7.63 (d, J=2.4 Hz, 1 H), 7.33 (d, J=8.2 Hz, 1 H), 6.87 (dd, J=5.7, 2.4 Hz, 1 H), 3.92-3.77 (m, 5 H), 3.48-3.34 (m, 4 H), 2.50 (s, 3 H), 1.77-1.65 (m, 2 H), 1.62-1.55 (m, 2H); MS (ESI) m/z: 475.2 (M+H⁺).

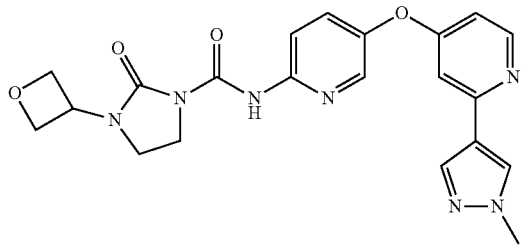 [SMILES: Cn1cc(-c2cc(Oc3ccc(NC(=O)N4CCN(C5COC5)C4=O)nc3)ccn2)cn1]

Example 50

A 0° C. solution of phosgene (15% in toluene, 1.0 mL, 1.401 mmol) in DCM (15 mL) was treated drop-wise with a solution of Example B10 (0.1215 g, 0.855 mmol) and pyridine (0.138 mL, 1.709 mmol) in DCM (2 mL), stirred at 0° C. for 0.5 h then concentrated to dryness. The residue was dissolved in DCM (2 mL), added to a 0° C. solution of Example A2 (0.200 g, 0.748 mmol) and pyridine (0.1 mL, 1.239 mmol) in DCM (5 mL), stirred at 0° C. for 0.5 h, then warmed to RT for 12 h. The mixture was treated with satd. NaHCO₃, the layers separated and the aqueous layer extracted with DCM (3×). The combined organics were dried over Na₂SO₄, concentrated to dryness and purified via silica gel chromatography (MeOH/DCM). The material was dissolved in toluene, concentrated to dryness, dissolved in MeOH and concentrated to dryness to afford N-(5-((2-(1-methyl-1H-pyrazol-4-yl)pyridin-4-yl)oxy)pyridin-2-yl)-3-(oxetan-3-yl)-2-oxoimidazolidine-1-carboxamide (94 mg, 29%). ¹H NMR (400 MHz, DMSO-d₆): δ 10.81 (s, 1 H), 8.32 (d, J=5.7 Hz, 1 H), 8.21 (s, 1 H), 8.18 (d, J=2.9 Hz, 1 H), 8.02 (d, J=9.0 Hz, 1 H), 7.91 (s, 1 H), 7.67 (dd, J=9.0, 2.9 Hz, 1 H), 7.19 (d, J=2.4 Hz, 1 H), 6.65 (dd, J=5.7, 2.5 Hz, 1 H), 5.03-4.95 (m, 1 H), 4.72 (t, J=6.6 Hz, 2 H), 4.64 (t, J=7.4 Hz, 2 H), 3.84-3.78 (m, 5 H), 3.74-3.67 (m, 2H); MS (ESI) m/z: 436.2 (M+H⁺).

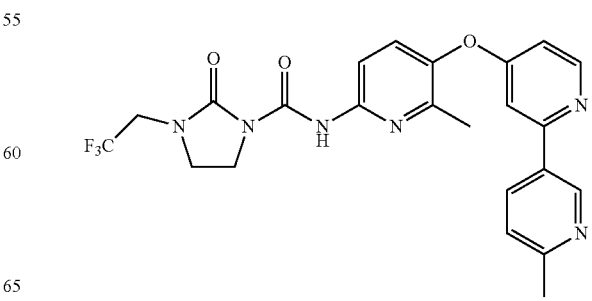

Example 53

A 0° C. solution of phosgene (15% in toluene, 2 mL, 2.84 mmol) in DCM (5 mL) was treated drop-wise with a solution of pyridine (0.1 mL, 1.236 mmol) and Example B19 (0.086 g, 0.513 mmol) in DCM (5 mL), stirred at RT for 1 h, then concentrated to dryness. The residue was dissolved in DCM (5 mL), cooled to 0° C., treated with a solution of Example A10 (0.1 g, 0.342 mmol) and pyridine (0.1 mL) in DCM (5 mL), warmed to RT and stirred overnight. The mixture was concentrated to dryness and purified via reverse-phase chromatography (MeCN/H$_2$O with 0.1% TFA). The combined fractions were treated with satd. NaHCO$_3$, extracted with EtOAc (3×) and the combined organics were dried over Na$_2$SO$_4$ and concentrated to dryness. The material was treated with MeCN and the solid collected via filtration to afford N-(6-methyl-5-((6'-methyl-[2,3'-bipyridin]-4-yl)oxy)pyridin-2-yl)-2-oxo-3-(2,2,2-trifluoroethyl)imidazolidine-1-carboxamide (53 mg, 31%). $^1$H NMR (400 MHz, Acetone-d$_6$): 10.80 (s, 1 H), 9.13 (d, J=2.4 Hz, 1 H), 8.55 (d, J=5.6 Hz, 1 H), 8.28 (dd, J=8.1, 2.4 Hz, 1 H), 8.04 (d, J=8.8 Hz, 1 H), 7.60 (d, J=8.8 Hz, 1 H), 7.49 (d, J=2.4 Hz, 1 H), 7.31 (d, J=8.1 Hz, 1 H), 6.82 (dd, J=5.6, 2.4 Hz, 1 H), 4.12 (q, J=9.4 Hz, 2H), 4.02 (m, 2 H), 3.78 (m, 2 H), 2.53 (s, 3 H), 2.31 (s, 3H); MS (ESI) m/z: 487.2 (M+H$^+$).

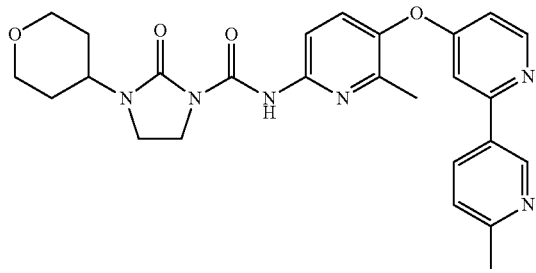

Example 54

A 0° C. solution of Example B1 (0.18 g, 1.058 mmol) and pyridine (0.25 mL, 3.09 mmol) in DCM (5 mL) was treated drop-wise with phosgene (20% in toluene, 1.3 mL, 2.458 mmol), warmed to RT as the cooling bath expired, treated slowly with a solution of Example A10 (0.15 g, 0.513 mmol) and pyridine (0.15 mL, 1.855 mmol) in DCM (5 mL) and stirred at RT overnight. The mixture was treated with satd. NaHCO$_3$, the layers separated and the aqueous layer extracted with EtOAc (4×). The combined organics were dried over Na$_2$SO$_4$, concentrated to dryness and treated with MeCN. The resulting solid was collected via filtration and dried to afford N-(6-methyl-5-((6'-methyl-[2,3'-bipyridin]-4-yl)oxy)pyridin-2-yl)-2-oxo-3-(tetrahydro-2H-pyran-4-yl)imidazolidine-1-carboxamide (74 mg, 29%). $^1$H NMR (400 MHz, DMSO-d$_6$): δ 10.91 (s, 1 H), 9.10 (s, 1 H), 8.55 (s, 1 H), 8.28 (d, J=2.4 Hz, 1 H), 7.92 (s, 1 H), 7.65 (s, 1 H), 7.59 (s, 1 H), 7.36 (s, 1 H), 6.78 (d, J=2.8 Hz, 1 H), 3.93 (m, 3 H), 3.82 (m, 2 H), 3.48 (m, 2 H), 3.40 (m, 2 H), 2.51 (s, 3 H), 2.26 (s, 3 H), 1.73 (m, 2 H), 1.64 (m, 2H); MS (ESI) m/z: 489.2 (M+H$^+$).

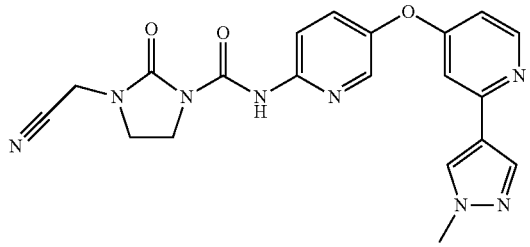 [SMILES: Cn1cc(-c2cc(Oc3ccc(NC(=O)N4CCN(CC#N)C4=O)nc3)ccn2)cn1]

Example 55

A solution of imidazolidin-2-one (0.75 g, 8.71 mmol) in DMF (17 mL) was treated drop-wise with LiHMDS (1M THF, 10.45 mL, 10.45 mmol), stirred for 2 h, treated with bromoacetonitrile (0.607 mL, 8.71 mmol) and heated at 45° C. overnight. The mixture was cooled to RT, treated with satd. NH$_4$Cl, extracted with EtOAc (4×) and the combined organics were washed with brine, dried over Na$_2$SO$_4$, concentrated to dryness and purified via silica gel chromatography (MeOH/DCM) to afford 2-(2-oxoimidazolidin-1-yl)acetonitrile (65 mg, 6%). $^1$H NMR (400 MHz, DMSO-d$_6$): δ 6.38 (s, 1 H), 4.66 (s, 2 H), 3.98-3.93 (m, 2H), 3.91-3.86 (m, 2H); MS (ESI) m/z: 126.1 (M+H$^+$).

A 0° C. solution of phosgene (15% in toluene, 1.37 mL, 1.948 mmol) in DCM (5 mL) was treated drop-wise with a solution of 2-(2-oxoimidazolidin-1-yl)acetonitrile (0.065 g, 0.519 mmol) and pyridine (0.2 mL, 2.473 mmol) in DCM (5 mL), warmed to RT, stirred for 2 h, then concentrated to dryness. The residue was dissolved in DCM (5 mL), cooled to 0° C., treated with a solution of Example A2 (0.069 g, 0.260 mmol) and pyridine (0.2 mL) in DCM (5 mL), warmed to RT and stirred for 3 h. The mixture was treated with satd. NaHCO$_3$, extracted with DCM (3×) and the combined organics were dried over Na$_2$SO$_4$, concentrated to dryness and purified via silica gel chromatography (MeOH/EtOAc) to afford 3-(cyanomethyl)-N-(5-((2-(1-methyl-1H-pyrazol-4-yl)pyridin-4-yl)oxy)pyridin-2-yl)-2-oxoimidazolidine-1-carboxamide (25 mg, 22%). $^1$H NMR (400 MHz, DMSO-d$_6$): δ 10.69 (s, 1 H), 8.37 (d, J=5.7 Hz, 1 H), 8.25-8.24 (m, 2 H), 8.07 (d, J=9.0 Hz, 1 H), 7.96 (d, J=0.7 Hz, 1 H), 7.74 (dd, J=9.0, 2.9 Hz, 1 H), 7.23 (d, J=2.4 Hz, 1 H), 6.70 (dd, J=5.7, 2.4 Hz, 1H), 4.47 (s, 2 H), 3.93-3.84 (m, 5 H), 3.54 (t, J=8.2 Hz, 2H); MS (ESI) m/z: 419.2 (M+H$^+$).

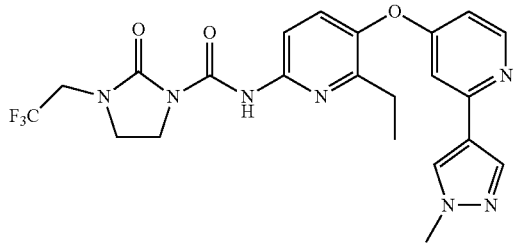 [SMILES: CCc1nc(NC(=O)N2CCN(CC(F)(F)F)C2=O)ccc1Oc1ccnc(-c2cnn(C)c2)c1]

Example 56

A 0° C. solution of phosgene (15% in toluene, 2.0 mL, 2.84 mmol) in DCM (5 mL) was treated drop-wise with a solution of Example B19 (88 mg, 0.523 mmol) and pyridine (110 mg, 1.395 mmol) in DCM (5 mL), warmed to RT, stirred for 1 h, then concentrated to dryness. The residue was dissolved in DCM (5 mL), cooled to 0° C., treated with a solution of Example A9 (103 mg, 0.349 mmol) and pyridine (110 mg, 1.395 mmol) in DCM (5 mL), warmed to RT and stirred overnight. The mixture was concentrated to dryness and purified via reverse-phase chromatography (MeCN/H₂O with 0.1% TFA). The organics were removed under reduced pressure and the aqueous residue was treated with satd. NaHCO₃ and extracted with EtOAc (3×). The combined organics were washed with brine, dried over Na₂SO₄ and concentrated to dryness to afford N-(6-ethyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide (101 mg, 59%). $^1$H NMR (400 MHz, DMSO-d₆): δ 10.71 (s, 1 H), 8.35 (d, J=5.7 Hz, 1 H), 8.25 (s, 1 H), 7.95 (s, 1 H), 7.90 (d, J=8.8 Hz, 1 H), 7.62 (d, J=8.8 Hz, 1 H), 7.18 (d, J=2.4 Hz, 1 H), 6.59 (dd, J=5.7, 2.4 Hz, 1 H), 4.11 (q, J=9.6 Hz, 2 H), 3.88-3.86 (m, 2 H), 3.84 (s, 3 H), 3.60 (t, J=8.2 Hz, 2 H), 2.57 (q, J=7.5 Hz, 2 H), 1.11 (t, J=7.5 Hz, 3H); MS (ESI) m/z: 490.2 (M+H⁺).

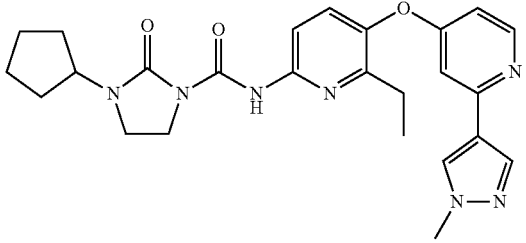 [SMILES: CCc1nc(NC(=O)N2CCN(C3CCCC3)C2=O)ccc1Oc1ccnc(-c2cnn(C)c2)c1]

Example 57

A 0° C. solution of phosgene (15% in toluene, 2.19 mmol, 3.12 mmol) in DCM (5 mL) was treated drop-wise with a solution of Example B14 (90 mg, 0.584 mmol) and pyridine (123 mg, 1.395 mmol) in DCM (5 mL), warmed to RT, stirred for 1 h, then concentrated to dryness. The residue was dissolved in DCM (5 mL), cooled to 0° C., treated with a solution of Example A9 (115 mg, 0.389 mmol) and pyridine (123 mg, 1.558 mmol) in DCM (5 mL), warmed to RT and stirred overnight. The mixture was concentrated to dryness and purified via reverse-phase chromatography (MeCN/H₂O with 0.1% TFA). The organics were removed under reduced pressure and the aqueous residue was treated with satd. NaHCO₃ and extracted with EtOAc (3×). The combined organics were washed with brine, dried over Na₂SO₄ and concentrated to dryness to afford 3-cyclopentyl-N-(6-ethyl-5-((2-(1-methyl-1H-pyrazol-4-yl)pyridin-4-yl)oxy)pyridin-2-yl)-2-oxoimidazolidine-1-carboxamide (118 mg, 63%). $^1$H NMR (400 MHz, DMSO-d₆): δ 10.94 (s, 1 H), 8.34 (d, J=5.7 Hz, 1 H), 8.25 (s, 1 H), 7.95 (s, 1 H), 7.90 (d, J=8.8 Hz, 1 H), 7.60 (d, J=8.8 Hz, 1 H), 7.18 (d, J=2.4 Hz, 1 H), 6.59 (dd, J=5.7, 2.4 Hz, 1 H), 4.19 (t, J=7.4 Hz, 1 H), 3.84 (s, 3 H), 3.80 (t, J=8.2 Hz, 2 H), 3.45 (t, J=8.2 Hz, 2 H), 2.56 (q, J=7.5 Hz, 2 H), 1.78 (d, J=10.8 Hz, 2 H), 1.67-1.52 (br m, 6 H), 1.11 (t, J=7.5 Hz, 3H); MS (ESI) m/z: 476.2 (M+H⁺).

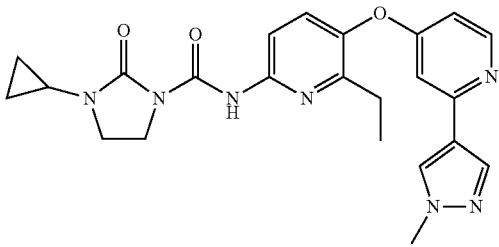 [SMILES: CCc1nc(NC(=O)N2CCN(C3CC3)C2=O)ccc1Oc1ccnc(-c2cnn(C)c2)c1]

Example 58

A 0° C. solution of phosgene (15% in toluene, 2.87 mmol, 4.06 mmol) in DCM (5 mL) was treated drop-wise with a solution of Example B20 (96 mg, 0.762 mmol) and pyridine (161 mg, 2.032 mmol) in DCM (5 mL), warmed to RT, stirred for 1 h, then concentrated to dryness. The residue was dissolved in DCM (5 mL), cooled to 0° C., treated with a solution of Example A9 (150 mg, 0.508 mmol) and pyridine (161 mg, 2.032 mmol) in DCM (5 mL), warmed to RT and stirred overnight. The mixture was concentrated to dryness and purified via reverse-phase chromatography (MeCN/H₂O with 0.1% TFA). The organics were removed under reduced pressure and the aqueous residue was treated with satd. NaHCO₃ and extracted with EtOAc (3×). The combined organics were washed with brine, dried over Na₂SO₄ and concentrated to dryness to afford 3-cyclopropyl-N-(6-ethyl-5-((2-(1-methyl-1H-pyrazol-4-yl)pyridin-4-yl)oxy)pyridin-2-yl)-2-oxoimidazolidine-1-carboxamide (165 mg, 72%). $^1$H NMR (400 MHz, DMSO-d₆): δ 10.90 (s, 1 H), 8.34 (d, J=5.7 Hz, 1 H), 8.25 (s, 1 H), 7.95 (s, 1 H), 7.89 (d, J=8.8 Hz, 1 H), 7.60 (d, J=8.8 Hz, 1 H), 7.18 (d, J=2.4 Hz, 1 H), 6.59 (dd, J=5.7, 2.4 Hz, 1 H), 3.84 (s, 3 H), 3.74-3.73 (m, 2 H), 3.41 (t, J=8.2 Hz, 2 H), 2.58-2.57 (m, 3 H), 1.11 (t, J=7.5 Hz, 3 H), 0.71 (d, J=5.3 Hz, 4H); MS (ESI) m/z: 448.2 (M+H⁺).

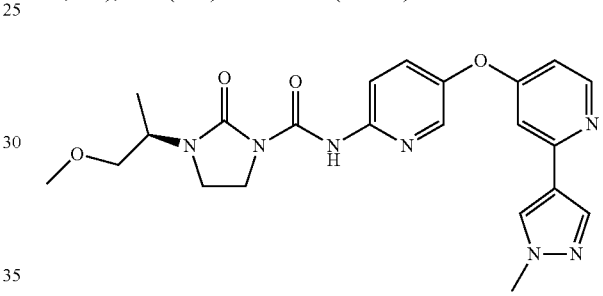

Example 59

A mixture of (R)-1-methoxypropan-2-amine hydrochloride (500 mg, 3.98 mmol) and pyridine (315 mg, 3.98 mmol) in THF (15 mL) was treated drop-wise with 2-chloroethylisocyanate (420 mg, 3.98 mmol) and stirred at RT overnight. The mixture was concentrated to dryness, partitioned between EtOAc and brine and the organic layer dried over Na₂SO₄ and concentrated to dryness to afford (S)-1-(2-chloroethyl)-3-(1-methoxypropan-2-yl)urea (393 mg, 50%). $^1$H NMR (400 MHz, DMSO-d₆): δ 6.08 (s, 1 H), 5.93 (d, J=8.1 Hz, 1 H), 3.71 (m, 1 H), 3.56-3.51 (m, 3 H), 3.30-3.23 (m, 3 H), 3.22 (s, 3 H), 0.98 (d, J=6.7 Hz, 3H).

A −20° C. solution of (S)-1-(2-chloroethyl)-3-(1-methoxypropan-2-yl)urea (393 mg, 2.019 mmol) in THF (10 mL) was treated portion-wise with NaH (60% in mineral oil, 178 mg, 4.44 mmol), warmed to RT and stirred overnight. The mixture was treated with EtOAc, washed with water, then brine, dried over Na₂SO₄ and concentrated to dryness to afford crude (R)-1-(1-methoxypropan-2-yl)imidazolidin-2-one (100% yield assumed) which was used without further purification. MS (ESI) m/z: 159.1 (M+H⁺).

Phosgene (15% in toluene, 1.75 mL, 2.449 mmol) was treated with a solution of (R)-1-(1-methoxypropan-2-yl)imidazolidin-2-one (155 mg, 0.980 mmol) and pyridine (116 mg, 1.470 mmol) in DCM (2 mL), stirred at RT for 15 min, then concentrated to dryness. The residue was dissolved in DCM (2 mL), treated with a solution of Example A2 (131 mg, 0.490 mmol) and TEA (248 mg, 2.449 mmol) in DCM (2 mL) and stirred at RT for 4 h. The mixture was treated with EtOAc, washed with satd. NaHCO₃, then brine, dried over Na₂SO₄, concentrated to dryness and purified via silica gel chromatography (MeOH/EtOAc) to afford (R)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide (38 mg, 17%). ¹H NMR (400 MHz, DMSO-d₆): δ 10.98 (s, 1 H), 8.37 (d, J=5.7 Hz, 1 H), 8.25 (s, 1 H), 8.22-8.21 (m, 1 H), 8.06-8.05 (m, 1 H), 7.95 (d, J=0.7 Hz, 1 H), 7.72 (dd, J=9.0, 2.9 Hz, 1 H), 7.22 (d, J=2.4 Hz, 1 H), 6.69 (dd, J=5.7, 2.4 Hz, 1 H), 4.10-4.09 (m, 1 H), 3.84 (s, 3 H), 3.81-3.79 (m, 2 H), 3.40-3.39 (m, 4 H), 3.26 (s, 3 H), 1.09 (d, J=6.9 Hz, 3H); MS (ESI) m/z: 452.2 (M+H⁺).

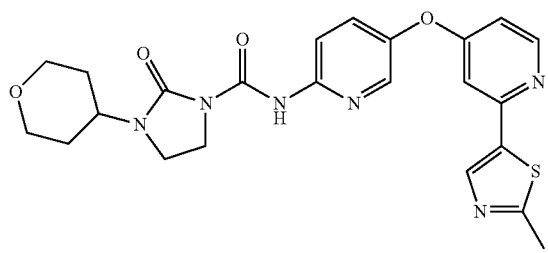 [SMILES: Cc1ncc(-c2cc(Oc3ccc(NC(=O)N4CCN(C5CCOCC5)C4=O)nc3)ccn2)s1]

Example 60

A 0° C. solution of phosgene (15% in toluene, 0.650 mL, 0.911 mmol) in DCM (8 mL) was treated with a solution of Example B1 (0.135 g, 0.793 mmol) and pyridine (0.080 mL, 0.991 mmol) in DCM (2 mL), stirred for 0.5 h, then warmed to RT and concentrated to dryness. The residue was dissolved in DCM (2 mL), added to a solution of Example A11 (0.200 g, 0.703 mmol) and pyridine (0.06 mL, 0.743 mmol) in DCM (5 mL) and stirred at RT overnight. The mixture was treated with satd. NaHCO₃, extracted with EtOAc (3×) and the combined organics were dried over Na₂SO₄, concentrated to dryness and purified via silica gel chromatography (MeOH/EtOAc). The material was re-purified via silica gel chromatography (MeOH/DCM) to afford N-(5-((2-(2-methylthiazol-5-yl)pyridin-4-yl)oxy)pyridin-2-yl)-2-oxo-3-(tetrahydro-2H-pyran-4-yl)imidazolidine-1-carboxamide (63 mg, 19%). ¹H NMR (400 MHz, DMSO-d₆): δ 10.97 (s, 1 H), 8.40 (d, J=5.8 Hz, 1 H), 8.32 (s, 1 H), 8.25-8.24 (m, 1 H), 8.07-8.06 (m, 1 H), 7.74 (dd, J=9.0, 2.9 Hz, 1 H), 7.59 (d, J=2.4 Hz, 1 H), 6.80 (dd, J=5.8, 2.4 Hz, 1 H), 3.93-3.78 (m, 5 H), 3.48-3.35 (m, 4 H), 2.65 (s, 3 H), 1.77-1.65 (m, 2 H), 1.62-1.58 (m, 2H); MS (ESI) m/z: 481.1 (M+H⁺).

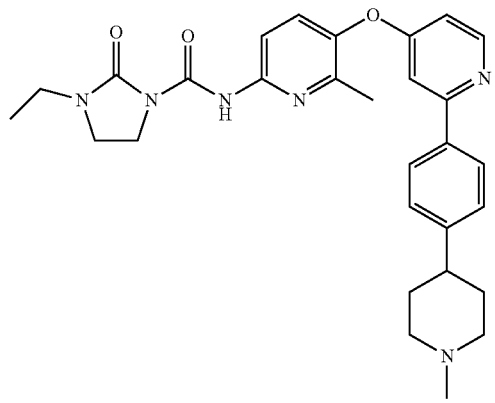 [SMILES: CCN1CCN(C(=O)Nc2ccc(Oc3ccnc(-c4ccc(C5CCN(C)CC5)cc4)c3)c(C)n2)C1=O]

Example 61

A 0° C. solution of phosgene (15% in toluene, 1.41 mL, 2.003 mmol) in DCM (5 mL) was treated drop-wise with a solution of Example B18 (61 mg, 0.534 mmol) and pyridine (0.2 mL, 2.473 mmol) in DCM (5 mL), warmed to RT, stirred for 2 h, then concentrated to dryness. The residue was dissolved in DCM (5 mL), cooled to 0° C., treated with a solution of Example A12 (0.10 g, 0.267 mmol), pyridine (0.2 mL, 2.473 mmol) and DIEA (0.2 mL, 1.145 mmol) in DCM (5 mL), warmed to RT and stirred for 3 h. The mixture was treated with satd. NaHCO₃, extracted with EtOAc (3×) and the combined organics were washed with 1N NaOH, then brine, dried over Na₂SO₄ and concentrated to dryness. The material was treated with EtOAc and the resulting solid collected via filtration to afford 3-ethyl-N-(6-methyl-5-((2-(4-(1-methylpiperidin-4-yl)phenyl)pyridin-4-yl)oxy)pyridin-2-yl)-2-oxoimidazolidine-1-carboxamide (35 mg, 26%). ¹H NMR (400 MHz, DMSO-d₆): δ 10.91 (s, 1 H), 8.50 (d, J=5.6 Hz, 1 H), 7.96 (d, J=8.1 Hz, 2 H), 7.91 (d, J=8.8 Hz, 1 H), 7.64 (d, J=8.9 Hz, 1 H), 7.41 (d, J=2.4 Hz, 1 H), 7.32 (d, J=8.1 Hz, 2 H), 6.75 (dd, J=5.7, 2.4 Hz, 1H), 3.80 (m, 2 H), 3.46 (m, 2 H), 3.26 (m, 2 H), 3.11 (br m, 2 H), 2.62 (br m, 2 H), 2.43 (s, 3H), 2.25 (s, 3 H), 1.89-1.68 (m, 5 H), 1.09 (t, J=7.2 Hz, 3H); MS (ESI) m/z: 515.3 (M+H⁺).

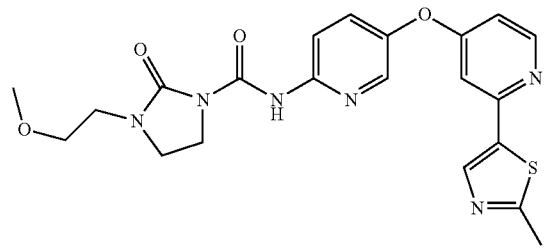

Example 62

A 0° C. solution of phosgene (15% in toluene, 0.341 mL, 0.478 mmol) in DCM (2 mL) was treated with a solution of Example B3 (0.060 g, 0.416 mmol) and pyridine (0.042 mL, 0.520 mmol) in DCM (0.5 mL), stirred for 0.5 h, then warmed to RT and concentrated to dryness. The residue was dissolved in DCM (2 mL), added to a solution of Example A11 (0.100 g, 0.352 mmol) and pyridine (0.06 mL, 0.743 mmol) in DCM (5 mL) and stirred at RT for 1 h. The mixture was treated with water, extracted with DCM (3×) and the combined organics were dried over Na₂SO₄, concentrated to dryness and purified via silica gel chromatography (MeOH/EtOAc) to afford 3-(2-methoxyethyl)-N-(5-((2-(2-methylthiazol-5-yl)pyridin-4-yl)oxy)pyridin-2-yl)-2-oxoimidazolidine-1-carboxamide (47 mg, 29%). ¹H NMR (400 MHz, DMSO-d₆): δ 10.96 (s, 1 H), 8.40 (d, J=5.8 Hz, 1 H), 8.32 (s, 1 H), 8.25 (d, J=2.9 Hz, 1 H), 8.08 (d, J=9.0 Hz, 1 H), 7.74 (dd, J=9.0, 2.9 Hz, 1 H), 7.60 (d, J=2.4 Hz, 1 H), 6.80 (dd, J=5.8, 2.4 Hz, 1 H), 3.83-3.78 (m, 2 H), 3.53-3.47 (m, 4H), 3.41-3.37 (m, 2 H), 3.26 (s, 3 H), 2.65 (s, 3H); MS (ESI) m/z: 455.2 (M+H⁺).

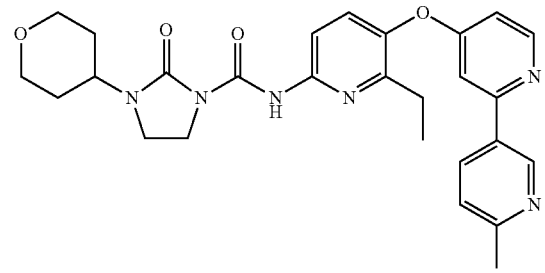 [SMILES: CCc1nc(NC(=O)N2CCN(C3CCOCC3)C2=O)ccc1Oc1ccnc(-c2ccc(C)nc2)c1]

Example 63

A mixture of Example A13 (0.5 g, 2.002 mmol), 2-methyl-5-(4,4,5,5-tetramethyl-1,3,2-dioxaborolan-2-yl)pyridine (0.570 g, 2.60 mmol) and $K_2CO_3$ (0.720 g, 5.21 mmol) in dioxane (17 mL) and water (3 mL) was sparged with Ar, treated with $Pd(PPh_3)_4$ (0.23 g, 0.199 mmol) and heated at 85° C. overnight. The mixture was cooled to RT, diluted with EtOAc and the solids removed via filtration through diatomaceous earth. The filtrate was concentrated to dryness, purified via silica gel chromatography (MeOH/DCM), then further purified via reverse-phase chromatography (MeCN/$H_2O$ with 0.1% TFA). The material was treated with MeCN, heated, then cooled to RT and the solid collected via filtration to afford 6-ethyl-5-((6'-methyl-[2,3'-bipyridin]-4-yl)oxy)pyridin-2-amine (320 mg, 52%). $^1$H NMR (400 MHz, DMSO-$d_6$): δ 9.07 (d, J=2.4 Hz, 1 H), 8.48 (d, J=5.7 Hz, 1 H), 8.25 (dd, J=8.1, 2.4 Hz, 1 H), 7.51 (d, J=2.4 Hz, 1 H), 7.33 (d, J=8.1 Hz, 1 H), 7.20 (d, J=8.7 Hz, 1 H), 6.68 (dd, J=5.7, 2.4 Hz, 1 H), 6.36 (d, J=8.7 Hz, 1 H), 5.96-5.94 (m, 2 H), 2.50 (s, 3 H), 2.41 (q, J=7.5 Hz, 2 H), 1.05 (t, J=7.5 Hz, 3H); MS (ESI) m/z: 307.2 (M+H$^+$).

A 0° C. solution of Example B1 (0.19 g, 1.116 mmol) and pyridine (0.26 mL, 3.21 mmol) in DCM (5 mL) was treated drop-wise with phosgene (20% in toluene, 1.4 mL, 2.65 mmol) and warmed to RT over 0.5 h. The mixture was treated slowly with a solution of 6-ethyl-5-((6'-methyl-[2,3'-bipyridin]-4-yl)oxy)pyridin-2-amine (0.16 g, 0.522 mmol) and pyridine (0.16 mL, 1.978 mmol) in DCM (5 mL) and stirred at RT overnight. The mixture was treated with satd. NaHCO$_3$, extracted with EtOAc (4×) and the combined organics were dried over MgSO$_4$, concentrated to dryness, purified via silica gel chromatography (MeOH/DCM), then re-purified via reverse-phase chromatography (MeCN/H$_2$O with 0.1% TFA). The combined fractions were treated with satd. NaHCO$_3$, extracted with DCM (5×) and the combined organics were dried over MgSO$_4$ and concentrated to dryness to afford N-(6-ethyl-5-((6'-methyl-[2,3'-bipyridin]-4-yl)oxy)pyridin-2-yl)-2-oxo-3-(tetrahydro-2H-pyran-4-yl)imidazolidine-1-carboxamide (19 mg, 7%). $^1$H NMR (400 MHz, DMSO-$d_6$): δ 10.93 (s, 1 H), 9.09 (d, J=2.4 Hz, 1 H), 8.52 (d, J=5.7 Hz, 1 H), 8.28 (dd, J=8.1, 2.4 Hz, 1 H), 7.90 (d, J=8.8 Hz, 1 H), 7.64 (d, J=8.8 Hz, 1 H), 7.59 (d, J=2.4 Hz, 1 H), 7.33 (d, J=8.2 Hz, 1H), 6.77 (dd, J=5.7, 2.4 Hz, 1 H), 3.94-3.84 (m, 3 H), 3.83-3.79 (m, 2 H), 3.46 (t, J=8.2 Hz, 2 H), 3.38 (t, J=11.6 Hz, 2 H), 2.58 (q, J=7.5 Hz, 2 H), 2.50 (s, 3 H), 1.72 (dd, J=12.3, 4.5 Hz, 2 H), 1.62 (s, 2 H), 1.12 (t, J=7.5 Hz, 3H); MS (ESI) m/z: 503.3 (M+H$^+$).

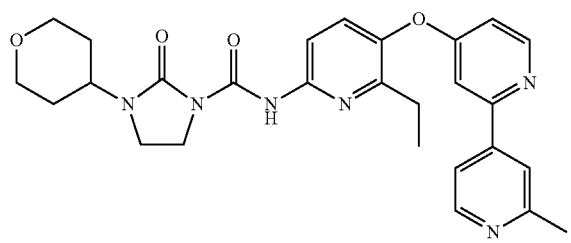 [SMILES: CCc1nc(NC(=O)N2CCN(C3CCOCC3)C2=O)ccc1Oc1ccnc(-c2ccnc(C)c2)c1]

Example 64

A mixture of Example A13 (0.5 g, 2.002 mmol), 2-methyl-4-(4,4,5,5-tetramethyl-1,3,2-dioxaborolan-2-yl)pyridine (0.570 g, 2.60 mmol) and K$_2$CO$_3$ (0.720 g, 5.21 mmol) in dioxane (17 mL) and water (3 mL) was sparged with Ar, treated with Pd(PPh$_3$)$_4$ (0.23 g, 0.199 mmol) and heated at 85° C. overnight. The mixture was cooled to RT, diluted with EtOAc and the solids removed via filtration through diatomaceous earth. The filtrate was concentrated to dryness, purified twice via silica gel chromatography (MeOH/DCM), then further purified via reverse-phase chromatography (MeCN/H$_2$O with 0.1% TFA). Combined fractions were neutralized, pooled and concentrated to dryness. The material was treated with MeCN, heated, then cooled to RT and the solid collected via filtration to afford 6-ethyl-5-((2'-methyl-[2,4'-bipyridin]-4-yl)oxy)pyridin-2-amine (260 mg, 42%). $^1$H NMR (400 MHz, DMSO-$d_6$): δ 8.52 (m, 2 H), 7.88 (s, 1 H), 7.77 (d, J=5.4 Hz, 1 H), 7.60 (d, J=2.4 Hz, 1 H), 7.21 (d, J=8.7 Hz, 1 H), 6.76 (dd, J=5.7, 2.4 Hz, 1 H), 6.36 (d, J=8.7 Hz, 1H), 5.98-5.96 (m, 2 H), 2.53 (s, 3 H), 2.40 (q, J=7.6 Hz, 2 H), 1.05 (t, J=7.5 Hz, 3H); MS (ESI) m/z: 307.2 (M+H$^+$).

A 0° C. solution of Example B1 (0.19 g, 1.116 mmol) and pyridine (0.26 mL, 3.21 mmol) in DCM (5 mL) was treated drop-wise with phosgene (20% in toluene, 1.4 mL, 2.65 mmol), warmed to RT over 0.5 h, then treated slowly with a solution of 6-ethyl-5-((2'-methyl-[2,4'-bipyridin]-4-yl)oxy)pyridin-2-amine (0.13 g, 0.424 mmol) and pyridine (0.16 mL, 1.978 mmol) in DCM (5 mL) and stirred at RT overnight. The mixture was treated with satd. NaHCO$_3$, extracted with EtOAc (4×) and the combined organics were dried over MgSO$_4$, concentrated to dryness, purified via silica gel chromatography (MeOH/DCM), then re-purified via reverse-phase chromatography (MeCN/H$_2$O with 0.1% TFA). The organics were removed under reduced pressure, the aqueous residue treated with satd. NaHCO$_3$, extracted with DCM (5×) and the combined organics were dried over MgSO$_4$ and concentrated to dryness to afford N-(6-ethyl-5-((2'-methyl-[2,4'-bipyridin]-4-yl)oxy)pyridin-2-yl)-2-oxo-3-(tetrahydro-2H-pyran-4-yl)imidazolidine-1-carboxamide (8 mg, 4%). $^1$H NMR (400 MHz, DMSO-$d_6$): δ 10.93 (s, 1 H), 8.56 (d, J=5.7 Hz, 1 H), 8.52 (d, J=5.3 Hz, 1 H), 7.93-7.89 (m, 2 H), 7.67 (d, J=2.4 Hz, 1 H), 7.68-7.66 (m, 1 H), 7.64 (s, 1 H), 6.86 (dd, J=5.7, 2.4 Hz, 1 H), 3.94-3.78 (m, 5 H), 3.49-3.34 (m, 4 H), 2.58 (q, J=7.5 Hz, 2 H), 2.53 (s, 3H), 1.78-1.66 (m, 2 H), 1.64-1.57 (m, 2 H), 1.12 (t, J=7.5 Hz, 3H); MS (ESI) m/z: 503.3 (M+H$^+$).

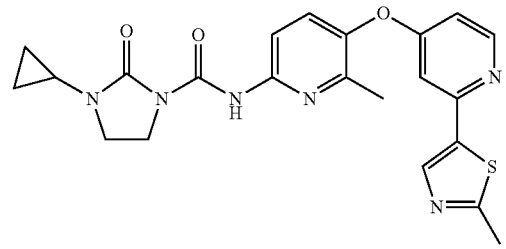 [SMILES: Cc1ncc(-c2cc(Oc3ccc(NC(=O)N4CCN(C5CC5)C4=O)nc3C)ccn2)s1]

Example 65

A 0° C. solution of phosgene (15% in toluene, 2 mL, 2.84 mmol) in DCM (5 mL) was treated drop-wise with a solution of pyridine (0.1 mL, 1.236 mmol) and Example B20 (0.063 g, 0.503 mmol) in DCM (5 mL), stirred at RT for 1.5 h, then concentrated to dryness. The residue was dissolved in DCM (5 mL), cooled to 0° C., treated with a solution of Example A14 (0.1 g, 0.335 mmol) and pyridine (0.1 mL) in DCM (5 mL), warmed to RT and stirred overnight. The mixture was treated with EtOAc, washed with satd. NaHCO$_3$, then brine, dried over Na$_2$SO$_4$, concentrated to dryness and purified via reverse-phase chromatography (MeCN/H₂O with 0.1% TFA). The combined fractions were treated with satd. NaHCO₃, extracted with EtOAc and the organic layer was washed with brine, dried over Na₂SO₄ and concentrated to dryness to afford 3-cyclopropyl-N-(6-methyl-5-((2-(2-methylthiazol-5-yl)pyridin-4-yl)oxy)pyridin-2-yl)-2-oxoimidazolidine-1-carboxamide (70 mg, 46%). ¹H NMR (400 MHz, DMSO-d₆): δ 10.90 (s, 1 H), 8.38 (d, J=5.8 Hz, 1 H), 8.33 (s, 1 H), 7.90 (d, J=8.8 Hz, 1 H), 7.63 (d, J=8.8 Hz, 1 H), 7.56 (d, J=2.4 Hz, 1 H), 6.70 (dd, J=5.8, 2.4 Hz, 1 H), 3.75 (m, 2 H), 3.41 (m, 2 H), 2.65 (s, 3 H), 2.60 (m, 1 H), 2.25 (s, 3H), 0.71 (m, 4H); MS (ESI) m/z: 451.2 (M+H⁺).

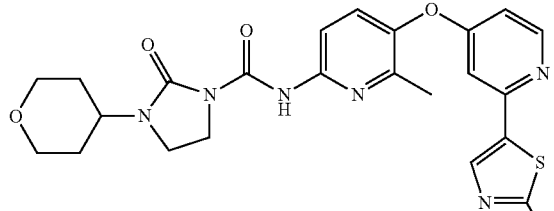

Example 66

A 0° C. solution of phosgene (15% in toluene, 0.849 mL, 1.190 mmol) in DCM (5 mL) was treated drop-wise with a solution of Example B1 (0.150 g, 0.881 mmol) and pyridine (0.10 mL, 1.234 mmol) in DCM (2 mL), stirred for 0.5 h, then concentrated to dryness. The residue was dissolved in DCM (1 mL), added to a solution of Example A14 (0.110 g, 0.369 mmol) and pyridine (0.044 mL, 0.542 mmol) in DCM (3 mL) and stirred at RT overnight. The mixture was treated with satd. NaHCO₃, the layers separated and the aqueous layer was extracted with additional DCM (3×). The combined organics were dried over Na₂SO₄, concentrated to dryness and purified via silica gel chromatography (MeOH/EtOAc) to afford N-(6-methyl-5-((2-(2-methylthiazol-5-yl)pyridin-4-yl)oxy)pyridin-2-yl)-2-oxo-3-(tetrahydro-2H-pyran-4-yl)imidazolidine-1-carboxamide (141 mg, 77%). ¹H NMR (400 MHz, DMSO-d₆): δ 10.90 (s, 1 H), 8.38 (d, J=5.8 Hz, 1 H), 8.32 (s, 1 H), 7.90 (d, J=8.8 Hz, 1 H), 7.63 (d, J=8.8 Hz, 1 H), 7.55 (d, J=2.4 Hz, 1 H), 6.69 (dd, J=5.8, 2.4 Hz, 1 H), 3.94-3.77 (m, 5 H), 3.49-3.34 (m, 4 H), 2.65 (s, 3 H), 2.24 (s, 3 H), 1.77-1.66 (m, 2H), 1.63-1.57 (m, 2H); MS (ESI) m/z: 495.2 (M+H⁺).

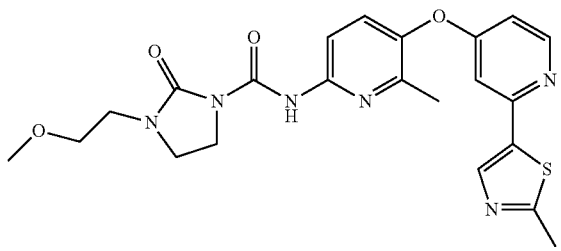

Example 67

A 0° C. solution of phosgene (15% in toluene, 1.00 mL, 1.405 mmol) in DCM (10 mL) was treated drop-wise with a solution of Example B3 (0.150 g, 1.040 mmol) and pyridine (0.118 mL, 1.457 mmol) in DCM (2 mL), stirred for 0.5 h, then concentrated to dryness. The residue was dissolved in DCM (1 mL), added to a solution of Example A14 (0.110 g, 0.369 mmol) and pyridine (0.057 mL, 0.71 mmol) in DCM (3 mL) and stirred at RT overnight. The mixture was treated with satd. NaHCO₃, the layers separated and the aqueous layer was extracted with additional DCM (3×). The combined organics were dried over Na₂SO₄, concentrated to dryness and purified via silica gel chromatography (MeOH/EtOAc). The material was lyophilized and dried, treated with toluene, sonicated and concentrated to dryness to afford 3-(2-methoxyethyl)-N-(6-methyl-5-((2-(2-methylthiazol-5-yl)pyridin-4-yl)oxy)pyridin-2-yl)-2-oxoimidazolidine-1-carboxamide (91 mg, 52%). ¹H NMR (400 MHz, DMSO-d₆): δ 10.89 (s, 1 H), 8.38 (d, J=5.8 Hz, 1 H), 8.32 (s, 1 H), 7.90 (d, J=8.8 Hz, 1 H), 7.63 (d, J=8.8 Hz, 1 H), 7.55 (d, J=2.4 Hz, 1 H), 6.70 (dd, J=5.8, 2.4 Hz, 1 H), 3.83-3.77 (m, 2 H), 3.54-3.47 (m, 4 H), 3.41-3.36 (m, 2 H), 3.26 (s, 3 H), 2.65 (s, 3 H), 2.25 (s, 3H); MS (ESI) m/z: 469.2 (M+H⁺).

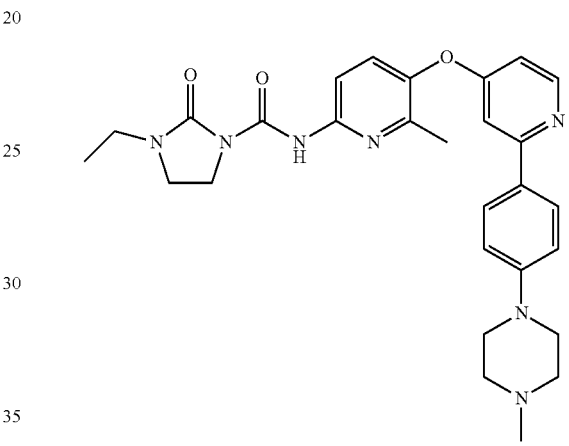

Example 68

A mixture of Example A6 (0.676 g, 2.55 mmol), 1-methyl-4-(4-(4,4,5,5-tetramethyl-1,3,2-dioxaborolan-2-yl)phenyl)piperazine (1 g, 3.31 mmol), K₂CO₃ (1.055 g, 7.64 mmol) and Pd(PPh₃)₄ (0.147 g, 0.127 mmol) in dioxane (8 mL) was sparged with Ar and heated at 90° C. overnight. The mixture was cooled to RT, treated with brine, extracted with EtOAc (4×) and the combined organics were dried over Na₂SO₄, concentrated to dryness and purified via silica gel chromatography (MeOH/DCM) to afford 1-methyl-4-(4-(4-((2-methyl-6-nitropyridin-3-yl)oxy)pyridin-2-yl)phenyl)piperazine (333 mg, 32%). ¹H NMR (400 MHz, DMSO-d₆): δ 8.55 (d, J=5.6 Hz, 1 H), 8.22 (d, J=8.7 Hz, 1 H), 7.95 (d, J=8.8 Hz, 2 H), 7.81 (d, J=8.7 Hz, 1 H), 7.58 (d, J=2.3 Hz, 1 H), 6.98 (d, J=8.8 Hz, 2 H), 6.94 (dd, J=5.6, 2.3 Hz, 1 H), 3.24-3.18 (m, 4 H), 2.52 (s, 3 H), 2.45-2.41 (m, 4 H), 2.21 (s, 3H); MS (ESI) m/z: 406.2 (M+H⁺).

A solution of 1-methyl-4-(4-(4-((2-methyl-6-nitropyridin-3-yl)oxy)pyridin-2-yl)phenyl)piperazine (0.333 g, 0.821 mmol) in MeOH (20 mL) was treated with 10% Pd/C (50% w/w water, 0.087 g, 0.082 mmol) and hydrogenated (1 atm) overnight. The solids were removed via filtration through diatomaceous earth, washed with MeOH and the filtrate concentrated to dryness to afford 6-methyl-5-((2-(4-(4-methylpiperazin-1-yl)phenyl)pyridin-4-yl)oxy)pyridin-2-amine (247 mg, 80%). ¹H NMR (400 MHz, DMSO-d₆): δ 8.38 (d, J=5.7 Hz, 1 H), 7.85 (d, J=8.8 Hz, 2 H), 7.21-7.20 (m, 2 H), 6.98 (d, J=8.8 Hz, 2 H), 6.57 (dd, J=5.6, 2.4 Hz, 1 H), 6.35 (d, J=8.7 Hz, 1 H), 5.94 (s, 2 H), 3.20 (t, J=4.7 Hz, 4 H), 2.45 (s, 4H), 2.22 (s, 3 H), 2.07 (s, 3H); MS (ESI) m/z: 376.2 (M+H$^+$).

A 0° C. solution of phosgene (15% in toluene, 1.41 mL, 2.003 mmol) in DCM (5 mL) was treated drop-wise with a solution of Example B18 (61 mg, 0.534 mmol) and pyridine (0.2 mL, 2.473 mmol) in DCM (5 mL), warmed to RT, stirred for 2 h, then concentrated to dryness. The residue was dissolved in DCM (5 mL), cooled to 0° C., treated with a solution of 6-methyl-5-((2-(4-(4-methylpiperazin-1-yl)phenyl)pyridin-4-yl)oxy)pyridin-2-amine (0.10 g, 0.266 mmol) and DIEA (0.2 mL, 1.145 mmol) in DCM (5 mL), warmed to RT and stirred overnight. The mixture was treated with 1N NaOH, extracted with EtOAc (3×) and the combined organics were washed with 1N NaOH, then brine, dried over Na$_2$SO$_4$, concentrated to dryness and purified via reverse-phase chromatography (MeCN/H$_2$O with 0.1% TFA). The organics were removed under reduced pressure and the aqueous residue was treated with K$_2$CO$_3$ and extracted with 5:1 DCM/THF (3×). The combined organics were dried over Na$_2$SO$_4$ and concentrated to dryness to afford 3-ethyl-N-(6-methyl-5-((2-(4-(4-methylpiperazin-1-yl)phenyl)pyridin-4-yl)oxy)pyridin-2-yl)-2-oxoimidazolidine-1-carboxamide (54 mg, 39%). $^1$H NMR (400 MHz, DMSO-d$_6$): δ 10.90 (s, 1 H), 8.42 (d, J=5.6 Hz, 1 H), 7.92-7.86 (m, 3 H), 7.62 (d, J=8.9 Hz, 1 H), 7.32 (d, J=2.4 Hz, 1 H), 6.97 (d, J=8.8 Hz, 2 H), 6.63 (dd, J=5.7, 2.3 Hz, 1 H), 3.80 (t, J=8.3 Hz, 2 H), 3.46 (t, J=8.2 Hz, 2 H), 3.26-3.25 (m, 2 H), 3.20 (s, 4 H), 2.43 (s, 4 H), 2.25 (s, 3 H), 2.21 (s, 3 H), 1.09 (t, J=7.2 Hz, 3H); MS (ESI) m/z: 516.3 (M+H$^+$).

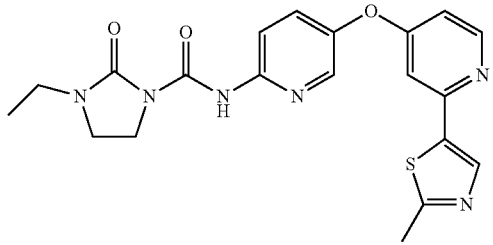

Example 69

A solution of phosgene (15% in toluene, 0.928 g, 1.407 mmol) was treated with a solution of Example B18 (0.080 g, 0.703 mmol) and pyridine (0.028 mL, 0.352 mmol) in DCM (3 mL), stirred at RT for 15 min, then concentrated to dryness. The residue was treated with a solution of Example A11 (0.1 g, 0.352 mmol) and TEA (0.178 g, 1.758 mmol) in DCM (3 mL) and stirred at RT for 1 h. The mixture was treated with water, extracted with DCM (2×) and the combined organics were washed with brine, dried over Na$_2$SO$_4$, concentrated to dryness and purified via silica gel chromatography (MeOH/DCM). The material was further purified via reverse-phase chromatography (MeCN/H$_2$O with 0.1% TFA); combined fractions were treated with satd. NaHCO$_3$, extracted with EtOAc (2×) and the combined organics were washed with brine, dried over Na$_2$SO$_4$ and concentrated to dryness to afford 3-ethyl-N-(5-((2-(2-methylthiazol-5-yl)pyridin-4-yl)oxy)pyridin-2-yl)-2-oxoimidazolidine-1-carboxamide (72 mg, 48%). $^1$H NMR (400 MHz, DMSO-d$_6$): δ 10.99 (s, 1 H), 8.40 (d, J=5.8 Hz, 1 H), 8.32 (s, 1 H), 8.24 (d, J=2.9 Hz, 1 H), 8.07 (d, J=9.0 Hz, 1H), 7.74 (dd, J=9.0, 2.9 Hz, 1 H), 7.60 (d, J=2.4 Hz, 1 H), 6.80 (dd, J=5.8, 2.4 Hz, 1 H), 3.80-3.79 (m, 2 H), 3.46 (m, 2 H), 3.26 (q, J=7.0 Hz, 2 H), 2.65 (s, 3 H), 1.09 (t, J=7.2 Hz, 3H); MS (ESI) m/z: 425.1 (M+H$^+$).

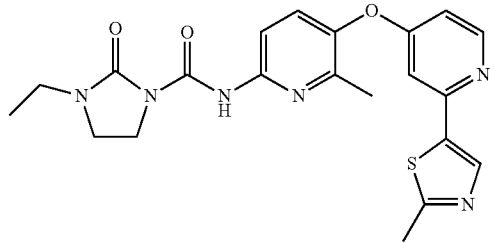 [SMILES: CCN1CCN(C(=O)Nc2ccc(Oc3ccnc(-c4cnc(C)s4)c3)c(C)n2)C1=O]

Example 70

A solution of phosgene (15% in toluene, 1.105 g, 1.676 mmol) was treated with a solution of Example B18 (0.057 g, 0.503 mmol) and pyridine (0.136 mL, 1.676 mmol) in DCM (3 mL), stirred at RT for 15 min, then concentrated to dryness. The residue was treated with a solution of Example A14 (0.1 g, 0.335 mmol) and TEA (0.140 mL, 1.005 mmol) in DCM (3 mL) and stirred at RT for 1 h. The mixture was treated with water, extracted with DCM (2×) and the combined organics were washed with brine, dried over Na$_2$SO$_4$, concentrated to dryness and purified reverse-phase chromatography (MeCN/H$_2$O with 0.1% TFA). The combined fractions were treated with satd. NaHCO$_3$, extracted with EtOAc (2×) and the combined organics were washed with brine, dried over Na$_2$SO$_4$ and concentrated to dryness to afford 3-ethyl-N-(6-methyl-5-((2-(2-methylthiazol-5-yl)pyridin-4-yl)oxy)pyridin-2-yl)-2-oxoimidazolidine-1-carboxamide (101 mg, 69%). $^1$H NMR (400 MHz, DMSO-d$_6$): δ 10.91 (s, 1 H), 8.38 (d, J=5.8 Hz, 1 H), 8.32 (s, 1 H), 7.90 (d, J=8.8 Hz, 1 H), 7.62 (d, J=8.8 Hz, 1 H), 7.55 (d, J=2.4 Hz, 1 H), 6.69 (dd, J=5.8, 2.4 Hz, 1 H), 3.80-3.79 (m, 2 H), 3.46-3.45 (m, 2 H), 3.25 (q, J=7.2 Hz, 2 H), 2.65 (s, 3 H), 2.24 (s, 3 H), 1.09 (t, J=7.2 Hz, 3H); MS (ESI) m/z: 439.2 (M+H$^+$).

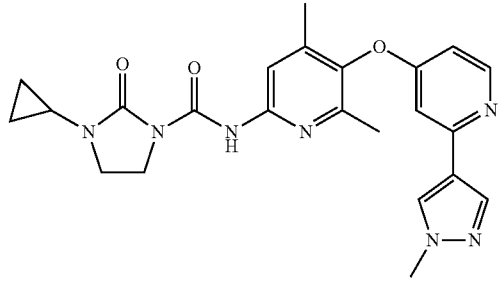 [SMILES: Cc1cc(NC(=O)N2CCN(C3CC3)C2=O)nc(C)c1Oc1ccnc(-c2cnn(C)c2)c1]

Example 71

A 0° C. solution of phosgene (15% in toluene, 268 mg, 0.593 mmol) in DCM (2 mL) was treated drop-wise with a solution of Example B20 (75 mg, 0.593 mmol) and pyridine (107 mg, 1.354 mmol) in DCM (2 mL), warmed to RT, stirred for 1 h, then concentrated to dryness. The residue was dissolved in DCM (2 mL), cooled to 0° C., treated with a solution of Example A15 (100 mg, 0.339 mmol) and pyridine (107 mg, 1.354 mmol) in DCM (2 mL), warmed to RT and stirred overnight. The mixture was treated with EtOAc, washed with 50% satd. NaHCO$_3$, then brine, dried over Na$_2$SO$_4$, concentrated to dryness and purified via silica gel chromatography (MeOH/EtOAc) to afford 3-cyclopropyl-N-(4,6-dimethyl-5-((2-(1-methyl-1H-pyrazol-4-yl)pyridin-4-yl)oxy)pyridin-2-yl)-2-oxoimidazolidine-1-carboxamide (45 mg, 28%). $^1$H NMR (400 MHz, DMSO-d$_6$): δ 10.82 (s, 1 H), 8.32 (d, J=5.7 Hz, 1 H), 8.25 (s, 1 H), 7.95 (s, 1 H), 7.83 (s, 1 H), 7.12 (d, J=2.4 Hz, 1H), 6.50 (dd, J=5.7, 2.4 Hz, 1 H), 3.84 (s, 3 H), 3.76-3.71 (m, 2 H), 3.44-3.38 (m, 2 H), 2.61-2.55 (m, 1 H), 2.17 (s, 3 H), 2.09 (s, 3 H), 0.70 (d, J=5.4 Hz, 4H); MS (ESI) m/z: 448.2 (M+H$^+$).

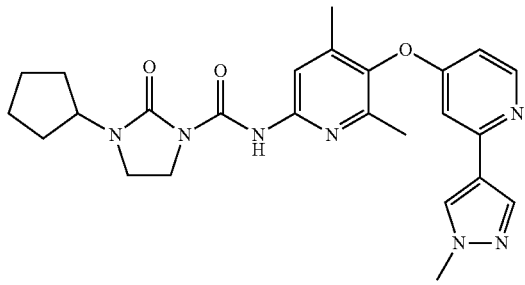 [SMILES: Cc1cc(NC(=O)N2CCN(C3CCCC3)C2=O)nc(C)c1Oc1ccnc(-c2cnn(C)c2)c1]

Example 72

A 0° C. solution of phosgene (15% in toluene, 1.19 mL, 1.693 mmol) in DCM (3 mL) was treated drop-wise with a solution of Example B14 (91 mg, 0.593 mmol) and pyridine (107 mg, 1.354 mmol) in DCM (2 mL), warmed to RT, stirred for 1 h, then concentrated to dryness. The residue was dissolved in DCM (3 mL), cooled to 0° C., treated with a solution of Example A15 (100 mg, 0.339 mmol) and pyridine (107 mg, 1.354 mmol) in DCM (2 mL), warmed to RT and stirred overnight. The mixture was concentrated to dryness and purified via reverse-phase chromatography (MeCN/H$_2$O with 0.1% TFA). The organics were removed under reduced pressure and the aqueous residue was treated with satd. NaHCO$_3$, and allowed to stand for 0.5 h. The resulting solid was collected via filtration, washed with water and dried to afford 3-cyclopentyl-N-(4,6-dimethyl-5-((2-(1-methyl-1H-pyrazol-4-yl)pyridin-4-yl)oxy)pyridin-2-yl)-2-oxoimidazolidine-1-carboxamide (61 mg, 37%). $^1$H NMR (400 MHz, DMSO-d$_6$): δ 10.85 (s, 1 H), 8.32 (d, J=5.7 Hz, 1 H), 8.25 (s, 1H), 7.95 (s, 1 H), 7.83 (s, 1 H), 7.12 (d, J=2.4 Hz, 1 H), 6.50 (dd, J=5.7, 2.4 Hz, 1 H), 4.18 (t, J=7.6 Hz, 1 H), 3.84 (s, 3 H), 3.79 (t, J=8.2 Hz, 2 H), 3.44 (t, J=8.2 Hz, 2 H), 2.16 (s, 3H), 2.09 (s, 3 H), 1.69-1.60 (m, 8H); MS (ESI) m/z: 476.3 (M+H$^+$).

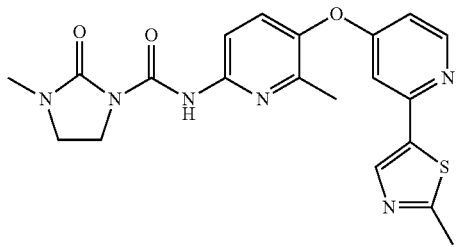

Example 73

A 0° C. solution of phosgene (15% in toluene, 2 mL, 2.84 mmol) in DCM (5 mL) was treated drop-wise with a solution of pyridine (0.1 mL, 1.236 mmol) and 1-methylimidazolidin-2-one (0.038 g, 0.377 mmol) in DCM (5 mL), warmed to RT, stirred for 1.5 h, then concentrated to dryness. The residue was dissolved in DCM (5 mL), cooled to 0° C., treated with a solution of Example A14 (0.075 g, 0.251 mmol) and pyridine (0.1 mL) in DCM (5 mL), warmed to RT and stirred overnight. The mixture was treated with satd. NaHCO$_3$, extracted with DCM (2×) and the combined organics were dried over Na$_2$SO$_4$, concentrated to dryness and purified via reverse-phase chromatography (MeCN/H$_2$O with 0.1% TFA). The combined fractions were treated with satd. NaHCO$_3$, extracted with EtOAc and the organic layer was dried over Na$_2$SO$_4$ and concentrated to dryness to afford 3-methyl-N-(6-methyl-5-((2-(2-methylthiazol-5-yl)pyridin-4-yl)oxy)pyridin-2-yl)-2-oxoimidazolidine-1-carboxamide (56 mg, 53%). $^1$H NMR (400 MHz, DMSO-d$_6$): δ 10.90 (s, 1 H), 8.38 (d, J=5.8 Hz, 1 H), 8.33 (s, 1 H), 7.91 (d, J=8.8 Hz, 1 H), 7.63 (d, J=8.8 Hz, 1 H), 7.56 (d, J=2.4 Hz, 1 H), 6.70 (dd, J=5.8, 2.4 Hz, 1 H), 3.80 (m, 2 H), 3.45 (m, 2 H), 2.81 (s, 3 H), 2.65 (s, 3H), 2.25 (s, 3H); MS (ESI) m/z: 425.2 (M+H$^+$).

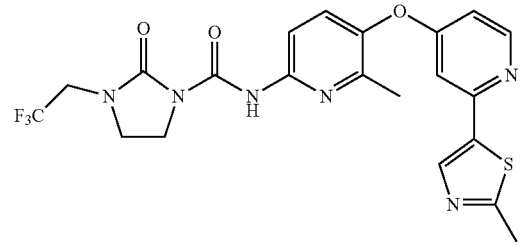 [SMILES: Cc1ncc(-c2cc(Oc3ccc(NC(=O)N4CCN(CC(F)(F)F)C4=O)nc3C)ccn2)s1]

Example 74

A 0° C. solution of phosgene (15% in toluene, 2 mL, 2.84 mmol) in DCM (5 mL) was treated drop-wise with a solution of pyridine (0.1 mL, 1.236 mmol) and Example B19 (0.063 g, 0.377 mmol) in DCM (5 mL), warmed to RT, stirred for 1.5 h, then concentrated to dryness. The residue was dissolved in DCM (5 mL), cooled to 0° C., treated with a solution of Example A14 (0.075 g, 0.251 mmol) and pyridine (0.1 mL) in DCM (5 mL), warmed to RT and stirred overnight. The mixture was treated with satd. NaHCO$_3$, extracted with DCM (2×) and the combined organics were dried over Na$_2$SO$_4$, concentrated to dryness and purified via reverse-phase chromatography (MeCN/H$_2$O with 0.1% TFA). The combined fractions were treated with satd. NaHCO$_3$, extracted with EtOAc (2×) and the combined organics were dried over Na$_2$SO$_4$ and concentrated to dryness to afford N-(6-methyl-5-((2-(2-methylthiazol-5-yl)pyridin-4-yl)oxy)pyridin-2-yl)-2-oxo-3-(2,2,2-trifluoroethyl)imidazolidine-1-carboxamide (68 mg, 54%). $^1$H NMR (400 MHz, DMSO-d$_6$): δ 10.70 (s, 1 H), 8.39 (d, J=5.8 Hz, 1 H), 8.33 (s, 1 H), 7.91 (d, J=8.8 Hz, 1 H), 7.65 (d, J=8.8 Hz, 1 H), 7.56 (d, J=2.4 Hz, 1 H), 6.71 (dd, J=5.8, 2.4 Hz, 1 H), 4.11 (q, J=9.6 Hz, 2H), 3.89 (m, 2 H), 3.60 (m 2 H), 2.65 (s, 3 H), 2.26 (s, 3H); MS (ESI) m/z: 493.1 (M+H$^+$).

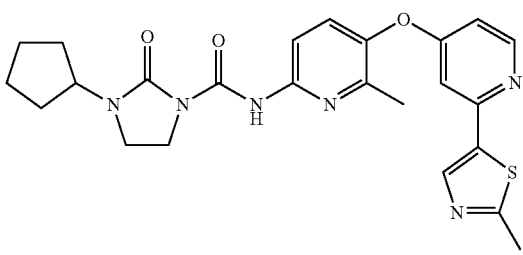 [SMILES: Cc1ncc(-c2cc(Oc3ccc(NC(=O)N4CCN(C5CCCC5)C4=O)nc3C)ccn2)s1]

Example 75

A 0° C. solution of phosgene (15% in toluene, 2 mL, 2.84 mmol) in DCM (5 mL) was treated drop-wise with a solution of pyridine (0.1 mL, 1.236 mmol) and Example B14 (0.058 g, 0.377 mmol) in DCM (5 mL), warmed to RT, stirred for 1.5 h, then concentrated to dryness. The residue was dissolved in DCM (5 mL), cooled to 0° C., treated with a solution of Example A14 (0.075 g, 0.251 mmol) and pyridine (0.1 mL) in DCM (5 mL), warmed to RT and stirred overnight. The mixture was treated with satd. NaHCO$_3$, extracted with DCM (2×) and the combined organics were dried over Na$_2$SO$_4$, concentrated to dryness and purified via reverse-phase chromatography (MeCN/H$_2$O with 0.1% TFA). The combined fractions were treated with satd. NaHCO$_3$, extracted with EtOAc (2×) and the combined organics were dried over Na$_2$SO$_4$ and concentrated to dryness to afford 3-cyclopentyl-N-(6-methyl-5-((2-(2-methylthiazol-5-yl)pyridin-4-yl)oxy)pyridin-2-yl)-2-oxoimidazolidine-1-carboxamide (40 mg, 33%). $^1$H NMR (400 MHz, DMSO-d$_6$): δ 10.94 (s, 1 H), 8.38 (d, J=5.8 Hz, 1 H), 8.33 (s, 1 H), 7.91 (d, J=8.8 Hz, 1 H), 7.63 (d, J=8.8 Hz, 1H), 7.56 (d, J=2.4 Hz, 1 H), 6.70 (dd, J=5.8, 2.4 Hz, 1 H), 4.19 (m, 1 H), 3.80 (m, 2 H), 3.45 (m, 2 H), 2.65 (s, 3 H), 2.25 (s, 3 H), 1.78 (m, 2 H), 1.67-1.52 (m, 6H); MS (ESI) m/z: 479.2 (M+H$^+$).

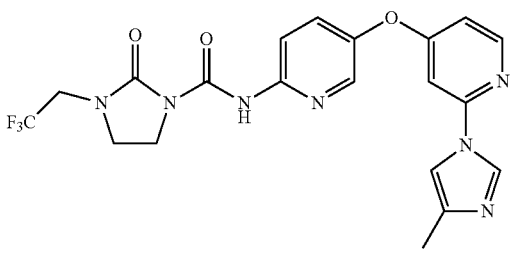 [SMILES: Cc1cn(-c2cc(Oc3ccc(NC(=O)N4CCN(CC(F)(F)F)C4=O)nc3)ccn2)cn1]

Example 76

A 0° C. solution of phosgene (15% in toluene, 2 mL, 2.84 mmol) in DCM (5 mL) was treated drop-wise with a solution of pyridine (0.1 mL, 1.236 mmol) and Example B19 (0.066 g, 0.393 mmol) in DCM (5 mL), warmed to RT, stirred for 1.5 h, then concentrated to dryness. The residue was dissolved in DCM (5 mL), cooled to 0° C., treated with a solution of Example A16 (0.070 g, 0.262 mmol) and pyridine (0.1 mL) in DCM (5 mL), warmed to RT and stirred overnight. The mixture was treated with satd. NaHCO$_3$, extracted with DCM (2×) and the combined organics were dried over Na$_2$SO$_4$ and concentrated to dryness. The material was treated with EtOAc and the resulting solid collected via filtration and dried to afford N-(5-((2-(4-methyl-1H-imidazol-1-yl)pyridin-4-yl)oxy)pyridin-2-yl)-2-oxo-3-(2,2,2-trifluoroethyl)imidazolidine-1-carboxamide (66 mg, 54%). $^1$H NMR (400 MHz, DMSO-d$_6$): δ 10.77 (s, 1 H), 8.41 (d, J=1.4 Hz, 1 H), 8.34 (d, J=5.8 Hz, 1 H), 8.29 (d, J=2.9 Hz, 1 H), 8.09 (d, J=9.1 Hz, 1 H), 7.78 (dd, J=9.1, 2.9 Hz, 1H), 7.65 (s, 1 H), 7.40 (d, J=2.2 Hz, 1 H), 6.84 (dd, J=5.8, 2.2 Hz, 1 H), 4.12 (q, J=9.6 Hz, 2 H), 3.89 (m, 2 H), 3.60 (m, 2 H), 2.14 (d, J=1.0 Hz, 3H); MS (ESI) m/z: 462.2 (M+H$^+$).

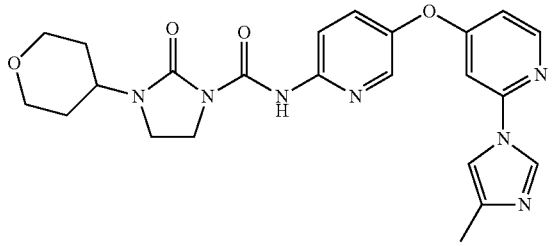 [SMILES: Cc1cn(-c2cc(Oc3ccc(NC(=O)N4CCN(C5CCOCC5)C4=O)nc3)ccn2)cn1]

Example 77

A 0° C. solution of phosgene (15% in toluene, 2 mL, 2.84 mmol) in DCM (5 mL) was treated drop-wise with a solution of pyridine (0.1 mL, 1.236 mmol) and Example B1 (0.067 g, 0.393 mmol) in DCM (5 mL), warmed to RT, stirred for 1.5 h, then concentrated to dryness. The residue was dissolved in DCM (5 mL), cooled to 0° C., treated with a solution of Example A16 (0.070 g, 0.262 mmol) and pyridine (0.1 mL) in DCM (5 mL), warmed to RT and stirred overnight. The mixture was treated with satd. NaHCO$_3$, extracted with DCM (2×) and the combined organics were dried over Na$_2$SO$_4$, concentrated to dryness and purified via silica gel chromatography (MeOH/DCM). The material was treated with EtOAc, allowed to stand at RT and the resulting solid collected via filtration and dried to afford N-(5-((2-(4-methyl-1H-imidazol-1-yl)pyridin-4-yl)oxy)pyridin-2-yl)-2-oxo-3-(tetrahydro-2H-pyran-4-yl)imidazolidine-1-carboxamide (53 mg, 44%). $^1$H NMR (400 MHz, DMSO-d$_6$): δ 10.99 (s, 1 H), 8.40 (d, J=1.4 Hz, 1 H), 8.33 (d, J=5.8 Hz, 1 H), 8.27 (d, J=2.9 Hz, 1 H), 8.09 (d, J=9.1 Hz, 1 H), 7.76 (dd, J=9.0, 2.9 Hz, 1 H), 7.65 (d, J=1.4 Hz, 1 H), 7.40 (d, J=2.2 Hz, 1H), 6.83 (dd, J=5.8, 2.2 Hz, 1 H), 3.93-3.89 (m, 3 H), 3.82 (m, 2 H), 3.35-3.50 (m, 4 H), 2.14 (d, J=1.0 Hz, 3 H), 1.72 (m, 2 H), 1.60 (m, 2H); MS (ESI) m/z: 464.2 (M+H$^+$).

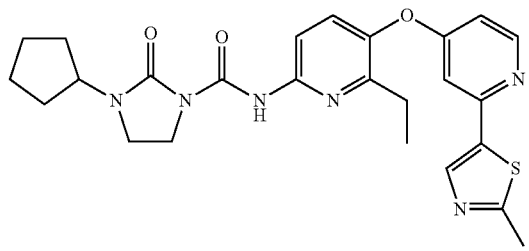 [SMILES: CCc1nc(NC(=O)N2CCN(C3CCCC3)C2=O)ccc1Oc1ccnc(-c2cnc(C)s2)c1]

Example 78

A mixture of Example A8 (1.35 g, 4.83 mmol), Example C6 (1.874 g, 4.83 mmol) and Pd(PPh$_3$)$_4$ (279 mg, 0.241 mmol) in toluene (15 mL) was sparged with Ar and heated at 105° C. overnight. The mixture was cooled to RT, treated with 10% KF and EtOAc and stirred vigorously for 2 h. The mixture was diluted with additional EtOAc, the solids removed via filtration through diatomaceous earth, the layers of the filtrate separated and the organic layer washed with satd. NaHCO₃, then brine, dried over Na₂SO₄, concentrated to dryness and purified via silica gel chromatography (EtOAc/Hex) to afford 5-(4-((2-ethyl-6-nitropyridin-3-yl)oxy)pyridin-2-yl)-2-methylthiazole (756 mg, 45%). ¹H NMR (400 MHz, DMSO-d₆): δ 8.50 (d, J=5.7 Hz, 1 H), 8.35 (s, 1 H), 8.24 (d, J=8.7 Hz, 1 H), 7.89 (d, J=8.7 Hz, 1 H), 7.73 (d, J=2.4 Hz, 1 H), 7.02 (dd, J=5.7, 2.4 Hz, 1 H), 2.84 (q, J=7.5 Hz, 2H), 2.65 (s, 3 H), 1.24 (t, J=7.5 Hz, 3H); MS (ESI) m/z: 343.1 (M+H⁺).

A mixture of 5-(4-((2-ethyl-6-nitropyridin-3-yl)oxy)pyridin-2-yl)-2-methylthiazole (756 mg, 2.208 mmol) and 10% Pd/C (50% w/w with water, 235 mg, 0.221 mmol) in MeOH (15 mL) was hydrogenated (1 atm) at RT overnight, then warmed to 50° C. for 4 h. The mixture was cooled to RT, the solids removed via filtration through diatomaceous earth, washed with MeOH and the filtrate concentrated to dryness to afford 6-ethyl-5-((2-(2-methylthiazol-5-yl)pyridin-4-yl)oxy)pyridin-2-amine (79 mg, 11%). MS (ESI) m/z: 313.1 (M+H⁺).

A 0° C. solution of phosgene (15% in toluene, 0.88 mL, 1.248 mmol) in DCM (2 mL) was treated drop-wise with a solution of Example B14 (67 mg, 0.437 mmol) and pyridine (79 mg, 0.999 mmol) in DCM (1 mL), warmed to RT, stirred for 1 h, then concentrated to dryness. The residue was dissolved in DCM (1 mL), added to a 0° C. solution of 6-ethyl-5-((2-(2-methylthiazol-5-yl)pyridin-4-yl)oxy)pyridin-2-amine (78 mg, 0.339 mmol) and pyridine (79 mg, 0.999 mmol) in DCM (2 mL) and THF (1 mL), warmed to RT and stirred overnight. The mixture was concentrated to dryness and purified via silica gel chromatography (EtOAc/Hex) to afford 3-cyclopentyl-N-(6-ethyl-5-((2-(2-methylthiazol-5-yl)pyridin-4-yl)oxy)pyridin-2-yl)-2-oxoimidazolidine-1-carboxamide (42 mg, 34%). ¹H NMR (400 MHz, DMSO-d₆): δ 10.94 (s, 1 H), 8.37 (d, J=5.8 Hz, 1 H), 8.32 (s, 1 H), 7.90 (d, J=8.8 Hz, 1 H), 7.62 (d, J=8.8 Hz, 1 H), 7.57 (d, J=2.4 Hz, 1 H), 6.69 (dd, J=5.8, 2.4 Hz, 1 H), 4.18 (t, J=7.6 Hz, 1 H), 3.80-3.78 (m, 2 H), 3.45 (t, J=8.2 Hz, 2 H), 2.65 (s, 3 H), 2.57 (q, J=7.6 Hz, 2 H), 1.78 (d, J=11.0 Hz, 2 H), 1.65-1.52 (m, 6 H), 1.11 (t, J=7.5 Hz, 3H); MS (ESI) m/z: 493.2 (M+H⁺).

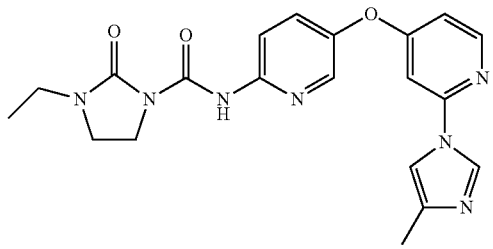 [SMILES: CCN1CCN(C(=O)Nc2ccc(Oc3ccnc(-n4cnc(C)c4)c3)cn2)C1=O]

Example 79

A 0° C. solution of phosgene (15% in toluene, 2 mL, 2.84 mmol) in DCM (5 mL) was treated drop-wise with a solution of pyridine (0.1 mL, 1.236 mmol) and Example B18 (0.045 g, 0.393 mmol) in DCM (5 mL), warmed to RT, stirred for 1.5 h, then concentrated to dryness. The residue was dissolved in DCM (5 mL), cooled to 0° C., treated with a solution of Example A16 (0.070 g, 0.262 mmol) and pyridine (0.1 mL) in DCM (5 mL), warmed to RT and stirred overnight. The mixture was treated with satd. NaHCO₃, extracted with DCM (2×) and the combined organics were dried over Na₂SO₄, concentrated to dryness and purified via reverse-phase chromatography (MeCN/H₂O with 0.1% TFA). The combined fractions were treated with satd. NaHCO₃, extracted with EtOAc (2×) and the combined organics were dried over Na₂SO₄ and concentrated to dryness to afford 3-ethyl-N-(5-((2-(4-methyl-1H-imidazol-1-yl)pyridin-4-yl)oxy)pyridin-2-yl)-2-oxoimidazolidine-1-carboxamide (53 mg, 50%). ¹H NMR (400 MHz, DMSO-d₆): δ 11.00 (s, 1 H), 8.40 (s, 1 H), 8.33 (d, J=5.8 Hz, 1 H), 8.26 (d, J=2.9 Hz, 1 H), 8.09 (d, J=9.0 Hz, 1 H), 7.76 (dd, J=9.0, 2.9 Hz, 1 H), 7.65 (s, 1 H), 7.39 (d, J=2.2 Hz, 1 H), 6.83 (dd, J=5.8, 2.2 Hz, 1 H), 3.81 (m, 2 H), 3.47 (m, 2 H), 3.27 (m, 2 H), 2.14 (d, J=1.0 Hz, 3 H), 1.10 (t, J=7.2 Hz, 3H); MS (ESI) m/z: 408.2 (M+H⁺).

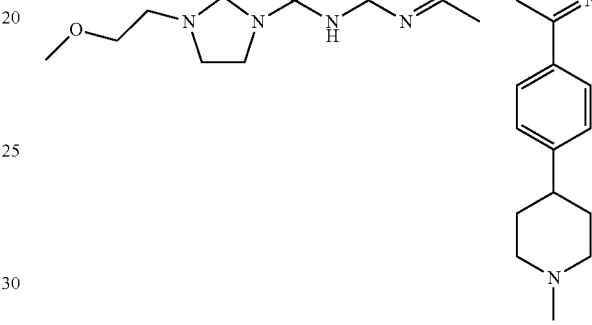

Example 80

A mixture of Example C5 (0.150 g, 0.370 mmol), Example C7 (0.145 g, 0.480 mmol), K₂CO₃ (0.153 g, 1.109 mmol) and Pd(PPh₃)₄ (0.043 g, 0.037 mmol) in dioxane (6 mL) and water (1.5 mL) was sparged with Ar and heated at 90° C. overnight. The mixture was cooled to RT, treated with 1N NaOH, extracted with EtOAc (4×) and the combined organics were washed with brine, dried over Na₂SO₄, concentrated to dryness and purified via silica gel chromatography (MeOH/DCM) to afford 3-(2-methoxyethyl)-N-(6-methyl-5-((2-(4-(1-methylpiperidin-4-yl)phenyl)pyridin-4-yl)oxy)pyridin-2-yl)-2-oxoimidazolidine-1-carboxamide (125 mg, 62%). ¹H NMR (400 MHz, DMSO-d₆): δ 10.89 (s, 1 H), 8.49 (d, J=5.7 Hz, 1 H), 7.92-7.91 (m, 3 H), 7.64 (d, J=8.8 Hz, 1 H), 7.40 (d, J=2.4 Hz, 1 H), 7.31 (d, J=8.2 Hz, 2 H), 6.75 (dd, J=5.7, 2.4 Hz, 1 H), 3.81-3.79 (m, 2 H), 3.51-3.49 (m, 4 H), 3.39 (m, 2 H), 3.26 (s, 3 H), 2.85 (m, 2 H), 2.25 (s, 3 H), 2.17 (s, 3 H), 1.96-1.93 (m, 2 H), 1.71-1.66 (m, 5H); MS (ESI) m/z: 545.3 (M+H⁺).

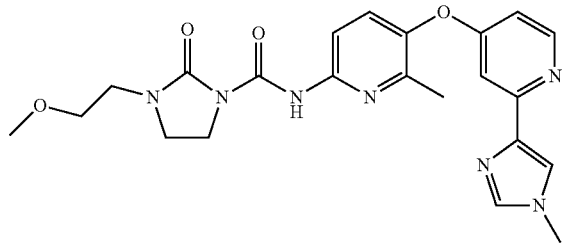

Example 81

A mixture of Example C5 (0.150 g, 0.370 mmol), N-methyl-4-(tributylstannyl)imidazole (0.178 g, 0.480 mmol) and Pd(PPh$_3$)$_4$ (0.021 g, 0.018 mmol) in toluene (4 mL) was sparged with Ar and heated at 105° C. overnight. The mixture was cooled to RT, treated with 10% KF and EtOAc, stirred for 2 h and the solids removed via filtration through diatomaceous earth. The filtrate was extracted with EtOAc (3×) and the combined organics were washed with 10% KF, then brine, dried over Na$_2$SO$_4$ and concentrated to dryness. The material was treated with MeCN, sonicated, the solid removed via filtration and the filtrate concentrated to dryness and purified via silica gel chromatography (MeOH/DCM). The material was suspended in MeCN, sonicated and the solid collected via filtration. The filtrate was concentrated to dryness and further purified via reverse-phase chromatography (MeCN/H$_2$O with 0.1% TFA). The organics were removed under reduced pressure, the aqueous residue treated with satd. NaHCO$_3$, extracted with EtOAc (3×) and the combined organics were dried over Na$_2$SO$_4$, concentrated to dryness and combined with the above-isolated solid to afford 3-(2-methoxyethyl)-N-(6-methyl-5-((2-(1-methyl-1H-imidazol-4-yl)pyridin-4-yl)oxy)pyridin-2-yl)-2-oxoimidazolidine-1-carboxamide (61 mg, 36%). $^1$H NMR (400 MHz, DMSO-d$_6$): δ 10.89 (s, 1 H), 8.35 (d, J=5.7 Hz, 1 H), 7.91 (d, J=8.8 Hz, 1H), 7.67 (d, J=1.3 Hz, 1 H), 7.64 (d, J=8.8 Hz, 1 H), 7.59 (d, J=1.3 Hz, 1 H), 7.16 (d, J=2.6 Hz, 1 H), 6.74 (dd, J=5.7, 2.6 Hz, 1 H), 3.84-3.78 (m, 2 H), 3.67 (s, 3 H), 3.54-3.47 (m, 4 H), 3.41-3.37 (m, 2 H), 3.26 (s, 3 H), 2.23 (s, 3H); MS (ESI) m/z: 452.2 (M+H$^+$).

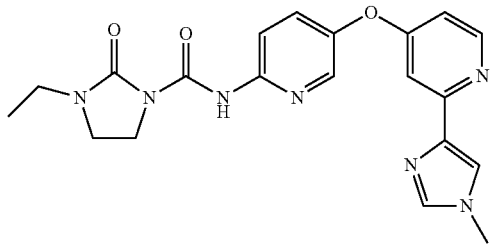 [SMILES: CCN1CCN(C(=O)Nc2ccc(Oc3ccnc(-c4cn(C)cn4)c3)cn2)C1=O]

Example 82

A 0° C. solution of phosgene (15% in toluene, 2.375 mL, 3.37 mmol) in DCM (5 mL) was treated drop-wise with a solution of Example B18 (0.102 g, 0.898 mmol) and pyridine (0.2 mL, 2.473 mmol) in DCM (5 mL), warmed to RT, stirred for 0.5 h, then concentrated to dryness. The residue was dissolved in DCM (5 mL), cooled to 0° C., treated with a solution of Example A17 (0.12 g, 0.449 mmol) and DIEA (0.2 mL, 1.145 mmol) in DCM (5 mL) and stirred at RT overnight. The mixture was treated with 1N NaOH, extracted with EtOAc (4×) and the combined organics were washed with 1N NaOH, then brine, dried over Na$_2$SO$_4$, concentrated to dryness and purified via silica gel chromatography (MeOH/DCM) to afford 3-ethyl-N-(5-((2-(1-methyl-1H-imidazol-4-yl)pyridin-4-yl)oxy)pyridin-2-yl)-2-oxoimidazolidine-1-carboxamide (150 mg, 82%). $^1$H NMR (400 MHz, DMSO-d$_6$): δ 10.99 (s, 1H), 8.36 (d, J=5.6 Hz, 1 H), 8.24 (d, J=2.9 Hz, 1 H), 8.08 (d, J=9.0 Hz, 1 H), 7.75 (dd, J=9.0, 2.9 Hz, 1 H), 7.67 (d, J=1.3 Hz, 1 H), 7.59 (d, J=1.3 Hz, 1 H), 7.23 (d, J=2.6 Hz, 1 H), 6.80 (dd, J=5.7, 2.6 Hz, 1 H), 3.81-3.80 (m, 2 H), 3.67 (s, 3 H), 3.46 (t, J=8.2 Hz, 2 H), 3.26-3.25 (m, 2 H), 1.09 (t, J=7.2 Hz, 3H); MS (ESI) m/z: 408.2 (M+H$^+$).

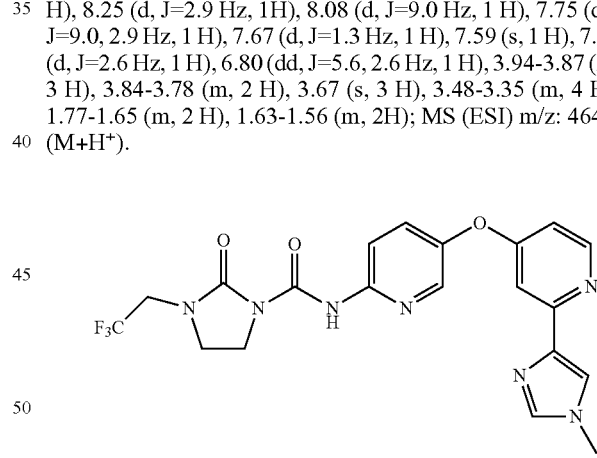

Example 83

A 0° C. solution of phosgene (15% in toluene, 2.375 mL, 3.37 mmol) in DCM (5 mL) was treated drop-wise with a solution of Example B1 (0.153 g, 0.898 mmol) and pyridine (0.2 mL, 2.473 mmol) in DCM (5 mL), warmed to RT, stirred for 0.5 h, then concentrated to dryness. The residue was dissolved in DCM (5 mL), cooled to 0° C., treated with a solution of Example A17 (0.12 g, 0.449 mmol) and DIEA (0.2 mL, 1.145 mmol) in DCM (5 mL) and stirred at RT overnight. The mixture was treated with 1N NaOH, extracted with EtOAc (4×) and the combined organics were washed with 1N NaOH, then brine, dried over Na$_2$SO$_4$, concentrated to dryness and purified via silica gel chromatography (MeOH/DCM) to afford N-(5-((2-(1-methyl-1H-imidazol-4-yl)pyridin-4-yl)oxy)pyridin-2-yl)-2-oxo-3-(tetrahydro-2H-pyran-4-yl)imidazolidine-1-carboxamide (180 mg, 87%). $^1$H NMR (400 MHz, DMSO-d$_6$): δ 10.98 (s, 1 H), 8.36 (d, J=5.7 Hz, 1 H), 8.25 (d, J=2.9 Hz, 1H), 8.08 (d, J=9.0 Hz, 1 H), 7.75 (dd, J=9.0, 2.9 Hz, 1 H), 7.67 (d, J=1.3 Hz, 1 H), 7.59 (s, 1 H), 7.23 (d, J=2.6 Hz, 1 H), 6.80 (dd, J=5.6, 2.6 Hz, 1 H), 3.94-3.87 (m, 3 H), 3.84-3.78 (m, 2 H), 3.67 (s, 3 H), 3.48-3.35 (m, 4 H), 1.77-1.65 (m, 2 H), 1.63-1.56 (m, 2H); MS (ESI) m/z: 464.2 (M+H$^+$).

Example 84

A 0° C. solution of phosgene (15% in toluene, 2.375 mL, 3.37 mmol) in DCM (5 mL) was treated drop-wise with a solution of Example B19 (0.075 g, 0.449 mmol) and pyridine (0.2 mL, 2.473 mmol) in DCM (5 mL), warmed to RT, stirred for 0.5 h, then concentrated to dryness. The residue was dissolved in DCM (5 mL), cooled to 0° C., treated with a solution of Example A17 (0.12 g, 0.449 mmol) and DIEA (0.2 mL, 1.145 mmol) in DCM (5 mL) and stirred at RT overnight. The mixture was treated with 1N NaOH, extracted with EtOAc (4×) and the combined organics were washed with 1N NaOH, then brine, dried over Na$_2$SO$_4$, concentrated to dryness and purified via silica gel chromatography (MeOH/DCM) to afford N-(5-((2-(1-methyl-1H-imidazol-4-yl)pyridin-4-yl)oxy)pyridin-2-yl)-2-oxo-3-(2,2,2-trifluoroethyl)imidazolidine-1-carboxamide (114 mg, 55%). $^1$H NMR (400 MHz, DMSO-$d_6$): δ 10.76 (s, 1 H), 8.37 (d, J=5.6 Hz, 1 H), 8.26 (d, J=2.9 Hz, 1 H), 8.08 (d, J=9.0 Hz, 1 H), 7.77 (dd, J=9.0, 2.9 Hz, 1 H), 7.68 (d, J=1.4 Hz, 1 H), 7.60 (d, J=1.3 Hz, 1 H), 7.24 (d, J=2.6 Hz, 1 H), 6.80 (dd, J=5.7, 2.6 Hz, 1 H), 4.11 (q, J=9.6 Hz, 2H), 3.88-3.87 (m, 2 H), 3.67 (s, 3 H), 3.59 (t, J=8.2 Hz, 2H); MS (ESI) m/z: 462.2 (M+H$^+$).

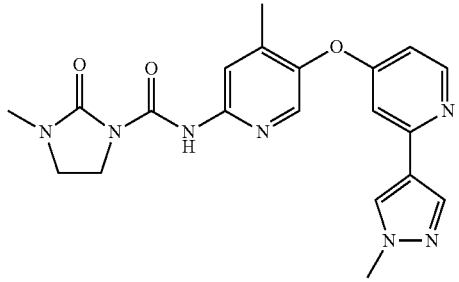 [SMILES: Cc1cc(NC(=O)N2CCN(C)C2=O)ncc1Oc1ccnc(-c2cnn(C)c2)c1]

Example 85

A solution of Example A18 (1.5 g, 5.65 mmol) and 1-methyl-4-(4,4,5,5-tetramethyl-1,3,2-dioxaborolan-2-yl)-1H-pyrazole (1.527 g, 7.34 mmol) in dioxane (20 mL) was sparged with Ar, treated with a solution of $K_2CO_3$ (1.171 g, 8.47 mmol) in water (5 mL) and Pd(PPh$_3$)$_4$ (0.326 g, 0.282 mmol) and heated at 80° C. overnight. The mixture was cooled to RT, treated with water, extracted with DCM (4×) and the combined organics were dried over Na$_2$SO$_4$, concentrated to dryness and purified via silica gel chromatography (MeOH/DCM) to afford 4-methyl-5-((2-(1-methyl-1H-pyrazol-4-yl)pyridin-4-yl)oxy)-2-nitropyridine (2.3 g, 75%). $^1$H NMR (400 MHz, DMSO-$d_6$): δ 8.48 (s, 1 H), 8.43-8.42 (m, 2H), 8.27 (s, 1 H), 7.98 (s, 1 H), 7.30 (d, J=2.4 Hz, 1 H), 6.83 (dd, J=5.7, 2.4 Hz, 1 H), 3.84 (s, 3 H), 2.34 (s, 3H); MS (ESI) m/z: 312.1 (M+H$^+$).

A solution of 4-methyl-5-((2-(1-methyl-1H-pyrazol-4-yl)pyridin-4-yl)oxy)-2-nitropyridine (2.3 g, 7.39 mmol) in MeOH (37 mL) and THF (37 mL) was treated with NH$_4$Cl (11.86 g, 222 mmol) followed by the portion-wise addition of zinc dust (4.83 g, 73.9 mmol) and the mixture stirred at RT overnight. The mixture was diluted with EtOAc, the solids removed via filtration through diatomaceous earth and the filtrate concentrated to dryness and purified via silica gel chromatography (MeOH/DCM) to afford 4-methyl-5-((2-(1-methyl-1H-pyrazol-4-yl)pyridin-4-yl)oxy)pyridin-2-amine (1.4 g, 67%). MS (ESI) m/z: 282.1 (M+H$^+$).

A 0° C. solution of phosgene (15% in toluene, 2.82 mL, 4.00 mmol) in DCM (3 mL) was treated drop-wise with a solution of 1-methyl-2-imidazolidinone (0.107 g, 1.066 mmol) and pyridine (0.2 mL, 2.473 mmol) in DCM (3 mL), warmed to RT, stirred for 0.5 h, then concentrated to dryness. The residue was dissolved in DCM (3 mL), cooled to 0° C., treated with a solution of 4-methyl-5-((2-(1-methyl-1H-pyrazol-4-yl)pyridin-4-yl)oxy)pyridin-2-amine (0.15 g, 0.533 mmol) and DIEA (0.2 mL, 1.145 mmol) in DCM (3 mL), warmed to RT and stirred for 3 h. The mixture was treated with satd. NaHCO$_3$, extracted with DCM (4×) and the combined organics were dried over Na$_2$SO$_4$ and concentrated to dryness. The material was treated with MeCN and the resulting solid was collected via filtration to afford 3-methyl-N-(4-methyl-5-((2-(1-methyl-1H-pyrazol-4-yl)pyridin-4-yl)oxy)pyridin-2-yl)-2-oxoimidazolidine-1-carboxamide (116 mg, 52%). $^1$H NMR (400 MHz, DMSO-$d_6$): δ 10.90 (s, 1 H), 8.34 (d, J=5.7 Hz, 1 H), 8.25 (s, 1 H), 8.10 (s, 1 H), 8.01 (s, 1 H), 7.95 (s, 1 H), 7.16 (d, J=2.4 Hz, 1 H), 6.59 (dd, J=5.7, 2.5 Hz, 1 H), 3.84 (s, 3 H), 3.79-3.78 (m, 2 H), 3.45 (t, J=8.2 Hz, 2 H), 2.80 (s, 3 H), 2.14 (s, 3H); MS (ESI) m/z: 408.2 (M+H$^+$).

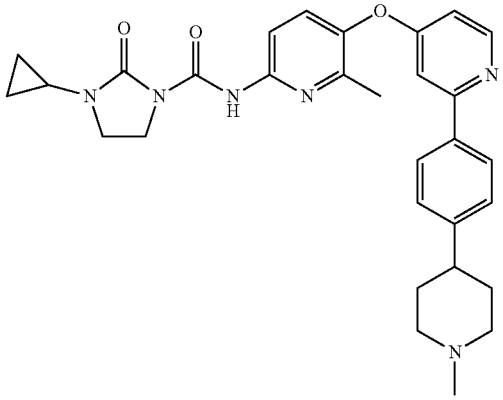 [SMILES: Cc1nc(NC(=O)N2CCN(C3CC3)C2=O)ccc1Oc1ccnc(-c2ccc(C3CCN(C)CC3)cc2)c1]

Example 86

A 0° C. solution of phosgene (15% in toluene, 1.695 mL, 2.403 mmol) in DCM (5 mL) was treated drop-wise with a solution of Example B20 (0.081 g, 0.641 mmol) and pyridine (0.2 mL, 2.473 mmol) in DCM (5 mL), warmed to RT, stirred for 0.5 h, then concentrated to dryness. The residue was dissolved in DCM (5 mL), cooled to 0° C., treated with a solution of Example A12 (0.12 g, 0.320 mmol) and DIEA (0.2 mL, 1.145 mmol) in DCM (5 mL), warmed to RT and stirred overnight. The mixture was treated with 1N NaOH, extracted with EtOAc (4×) and the combined organics were washed with 1N NaOH, then brine, dried over Na$_2$SO$_4$, concentrated to dryness and purified via silica gel chromatography (MeOH/DCM. The material was treated with MTBE, sonicated, stirred vigorously overnight and the resulting solid collected via filtration to afford 3-cyclopropyl-N-(6-methyl-5-((2-(4-(1-methylpiperidin-4-yl)phenyl)pyridin-4-yl)oxy)pyridin-2-yl)-2-oxoimidazolidine-1-carboxamide (67 mg, 40%). $^1$H NMR (400 MHz, DMSO-$d_6$): δ 10.90 (s, 1 H), 8.49 (d, J=5.7 Hz, 1 H), 7.92-7.91 (m, 3 H), 7.64 (d, J=8.9 Hz, 1 H), 7.40 (d, J=2.4 Hz, 1 H), 7.32 (d, J=8.1 Hz, 2 H), 6.75 (dd, J=5.6, 2.4 Hz, 1 H), 3.75-3.73 (m, 2 H), 3.41 (t, J=8.2 Hz, 2 H), 2.90-2.88 (m, 2 H), 2.58 (m, 1 H), 2.26 (s, 3 H), 2.25 (br s, 3 H), 2.04-2.02 (m, 2 H), 1.78-1.63 (m, 5 H), 0.71 (m, 4H); MS (ESI) m/z: 527.3 (M+H$^+$).

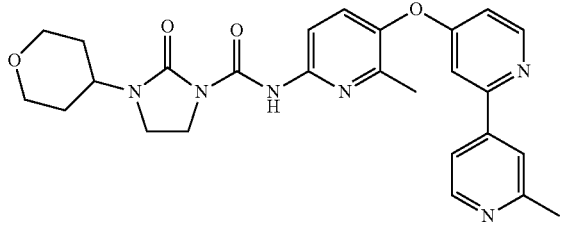 [SMILES: Cc1cc(-c2cc(Oc3ccc(NC(=O)N4CCN(C5CCOCC5)C4=O)nc3C)ccn2)ccn1]

Example 87

A mixture of Example C3 (0.377 g, 0.873 mmol) and K$_2$CO$_3$ (0.362 g, 2.62 mmol) in dioxane (4 mL) and water (1 mL) was sparged with Ar, treated with 2-methyl-4-(4,4,5,5-tetramethyl-1,3,2-dioxaborolan-2-yl)pyridine (0.201 g, 0.917 mmol) and Pd(Ph$_3$P)$_4$ (0.101 g, 0.087 mmol), sparged again with Ar and heated at 80° C. overnight. The mixture was cooled to RT, diluted with EtOAc, dried over Na$_2$SO$_4$, concentrated to dryness and purified via silica gel chromatography (MeOH/EtOAc). The material was treated with Et$_2$O, stirred at RT and the resulting solid collected via filtration and dried to afford N-(6-methyl-5-((2'-methyl-[2,4'-bipyridin]-4-yl)oxy)pyridin-2-yl)-2-oxo-3-(tetrahydro-2H-pyran-4-yl)imidazolidine-1-carboxamide (151 mg, 35%). $^1$H NMR (400 MHz, DMSO-d$_6$): δ 10.90 (s, 1 H), 8.56 (d, J=5.6 Hz, 1 H), 8.52 (d, J=5.2 Hz, 1 H), 7.93-7.88 (m, 2 H), 7.79 (dd, J=5.3, 1.6 Hz, 1 H), 7.66-7.63 (m, 2 H), 6.86 (dd, J=5.6, 2.4 Hz, 1 H), 3.93-3.77 (m, 5 H), 3.49-3.34 (m, 4 H), 2.52 (s, 3 H), 2.26 (s, 3 H), 1.78-1.66 (m, 2 H), 1.63-1.57 (m, 2H); MS (ESI) m/z: 489.2 (M+H$^+$).

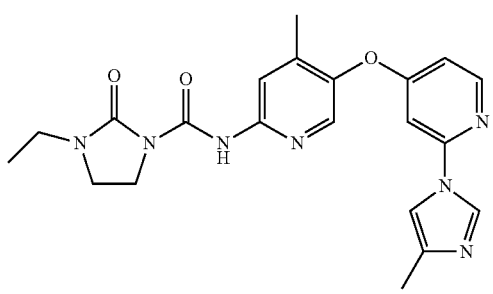 [SMILES: CCN1CCN(C(=O)Nc2cc(C)c(Oc3ccnc(-n4cnc(C)c4)c3)cn2)C1=O]

Example 88

A 0° C. solution of phosgene (15% in toluene, 5 mL, 7.09 mmol) in DCM (8 mL) was treated drop-wise with a solution of Example B18 (0.2 g, 1.752 mmol) and pyridine (0.5 mL, 6.18 mmol) in DCM (8 mL), warmed to RT, stirred for 0.5 h, then concentrated to dryness. The residue was dissolved in DCM (8 mL), cooled to 0° C., treated with a solution of Example A19 (0.2 g, 0.849 mmol) and DIEA (0.5 mL, 2.86 mmol) in DCM (8 mL), warmed to RT and stirred for 3 h. The mixture was treated with satd. NaHCO$_3$, extracted with DCM (5×) and the combined organics were dried over Na$_2$SO$_4$, concentrated to dryness and purified via silica gel chromatography (MeOH/DCM) to afford N-(5-((2-chloropyridin-4-yl)oxy)-4-methylpyridin-2-yl)-3-ethyl-2-oxoimidazolidine-1-carboxamide (300 mg, 94%). MS (ESI) m/z: 376.1 (M+H$^+$).

A solution of Pd$_2$(dba)$_3$ (0.029 g, 0.032 mmol) and Me$_4$t-BuXPhos (0.034 g, 0.072 mmol) in toluene (0.6 mL) and dioxane (1.2 mL) was heated at 120° C. for 3 min, cooled to RT, added to a degassed suspension of N-(5-((2-chloropyridin-4-yl)oxy)-4-methylpyridin-2-yl)-3-ethyl-2-oxoimidazolidine-1-carboxamide (0.3 g, 0.798 mmol), 4-methyl imidazole (0.085 g, 1.038 mmol) and K$_3$PO$_4$ (0.339 g, 1.597 mmol) in toluene (1.2 mL) and dioxane (2.4 mL) and heated at 110° C. overnight. The mixture was treated with additional catalyst (synthesized from Pd$_2$(dba)$_3$ (0.029 g, 0.032 mmol) and Me$_4$t-BuXPhos (0.034 g, 0.072 mmol) in toluene (0.6 mL) and dioxane (1.2 mL) as above) and heated at 110° C. overnight. The mixture was cooled to RT, treated with satd. NaHCO$_3$, extracted with EtOAc (5×) and the combined organics were dried over Na$_2$SO$_4$, concentrated to dryness and purified twice via silica gel chromatography (MeOH/DCM). The material was further purified via reverse-phase chromatography (MeCN/H$_2$O with 0.1% TFA); the organics were removed under reduced pressure and the aqueous residue was treated with satd. NaHCO$_3$ and extracted with DCM (3×). The combined organics were dried over Na$_2$SO$_4$ and concentrated to dryness to afford 3-ethyl-N-(4-methyl-5-((2-(4-methyl-1H-imidazol-1-yl)pyridin-4-yl)oxy)pyridin-2-yl)-2-oxoimidazolidine-1-carboxamide (112 mg, 32%). $^1$H NMR (400 MHz, DMSO-d$_6$): δ 10.93 (s, 1 H), 8.39 (d, J=1.4 Hz, 1 H), 8.30 (d, J=5.8 Hz, 1 H), 8.13 (s, 1 H), 8.02 (s, 1 H), 7.64 (s, 1 H), 7.33 (d, J=2.2 Hz, 1 H), 6.73 (dd, J=5.8, 2.2 Hz, 1 H), 3.80 (t, J=8.3 Hz, 2H), 3.46 (t, J=8.2 Hz, 2 H), 3.26-3.25 (q, J=7.2 Hz, 2 H), 2.15 (s, 3 H), 2.13 (s, 3 H), 1.09 (t, J=7.2 Hz, 3H); MS (ESI) m/z: 422.2 (M+H$^+$).

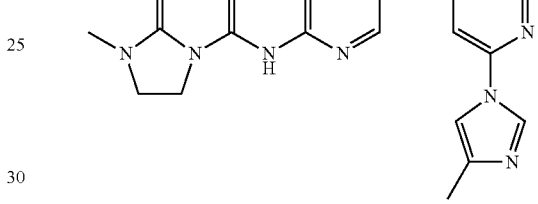

Example 89

A 0° C. solution of phosgene (15% in toluene, 5 mL, 7.09 mmol) in DCM (8 mL) was treated drop-wise with a solution of 1-methyl-2-imidazolidinone (0.2 g, 1.998 mmol) and pyridine (0.5 mL, 6.18 mmol) in DCM (8 mL), warmed to RT, stirred for 0.5 h, then concentrated to dryness. The residue was dissolved in DCM (8 mL), cooled to 0° C., treated with a solution of Example A19 (0.2 g, 0.849 mmol) and DIEA (0.5 mL, 2.86 mmol) in DCM (8 mL), warmed to RT and stirred for 3 h. The mixture was treated with satd. NaHCO$_3$, extracted with DCM (5×) and the combined organics were dried over Na$_2$SO$_4$, concentrated to dryness and purified via silica gel chromatography (MeOH/DCM) to afford N-(5-((2-chloropyridin-4-yl)oxy)-4-methylpyridin-2-yl)-3-methyl-2-oxoimidazolidine-1-carboxamide (100 mg, 33%). MS (ESI) m/z: 362.1 (M+H$^+$).

A solution of Pd$_2$(dba)$_3$ (10.12 mg, 0.011 mmol) and Me$_4$t-BuXPhos (0.012 g, 0.025 mmol) in toluene (0.2 mL) and dioxane (0.4 mL) was heated at 120° C. for 3 min, cooled to RT, added to a degassed suspension of N-(5-((2-chloropyridin-4-yl)oxy)-4-methylpyridin-2-yl)-3-methyl-2-oxoimidazolidine-1-carboxamide (0.1 g, 0.276 mmol), 4-methyl imidazole (0.030 g, 0.359 mmol) and K$_3$PO$_4$ (0.117 g, 0.553 mmol) in toluene (0.4 mL) and dioxane (0.8 mL) and heated at 110° C. overnight. The mixture was treated with additional catalyst (synthesized from Pd$_2$(dba)$_3$ (10.12 mg, 0.011 mmol) and Me$_4$t-BuXPhos (0.012 g, 0.025 mmol) in toluene (0.2 mL) and dioxane (0.4 mL) as above) and heated at 110° C. overnight. The mixture was cooled to RT, treated with satd. NaHCO$_3$, extracted with EtOAc (5×) and the combined organics were dried over Na$_2$SO$_4$, concentrated to dryness and purified twice via silica gel chromatography (MeOH/DCM). The material was treated with MeCN, heated to reflux, cooled to RT and the resulting solid collected via filtration and dried to afford 3-methyl-N-(4-methyl-5-((2-(4-methyl-1H-imidazol-1-yl)pyridin-4-yl)oxy)pyridin-2-yl)-2-oxoimidazolidine-1-carboxamide (20 mg, 17%). ¹H NMR (400 MHz, DMSO-d₆): δ 10.92 (s, 1 H), 8.39 (d, J=1.4 Hz, 1 H), 8.30 (d, J=5.8 Hz, 1 H), 8.13 (s, 1 H), 8.02 (s, 1 H), 7.64 (t, J=1.3 Hz, 1 H), 7.33 (d, J=2.2 Hz, 1 H), 6.73 (dd, J=5.8, 2.2 Hz, 1 H), 3.79-3.78 (m, 2 H), 3.46-3.44 (m, 2 H), 2.80 (s, 3 H), 2.15 (s, 3 H), 2.13 (s, 3H); MS (ESI) m/z: 408.2 (M+H⁺).

tography (MeOH/DCM), treated with Et₂O, sonicated and the resulting solid collected via filtration to afford N-(2,5-difluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (263 mg, 80%). ¹H NMR (400 MHz, DMSO-d₆): δ 10.94 (s, 1 H), 8.37 (d, J=5.7 Hz, 1 H), 8.27 (s, 1 H), 8.20 (dd, J=12.5, 7.4 Hz, 1 H), 7.97 (s, 1 H), 7.58 (dd, J=11.1, 7.4 Hz, 1 H), 7.23 (d, J=2.5 Hz, 1 H), 6.70 (dd, J=5.7, 2.5 Hz, 1 H), 3.94-3.77 (m, 8 H), 3.47 (t, J=8.2 Hz, 2 H), 3.38 (t, J=11.7 Hz, 2 H), 1.71 (m, 2 H), 1.59 (br d, J=12.4 Hz, 2H); MS (ESI) m/z: 499.2 (M+H⁺).

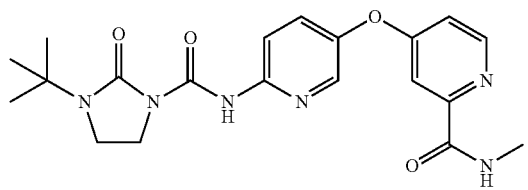 [SMILES: CNC(=O)c1cc(Oc2ccc(NC(=O)N3CCN(C(C)(C)C)C3=O)nc2)ccn1]

Example 90

A 0° C. solution of phosgene (15% in toluene, 2 mL, 2.84 mmol) in DCM (5 mL) was treated drop-wise with a solution of pyridine (0.1 mL, 1.236 mmol) and Example B16 (0.116 g, 0.819 mmol) in DCM (5 mL), warmed to RT, stirred for 1 h, then concentrated to dryness. The residue was dissolved in DCM (5 mL), cooled to 0° C., treated with a solution of Example A23 (0.10 g, 0.409 mmol) and pyridine (0.1 mL) in DCM (5 mL), warmed to RT and stirred overnight. The mixture was treated with satd. NaHCO₃, extracted with EtOAc (3×) and the combined organics were dried over Na₂SO₄, concentrated to dryness and purified via silica gel chromatography (EtOAc/Hex). The material was treated with Et₂O, sonicated and the resulting solid collected via filtration to afford 4-((6-(3-(tert-butyl)-2-oxoimidazolidine-1-carboxamido)pyridin-3-yl)oxy)-N-methylpicolinamide (138 mg, 81%). ¹H NMR (400 MHz, DMSO-d₆): δ 11.08 (s, 1 H), 8.77 (q, J=4.9 Hz, 1 H), 8.52 (d, J=5.6 Hz, 1 H), 8.26 (d, J=2.9 Hz, 1 H), 8.09 (d, J=9.0 Hz, 1 H), 7.76 (dd, J=9.0, 2.9 Hz, 1 H), 7.41 (d, J=2.6 Hz, 1 H), 7.18 (dd, J=5.6, 2.7 Hz, 1 H), 3.73 (m, 2 H), 3.52 (m, 2 H), 2.78 (d, J=4.9 Hz, 3 H), 1.37 (s, 9H); MS (ESI) m/z: 413.2 (M+H⁺).

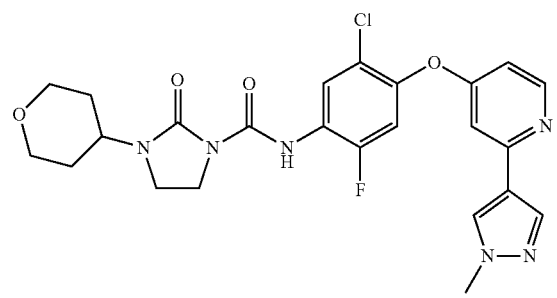 [SMILES: Cn1cc(-c2cc(Oc3cc(F)c(NC(=O)N4CCN(C5CCOCC5)C4=O)cc3F)ccn2)cn1]

Example 92

A 0° C. suspension of Example A22 (0.100 g, 0.314 mmol) and TEA (0.131 mL, 0.941 mmol) in DCM (3 mL) was treated with a thin suspension of crude Example B2 (0.117 g, 0.502 mmol) in DCM (4 mL). The mixture was warmed to RT, stirred overnight, treated with a solution of additional Example B2 (34 mg, 0.147 mmol) in DCM (2 mL) and stirred for 1 h. The mixture was concentrated to dryness, purified via silica gel chromatography (MeOH/DCM), the resulting solid triturated with MTBE, collected via filtration, rinsed with MTBE and dried to afford N-(5-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide as a white solid (136 mg, 84%). ¹H NMR (400 MHz, DMSO-d₆): δ 10.92 (d, J=2.7 Hz, 1 H), 8.38-8.37 (m, 2 H), 8.26 (s, 1 H), 7.97 (d, J=0.7 Hz, 1 H), 7.57 (d, J=11.3 Hz, 1 H), 7.20 (d, J=2.5 Hz, 1 H), 6.64 (dd, J=5.7, 2.5 Hz, 1 H), 3.93-3.77 (m, 8 H), 3.47 (m, 2 H), 3.37 (m, 2 H), 1.70 (m, 2 H), 1.59 (m, 2H); MS (ESI) m/z: 515.2 (M+H⁺).

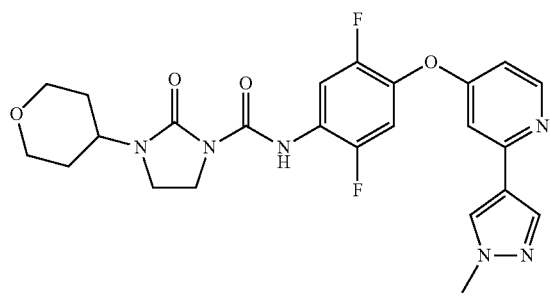

Example 91

A 0° C. mixture of Example A20 (0.200 g, 0.662 mmol) and TEA (0.277 mL, 1.985 mmol) in DCM (3 mL) was treated with a solution of Example B2 (0.246 g, 1.059 mmol) in THF (5 mL), warmed to RT and stirred for 1 h. The mixture was concentrated to dryness, purified via silica gel chroma-

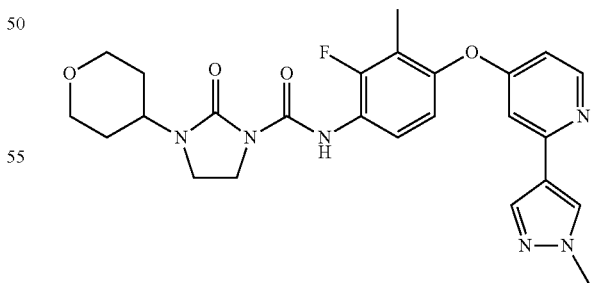

Example 93

A solution of 1,3-difluoro-2-methyl-benzene (15 g, 0.12 mol) in H₂SO₄ (100 mL) was treated drop-wise with 65% HNO₃ (11.4 g, 0.12 mol) at −10° C. and the resultant mixture was stirred for 30 min. The mixture was poured into ice-water and extracted with EtOAc (3×). The combined organic layers were washed with brine, dried over Na$_2$SO$_4$ and concentrated in vacuo to give 1,3-difluoro-2-methyl-4-nitro-benzene (16 g, 78%). $^1$H NMR (400 MHz, CDCl$_3$): δ 7.80 (m, 1 H), 6.95 (m, 1 H), 2.30 (s, 3H).

1,3-Difluoro-2-methyl-4-nitro-benzene (16 g, 0.092 mol), benzyl alcohol (10 g, 0.092 mol) and K$_2$CO$_3$ (25.3 g, 0.18 mol), were combined in DMF (300 mL) and heated to 100° C. overnight. The mixture was poured into water and extracted with EtOAc (3×). The combined organic layers were washed with brine, dried over Na$_2$SO$_4$, concentrated in vacuo and purified by silica gel chromatography to give 1-benzyloxy-3-fluoro-2-methyl-4-nitro-benzene (8 g, 33%). $^1$H NMR (400 MHz, DMSO-d$_6$): δ 8.04 (t, J=8.8 Hz, 1 H), 7.30-7.46 (m, 5 H), 7.08 (d, J=9.2 Hz, 1 H), 5.28 (s, 2 H), 2.13 (s, 3H).

A solution of 1-benzyloxy-3-fluoro-2-methyl-4-nitro-benzene (8 g, 0.031 mol) in MeOH (100 mL) was treated with Pd/C (10%) and hydrogenated (30 psi) for 2 h. The catalyst was removed by filtration, and the filtrate was concentrated in vacuo to afford 4-amino-3-fluoro-2-methyl-phenol (4.2 g, 96% yield). $^1$H NMR (300 MHz, DMSO-d$_6$): δ 8.61 (s, 1 H), 6.36 (m, 2 H), 4.28 (s, 2 H), 1.96 (s, 3H); MS (ESI) m/z: 142.1 [M+H]$^+$.

Potassium tert-butoxide (3.5 g, 31 mmol) was added to a solution of 4-amino-3-fluoro-2-methyl-phenol (4.2 g, 30 mmol) in DMA, and stirred at RT for 0.5 h. A solution of 2,4-dichloropyridine (4.38 g, 30 mmol) in DMA was added and the mixture was heated at 100° C. overnight. The reaction mixture was concentrated in vacuo and the residue was dissolved in EtOAc (200 mL) and filtered through silica gel. The filter cake was washed with EtOAc, and the combined filtrates were concentrated in vacuo and purified by silica gel chromatography to give 4-(2-chloro-pyridin-4-yloxy)-2-fluoro-3-methyl-phenylamine (3.2 g, 42% yield). $^1$H NMR (400 MHz, DMSO-d$_6$): δ 8.21 (d, J=6.4 Hz, 1 H), 6.84 (d, J=2.0 Hz, 1H), 6.81 (dd, J=5.6, 2.4 Hz, 1 H), 6.67-6.65 (m, 2 H), 5.13 (s, 2 H), 1.91 (s, 3H); MS (ESI): m/z 253.2 [M+H]$^+$.

Using a procedure analogous to Example 95, 4-(2-chloro-pyridin-4-yloxy)-2-fluoro-3-methyl-phenylamine (1.0 g, 3.3 mmol), 1-methyl-4-(4,4,5,5-tetramethyl-[1,3,2]dioxaborolan-2-yl)-1H-pyrazole (1 g, 4.8 mmol), Na$_2$CO$_3$ (0.84 g, 6.6 mmol) and Pd(PPh$_3$)$_4$ (0.25 g, 0.2 mmol) were combined to give 2-fluoro-3-methyl-4-[2-(1-methyl-1H-pyrazol-4-yl)-pyridin-4-yloxy]-phenylamine (0.74 g, 75%). $^1$H NMR (400 MHz, DMSO-d$_6$): δ 8.27 (d, J=6.4 Hz, 1 H), 8.18 (s, 1 H), 7.90 (s, 1 H), 7.07 (s, 1 H), 6.68-6.61 (m, 2 H), 6.45 (dd, J=5.6, 2.4 Hz, 1 H), 5.06 (s, 2 H), 3.82 (s, 3 H), 1.95 (s, 3H); MS (ESI) m/z: 299.2 [M+H]$^+$.

Phosgene (20% in toluene, 0.798 mL, 1.508 mmol) was treated drop-wise with a solution of Example B1 (0.128 g, 0.754 mmol) and pyridine (0.244 mL, 3.02 mmol) in DCM (5 mL), stirred at RT for 10 min, then concentrated to dryness. The residue was dissolved in DCM (5 mL), treated drop-wise with a solution of 2-fluoro-3-methyl-4-((2-(1-methyl-1H-pyrazol-4-yl)pyridin-4-yl)oxy)aniline (0.15 g, 0.503 mmol) and DIEA (0.527 mL, 3.02 mmol) in DCM (5 mL) stirred at RT for 3 h. The mixture was treated with satd. NaHCO$_3$, extracted with DCM (3×) and the combined organics were dried over Na$_2$SO$_4$, concentrated to dryness and purified via silica gel chromatography (MeOH/DCM) to afford N-(2-fluoro-3-methyl-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (0.188 g, 76%). $^1$H NMR (400 MHz, DMSO-d$_6$): δ 10.76 (d, J=2.7 Hz, 1 H), 8.33 (d, J=5.7 Hz, 1 H), 8.24 (s, 1 H), 8.05 (t, J=9.0 Hz, 1 H), 7.95 (d, J=0.7 Hz, 1 H), 7.16 (d, J=2.4 Hz, 1 H), 6.98 (d, J=9.0 Hz, 1 H), 6.57 (dd, J=5.7, 2.4 Hz, 1 H), 3.93-3.83 (m, 6 H), 3.82-3.77 (m, 2 H), 3.46 (t, J=8.2 Hz, 2 H), 3.38 (dd, J=12.6, 10.8 Hz, 2 H), 2.05 (d, J=2.0 Hz, 3 H), 1.71 (m, 2 H), 1.59 (br d, J=12.3 Hz, 2H); MS (ESI) m/z: 495.2 (M+H$^+$).

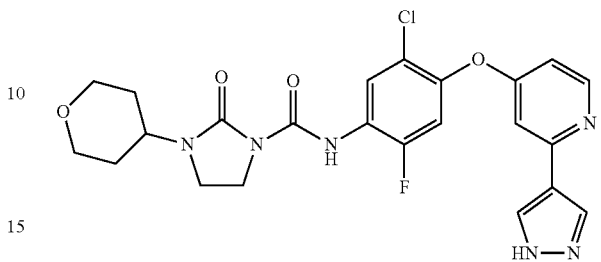

Example 94

A mixture of Example C8 (0.200 g, 0.426 mmol), 4-(4,4,5,5-tetramethyl-1,3,2-dioxaborolan-2-yl)-1H-pyrazole (0.124 g, 0.639 mmol) and K$_2$CO$_3$ (0.177 g, 1.279 mmol) in dioxane (4 mL) and water (1 mL) was sparged with Ar, treated with Pd(PPh$_3$)$_4$ (0.025 g, 0.021 mmol), sparged again with Ar and heated at 80° C. overnight. The mixture was cooled to RT, treated with satd. NaHCO$_3$, extracted with EtOAc (2×) and the combined organics were washed with brine, dried over MgSO$_4$, concentrated to dryness and purified via silica gel chromatography (MeOH/DCM) to afford N-(4-((2-(1H-pyrazol-4-yl)pyridin-4-yl)oxy)-5-chloro-2-fluorophenyl)-2-oxo-3-(tetrahydro-2H-pyran-4-yl)imidazolidine-1-carboxamide (160 mg, 75%) as a white solid. $^1$H NMR (400 MHz, DMSO-d$_6$): δ 13.05 (s, 1H), 10.91 (d, J=2.7 Hz, 1 H), 8.40 (1H, d, J=8.1 Hz, 1 H), 8.36 (d, J=5.7 Hz, 1 H), 8.33 (s, 1 H), 8.04 (s, 1 H), 7.57 (d, J=11.2 Hz, 1 H), 7.30 (d, J=2.5 Hz, 1 H), 6.61 (dd, J=5.7, 2.5 Hz, 1 H), 3.94-3.77 (m, 5 H), 3.47 (t, J=8.2 Hz, 2 H), 3.37 (t, J=11.8 Hz, 2 H), 1.75-1.64 (m, 2 H), 1.59 (m, 2H); MS (ESI) m/z: 501.1 (M+H+).

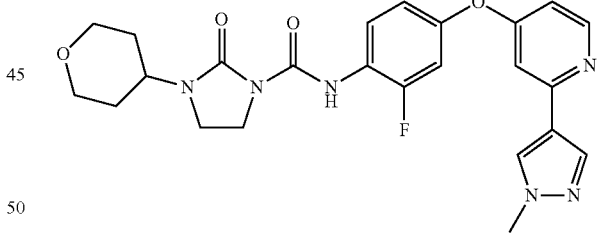

Example 95

A suspension of 3-fluoro-4-aminophenol (8.0 g, 63.0 mmol) in dimethylacetamide (80 mL) was de-gassed in vacuo and treated with potassium tert-butoxide (7.3 g, 65 mmol). The resultant mixture was stirred at RT for 30 min. 2,4-Dichloropyridine (8 g, 54 mmol) was added and the mixture was heated to 80° C. for 12 h. The solvent was removed under reduced pressure to give a residue which was partitioned between water and EtOAc (3×). The organic layers were washed with satd. brine, dried over MgSO$_4$, concentrated in vacuo and purified by silica gel column chromatography to give 4-(2-chloropyridin-4-yloxy)-2-fluorobenzenamine (11 g, 86% yield). $^1$H NMR (300 MHz, DMSO-d$_6$): δ 8.24 (d, J=5.7 Hz, 1 H), 7.00 (dd, J=9.0, 2.7 Hz, 1 H), 6.89-6.73 (m, 4 H), 5.21 (br s, 2H); MS (ESI) m/z: 239.2 (M+H+).

A solution of 4-(2-chloropyridin-4-yloxy)-2-fluorobenzenamine (3 g, 12.6 mmol), 1-methyl-3-(4,4,5,5-tetramethyl-[1,3,2]dioxaborolan-2-yl)-1H-pyrazole (5.2 g, 25.2 mmol), and Na$_2$CO$_3$ (2.7 g, 25.2 mmol) in DME (18 mL)/water (6 mL) was sparged with nitrogen for 20 min. Pd(PPh$_3$)$_4$ (729 mg, 0.63 mmol) was added and the resulting mixture was heated to 100° C. for 16 h. The solvent was removed under reduced pressure and the crude product was suspended in water and extracted with EtOAc. The organic layer was washed with brine, dried over Na$_2$SO$_4$, concentrated in vacuo and purified via silica gel chromatography to give 2-fluoro-4-((2-(1-methyl-1H-pyrazol-4-yl)pyridin-4-yl)oxy)aniline (2 g, 56% yield). $^1$H NMR (300 MHz, DMSO-d$_6$): δ 8.31 (d, J=5.7 Hz, 1 H), 8.21 (s, 1 H), 7.92 (s, 1 H), 7.12 (d, J=2.4 Hz, 1 H), 6.96 (m, 1 H), 6.85-6.72 (m, 2 H), 6.56 (m, 1 H), 5.15 (s, 2 H), 3.84 (s, 3H); MS (ESI) m/z: 285.0 (M+H$^+$).

A mixture of 2-fluoro-4-((2-(1-methyl-1H-pyrazol-4-yl)pyridin-4-yl)oxy)aniline (0.150 g, 0.528 mmol) and TEA (3.2 mL, 22.93 mmol) in DCM (5 mL) was cooled to 0° C., treated with a solution of Example B2 (0.164 g, 0.705 mmol) in DCM (1.5 mL), warmed to RT and stirred for 1 h. The mixture was treated with water, stirred for 10 min, the layers separated and the organic layer dried over Na$_2$SO$_4$, concentrated to dryness and purified via silica gel chromatography (MeOH/DCM). The material was treated with Et2O, sonicated and the resulting solid collected via filtration to afford N-(2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (167 mg, 66%). $^1$H NMR (400 MHz, DMSO-d$_6$): δ 10.74 (d, J=2.5 Hz, 1 H), 8.36 (d, J=5.7 Hz, 1 H), 8.25 (s, 1 H), 8.19 (t, J=9.1 Hz, 1 H), 7.95 (d, J=0.7 Hz, 1 H), 7.28 (dd, J=11.7, 2.7 Hz, 1 H), 7.22 (d, J=2.4 Hz, 1 H), 7.03 (dd, J=9.1, 2.5 Hz, 1 H), 6.67 (dd, J=5.7, 2.4 Hz, 1 H), 3.93-3.77 (m, 8 H), 3.46 (t, J=8.2 Hz, 2 H), 3.38 (dd, J=12.5, 10.6 Hz, 2 H), 1.71 (qd, J=12.2, 4.5 Hz, 2 H), 1.60-1.57 (m, 2H); MS (ESI) m/z: 481.2 (M+H$^+$).

NMR (400 MHz, DMSO-d$_6$): δ 8.24 (d, J=5.7 Hz, 1 H), 7.02 (d, J=8.7 Hz, 1 H), 6.87-6.82 (m, 2 H), 6.73-6.72 (m, 1 H), 6.58-6.56 (m, 1 H), 5.50 (br s, 2H); MS (ESI) m/z: 254.9 (M+H$^+$); 256.9 (M+2+H$^+$).

3-Chloro-4-(2-chloropyridin-4-yloxy)benzenamine (0.89 g, 3.49 mmol), 1-methyl-4-(4,4,5,5-tetramethyl-1,3,2-dioxaborolan-2-yl)-pyrazole (0.871 g, 4.19 mmol) and K$_2$CO$_3$ (1.302 g, 9.42 mmol) were combined in DME (6 mL)/H$_2$O (7.5 mL) and the headspace was flushed with Ar for 10 min. Pd(Ph$_3$P)$_4$ (0.202 g, 0.174 mmol) was then added and the biphasic reaction was heated at 90° C. overnight. The mixture was cooled to RT and filtered to remove insoluble material. The filtrate was diluted with THF, washed with brine (3×) and the combined aqueous phases were back-extracted with THF (2×). The combined organics were washed with brine (1×), dried over MgSO$_4$, concentrated in vacuo and purified by silica gel chromatography (MeOH/CHCl$_3$) to afford 3-chloro-4-((2-(1-methyl-1H-pyrazol-4-yl)pyridin-4-yl)oxy)aniline (1.10 g, 83%). $^1$H NMR (400 MHz, DMSO-d$_6$): δ 8.30-8.29 (m, 1 H), 8.22 (s, 1 H), 7.92 (s, 1 H), 7.12 (m, 1 H), 7.00-6.98 (m, 1 H), 6.72 (br s, 1 H), 6.58-6.54 (m, 1 H), 6.47-6.44 (m, 1 H), 5.44 (s, 2 H), 3.84 (s, 3H); MS (ESI) m/z: 301.1 (M+H$^+$); 303.0 (M+2+H$^+$).

A 0° C. mixture of 3-chloro-4-((2-(1-methyl-1H-pyrazol-4-yl)pyridin-4-yl)oxy)aniline (0.150 g, 0.499 mmol) and TEA (0.1 mL, 0.716 mmol) in DCM (5 mL) was treated with a solution of Example B2 (0.164 g, 0.705 mmol) in DCM (1.5 mL), warmed to RT and stirred for 1 h. The mixture was treated with water, stirred for 10 min, the layers separated and the organic layer dried over Na$_2$SO$_4$, concentrated to dryness and purified via silica gel chromatography (MeOH/DCM) to afford N-(3-chloro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (176 mg, 71%). $^1$H NMR (400 MHz, DMSO-d$_6$): δ 10.57 (s, 1 H), 8.34 (d, J=5.7 Hz, 1 H), 8.25 (s, 1 H), 7.96 (s, 1 H), 7.92 (d, J=2.6 Hz, 1 H), 7.46 (dd, J=8.8, 2.6 Hz, 1H), 7.32 (d, J=8.8 Hz, 1 H), 7.19 (d, J=2.4 Hz, 1 H), 6.55 (dd, J=5.7, 2.5 Hz, 1 H), 3.94-3.76 (m, 8 H), 3.46 (t, J=8.2 Hz, 2 H), 3.37 (t, J=11.7 Hz, 2 H), 1.76-1.66 (m, 2 H), 1.59 (d, J=12.4 Hz, 2H); MS (ESI) m/z: 497.2 (M+H$^+$).

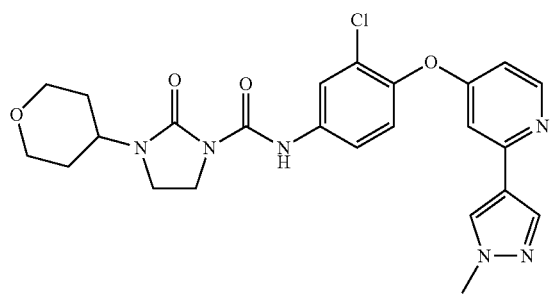 [SMILES: Cn1cc(-c2cc(Oc3ccc(NC(=O)N4CCN(C5CCOCC5)C4=O)cc3Cl)ccn2)cn1]

Example 96

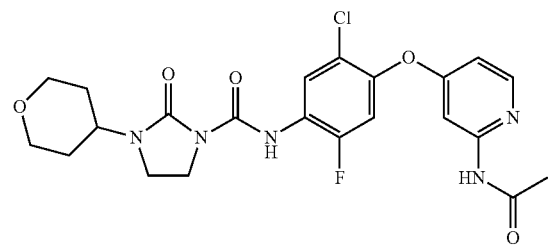 [SMILES: CC(=O)Nc1cc(Oc2cc(F)c(NC(=O)N3CCN(C4CCOCC4)C3=O)cc2Cl)ccn1]

Example 97

KOtBu (1.016 g, 9.05 mmol) was added to a solution of 4-amino-2-chlorophenol (1.00 g, 6.97 mmol) in DMF (35 mL) at RT and stirred 45 min. 2,4-Dichloropyridine (1.340 g, 9.05 mmol) was then added and the reaction was heated at 90° C. overnight. The mixture was cooled to RT, diluted with H$_2$O and EtOAc, the layers separated and the aqueous layer was extracted with EtOAc (3×). The combined organics were washed with H$_2$O (1×), then brine (2×), dried over MgSO$_4$, concentrated in vacuo and purified by silica gel chromatography (EtOAc/Hex) to afford 3-chloro-4-(2-chloropyridin-4-yloxy)benzenamine (0.89 g, 50%) as a waxy yellow solid. $^1$H A mixture of Example C8 (0.243 g, 0.518 mmol), acetamide (0.184 g, 3.11 mmol), Cs$_2$CO$_3$ (0.422 g, 1.294 mmol) and Xantphos (0.090 g, 0.155 mmol) in dioxane (3 mL) was sparged with Ar, treated with Pd$_2$(dba)$_3$ (0.062 g, 0.067 mmol), sparged again with Ar and heated at 100° C. overnight. The mixture was cooled to RT, treated with brine, extracted with EtOAc (3×) and the combined organics were dried over Na$_2$SO$_4$, concentrated to dryness and purified twice via silica gel chromatography (MeOH/DCM, then MeOH/EtOAc) to afford N-(4-((2-acetamidopyridin-4-yl)oxy)-5-chloro-2-fluorophenyl)-2-oxo-3-(tetrahydro-2H-pyran-4-yl)imidazolidine-1-carboxamide (74 mg, 29%). ¹H NMR (400 MHz, DMSO-d₆): δ 10.92 (d, J=2.7 Hz, 1 H), 10.57 (s, 1 H), 8.39 (d, J=8.1 Hz, 1 H), 8.17 (d, J=5.7 Hz, 1 H), 7.61 (d, J=2.4 Hz, 1 H), 7.58 (d, J=11.2 Hz, 1 H), 6.64 (dd, J=5.7, 2.4 Hz, 1 H), 3.93-3.83 (m, 3 H), 3.81 (m, 2 H), 3.48 (t, J=8.2 Hz, 2 H), 3.37 (dd, J=12.4, 10.6 Hz, 2 H), 2.03 (s, 3 H), 1.71 (qd, J=12.2, 4.5 Hz, 2 H), 1.62-1.56 (m, 2H); MS (ESI) m/z: 492.1 (M+H⁺).

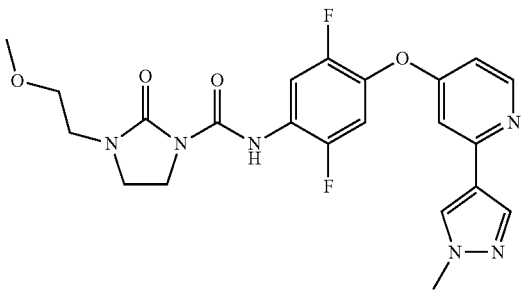 [SMILES: COCCN1CCN(C(=O)Nc2cc(F)c(Oc3ccnc(-c4cnn(C)c4)c3)cc2F)C1=O]

Example 98

A 0° C. solution of Example A20 (0.170 g, 0.562 mmol) and TEA (0.1 mL, 0.716 mmol) in DCM (5 mL) was treated with a solution of Example B4 (0.165 g, 0.799 mmol) in DCM (1.5 mL), warmed to RT and stirred for 1 h. The mixture was treated with water, stirred for 10 min, the layers separated and the organic layer dried over Na₂SO₄, concentrated to dryness and purified via silica gel chromatography (MeOH/DCM). The material was treated with Et2O, sonicated and the resulting solid collected via filtration to afford N-(2,5-difluoro-4-((2-(1-methyl-1H-pyrazol-4-yl)pyridin-4-yl)oxy)phenyl)-3-(2-methoxyethyl)-2-oxoimidazolidine-1-carboxamide (170 mg, 64%). ¹H NMR (400 MHz, DMSO-d₆): δ 10.90 (s, 1 H), 8.37 (d, J=5.7 Hz, 1 H), 8.26 (s, 1 H), 8.20 (dd, J=12.5, 7.4 Hz, 1 H), 7.97 (s, 1 H), 7.57 (dd, J=11.2, 7.4 Hz, 1 H), 7.23 (d, J=2.5 Hz, 1 H), 6.71 (dd, J=5.7, 2.5 Hz, 1 H), 3.84 (s, 3 H), 3.83-3.78 (m, 2 H), 3.50-3.46 (m, 4 H), 3.40-3.37 (m, 2 H), 3.26 (s, 3H); MS (ESI) m/z: 473.1 (M+H⁺).

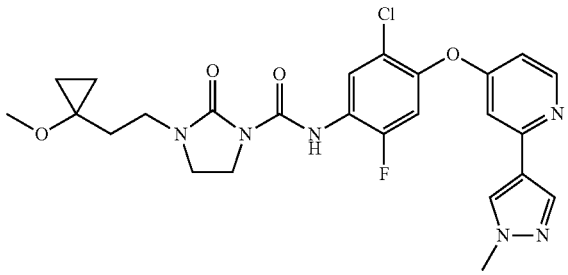 [SMILES: COC1(CCN2CCN(C(=O)Nc3cc(Cl)c(Oc4ccnc(-c5cnn(C)c5)c4)cc3F)C2=O)CC1]

Example 99

A 0° C. solution of phosgene (20% in toluene, 0.711 mL, 0.980 mmol) in DCM (6 mL) was treated slowly drop-wise with a solution of Example B9 (0.129 g, 0.700 mmol) and pyridine (0.113 mL, 1.400 mmol) in DCM (2 mL) warmed to RT, and stirred for 0.5 h. The mixture was concentrated to dryness, dissolved in DCM (2 mL), added to a 0° C. solution of Example A22 (0.069 g, 0.218 mmol) and TEA (0.091 mL, 0.654 mmol) in DCM (1 mL), warmed to RT and stirred overnight. The mixture was diluted with additional DCM, washed with water (3×), dried over MgSO₄, concentrated to dryness and purified via reverse-phase chromatography (MeCN/H₂O with 0.1% TFA). The organic were removed under reduced pressure and the aqueous residue was treated with satd. NaHCO₃, extracted with EtOAc (3×) and the combined organics dried over MgSO₄ and concentrated to dryness to afford N-(5-chloro-2-fluoro-4-((2-(1-methyl-1H-pyrazol-4-yl)pyridin-4-yl)oxy)phenyl)-3-(2-(1-methoxycyclopropyl)ethyl)-2-oxoimidazolidine-1-carboxamide (69 mg, 60%). ¹H NMR (400 MHz, DMSO-d₆): δ 10.90 (d, J=2.7 Hz, 1 H), 8.41 (d, J=8.1 Hz, 1 H), 8.36 (d, J=5.7 Hz, 1 H), 8.27 (s, 1 H), 7.97 (d, J=0.7 Hz, 1 H), 7.57 (d, J=11.3 Hz, 1 H), 7.20 (d, J=2.4 Hz, 1 H), 6.64 (dd, J=5.7, 2.5 Hz, 1 H), 3.84 (s, 3 H), 3.81-3.79 (m, 2 H), 3.51 (t, J=8.3 Hz, 2 H), 3.34 (t, J=7.5 Hz, 2 H), 3.16 (s, 3 H), 1.77 (t, J=7.4 Hz, 2 H), 0.67-0.66 (m, 2 H), 0.42-0.41 (m, 2H); MS (ESI) m/z: 529.2 (M+H⁺).

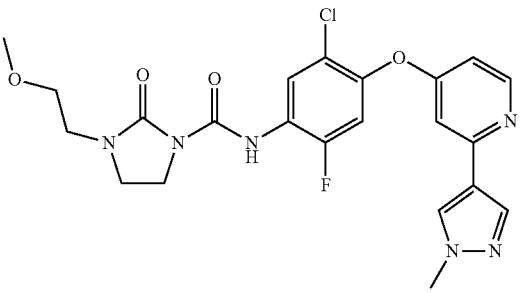 [SMILES: COCCN1CCN(C(=O)Nc2cc(Cl)c(Oc3ccnc(-c4cnn(C)c4)c3)cc2F)C1=O]

Example 100

A 0° C. solution of Example A22 (0.170 g, 0.533 mmol) and TEA (0.1 mL, 0.716 mmol) in DCM (5 mL) was treated with a solution of Example B4 (0.165 g, 0.799 mmol) in DCM (1.5 mL), warmed to RT and stirred for 1 h. The mixture was treated with water, stirred for 10 min, the layers separated and the organic layer dried over Na₂SO₄, concentrated to dryness and purified via silica gel chromatography (MeOH/DCM). The material was treated with Et₂O, sonicated and the resulting solid collected via filtration to afford N-(5-chloro-2-fluoro-4-((2-(1-methyl-1H-pyrazol-4-yl)pyridin-4-yl)oxy)phenyl)-3-(2-methoxyethyl)-2-oxoimidazolidine-1-carboxamide (152 mg, 58%). ¹H NMR (400 MHz, DMSO-d₆): δ 10.88 (d, J=2.7 Hz, 1 H), 8.40 (d, J=8.1 Hz, 1 H), 8.36 (d, J=5.7 Hz, 1 H), 8.27 (s, 1 H), 7.98 (s, 1 H), 7.58 (d, J=11.3 Hz, 1 H), 7.20 (d, J=2.4 Hz, 1 H), 6.64 (dd, J=5.7, 2.5 Hz, 1 H), 3.84 (s, 3 H), 3.82-3.80 (m, 2 H), 3.51-3.49 (m, 4 H), 3.40-3.37 (m, 2 H), 3.26 (s, 3H); MS (ESI) m/z: 489.1 (M+H⁺).

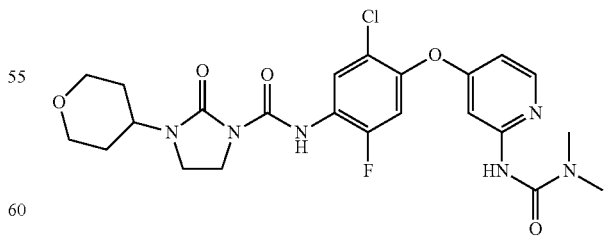

Example 101

A mixture of Example C8 (0.200 g, 0.426 mmol), N,N-dimethyl urea (0.225 g, 2.56 mmol), Cs₂CO₃ (0.347 g, 1.065 mmol) and Xantphos (0.074 g, 0.128 mmol) in dioxane (3 mL) was sparged with Ar, treated Pd₂(dba)₃ (0.051 g, 0.055 mmol), sparged again with Ar and heated at 100° C. overnight. The mixture was cooled to RT, treated with brine, extracted with EtOAc (3×) and the combined organics were dried over Na₂SO₄, concentrated to dryness and purified twice via silica gel chromatography (MeOH/DCM, then MeOH/EtOAc). The material was suspended in 1:1 EtOAc/Et₂O, sonicated and the resulting solid collected via filtration to afford N-(5-chloro-4-((2-(3,3-dimethylureido)pyridin-4-yl)oxy)-2-fluorophenyl)-2-oxo-3-(tetrahydro-2H-pyran-4-yl)imidazolidine-1-carboxamide (98 mg, 44%). ¹H NMR (400 MHz, DMSO-d₆): δ 10.92 (d, J=2.7 Hz, 1 H), 8.91 (s, 1 H), 8.39 (d, J=8.0 Hz, 1 H), 8.10 (d, J=5.7 Hz, 1 H), 7.56 (d, J=11.2 Hz, 1 H), 7.34 (d, J=2.4 Hz, 1 H), 6.56 (dd, J=5.7, 2.4 Hz, 1 H), 3.93-3.86 (m, 3 H), 3.83-3.81 (m, 2 H), 3.47 (m, 2H), 3.37 (m, 2 H), 2.87 (s, 6 H), 1.71 (m, 2 H), 1.59 (m, 2H); MS (ESI) m/z: 521.2 (M+H⁺).

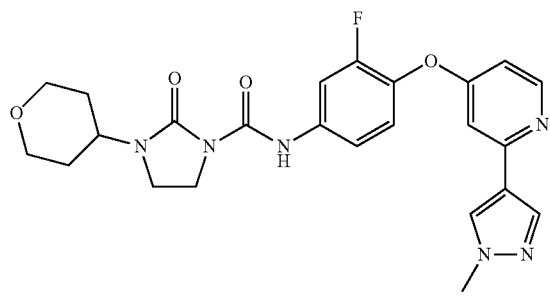 [SMILES: Cn1cc(-c2cc(Oc3ccc(NC(=O)N4CCN(C5CCOCC5)C4=O)cc3F)ccn2)cn1]

Example 102

Using a procedure analogous to Example 95, 2-fluoro-4-aminophenol (2.6 g, 24 mmol) and 2,4-dichloropyridine (2.88 g, 20 mol) were combined to provide 4-(2-chloropyridin-4-yloxy)-3-fluoroaniline (3.2 g, 67%). ¹H NMR (400 MHz, DMSO-d₆): δ 8.25 (d, J=5.6 Hz, 1 H), 6.99 (m, 1 H), 6.90 (m, 2 H), 6.50 (d, J=1.6 Hz, 1 H), 6.41 (d, J=10.4 Hz, 1 H), 5.51 (s, 2H); MS (ESI) m/z: 239.1 (M+H⁺).

Using a procedure analogous to Example 95, 4-(2-chloropyridin-4-yloxy)-3-fluoroaniline (3 g, 11.6 mmol), 1-methyl-4-(4,4,5,5-tetramethyl-1,3,2-dioxaborolan-2-yl)-1H-pyrazole (3.4 g, 16.4 mmol), Na₂CO₃ (2.7 g, 25.2 mmol) and Pd(Ph₃)₄ (1.5 g, 0.1 eq) were combined to give 3-fluoro-4-((2-(1-methyl-1H-pyrazol-4-yl)pyridin-4-yl)oxy)aniline (1.1 g, 34%). ¹H NMR (400 MHz, DMSO-d₆): 6 (8.31 (d, J=5.6 Hz, 1 H), 8.22 (s, 1 H), 7.93 (s, 1 H), 7.14 (s, 1 H), 6.98 (m, 1 H), 6.55-6.49 (m, 2 H), 6.42 (d, J=7.2 Hz, 1 H), 5.44 (s, 2H), 3.86 (s, 3H); MS (ESI) m/z: (M+H⁺): 285.2.

A 0° C. mixture of 3-fluoro-4-((2-(1-methyl-1H-pyrazol-4-yl)pyridin-4-yl)oxy)aniline (0.150 g, 0.528 mmol) and TEA (0.1 mL, 0.716 mmol) in DCM (5 mL) was treated with a solution of Example B2 (0.164 g, 0.705 mmol) in DCM (1.5 mL), warmed to RT and stirred for 1 h. The mixture was treated with water, stirred for 10 min, the layers separated and the organic layer dried over Na₂SO₄, concentrated to dryness and purified via silica gel chromatography (MeOH/DCM). The material was treated with DCM, sonicated and allowed to evaporate overnight. The residue was treated with Et₂O, sonicated and the resulting solid collected via filtration to afford N-(3-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (154 mg, 61%). ¹H NMR (400 MHz, DMSO-d₆): δ 10.59 (s, 1 H), 8.35 (d, J=5.7 Hz, 1 H), 8.25 (s, 1 H), 7.95 (s, 1 H), 7.74 (dd, J=12.9, 2.2 Hz, 1 H), 7.36-7.28 (m, 2 H), 7.22 (d, J=2.5 Hz, 1 H), 6.62 (dd, J=5.7, 2.5 Hz, 1 H), 3.94-3.82 (m, 6 H), 3.79 (m, 2 H), 3.45 (m, 2 H), 3.37 (m, 2 H), 1.72 (m, 2 H), 1.59 (m, 2H); MS (ESI) m/z: (M+H⁺): 481.2.

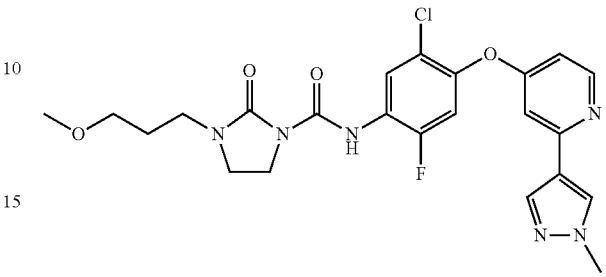

Example 103

A solution of Example B5 (0.071 g, 0.452 mmol) and pyridine (0.114 mL, 1.412 mmol) in DCM (2 mL) was added to phosgene (20% in toluene, 0.698 g, 1.412 mmol), stirred for 15 min, then concentrated to dryness. The residue was dissolved in DCM (2 mL), treated with a solution of Example A22 (0.09 g, 0.282 mmol) and TEA (0.118 mL, 0.847 mmol) in DCM (2 mL) and stirred at RT for 1 h. The mixture was diluted with water, extracted with DCM (2×) and the combined organics were washed with brine, dried over Na₂SO₄ and concentrated to dryness. The material was treated with 60% EtOAc/Hex, sonicated and the resulting solid collected via filtration to afford N-(5-chloro-2-fluoro-4-((2-(1-methyl-1H-pyrazol-4-yl)pyridin-4-yl)oxy)phenyl)-3-(3-methoxypropyl)-2-oxoimidazolidine-1-carboxamide (109 mg, 77%). ¹H NMR (400 MHz, DMSO-d₆): δ 10.91 (d, J=2.7 Hz, 1 H), 8.41 (d, J=8.1 Hz, 1 H), 8.36 (d, J=5.7 Hz, 1 H), 8.27 (s, 1 H), 7.98 (s, 1 H), 7.57 (d, J=11.3 Hz, 1 H), 7.20 (d, J=2.4 Hz, 1 H), 6.64 (dd, J=5.7, 2.5 Hz, 1 H), 3.84 (s, 3 H), 3.82-3.80 (m, 2 H), 3.47 (m, 2 H), 3.34 (m, 2 H), 3.27 (m, 2 H), 3.22 (s, 3 H), 1.73 (m, 2H); MS (ESI) m/z: (M+H⁺): 503.2.

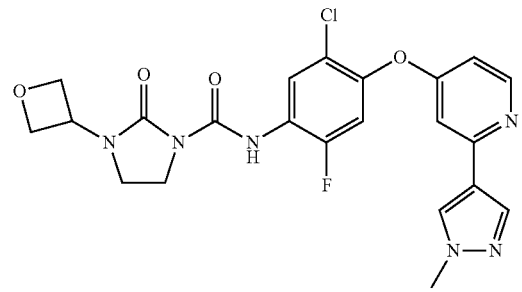 [SMILES: Cn1cc(-c2cc(Oc3cc(F)c(NC(=O)N4CCN(C5COC5)C4=O)cc3Cl)ccn2)cn1]

Example 104

A 0° C. solution of phosgene (20% in toluene, 0.853 mL, 1.177 mmol) in DCM (6 mL) was treated slowly drop-wise with a solution of Example B10 (0.119 g, 0.841 mmol) and pyridine (0.136 mL, 1.681 mmol) in DCM (2 mL), warmed to RT, stirred for 0.5 h, then concentrated to dryness. The residue was dissolved in DCM (2 mL), added to a 0° C. solution of Example A22 (0.084 g, 0.263 mmol) and TEA (0.110 mL, 0.788 mmol) in DCM (1 mL), warmed to RT and stirred overnight. The mixture was diluted with DCM, washed with water (3×), dried over MgSO₄, concentrated to dryness and purified via silica gel chromatography (MeOH/DCM) to afford N-(5-chloro-2-fluoro-4-((2-(1-methyl-1H-pyrazol-4-yl)pyridin-4-yl)oxy)phenyl)-3-(oxetan-3-yl)-2-oxoimidazolidine-1-carboxamide (44 mg, 34%). ¹H NMR (400 MHz, DMSO-d₆): δ 10.77 (d, J=2.7 Hz, 1 H), 8.39 (d, J=8.1 Hz, 1 H), 8.36 (d, J=5.7 Hz, 1 H), 8.26 (s, 1 H), 7.97 (s, 1 H), 7.57 (d, J=11.3 Hz, 1 H), 7.20 (d, J=2.4 Hz, 1 H), 6.64 (dd, J=5.7, 2.5 Hz, 1 H), 5.03 (m, 1 H), 4.77 (t, J=6.7 Hz, 2 H), 4.68 (t, J=7.3 Hz, 2H), 3.89-3.83 (m, 5 H), 3.77 (m, 2H); MS (ESI) m/z: (M+H⁺): 487.1.

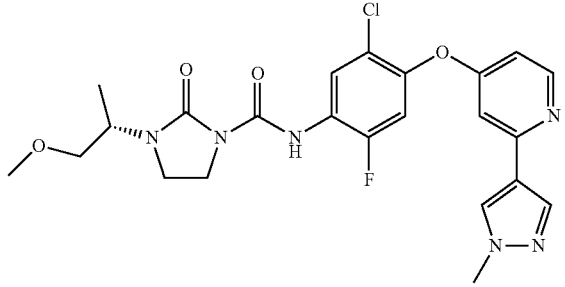 [SMILES: COC[C@H](C)N1CCN(C(=O)Nc2cc(Cl)c(Oc3ccnc(-c4cnn(C)c4)c3)cc2F)C1=O]

Example 105

A solution of Example B8 (298 mg, 0.941 mmol) and pyridine (112 mg, 1.412 mmol) in DCM (4 mL) was added to phosgene (20% in toluene, 1.164 g, 2.353 mmol), under Ar, stirred for 15 minutes, then concentrated to dryness. The residue was treated with a solution of Example A22 (150 mg, 0.471 mmol) and TEA (238 mg, 2.353 mmol) in DCM (4 mL) and stirred at RT overnight. The mixture was treated with water, extracted with EtOAc (2×) and the combined organics were washed with brine, dried over Na₂SO₄, concentrated to dryness and purified via reverse-phase chromatography (MeCN/H₂O with 0.1% TFA). The organics were removed under reduced pressure and the resulting aqueous residue was treated with satd. NaHCO₃, extracted with EtOAc (2×) and the combined organics were washed with brine, dried over Na₂SO₄ and concentrated to dryness. The material was further purified via silica gel chromatography (MeOH/EtOAc) to afford (S)—N-(5-chloro-2-fluoro-4-((2-(1-methyl-1H-pyrazol-4-yl)pyridin-4-yl)oxy)phenyl)-3-(1-methoxypropan-2-yl)-2-oxoimidazolidine-1-carboxamide (36 mg, 15%). ¹H NMR (400 MHz, DMSO-d₆): δ 10.90 (d, J=2.6 Hz, 1 H), 8.40 (d, J=8.0 Hz, 1 H), 8.36 (d, J=5.7 Hz, 1 H), 8.26 (s, 1 H), 7.97 (s, 1H), 7.56 (d, J=11.3 Hz, 1 H), 7.20 (d, J=2.5 Hz, 1 H), 6.64 (dd, J=5.7, 2.5 Hz, 1 H), 4.10-4.08 (m, 1 H), 3.84 (s, 3 H), 3.80 (m, 2H), 3.51-3.31 (m, 4 H), 3.25 (s, 3 H), 1.09 (d, J=6.9 Hz, 3H); MS (ESI) m/z: (M+H⁺): 503.1.

Example 106

A solution of Example B11 (0.103 g, 0.393 mmol) in DCM (4 mL) was treated with a solution of Example A22 (0.125 g, 0.393 mmol) and TEA (0.082 mL, 0.590 mmol) in DCM (4 mL), stirred at RT for 1 h, diluted with DCM, washed with water (2×), then brine (1×), dried over MgSO₄ and concentrated to dryness. The material was purified via silica gel chromatography (MeOH/EtOAc/Hex) to afford N-(5-chloro-2-fluoro-4-((2-(1-methyl-1H-pyrazol-4-yl)pyridin-4-yl)oxy)phenyl)-2-oxo-3-(2-(trifluoromethoxy)ethyl)imidazolidine-1-carboxamide (100 mg, 47%). ¹H NMR (400 MHz, DMSO-d₆): δ 10.80 (d, J=2.7 Hz, 1 H), 8.40-8.35 (m, 2 H), 8.27 (s, 1 H), 7.98 (s, 1 H), 7.58 (d, J=11.3 Hz, 1 H), 7.21 (d, J=2.4 Hz, 1 H), 6.65 (dd, J=5.7, 2.4 Hz, 1 H), 4.25 (t, J=5.1 Hz, 2 H), 3.86-3.80 (m, 5 H), 3.59-3.50 (m, 4H); MS (ESI) m/z: (M+H⁺): 543.1.

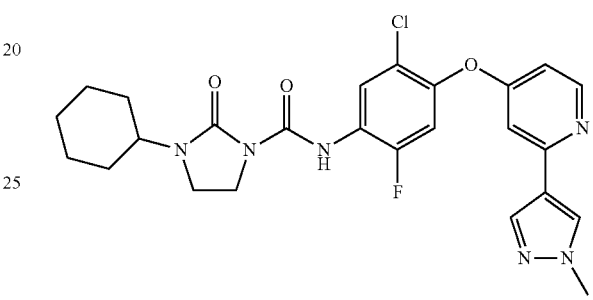

Example 107

A solution of Example B7 (0.076 g, 0.452 mmol) and pyridine (0.114 mL, 1.412 mmol) in DCM (2 mL) was added to phosgene (20% in toluene, 0.698 g, 1.412 mmol), under Ar, stirred for 15 min, then concentrated to dryness. The residue was dissolved in DCM (2 mL), treated with a solution of Example A22 (0.09 g, 0.282 mmol) and TEA (0.118 mL, 0.847 mmol) in DCM (2 mL) and stirred at RT for 1 h. The mixture was treated with water, extracted with DCM (2×) and the combined organics were washed with brine, dried over Na₂SO₄ and concentrated to dryness. The material was treated with 50% EtOAc/Hex, sonicated and the resulting solid collected via filtration to afford N-(5-chloro-2-fluoro-4-((2-(1-methyl-1H-pyrazol-4-yl)pyridin-4-yl)oxy)phenyl)-3-cyclohexyl-2-oxoimidazolidine-1-carboxamide (125 mg, 86%). ¹H NMR (400 MHz, DMSO-d₆): δ 10.95 (d, J=2.7 Hz, 1 H), 8.40 (d, J=8.1 Hz, 1 H), 8.36 (d, J=5.7 Hz, 1 H), 8.27 (s, 1 H), 7.98 (s, 1 H), 7.58 (d, J=11.2 Hz, 1 H), 7.21 (d, J=2.4 Hz, 1 H), 6.64 (dd, J=5.7, 2.4 Hz, 1 H), 3.84 (s, 3 H), 3.81-3.78 (m, 2 H), 3.63-3.60 (m, 1 H), 3.46-3.44 (m, 2 H), 1.71-1.67 (m, 5 H), 1.37-1.35 (m, 4H), 1.10-1.07 (m, 1H); MS (ESI) m/z: (M+H⁺): 513.2.

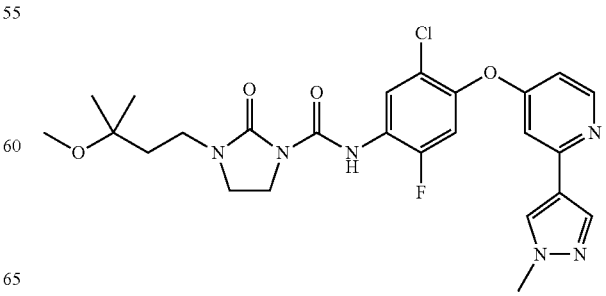

Example 108

A 0° C. solution of Example C9 (0.350 g, 0.812 mmol) in DMF (5 mL) was treated with NaH (60% in mineral oil, 0.100 g, 2.50 mmol), stirred at RT for 0.5 h, treated with Example C4 (0.500 g, 1.836 mmol) and stirred at RT overnight. The mixture was treated with water, extracted with EtOAc (3×) and the combined organics were dried over Na$_2$SO$_4$, concentrated to dryness and purified via silica gel chromatography (MeOH/DCM) to afford N-(5-chloro-2-fluoro-4-((2-(1-methyl-1H-pyrazol-4-yl)pyridin-4-yl)oxy)phenyl)-3-(3-methoxy-3-methylbutyl)-2-oxoimidazolidine-1-carboxamide (128 mg, 28%). $^1$H NMR (400 MHz, DMSO-d$_6$): δ 10.90 (s, 1 H), 8.38 (m, 2 H), 8.26 (s, 1 H), 7.97 (d, J=0.7 Hz, 1 H), 7.57 (d, J=11.3 Hz, 1 H), 7.20 (d, J=2.5 Hz, 1 H), 6.64 (dd, J=5.7, 2.5 Hz, 1 H), 3.84 (s, 3H), 3.80 (m, 2 H), 3.48 (t, J=8.2 Hz, 2 H), 3.28 (m, 2 H), 3.09 (s, 3 H), 1.70 (m, 2 H), 1.11 (s, 6H); MS (ESI) m/z: (M+H$^+$): 531.2.

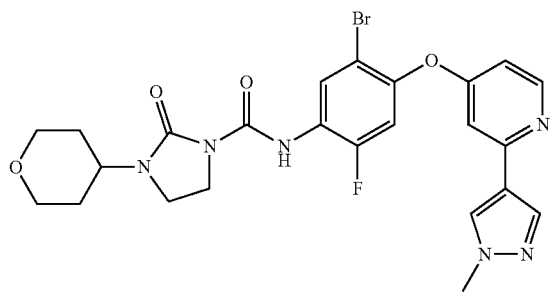 [SMILES: Cn1cc(-c2cc(Oc3cc(F)c(NC(=O)N4CCN(C5CCOCC5)C4=O)cc3Br)ccn2)cn1]

Example 109

A 0° C. mixture of 2-chloro-4-hydroxypyridine (817 mg, 6.30 mmol) in DMF (30 mL) was treated with NaH (60% in mineral oil, 277 mg, 6.93 mmol), stirred for 1 h, treated with 5-bromo-2,4-difluoronitrobenzene (1.50 g, 6.30 mmol) and heated at 90° C. overnight. The mixture was cooled to RT, diluted with water, extracted with EtOAc (2×) and the combined organics were washed with brine, dried over Na$_2$SO$_4$, concentrated to dryness and purified via silica gel chromatography (EtOAc/Hex) to afford 4-(2-bromo-5-fluoro-4-nitrophenoxy)-2-chloropyridine (1.16 g, 53%). MS (ESI) m/z: (M+H$^+$): 348.9.

A mixture of 4-(2-bromo-5-fluoro-4-nitrophenoxy)-2-chloropyridine (1.16 g, 3.34 mmol) and Raney Ni (0.5 g) in EtOH (40 mL) was hydrogenated (1 atm) overnight, the solids removed via filtration and washed with EtOH. The filtrate was concentrated to dryness, the residue dissolved in EtOAc, washed with brine, dried over Na$_2$SO$_4$ and concentrated to dryness to afford 5-bromo-4-((2-chloropyridin-4-yl)oxy)-2-fluoroaniline (994 mg, 94%). MS (ESI) m/z: (M+H$^+$): 318.9.

A mixture of 5-bromo-4-((2-chloropyridin-4-yl)oxy)-2-fluoroaniline (994 mg, 3.13 mmol), K$_3$PO$_4$ (1.993 g, 9.39 mmol) and 1-methyl-4-(4,4,5,5-tetramethyl-1,3,2-dioxaborolan-2-yl)-1H-pyrazole (716 mg, 3.44 mmol) in DMF (10 mL) and water (1.5 mL) was sparged with Ar, treated with Pd(PPh$_3$)$_4$ (362 mg, 0.313 mmol) and heated at 90° C. overnight. The mixture was cooled to RT, diluted with water, extracted with EtOAc (2×) and the combined organics were washed with brine, dried over Na$_2$SO$_4$, concentrated to dryness and purified via silica gel chromatography (EtOAc/Hex) to afford 5-bromo-2-fluoro-4-((2-(1-methyl-1H-pyrazol-4-yl)pyridin-4-yl)oxy)aniline (594 mg, 52%). MS (ESI) m/z: (M+H$^+$): 363.0.

A solution of Example B1 (141 mg, 0.826 mmol) and pyridine (98 mg, 1.239 mmol) in DCM (4 mL) was added to phosgene (20% in toluene, 1.021 g, 2.065 mmol), under Ar, stirred for 15 minutes, then concentrated to dryness. The residue was treated with a solution of 5-bromo-2-fluoro-4-((2-(1-methyl-1H-pyrazol-4-yl)pyridin-4-yl)oxy)aniline (150 mg, 0.413 mmol) and TEA (209 mg, 2.065 mmol) in DCM (4 mL) and stirred at RT for 0.5 h. The mixture was diluted with water, extracted with EtOAc (2×) and combined organics were washed with brine, dried over Na$_2$SO$_4$, concentrated to dryness and purified via silica gel chromatography (MeOH/EtOAc) to afford N-(5-bromo-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (134 mg, 58%). $^1$H NMR (400 MHz, DMSO-d$_6$): δ 10.90 (d, J=2.7 Hz, 1 H), 8.54 (d, J=8.2 Hz, 1 H), 8.36 (d, J=5.7 Hz, 1 H), 8.26 (s, 1 H), 7.97 (s, 1 H), 7.55 (d, J=11.3 Hz, 1 H), 7.19 (d, J=2.4 Hz, 1 H), 6.61 (dd, J=5.7, 2.5 Hz, 1 H), 3.93-3.87 (m, 3 H), 3.84 (s, 3 H), 3.83-3.78 (m, 2 H), 3.47 (m, 2 H), 3.37 (m, 2 H), 1.71 (m, 2 H), 1.59 (m, 2H); MS (ESI) m/z: (M+H$^+$): 559.1.

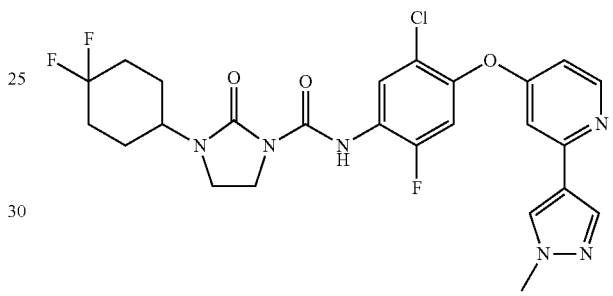

Example 110

A 0° C. solution of phosgene (20% in toluene, 1.50 mL, 2.84 mmol) was treated with a solution of Example B12 (0.200 g, 0.979 mmol) and pyridine (0.150 g, 1.896 mmol) in DCM (10 mL), stirred at RT for 0.5 h, then concentrated to dryness. The residue was treated with a solution of Example A22 (0.150 g, 0.471 mmol) and pyridine (0.150 g, 1.896 mmol) in DCM (10 mL) and stirred at RT for 2 h. The mixture was concentrated to dryness and purified via silica gel chromatography (EtOAc/DCM) to afford N-(5-chloro-2-fluoro-4-((2-(1-methyl-1H-pyrazol-4-yl)pyridin-4-yl)oxy)phenyl)-3-(4,4-difluorocyclohexyl)-2-oxoimidazolidine-1-carboxamide (63 mg, 24%). $^1$H NMR (400 MHz, DMSO-d$_6$): δ 10.91 (d, J=2.7 Hz, 1 H), 8.37 (m, 2 H), 8.26 (s, 1 H), 7.97 (s, 1 H), 7.57 (d, J 11.2 Hz, 1 H), 7.20 (d, J=2.5 Hz, 1 H), 6.64 (dd, J=5.7, 2.5 Hz, 1 H), 3.84 (m, 6 H), 3.46 (t, J=8.2 Hz, 2 H), 2.06-1.97 (m, 4 H), 1.68 (m, 4H); MS (ESI) m/z: (M+H$^+$): 549.2.

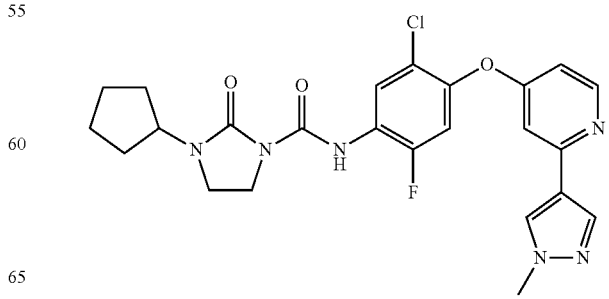

Example 111

A 0° C. solution of Example B14 (0.159 g, 1.031 mmol) and pyridine (0.272 mL, 3.37 mmol) in DCM (5 mL) was treated drop-wise with phosgene (20% in toluene, 1.579 mL, 2.99 mmol), warmed to RT, added to a solution of Example A22 (0.179 g, 0.561 mmol) and TEA (0.235 mL, 1.684 mmol) in DCM (5 mL) and stirred at RT for 2 h. The mixture was treated with satd. NaHCO$_3$, extracted with DCM (3×) and the combined organics were dried over Na$_2$SO$_4$, concentrated to dryness and purified via silica gel chromatography (MeOH/DCM) to afford N-(5-chloro-2-fluoro-4-((2-(1-methyl-1H-pyrazol-4-yl)pyridin-4-yl)oxy)phenyl)-3-cyclopentyl-2-oxoimidazolidine-1-carboxamide (137 mg, 49%). $^1$H NMR (400 MHz, DMSO-d$_6$): δ 10.93 (d, J=2.7 Hz, 1 H), 8.40 (d, J=8.0 Hz, 1 H), 8.36 (d, J=5.7 Hz, 1 H), 8.26 (s, 1 H), 7.97 (s, 1 H), 7.57 (d, J=11.3 Hz, 1 H), 7.20 (d, J=2.4 Hz, 1 H), 6.64 (dd, J=5.7, 2.5 Hz, 1 H), 4.19 (m, 1 H), 3.84 (s, 3 H), 3.81-3.79 (m, 2 H), 3.46 (m, 2H), 1.77-1.75 (m, 2 H), 1.69-1.50 (m, 6H); MS (ESI) m/z: (M+H$^+$): 499.2.

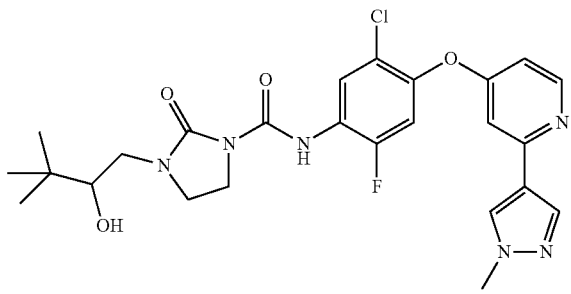 [SMILES: Cn1cc(-c2cc(Oc3cc(F)c(NC(=O)N4CCN(CC(O)C(C)(C)C)C4=O)cc3Cl)ccn2)cn1]

Example 112

A 0° C. solution of Example C9 (0.30 g, 0.696 mmol) in DMF (3 mL) was treated with NaH (60% in mineral oil, 0.070 g, 1.741 mmol), stirred at RT for 0.5 h, treated drop-wise with 2-(tert-butyl)oxirane (0.139 g, 1.393 mmol), stirred at RT for 1 h, then heated at 60° C. overnight. Additional 2-(tert-butyl) oxirane (0.1 mL) was added, the mixture heated at 60° C. for 7 h, cooled to RT, treated with additional NaH (60% in mineral oil, 0.070 g, 1.741 mmol), stirred for 20 min, treated with -(tert-butyl)oxirane (0.139 g, 1.393 mmol) and heated at 60° C. overnight. The mixture was cooled to RT, treated with water, extracted with EtOAc (3×) and the combined organics were washed with brine, dried over Na$_2$SO$_4$, concentrated to dryness and purified via silica gel chromatography (EtOAc, MeOH/DCM) to afford N-(5-chloro-2-fluoro-4-((2-(1-methyl-1H-pyrazol-4-yl)pyridin-4-yl)oxy)phenyl)-3-(2-hydroxy-3,3-dimethylbutyl)-2-oxoimidazolidine-1-carboxamide (29 mg, 7.5%). $^1$H NMR (400 MHz, DMSO-d$_6$): δ 10.95 (d, J=2.7 Hz, 1 H), 8.41 (d, J=8.1 Hz, 1 H), 8.36 (d, J=5.7 Hz, 1 H), 8.26 (s, 1 H), 7.97 (s, 1 H), 7.57 (d, J=11.3 Hz, 1 H), 7.20 (d, J=2.5 Hz, 1 H), 6.64 (dd, J=5.7, 2.5 Hz, 1 H), 4.84 (d, J=5.5 Hz, 1 H), 3.84 (s, 3 H), 3.80 (m, 2 H), 3.58 (m, 2 H), 3.31 (m, 2 H), 3.05 (m, 1 H), 0.87 (s, 9H); MS (ESI) m/z: (M+H$^+$): 531.2.

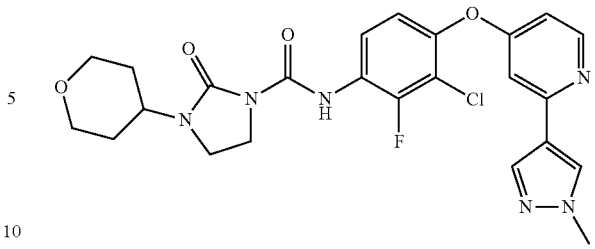

Example 113

A solution of 2-chloro-1,3-difluoro-4-nitrobenzene (80 g, 415 mmol) and benzyl alcohol (47 g, 435 mmol) in DMF (500 mL) was treated with K$_2$CO$_3$ (120 g, 870 mmol) and stirred at RT overnight. The mixture was poured into water, extracted with EtOAc (3×) and the combined organics were washed with brine, dried over Na$_2$SO$_4$, concentrated to dryness and purified via silica gel chromatography to afford 1-(benzyloxy)-2-chloro-3-fluoro-4-nitrobenzene (45 g, 39%). $^1$H NMR (400 MHz, DMSO-d$_6$): δ 8.21 (t, J=9.2 Hz, 1 H), 7.49-730 (m, 6 H), 5.40 (s, 2H).

A 0° C. solution of 1-(benzyloxy)-2-chloro-3-fluoro-4-nitrobenzene (45 g, 160 mmol) in DCM (200 mL) was treated drop-wise with tribromoborane (7.9 g, 320 mmol) over 0.5 h, stirred at 0° C. for 2 h, treated with satd. NaHCO$_3$ and was washed with brine. The organic layer was dried over Na$_2$SO$_4$ and concentrated to afford 2-chloro-3-fluoro-4-nitrophenol (25 g, 82%). $^1$H NMR (400 MHz, DMSO-d$_6$): δ 9.39 (s, 1 H), 6.95 (m, 2 H), 4.67 (brs, 2H).

A 0° C. solution of 2-chloro-3-fluoro-4-nitrophenol (25 g, 130.9 mmol) in 1:1 MeOH and THF (400 mL) was treated with NH$_4$Cl (70 g, 1.3 mol), followed by the portion-wise addition of zinc (83.2 g, 1.3 mol), then warmed to RT and stirred for 2 h. The solids were removed via filtration, the filtrate concentrated to dryness and the residue was dissolved in EtOAc, washed with brine, dried over Na$_2$SO$_4$ and concentrated to afford 4-amino-2-chloro-3-fluorophenol (16 g, 76%). $^1$H-NMR (400 MHz, DMSO-d$_6$): δ 9.41 (s, 1 H), 6.59-6.51 (m, 2 H), 4.65 (s, 2H); MS (ESI): m/z 162.2 [M+H]$^+$.

A mixture of 4-amino-2-chloro-3-fluorophenol (11 g, 68.3 mmol) and potassium 2-methylpropan-2-olate (8.4 g, 75.2 mmol) in DMA (120 mL) was stirred at RT under N$_2$ for 0.5 h, treated with 2,4-dichloropyridine (9.1 g, 62.1 mmol), and heated at 80° C. for 8 h. The mixture was concentrated to dryness, the residue treated with water, extracted with EtOAc (3×) and the combined organics were washed with brine, dried over Na$_2$SO$_4$, concentrated to dryness and purified via silica gel chromatography to afford 3-chloro-4-(2-chloropyridin-4-yloxy)-2-fluoroaniline (10 g, 59%). $^1$H NMR (400 MHz, DMSO-d$_6$): δ 8.26 (d, J=5.6 Hz, 1H), 6.98-6.96 (m, 2 H), 6.88 (dd, J=5.6 Hz, 2.0 Hz, 1 H), 6.80 (t, J=9.2 Hz, 1 H), 5.57 (s, 2H).

A solution of 3-chloro-4-(2-chloropyridin-4-yloxy)-2-fluoroaniline (10 g, 36.8 mmol) in DMF (140 mL) and water (30 mL) was treated with 1-methyl-4-(4,4,5,5-tetramethyl-1,3,2-dioxaborolan-2-yl)-1H-pyrazole (8.4 g, 40.5 mmol), K$_3$PO$_4$ (14.9 g, 73.6 mmol) and Pd(PPh$_3$)$_4$ (4.3 g, 3.7 mmol), sparged with N$_2$ and heated at 80° C. for 12 h. The mixture was cooled to RT, poured into water and extracted with EtOAc (3×). The combined organics were washed with brine, dried over Na$_2$SO$_4$, concentrated to dryness and purified via silica gel chromatography to afford 3-chloro-2-fluoro-4-((2-

(1-methyl-1H-pyrazol-4-yl)pyridin-4-yl)oxy)aniline (3.0 g, 26%). ¹H NMR (400 MHz, DMSO-d₆): δ 8.32 (d, J=6.0 Hz, 1 H), 8.24 (s, 1 H), 7.95 (s, 1 H), 7.15 (d, J=1.6 Hz, 1 H), 6.94 (d, J=8.8 Hz, 1 H), 6.80 (t, J=8.8 Hz, 1 H), 6.54-6.52 (m, 1 H), 5.51 (s, 2 H), 3.85 (s, 3H); MS (ESI): m/z 318.2 (M+H⁺).

A mixture of 3-chloro-2-fluoro-4-((2-(1-methyl-1H-pyrazol-4-yl)pyridin-4-yl)oxy)aniline (0.250 g, 0.784 mmol) and TEA (0.150 mL, 1.076 mmol) in DCM (5 mL) was treated drop-wise with a solution of Example B2 (0.219 g, 0.941 mmol) in DCM (5 mL), warmed to RT and stirred overnight. The mixture was treated with water, extracted with DCM (3×) and the combined organics were dried over Na₂SO₄, concentrated to dryness and purified via silica gel chromatography (MeOH/DCM). The material was treated with MeCN, sonicated and the resulting solid collected via filtration to afford N-(3-chloro-2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide (242 mg, 60%). ¹H NMR (400 MHz, DMSO-d₆): δ 10.86 (s, 1 H), 8.36 (d, J=5.7 Hz, 1 H), 8.26 (s, 1 H), 8.18 (t, J=8.9 Hz, 1 H), 7.97 (s, 1 H), 7.25-7.20 (m, 2 H), 6.65 (dd, J=5.7, 2.4 Hz, 1 H), 3.90 (m, 3 H), 3.84 (s, 3 H), 3.81 (m, 2 H), 3.47 (m, 2 H), 3.38 (m, 2 H), 1.77-1.65 (m, 2 H), 1.59 (m, 2H); MS (ESI) m/z: (M+H⁺): 515.1.

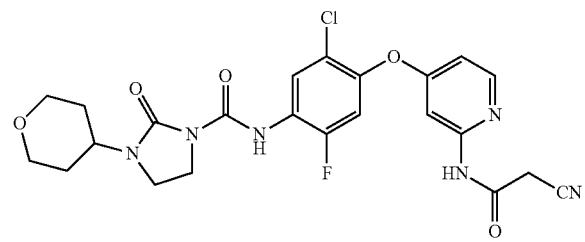 [SMILES: N#CCC(=O)Nc1cc(Oc2cc(F)c(NC(=O)N3CCN(C4CCOCC4)C3=O)cc2Cl)ccn1]

Example 114

A mixture of Example C8 (1 g, 2.131 mmol), t-butyl carbamate (0.749 g, 6.39 mmol), Cs₂CO₃ (2.083 g, 6.39 mmol) and Xantphos (0.555 g, 0.959 mmol) in dioxane (15 mL) was sparged with Ar, treated with Pd₂(dba)₃ (0.293 g, 0.320 mmol), sparged again with Ar and heated at 100° C. overnight. The mixture was cooled to RT, treated with satd. NaHCO₃, extracted with EtOAc (3×) and the combined organics were dried over Na₂SO₄, passed through a pad of silica gel and concentrated to dryness to afford crude tert-butyl (4-(2-chloro-5-fluoro-4-(2-oxo-3-(tetrahydro-2H-pyran-4-yl)imidazolidine-1-carboxamido)phenoxy)pyridin-2-yl)carbamate (1.32 g, 113%) which was used without further purification. MS (ESI) m/z: (M+H⁺): 550.1.

tert-Butyl(4-(2-chloro-5-fluoro-4-(2-oxo-3-(tetrahydro-2H-pyran-4-yl)imidazolidine-1-carboxamido)phenoxy)pyridin-2-yl)carbamate (1.32 g, 2.400 mmol) was combined with TFA (20 mL), stirred at RT overnight and concentrated to dryness. The residue was treated with DCM, sonicated, the solid removed via filtration and the filtrate concentrated to dryness and purified via silica gel chromatography (MeOH/EtOAc) to afford N-(4-((2-aminopyridin-4-yl)oxy)-5-chloro-2-fluorophenyl)-2-oxo-3-(tetrahydro-2H-pyran-4-yl)imidazolidine-1-carboxamide (382 mg, 35%). MS (ESI) m/z: (M+H⁺): 450.1.

A RT solution of cyanoacetic acid (0.500 g, 5.88 mmol) in DCM (20 mL) and DMF (0.1 mL) was treated drop-wise with oxalyl chloride (1.1 mL, 12.52 mmol), stirred at RT for 2.5 h, then concentrated to dryness. The residue was dissolved in DCM (5 mL), added drop-wise to a 0° C. solution of N-(4-((2-aminopyridin-4-yl)oxy)-5-chloro-2-fluorophenyl)-2-oxo-3-(tetrahydro-2H-pyran-4-yl)imidazolidine-1-carboxamide (0.210 g, 0.467 mmol) in pyridine (10 mL), stirred for 0.5 h, then concentrated to dryness. The residue was dissolved in DCM, washed with satd. NaHCO₃ and the aqueous layer extracted with EtOAc (3×). The combined organics were dried over Na₂SO₄, concentrated to dryness and purified twice via silica gel chromatography (MeOH/DCM, then MeOH/EtOAc). The material was further purified via silica gel chromatography (MeOH/DCM) to afford N-(5-chloro-4-((2-(2-cyanoacetamido)pyridin-4-yl)oxy)-2-fluorophenyl)-2-oxo-3-(tetrahydro-2H-pyran-4-yl)imidazolidine-1-carboxamide (120 mg, 49%). MS (ESI) m/z: (M+H⁺): 516.8.

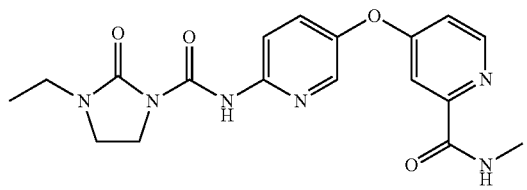 [SMILES: CCN1CCN(C(=O)Nc2ccc(Oc3ccnc(C(=O)NC)c3)cn2)C1=O]

Example 115

A 0° C. solution of phosgene (15% in toluene, 2 mL, 2.84 mmol) in DCM (5 mL) was treated drop-wise with a solution of pyridine (0.1 mL, 1.24 mmol) and Example B18 (0.095 g, 0.82 mmol) in DCM (5 mL), warmed to RT, stirred for 1 h, then concentrated to dryness. The residue was dissolved in DCM (5 mL), cooled to 0° C., treated with a solution of Example A23 (0.10 g, 0.409 mmol) and pyridine (0.1 mL) in DCM (5 mL), warmed to RT and stirred overnight. The mixture was treated with satd. NaHCO₃, extracted with EtOAc (3×) and the combined organics were dried over Na₂SO₄ and concentrated to dryness. The resultant material was treated with EtOAc and sonicated. The resulting solid was collected by filtration to afford 4-((6-(3-ethyl-2-oxoimidazolidine-1-carboxamido)pyridin-3-yl)oxy)-N-methylpicolinamide (105 mg, 66%). ¹H NMR (400 MHz, DMSO-d₆): δ 11.02 (s, 1 H), 8.79 (q, J=4.8 Hz, 1 H), 8.52 (d, J=5.6 Hz, 1 H), 8.27 (d, J=2.9 Hz, 1 H), 8.10 (d, J=9.0 Hz, 1 H), 7.77 (dd, J=9.0, 2.9 Hz, 1 H), 7.41 (d, J=2.6 Hz, 1 H), 7.18 (dd, J=5.6, 2.7 Hz, 1H), 3.81 (m, 2 H), 3.47 (m, 2 H), 3.26 (q, J=7.2 Hz, 2 H), 2.78 (d, J=4.8 Hz, 3 H), 1.09 (t, J=7.2 Hz, 3H); MS (ESI) m/z: 385.2 (M+H⁺).

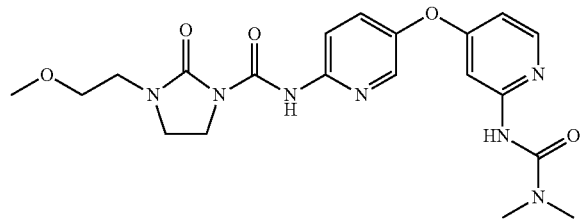

Example 116

A 0° C. solution of phosgene (15% in toluene, 3 mL, 4.21 mmol) in DCM (10 mL) was treated drop-wise with a solution of pyridine (0.350 mL, 4.35 mmol) and Example B3 (0.601 g, 4.17 mmol) in DCM (4 mL), stirred for 30 min, then concentrated to dryness. The residue was dissolved in DCM (4 mL)

and added drop-wise to a 0° C. solution of Example A24 (0.95 g, 3.48 mmol) and pyridine (0.35 mL, 4.35 mmol) in DCM (20 mL). After ~15 min of stirring, the reaction mixture was concentrated to dryness and left under high vacuum overnight. The product was dissolved in DCM and extracted with satd aq NaHCO₃. The aqueous layer was back-extracted with DCM (3×). The organic phases were combined, dried (Na₂SO₄) and concentrated to dryness to afford a red solid. The solid was purified via silica gel chromatography (1-6% MeOH/DCM) to afford a yellow oil which was further purified by reverse-phase silica gel chromatography (10-45% water/CH₃CN (0.1% TFA)). The enriched fractions were collected, concentrated, neutralized with sat'd NaHCO₃ and extracted with EtOAc (3×). The organic phases were combined, dried (Na₂SO₄) and concentrated to dryness to afford a white foam. The foam was dissolved in CH₃CN/H₂O, frozen and lyophilized overight to afford N-(5-((2-(3,3-dimethylureido)pyridin-4-yl)oxy)pyridin-2-yl)-3-(2-methoxyethyl)-2-oxoimidazolidine-1-carboxamide as a white solid. (0.246 g, 16%). ¹H NMR (400 MHz, DMSO-d₆): 10.96 (s, 1 H), 8.97 (s, 1 H), 8.20 (d, J=2.9 Hz, 1 H), 8.11 (d, J=5.8 Hz, 1 H), 8.06 (d, J=9.0 Hz, 1 H), 7.70 (dd, J=9.0, 2.9 Hz, 1H), 7.36 (d, J=2.3 Hz, 1 H), 6.62 (dd, J=5.8, 2.4 Hz, 1 H), 3.84-3.76 (m, 2 H), 3.53-3.45 (m, 4 H), 3.41-3.36 (m, 2 H), 3.26 (s, 3 H), 2.88 (s, 6H); MS (ESI) m/z: 444.2 (M+H⁺).

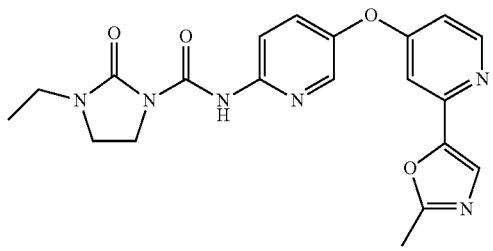 [SMILES: CCN1CCN(C(=O)Nc2ccc(Oc3ccnc(-c4cnc(C)o4)c3)cn2)C1=O]

Example 117

A 0° C. solution of phosgene (15% in toluene, 1.77 mL, 2.52 mmol) was treated drop-wise with a solution of pyridine (0.226 mL, 2.80 mmol) and Example B18 (158 mg, 1.23 mmol) in DCM (2 mL), warmed to RT, stirred for 1 h, then concentrated to dryness. The residue was dissolved in DCM (2 mL) and added drop-wise to a 0° C. solution of Example A25 (150 mg, 0.559 mmol) and pyridine (0.226 mL, 2.80 mmol), in DCM (2 mL). The reaction mixture was stirred at 0° C. for 15 min, then at room temperature for 22 h. The mixture was diluted with EtOAc (30 mL) and 1/2 saturated sodium bicarbonate (30 mL). The organic phase was washed with brine (30 mL), dried over sodium sulfate, and evaporated at reduced pressure. The residue was purified by chromatography (0-10% MeOH/EtOAc). The resultant material was dissolved in MeCN (2 mL) and then diluted with water (4 mL). The solution was quickly frozen and lyophilized, overnight to provide 3-ethyl-N-(5-((2-(2-methyloxazol-5-yl)pyridin-4-yl)oxy)pyridin-2-yl)-2-oxoimidazolidine-1-carboxamide (26 mg, 10%). ¹H NMR (400 MHz, DMSO-d₆): δ 11.01 (s, 1 H), 8.48 (d, J=5.7 Hz, 1 H), 8.26 (d, J=2.9 Hz, 1 H), 8.09 (d, J=9.0 Hz, 1 H), 7.76 (dd, J=9.0, 3.0 Hz, 1 H), 7.64 (s, 1 H), 7.16 (d, J=2.5 Hz, 1 H), 6.91 (dd, J=5.7, 2.5 Hz, 1 H), 3.81 (t, J=8.2 Hz, 2 H), 3.46 (t, J=8.2 Hz, 2 H), 3.26 (q, J=7.3 Hz, 2 H), 2.46 (s, 3 H), 1.09 (t, J=7.2 Hz, 3H). MS (ESI) m/z: 409.2 (M+H⁺).

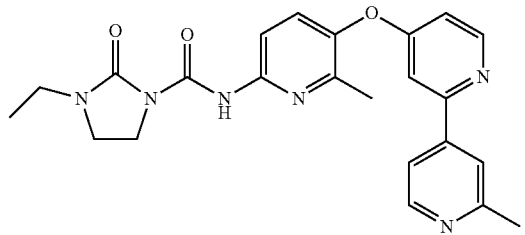 [SMILES: CCN1CCN(C(=O)Nc2ccc(Oc3ccnc(-c4ccnc(C)c4)c3)c(C)n2)C1=O]

Example 118

A solution of phosgene (15% in toluene, 2.41 mL, 3.42 mmol) was cooled to 0° C. A solution of pyridine (0.277 mL, 3.42 mmol) and Example B18 (158 mg, 1.23 mmol) in DCM (2 mL) was added drop-wise over 5 min. The reaction mixture was stirred for 1 h at RT and was evaporated at reduced pressure to near dryness. The residue was dissolved in DCM (2 mL) and added drop-wise to a 0° C. of Example A26 (150 mg, 0.559 mmol) and pyridine (0.277 mL, 3.42 mmol), in THF (2 mL). The reaction mixture was stirred at 0° C. for 15 min and at RT for 22 h. The mixture was diluted with EtOAc (30 mL) and half-saturated sodium bicarbonate (30 mL). The organic phase was washed with brine (30 mL), dried over sodium sulfate, and evaporated under reduced pressure. The residue was purified by silica gel chromatography (0-10% MeOH/EtOAc). The enriched fractions were combined and further purified by reverse phase silica gel chromatography (20-50% MeCN/water (0.1% TFA) to provide 3-ethyl-N-(6-methyl-5-((2'-methyl-[2,4'-bipyridin]-4-yl)oxy)pyridin-2-yl)-2-oxoimidazolidine-1-carboxamide (141 mg, 38%). ¹H NMR (400 MHz, DMSO-d₆): δ 10.92 (s, 1 H), 9.10 (d, J=2.3 Hz, 1 H), 8.52 (d, J=5.7 Hz, 1 H), 8.28 (dd, J=8.1, 2.4 Hz, 1 H), 7.91 (d, J=8.8 Hz, 1 H), 7.64 (d, J=8.8 Hz, 1 H), 7.58 (d, J=2.4 Hz, 1 H), 7.33 (d, J=8.2 Hz, 1 H), 6.77 (dd, J=5.7, 2.4 Hz, 1 H), 3.80 (t, J=8.3 Hz, 2 H), 3.46 (t, J=8.2 Hz, 2 H), 3.26 (q, J=7.3 Hz, 2 H), 2.50 (s, 3 H), 2.26 (s, 3 H), 1.09 (t, J=7.2 Hz, 3H). MS (ESI) m/z: 433.2 (M+H⁺).

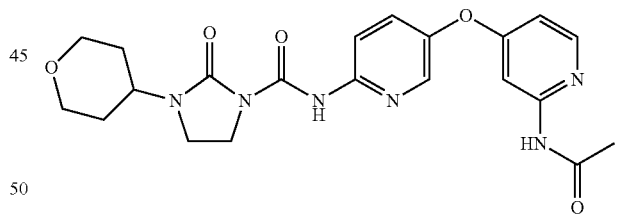

Example 119

A mixture of Example C1 (0.300 g, 0.718 mmol), acetamide (0.127 g, 2.154 mmol), Cs₂CO₃ (0.468 g, 1.436 mmol) and Xantphos (0.046 g, 0.079 mmol) in dioxane (7 mL) was sparged with Ar under sonication. Pd₂(dba)₃ 0.053 g, 0.057 mmol) was added, and the mixture was sparged again with Ar and heated at 93° C. overnight. The mixture was cooled to RT, and partitioned with EtOAc and brine. The aqueous layer was extracted with EtOAc (3×) and the combined organics were dried over Na₂SO₄, concentrated to dryness and purified by silica gel chromatography (MeOH/DCM). The material was suspended in 4:1 MeCN/water, frozen and lyophilized overnight, and further dried in a drying oven to afford N-(5-((2- acetamidopyridin-4-yl)oxy)pyridin-2-yl)-2-oxo-3-(tetrahydro-2H-pyran-4-yl)imidazolidine-1-carboxamide (0.287 g, 90%) as a white solid. ¹H NMR (400 MHz, DMSO-d₆): δ 10.98 (s, 1 H), 10.57 (s, 1 H), 8.23 (dd, J=2.9, 0.5 Hz, 1 H), 8.19 (d, J=5.7 Hz, 1 H), 8.08 (dd, J=9.0, 0.5 Hz, 1 H), 7.72 (dd, J=9.0, 2.9 Hz, 1 H), 7.66 (d, J=2.3 Hz, 1H), 6.69 (dd, J=5.7, 2.4 Hz, 1 H), 3.94-3.79 (m, 5 H), 3.49-3.37 (m, 4 H), 2.04 (s, 3 H), 1.78-1.67 (m, 2 H), 1.64-1.58 (m, 2H); MS (ESI) m/z: 441.2 (M+H⁺).

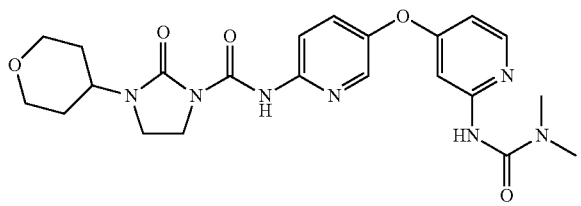 [SMILES: CN(C)C(=O)Nc1cc(Oc2ccc(NC(=O)N3CCN(C4CCOCC4)C3=O)nc2)ccn1]

Example 120

A mixture of Example C1 (0.150 g, 0.359 mmol), N,N-dimethyl urea (0.190 g, 2.154 mmol), Cs₂CO₃ (0.292 g, 0.897 mmol) and Xantphos (0.062 g, 0.108 mmol) in dioxane (7 mL) was sparged with Ar, treated Pd₂(dba)₃ (0.043 g, 0.047 mmol), sparged again with Ar and heated at 100° C. overnight. The mixture was cooled to RT, treated with aqueous saturated NaHCO₃, and extracted with EtOAc (3×). The combined organics were dried over Na₂SO₄, concentrated to dryness and purified via silica gel chromatography (MeOH/DCM). The yellowish solid was re-purified via reverse-phase chromatography (MeCN/H₂O with 0.1% TFA). The organics were removed under reduced pressure, the aqueous residue neutralized with satd. NaHCO₃ and extracted with EtOAc (3×). The combined organics were dried over Na₂SO₄, concentrated to dryness and dried in vacuo. The residue was dissolved in 4:1 MeCN/water, frozen and lyophilized overnight to afford N-(5-((2-(3,3-dimethylureido)pyridin-4-yl)oxy)pyridin-2-yl)-2-oxo-3-(tetrahydro-2H-pyran-4-yl)imidazolidine-1-carboxamide (110 mg, 54%) as a white solid. ¹H NMR (400 MHz, DMSO-d₆): δ 10.96 (s, 1 H), 8.90 (s, 1 H), 8.20 (d, J=2.5 Hz, 1 H), 8.10 (J=5.7 Hz, 1 H), 8.06 (d, J=9.0 Hz, 1 H), 7.69 (dd, J=9.0, 2.9 Hz, 1 H), 7.37 (d, J=2.4 Hz, 1 H), 6.60 (dd, J=5.7, 2.4 Hz, 1 H), 3.93-3.77 (m, 5 H), 3.47-3.35 (m, 4 H), 2.87 (s, 6 H), 1.76-1.65 (m, 2 H), 1.62-1.56 (m, 2H); MS (ESI) m/z: 470.2 (M+H⁺).

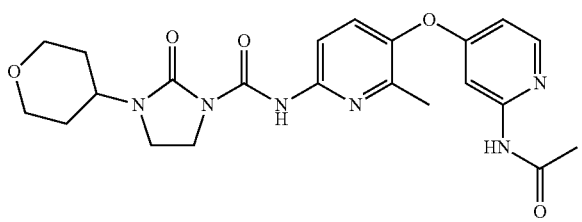 [SMILES: CC(=O)Nc1cc(Oc2ccc(NC(=O)N3CCN(C4CCOCC4)C3=O)nc2C)ccn1]

Example 121

To a degassed solution of Example C3 (0.12 g, 0.278 mmol) in dioxane (3 mL) was added acetamide (0.066 g, 1.111 mmol), Cs₂CO₃ (0.091 g, 0.278 mmol), X-Phos (0.013 g, 0.028 mmol), Pd₂(dba)₃ (0.025 g, 0.028 mmol) and the mixture was stirred at 80° C. for 16 h. The mixture was diluted with EtOAc (5 mL) and filtered through a pad of diatomaceous earth. The filter pad was washed with EtOAc (3×8 mL). The combined filtrates were washed with water and brine, dried (Na₂SO₄) and concentrated in vacuo. The residue was purified by chromatography (0-5% MeOH/DCM) to afford a colorless foam. The foam was dissolved in MeCN-water and the solution was frozen and lyophilized to provide N-(5-((2-acetamidopyridin-4-yl)oxy)-6-methylpyridin-2-yl)-2-oxo-3-(tetrahydro-2H-pyran-4-yl)imidazolidine-1-carboxamide (83 mg, 66%) as a white solid. ¹H NMR (400 MHz, DMSO-d₆): δ 10.89 (s, 1 H), 10.54 (s, 1 H), 8.16 (d, J=5.7 Hz, 1 H), 7.88 (d, J=8.8 Hz, 1 H), 7.60 (d, J=8.8 Hz, 1 H), 7.57 (d, J=2.4 Hz, 1 H), 6.61 (dd, J=5.7, 2.4 Hz, 1 H), 3.93-3.78 (m, 5H), 3.48-3.33 (m, 4 H), 2.20 (s, 3 H), 2.02 (s, 3 H), 1.78-1.67 (m, 2 H), 1.64-1.58 (m, 2H); MS (ESI) m/z: 455.1 (M+H⁺).

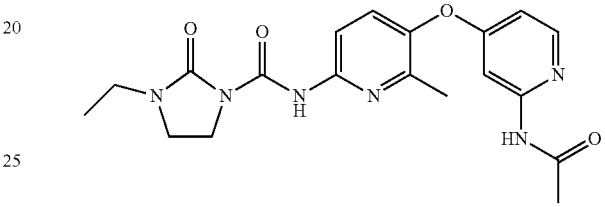

Example 122

A solution of Example B18 (0.088 g, 0.774 mmol) and pyridine (0.125 mL, 1.549 mmol) in DCM (2 mL) was added to a solution of phosgene (15% in toluene, 1.021 g, 1.549 mmol) under argon. The reaction mixture was stirred 15 minutes and then concentrated to dryness. The resultant solid was dissolved in DCM (2 mL) and was treated with a solution of Example A28 (0.10 g, 0.387 mmol) and triethylamine (0.162 mL, 1.162 mmol) in THF (4 mL). The mixture was stirred for 1 h at RT, was diluted with water (30 mL) and 10% MeOH-DCM (30 mL). The layers were separated and the aqueous layer was extracted with DCM (10 mL). The combined organics were washed with brine, dried (Na₂SO₄) and concentrated in vacuo. The residue was purified by slica gel chromatography (1-15% MeOH/DCM) to afford a foam. The foam was dissolved in MeCN-water and solution was frozen and lyophilized. The resultant solid was treated with 60% EtOAc-hexanes (~3 mL) with stirring. The resultant suspension was collected by filtration, washed with 30% EtOAc-hexanes, and dried overnight to provide N-(5-((2-acetamidopyridin-4-yl)oxy)-6-methylpyridin-2-yl)-3-ethyl-2-oxoimidazolidine-1-carboxamide (84 mg, 54.5%) as a white solid. ¹H NMR (400 MHz, DMSO-d₆): δ 10.90 (s, 1 H), 10.54 (s, 1 H), 8.16 (d, J=5.7 Hz, 1H), 7.89 (d, J=8.8 Hz, 1 H), 7.58-7.57 (m, 2 H), 6.61 (dd, J=5.7, 2.4 Hz, 1 H), 3.82-3.78 (m, 2 H), 3.48-3.44 (m, 2 H), 3.25 (q, J=7.2 Hz, 2 H), 2.20 (s, 3 H), 2.02 (s, 3 H), 1.09 (t, J=7.2 Hz, 3H); MS (ESI) m/z: 399.2 (M+H⁺).

The following assays demonstrate that certain compounds of Formula I inhibit kinase activity of c-FMS kinase, c-KIT kinase, or PDGFRβ kinase in enzymatic assays and also inhibit the activity of c-FMS kinase in M-NFS-60 and THP-1 cell lines. In vivo evaluations of certain compounds of Formula I also demonstrate inhibition of c-FMS in a pharmcodynamic model or also exhibit efficacy in a peritibial implant model, a U-251 or GL-261 glioma model, or in a MDA-MB-231 breast cancer xenograft model.

uFMS kinase (Seq. ID No. 1) Assay

Activity of unphosphorylated c-FMS kinase (uFMS, Seq. ID no. 1) was determined by following the production of ADP from the FMS kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained FMS (purchased from Millipore) (10 nM), polyE4Y (1 mg/mL), MgCl$_2$ (10 mM), pyruvate kinase (4 units), lactate dehydrogenase (0.7 units), phosphoenol pyruvate (1 mM), NADH (0.28 mM) and ATP (500 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader. The reaction rate was calculated using the 3 to 4 h time frame. Percent inhibition was obtained by comparison of reaction rate with that of a control (i.e., in the absence of test compound). IC$_{50}$ values were calculated from a series of percent inhibition values determined at a range of inhibitor concentrations using software routines as implemented in the GraphPad Prism software package.

uFMS Kinase Sequence (Y538-End) Used for Screening (Seq. ID No. 1)

```
YKYKQKPKYQ VRWKIIESYE GNSYTFIDPT QLPYNEKWEF
PRNNLQFGKT LGAGAFGKVV EATAFGLGKE DAVLKVAVKM
LKSTAHADEK EALMSELKIM SHLGQHENIV NLLGACTHGG
PVLVITEYCC YGDLLNFLRR KAEAMLGPSL SPGQDPEGGV
DYKNIHLEKK YVRRDSGFSS QGVDTYVEMR PVSTSSNDSF
SEQDLDKEDG RPLELRDLLH FSSQVAQGMA FLASKNCIHR
DVAARNVLLT NGHVAKIGDF GLARDIMNDS NYIVKGNARL
PVKWMAPESI FDCVYTVQSD VWSYGILLWE IFSLGLNPYP
GILVNSKFYK LVKDGYQMAQ PAFAPKNIYS IMQACWALEP
THRPTFQQIC SFLQEQAQED RRERDYTNLP SSSRSGGSGS
SSSELEEESS SEHLTCCEQG DIAQPLLQPN NYQFC
``` uKit Kinase (Seq. ID No. 2) Assay

Activity of unphosphorylated c-KIT kinase (uKIT, Seq. ID no. 2) was determined by following the production of ADP from the KIT kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μl) contained unphosphorylated KIT (12 nM), polyE4Y (1 mg/mL), MgCl$_2$ (10 mM), pyruvate kinase (4 units), lactate dehydrogenase (0.7 units), phosphoenol pyruvate (1 mM), and NADH (0.28 mM) and ATP (2000 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 4 hours at 30° C. on Synergy 2 plate reader (BioTech). Reaction rates around 3 to 4 h time frame were used to calculate % inhibitions, from which IC$_{50}$ values were generated.

uKit with N-Terminal GST Fusion Used for Screening (Seq ID No. 2)

```
LGYWKIKGLV QPTRLLLEYL EEKYEEHLYE RDEGDKWRNK
KFELGLEFPN LPYYIDGDVK LTQSMAIIRY IADKHNMLGG
CPKERAEISM LEGAVDIRYG VSRIAYSKDF ETLKVDFLSK
LPEMLKMFED RLCHKTYLNG DHVTHPDFML YDALDVVLYM
DPMCLDAFPK LVCFKKRIEA IPQIDKYLKS SKYIWPLQGW
QATFGGGDHP PKSDLVPRHN QTSLYKKAGS AAAVLEENLY
FQGTYKYLQK PMYEVQWKVV EEINGNNYVY IDPTQLPYDH
KWEFPRNRLS FGKTLGAGAF GKVVEATAYG LIKSDAAMTV
AVKMLKPSAH LTEREALMSE LKVLSYLGNH MNIVNLLGAC
TIGGPTLVIT EYCCYGDLLN FLRRKRDSFI CSKQEDHAEA
ALYKNLLHSK ESSCSDSTNE YMDMKPGVSY VVPTKADKRR
SVRIGSYIER DVTPAIMEDD ELALDLEDLL SFSYQVAKGM
AFLASKNCIH RDLAARNILL THGRITKICD FGLARDIKND
SNYVVKGNAR LPVKWMAPES IFNCVYTFESD VWSYGIFLWE
LFSLGSSPYP GMPVDSKFYK MIKEGFRMLS PEHAPAEMYD
IMKTCWDADP LKRPTFKQIV QLIEKQISES TNHIYSNLAN
CSPNRQKPVV DHSVRINSVG STASSSQPLL VHDDV
```

Unphosphorylated PDGFRβ (uPDGFRβ) Kinase (Seq. ID No. 3) Assay

Activity of unphosphorylated PDGFRβ kinase (uPDGFRβ, Seq. ID No. 3) was determined by following the production of ADP from the kinase reaction with ATP and poly E4Y as substrates through coupling with the pyruvate kinase/lactate dehydrogenase system (e.g., Schindler et al. Science (2000) 289: 1938-1942). In this assay, the oxidation of NADH (thus the decrease at A340 nm) was continuously monitored spectrophometrically. The reaction mixture (100 μL) contained PDGFRβ (DeCode, 15.7 nM), polyE4Y (2.5 mg/mL), MgCl$_2$ (10 mM), pyruvate kinase (4 units), lactate dehydrogenase (0.7 units), phosphoenol pyruvate (1 mM) and NADH (0.28 mM) and ATP (500 μM) in a 90 mM Tris buffer containing 0.2% octyl-glucoside and 1% DMSO, at pH 7.5. The inhibition reaction was started by mixing serial diluted test compound with the above reaction mixture. The absorption at 340 nm was monitored continuously for 4 h at 30° C. on a Polarstar Optima or Synergy 2 plate reader. The reaction rate was calculated using the 1.5 to 2.5 h time frame. Percent inhibition was obtained by comparison of reaction rate with that of a control (i.e., with no test compound). IC$_{50}$ values were calculated from a series of percent inhibition values determined at a range of inhibitor concentrations using software routines as implemented in the GraphPad Prism software package.

uPDGFRβ Kinase Sequence (Residues 557-1106) Used for Screening (Seq ID No. 3)

```
QKKP RYEIRW KVIE SVSSDG HEYI YVDPMQ LPYDSTWELP
RDQLVLGRTL GSGAFGQVVE ATAHGLSHSQ ATMKVAVKML
KSTARSSEKQ ALMSELKIMS HLGPHLNVVN LLGACTKGGP
```

```
IYIITEYCRY  GDLVDYLHRN  KHTFLQHHSD  KRRPPSAELY

SNALPVGLPL  PSHVSLTGE   SDGGYMDMSK  DESVDYVPML

DMKGDVKYAD  IESSNYMAPY  DNYVPSAPER  TCRAT LINES

PVLSYMDLVG  FSYQVANGME  FLASKNCVHR  DLAARNVLIC

EGKLVKICDF  GLARDIMRDS  NYISKGSTFL  PLKWMAPESI

FNSLYTTLSD  VWSFGILLWE  IFTLGGTPYP  ELPMNEQFYN

AIKRGYRMAQ  PAHASDEIYE  IMQKCWEEKF  EIRPPFSQLV

LLLERLLGEG  YKKKYQQVDE  EFLRSDHPAI  LRSQARLPGF

HGLRSPLDTS  SVLYTAVQPN  EGDNDYIIPL  PDPKPEVADE

GPLEGSPSLA  SSTLNEVNTS  STISCDSPLE  PQDEPEPEPQ

LELQVEPEPE  LEQLPDSGCP  APRAEAEDSF  L
```

Using the enzymatic protocols described above, compounds of Formula I are shown to be inhibitors in assays measuring the kinase activity of uFMS kinase, uKIT kinase, or uPDGFRβ kinase, as indicated below in Table 1.

TABLE 1

Activity of Compounds of Formula I in Enyzmatic Assays of uFMS kinase, uKIT kinase, or uPDGFRβ kinase.

| Example | uFMS | uKIT | uPDGFRβ |
|---|---|---|---|
| 1 | ++++ | +++ | ++ |
| 2 | +++ | +++ | + |
| 3 | ++++ | ++ | + |
| 4 | +++ | +++ | ++ |
| 5 | +++ | NT | ++ |
| 6 | +++ | NT | NT |
| 7 | +++ | +++ | + |
| 8 | +++ | NT | NT |
| 9 | +++ | NT | NT |
| 10 | +++ | ++ | + |
| 11 | +++ | +++ | + |
| 12 | +++ | +++ | + |
| 13 | +++ | NT | NT |
| 14 | +++ | NT | + |
| 15 | ++++ | NT | +++ |
| 16 | ++++ | ++++ | ++ |
| 17 | +++ | NT | NT |
| 18 | +++ | ++ | + |
| 19 | +++ | +++ | + |
| 20 | +++ | ++ | + |
| 21 | +++ | +++ | + |
| 22 | ++++ | +++ | + |
| 23 | +++ | + | + |
| 24 | +++ | +++ | ++ |
| 25 | ++++ | ++++ | +++ |
| 26 | ++++ | +++ | + |
| 27 | ++++ | NT | + |
| 28 | ++++ | ++ | + |
| 29 | ++++ | ++++ | + |
| 30 | ++++ | ++++ | ++ |
| 31 | +++ | ++ | + |
| 32 | ++ | ++ | + |
| 33 | ++++ | ++++ | ++ |
| 34 | ++++ | ++++ | +++ |
| 35 | ++++ | ++ | ++ |
| 36 | ++++ | +++ | ++ |
| 37 | +++ | ++ | + |
| 38 | +++ | ++++ | NT |
| 39 | +++ | ++ | + |
| 40 | ++++ | +++ | NT |
| 41 | +++ | + | + |
| 42 | ++++ | ++ | + |
| 43 | ++++ | ++ | + |
| 44 | +++ | ++ | + |
| 45 | ++++ | +++ | + |
| 46 | ++++ | +++ | ++ |
| 47 | ++++ | ++ | + |
| 48 | ++++ | ++++ | ++ |
| 49 | +++ | + | + |
| 50 | +++ | +++ | + |
| 51 | +++ | +++ | + |
| 52 | +++ | +++ | ++ |
| 53 | +++ | + | + |
| 54 | +++ | ++ | ++ |
| 55 | ++ | + | + |
| 56 | +++ | + | + |
| 57 | ++++ | + | + |
| 58 | +++ | + | + |
| 59 | ++++ | +++ | ++ |
| 60 | +++ | +++ | ++ |
| 61 | ++++ | ++ | + |
| 62 | ++ | ++ | NT |
| 63 | ++ | + | NT |
| 64 | ++ | + | NT |
| 65 | +++ | ++ | NT |
| 66 | +++ | ++ | NT |
| 67 | ++ | + | NT |
| 68 | ++++ | +++ | + |
| 69 | +++ | +++ | + |
| 70 | +++ | ++ | + |
| 71 | ++++ | +++ | ++ |
| 72 | ++++ | ++++ | +++ |
| 73 | ++ | + | NT |
| 74 | +++ | ++ | NT |
| 75 | ++++ | ++ | NT |
| 76 | +++ | ++ | NT |
| 77 | +++ | +++ | NT |
| 78 | +++ | + | NT |
| 79 | ++ | ++ | NT |
| 80 | ++++ | ++ | + |
| 81 | +++ | + | NT |
| 82 | +++ | ++++ | NT |
| 83 | +++ | +++ | ++ |
| 84 | +++ | +++ | + |
| 85 | ++++ | +++ | + |
| 86 | ++++ | +++ | + |
| 87 | ++++ | +++ | NT |
| 88 | +++ | ++ | + |
| 89 | ++ | ++ | + |
| 90 | ++++ | +++ | +++ |
| 91 | ++++ | ++ | NT |
| 92 | ++++ | +++ | NT |
| 93 | +++ | NT | NT |
| 94 | +++ | NT | NT |
| 95 | +++ | NT | NT |
| 96 | +++ | NT | NT |
| 97 | +++ | NT | NT |
| 98 | ++ | NT | NT |
| 99 | +++ | NT | NT |
| 100 | +++ | NT | NT |
| 101 | ++++ | NT | ++ |
| 102 | +++ | NT | NT |
| 103 | +++ | NT | + |
| 104 | ++ | NT | + |
| 105 | +++ | NT | + |
| 106 | +++ | NT | + |
| 107 | ++++ | NT | ++ |
| 108 | +++ | NT | + |
| 109 | +++ | +++ | + |
| 110 | ++++ | NT | + |
| 111 | ++++ | NT | + |
| 112 | +++ | +++ | ++ |
| 113 | ++++ | +++ | NT |
| 114 | + | + | NT |
| 115 | ++ | ++ | + |
| 116 | +++ | +++ | + |
| 117 | ++ | ++ | + |
| 118 | +++ | + | + |
| 119 | +++ | ++ | ++ |
| 120 | ++++ | +++ | +++ |

TABLE 1-continued

Activity of Compounds of Formula I in Enyzmatic Assays of uFMS kinase, uKIT kinase, or uPDGFRβ kinase.

| Example | uFMS | uKIT | uPDGFRβ |
|---------|------|------|---------|
| 121 | +++ | ++ | ++ |
| 122 | +++ | + | + |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM M-NFS-60 Cell Culture M-NFS-60 cells (catalog #CRL-1838) were obtained from the American Type Culture Collection (ATCC, Manassas, Va.). Briefly, cells were grown in suspension in RPMI 1640 medium supplemented with 10% characterized fetal bovine serum (Invitrogen, Carlsbad, Calif.), 0.05 mM 2-mercaptoethanol, and 20 ng/mL mouse recombinant macrophage colony stimulating factor (M-CSF) at 37° C., 5% $CO_2$, and 95% humidity. Cells were allowed to expand until reaching saturation at which point they were subcultured or harvested for assay use.

M-NFS-60 Cell Proliferation Assay

A serial dilution of test compound was dispensed into a 384-well black clear bottom plate (Corning, Corning, N.Y.). Two thousand five hundred cells were added per well in 50 μL complete growth medium. Plates were incubated for 67 h at 37° C., 5% $CO_2$, and 95% humidity. At the end of the incubation period 10 μL of a 440 μM solution of resazurin (Sigma, St. Louis, Mo.) in PBS was added to each well and incubated for an additional 5 h at 37° C., 5% $CO_2$, and 95% humidity. Plates were read on a Synergy2 reader (Biotek, Winooski, Vt.) using an excitation of 540 nM and an emission of 600 nM. $IC_{50}$ values were calculated from a series of percent inhibition values determined at a range of inhibitor concentrations using software routines as implemented in the GraphPad Prism software package.

THP-1 Cell Culture

THP-1 cells (catalog #TIB-202) were obtained from the ATCC. Briefly, cells were grown in RPMI 1640 supplemented with 10% characterized fetal bovine serum, 1% sodium pyruvate, 1% Penicillin-Streptomycin-Glutamine (PSG) and 55 uM 2-mercaptoethanol (Invitrogen, Carlsbad, Calif.) at 37 degrees Celsius, 5% $CO_2$, 95% humidity. Cells were allowed to expand until reaching 70-95% confluency at which point they were subcultured or harvested for assay use.

Phospho-FMS ELISA Assay

A serial dilution of test compound was diluted 1:100 in assay medium (RPMI 1640 supplemented with 10% characterized fetal bovine serum) in a 96 well black clear bottom plate (Corning, Corning, N.Y.). In a separate 96 well black clear bottom plate, one hundred and fifty thousand THP-1 cells were added per well in 100 μL in assay medium. Fifty microliters of diluted compound was then added to the cells. Plates were incubated for 4 hours at 37 degrees Celsius, 5% $CO_2$, 95% humidity. At the end of the incubation period, cells were stimulated with 50 μL of a 100 nM solution of recombinant human M-CSF (catalog #216-MC, R & D Systems, Minneapolis, Minn.) in assay medium and the plate was incubated for 5 minutes at 37 degrees Celsius, 5% $CO_2$, 95% humidity. Lysates were prepared and used to perform the phospho-FMS ELISA as described by the manufacturer (catalog #DYC3268, R & D Systems, Minneapolis, Minn.). GraphPad Prism was used to calculate $IC_{50}$ values obtained from data generated from the ELISA assay.

Osteoclast Tartrate-Resistant Acid Phosphatase Assay

A serial dilution of test compound was dispensed into a 384-well black clear bottom plate (Nalge Nunc International, Rochester, N.Y.). Compound was diluted by the addition of DMEM media supplemented with 10% characterized fetal bovine serum (Invitrogen, Carlsbad, Calif.). Diluted compound was transferred to a 384-well black clear bottom plate. Two-thousand five hundred osteoclast precursors (Lonza, Walkersville, Md.) were added per well in growth media containing Receptor Activator of Nuclear Factor Kappa-beta ligand (RANKL) and M-CSF (R&D Systems, Minneapolis, Minn.). Plates were incubated for 7-14 days at 37 degrees Celsius, 5% $CO_2$, and 95% humidity to allow differentiation of osteoclast precursors. At the end of the incubation period, 10 μL of supernatant from each well was transferred to a clear 384-well plate. Tartrate-resistant acid phosphatase activity in the supernatant samples was determined using an acid phosphatase assay kit (Sigma, St. Louis, Mo.). Absorbance was measured at 550 nm using a plate reader. Data was analyzed using Prism software (Graphpad, San Diego, Calif.) to calculate $IC_{50}$ values.

The compounds of Formula I are demonstrated to be functional inhibitors in one or more of the cellular assays described above, as indicated in Table 2.

TABLE 2

Inhibitory effects of compounds of Formula I versus M-NFS-60, THP-1 and Osteoclast Cells

| Example | M-NFS-60 cell proliferation | Osteoclast assay | pFMS inhibition in THP-1 cells |
|---------|-----------------------------|------------------|-------------------------------|
| 1 | +++ | +++ | +++ |
| 2 | +++ | ++++ | NT |
| 3 | +++ | +++ | +++ |
| 4 | +++ | +++ | ++++ |
| 5 | +++ | +++ | ++ |
| 6 | +++ | NT | NT |
| 7 | +++ | +++ | +++ |
| 8 | ++ | +++ | +++ |
| 9 | ++ | +++ | +++ |
| 10 | +++ | +++ | ++++ |
| 11 | +++ | ++++ | +++ |
| 12 | +++ | ++++ | +++ |
| 13 | ++ | +++ | NT |
| 14 | ++ | +++ | ++ |
| 15 | ++++ | ++++ | +++ |
| 16 | +++ | ++++ | +++ |
| 17 | +++ | +++ | NT |
| 18 | ++ | +++ | +++ |
| 19 | +++ | +++ | +++ |
| 20 | +++ | +++ | +++ |
| 21 | +++ | +++ | +++ |
| 22 | ++++ | ++++ | +++ |
| 23 | +++ | +++ | +++ |
| 24 | +++ | +++ | NT |
| 25 | ++++ | ++++ | +++ |
| 26 | ++++ | +++ | +++ |
| 27 | +++ | ++++ | NT |
| 28 | +++ | ++++ | +++ |
| 29 | ++++ | ++++ | +++ |
| 30 | ++++ | ++++ | NT |
| 31 | + | NT | NT |
| 33 | +++ | +++ | ++++ |
| 34 | +++ | +++ | ++++ |
| 35 | +++ | ++++ | ++++ |
| 36 | ++++ | ++++ | ++++ |
| 37 | +++ | +++ | +++ |
| 38 | +++ | ++++ | NT |
| 39 | ++ | +++ | +++ |
| 40 | +++ | NT | NT |
| 41 | ++ | +++ | +++ |
| 42 | +++ | ++++ | +++ |
| 43 | ++++ | ++++ | +++ |

TABLE 2-continued

Inhibitory effects of compounds of Formula I versus M-NFS-60, THP-1 and Osteoclast Cells

| Example | M-NFS-60 cell proliferation | Osteoclast assay | pFMS inhibition in THP-1 cells |
|---|---|---|---|
| 44 | ++ | +++ | NT |
| 45 | +++ | ++++ | NT |
| 46 | +++ | ++++ | NT |
| 47 | +++ | ++++ | NT |
| 48 | +++ | ++++ | NT |
| 49 | ++ | +++ | ++ |
| 50 | +++ | +++ | NT |
| 51 | +++ | ++ | NT |
| 52 | +++ | +++ | ++ |
| 53 | +++ | ++ | NT |
| 54 | +++ | +++ | ++ |
| 55 | ++ | ++ | NT |
| 56 | +++ | ++ | ++ |
| 57 | ++++ | +++ | +++ |
| 58 | +++ | +++ | +++ |
| 59 | ++++ | ++++ | NT |
| 60 | +++ | +++ | NT |
| 61 | ++++ | ++++ | ++++ |
| 62 | ++ | ++ | NT |
| 63 | + | + | NT |
| 64 | + | + | NT |
| 65 | ++ | +++ | NT |
| 66 | ++ | ++ | NT |
| 67 | ++ | ++ | NT |
| 68 | +++ | ++++ | NT |
| 69 | ++ | +++ | NT |
| 70 | ++ | +++ | NT |
| 71 | +++ | +++ | NT |
| 72 | ++++ | ++++ | NT |
| 73 | + | ++ | NT |
| 74 | ++ | +++ | NT |
| 75 | +++ | +++ | NT |
| 76 | ++ | ++ | NT |
| 77 | ++ | ++ | NT |
| 78 | + | ++ | NT |
| 79 | + | ++ | NT |
| 80 | +++ | +++ | NT |
| 81 | ++ | ++ | NT |
| 82 | +++ | +++ | NT |
| 83 | +++ | +++ | NT |
| 84 | +++ | +++ | NT |
| 85 | +++ | ++++ | +++ |
| 86 | ++++ | ++++ | NT |
| 87 | +++ | +++ | NT |
| 88 | +++ | +++ | +++ |
| 89 | + | ++ | NT |
| 90 | +++ | +++ | NT |
| 91 | +++ | +++ | +++ |
| 92 | +++ | +++ | +++ |
| 93 | ++ | +++ | NT |
| 94 | ++ | ++ | +++ |
| 95 | +++ | +++ | NT |
| 96 | + | ++ | +++ |
| 97 | ++ | ++ | ++ |
| 98 | ++ | +++ | NT |
| 99 | +++ | +++ | NT |
| 100 | ++ | +++ | NT |
| 101 | +++ | ++++ | +++ |
| 102 | + | ++ | NT |
| 103 | ++ | ++ | NT |
| 104 | + | ++ | NT |
| 105 | ++ | +++ | NT |
| 106 | + | ++ | NT |
| 107 | +++ | +++ | NT |
| 108 | ++ | ++ | NT |
| 109 | +++ | ++ | NT |
| 110 | +++ | NT | NT |
| 111 | +++ | ++++ | NT |
| 112 | ++ | NT | NT |
| 113 | ++ | NT | NT |
| 115 | + | +++ | NT |
| 116 | ++ | +++ | NT |
| 117 | ++ | +++ | +++ |
| 118 | +++ | +++ | +++ |
| 119 | +++ | +++ | +++ |
| 120 | +++ | ++++ | +++ |
| 121 | ++ | ++ | NT |
| 122 | ++ | ++ | NT |

NT: Not Tested;
+: $IC_{50} > 1$ uM;
++: $0.1$ uM $< IC_{50} \leq 1$ uM;
+++: $0.01$ uM $< IC_{50} \leq 0.1$ uM;
++++: $IC_{50} \leq 0.01$ uM Measurements of In Vivo Activity Analysis of cFOS mRNA Production in a c-FMS Mouse Spleen Pharmacodynamic Model To examine the in vivo modulation of FMS activity by compounds of formula I, spleen samples from female DBA/1 mice were collected and analyzed for M-CSF stimulated production of cFOS mRNA. Briefly, six to seven week old female Taconic DBA/1BO J Bom Tac mice were treated with a single oral dose (by gavage) of either vehicle or compound. Plasma and spleen samples were collected from four mice at each timepoint 2, 4, 6, 8, 12, 18, and 24 hours after dosing. Fifteen minutes prior to euthanasia, all mice were injected IV with 1 μg (100 μL fixed volume) of M-CSF. M-CSF, Recombinant Mouse Macrophage Colony Stimulating Factor (36.4 kDa homodimer, ≥98% purity) was obtained from Gibco. All procedures carried out in this experiment were conducted in compliance with all the laws, regulations and guidelines of the National Institutes of Health (NIH). cFOS mRNA levels in spleen extracts were determined using a quantitative reverse transcriptase PCR kit from Life Technologies. Plasma levels of FMS inhibitors were determined by mass spectrometer analysis. The degree of FMS inhibition was correlative to the amount of decrease observed in cFOS mRNA levels in the spleen samples of treated animals compared to vehicle.

In this model, Examples 18, 41, 42, and 118 afforded ≥70% inhibition of cFOS mRNA levels out to 8 h post 30 mg/kg dose.

PC-3 Peritibial Implant Model of Cancer Bone Metastasis

To evaluate in vivo anti-cancer activity of compounds of formula I, the PC-3 M-luc peritibial injection model of bone invasiveness model was employed. Briefly, PC-3 M-luc cells were obtained from Xenogen Corporation (Caliper Life Sciences) and expanded using MEM media modified with L-Glutamine (Cell Gro® #10-045-CV) supplemented with 10% fetal bovine serum, 1% penicillin-streptomycin-glutamine, 1% non-essential amino acids, and 1% MEM vitamins in 5% $CO_2$ atmosphere at 37° C. Six to 7 week old male nude mice (Crl:NU-Foxn1nu) were obtained from Charles River Laboratories. Test mice were implanted peritibially on Day 0 with $1 \times 10^6$ cells/mouse (0.1 ml) using an insulin syringe with a fixed 28-gauge needle. The needle was inserted at the ankle between the tibia and fibula until the bevel of the needle reached approximately half way between the knee and ankle. Treatments began on Day 0. Animals were dosed by oral gavage twice daily for the study duration. All procedures carried out in this experiment were conducted in compliance with all the laws, regulations and guidelines of the National Institutes of Health (NIH). When the primary tumor reached approximately 800 mg in size, ex-vivo micro-CT was performed on the tumor bearing fixed hind limb samples using a GE RS150 small animal micro-CT scanner using with the following settings:
X-ray tube voltage=70 kVp
X-ray tube current=25 mA
Exposure time=20 ms
Number of frames=500
Angle increment between frames=0.4o
Number of averages per frame=2
Acquisition method=Parker Images were then reconstructed at high resolution (100 microns; isotropic).

Isosurface volume renderings were used to delineate lesions in the hind limbs. A constant threshold was used to produce consistent representation of the isosurface between different anatomical sites and samples. Lesions in the right hind limb were scored with values of 0, 1, 2, 3, or 4 based on a qualitative assessment of lesion size as defined by:
0: Normal Bone
1: Minimal lesions. Some roughening of the isosurface. Small areas of apparent bone resorption.
2: Mild. More numerous lesions. Significant roughening of the isosurface. Full thickness lesions apparent.
3: Moderate. Full thickness lesions larger and more numerous.
4: Marked. Many, large, full thickness lesions. Significant distortion of remaining structure. Marked bone loss.

Example 42 was evaluated in this model at an oral dose of 30 mg/kg twice daily and demonstrated positive benefit with a lesion score of 2 compared to a lesion score of 4 in vehicle-treated animals.

U251 Intra-Cerebro-Ventricular Implant in Mice

To evaluate in vivo anti-cancer activity compounds of Formula I in combination with fractionated, localized head radiation, an orthotopic U251-luc (Luc) human glioma carcinoma model in female outbred nu/nu mice is employed. Briefly, U251 cells are obtained from the ATCC and altered to be luciferase expressing. They are grown in RPMI 1640 Media supplemented with 10% FBS and 1% PSG. The growth environment is maintained in an incubator with a 5% $CO_2$ atmosphere at 37° C. Female Harlan Nude mice (Hsd:Athymic-Nude-Fox1nu) 8-9 weeks old are used in this study. Test animals are implanted intracranially with U251-luc (Lucm-Cherry) cells. Briefly, animals are injected subcutaneously with 5 mg/kg carprofen and anesthetized using 2% isoflurane in air. The animals are then secured in a stereotaxic frame (ASIinstruments, Inc.) and a hole drilled 2 mm right lateral, 1 mm anterior to the coronal suture. The cell suspension (stored on wet ice) is mixed thoroughly and drawn up into a 50l syringe. The syringe needle is centered over the burr hole and lowered 3 mm into the brain and retracted 1 mm to form a "reservoir" for the deposition of the cell suspension. 10 µl of the cell suspension ($1 \times 10^6$ cells/mouse) is then injected slowly into the brain tissue. The tumor progression is tracked with in vivo bioluminescence imaging performed using an IVIS 50 optical imaging system (Xenogen, Alameda, Calif.). Bioluminescence images are acquired at periodic intervals for tumor burden estimation. All procedures carried out in this experiment are conducted in compliance with all the laws, regulations and guidelines of the National Institutes of Health (NIH). Treatment begins when the mean brain bioluminescence signal for all groups in the experiment is ~$1.3 \times 10^9$ photons/sec (typically 9 days post-implant). All mice receive 2Gy of radiation each day for five consecutive days from a RadSource RS-2000 irradiator. Additionally, mice receive test compound dosed by oral gavage or optionally with co-administered bevacizumab by tail vein injection. Bioluminescence images are acquired generally on days 8, 10, 14, 17, 21, 22, 24, 28 and 35 post-implant for tumor burden estimation. For each measurement, each mouse is injected subcutaneously with 150 mg/kg D-Luciferin (Promega) and imaged 10 minutes after the injection. Images are analyzed using Living Image (Xenogen, Alameda, Calif.) software. The BLI signal in the brain is calculated with a fixed area ROI to estimate the tumor burden. Average BLI signal for each group is compared to vehicle control to determine therapeutic benefit. Twenty-eight days after the first radiation treatment mice are euthanized, via over-exposure to carbon dioxide, for blood and brain collection. Whole blood is collected via terminal cardiac puncture and placed into EDTA Microtainer® tubes. Brains are excised and placed into 10% neutral buffered formalin.

GL261 Intracranial Implant Model

To evaluate the in vivo anti-cancer activity of compounds of formula I, an intracranial implant of GL261-luc2 murine glioma is employed. Briefly GL261-luc cells are obtained from Caliper Life Sciences, Inc and expaned in Dulbecco's Modified Eagle Media (DMEM) which is supplemented with 10% FBS and 1% PSG. The growth environment is maintained in an incubator with a 5% $CO_2$ atmosphere at 37° C. Following expansion, cells are re-suspended using serum-free media to generate a concentration of $1 \times 10^8$ cells/mL. Six to seven week old female C57BL/6J-Tyrc-2J/J from Jackson Labs are implanted intracranially on Day 0 with GL261-luc2 cells. For aseptic surgical implantation, animals are injected subcutaneously with 5 mg/kg carprofen, anesthetized using 2% isoflurane in air. The animals are then secured in a stereotaxic frame (ASIinstruments, Inc.) and a hole is drilled 2 mm right lateral, 1 mm anterior to the coronal suture. The cell suspension (stored on wet ice) is mixed thoroughly and drawn up into a 50 µL syringe. The syringe needle is centered over the burr hole and lowered 3 mm into the brain and retracted 1 mm to form a "reservoir" for the deposition of the cell suspension. 10 µL of the cell suspension ($1 \times 10^6$ cells/mouse) is then injected slowly into the brain tissue. The tumor progression is tracked with in vivo bioluminescence imaging performed using an IVIS 50 optical imaging system (Xenogen, Alameda, Calif.). Bioluminescence images are acquired at periodic intervals for tumor burden estimation. The quantity of emitted light from the tumor after systemic injection of D-Luciferin is expected to correlate with tumor size. Each mouse is injected intraperitoneally (IP) with 150 mg/kg D-Luciferin and imaged in the prone position 10 minutes after the injection. Medium and small binning of the CCD chip is used, and the exposure time is adjusted (10 seconds to 1 minute) to obtain at least several hundred counts from the tumors and to avoid saturation of the CCD chip. Images are analyzed using Living Image (Xenogen, Alameda, Calif.) software. Each unique signal is circled manually and labeled by group and mouse number. Treatment begins by oral gavage of test compound when the mean brain bioluminescence signal for all groups in the experiment is $280 \times 10^6$ photons/sec. All procedures carried out in this experiment are conducted in compliance with all the laws, regulations and guidelines of the National Institutes of Health (NIH). At the end of study all mice are euthanized via over-exposure to carbon dioxide for blood and brain collection. Whole blood is collected via terminal cardiac puncture and placed into EDTA Microtainer® tubes. Brains are excised and placed into 10% neutral buffered formalin.

MDA-MB-231 Xenograft Study

To evaluate the in vivo anti-cancer activity compounds of formula I, a MDA-MB-231-luc-D3H2LN human breast carcinoma xenograft was employed. Briefly, MDA-MB-231-luc-D3H2LN cells were obtained from Xenogen and expanded in Minimal Essential Media (MEM) with EBSS which was modified with 1% L-glutamine and supplemented with 10% FBS, 1% PSG, 1% non-essential amino acids, and 1% sodium pyruvate. The growth environment was maintained in an incubator with a 5% $CO_2$ atmosphere at 37° C. Cells were harvested and re-suspended using 50% serum-free media and 50% Matrigel® to generate a stock concentration of $5 \times 10^6$ cells/mL.

Six to 7 week old female C.B-17/IcrHsd-PrkdcscidLystbg mice were injected with 200 μL of cell suspension subcutaneously, just below the right axilla. All procedures carried out in this experiment were conducted in compliance with all the laws, regulations and guidelines of the National Institutes of Health (NIH). Treatment began when the mean tumor burden was approximately 150 mg. All mice were dosed with test compound by oral gavage. Body weights and tumor measurements were recorded three times weekly. Tumor burden (mg) was estimated from caliper measurements by the formula for the volume of a prolate ellipsoid assuming unit density as: Tumor burden (mg)=(L×W2)/2, where L and W were the respective orthogonal tumor length and width measurements (mm). The primary endpoints to evaluate efficacy was % T/C. % T/C was defined as the median tumor mass of a Treated Group divided by the median tumor mass of the Control Group×100. Ex vivo bioluminescence imaging was performed as animals exited the study, using an IVIS 50 optical imaging system (Xenogen, Alameda, Calif.). Animals were injected IP with 150 mg/kg D-Luciferin (Promega) and euthanized 10 minutes following the injection. The primary tumor was removed and snap frozen for future analysis and the mouse opened and imaged in the supine position. Large binning of the CCD chip was used, and the exposure time was adjusted (1 to 2 minutes) to obtain at least several hundred counts from the tumors and to avoid saturation of the CCD chip. Images were analyzed using Living Image (Xenogen, Alameda, Calif.) software. Each unique signal was circled manually and labeled by group and mouse number. Total BLI signal was correlative to tumor size and compared to vehicle control to determine treatment benefit.

Example 18 exhibited 51% tumor growth inhibition in this model when orally dosed at 30 mg/kg twice daily.

Compounds with structures similar to certain compounds of Formula I have been previously disclosed in US2008/0255155 as inhibitors of VEGFR (KDR) and cMET kinases. Representative examples are shown below. In addition, US2008/0255155 Examples 3 and 5 have also been reported to be inhibitors of TRK-A kinase (S. L. Raeppel, et. al. Internationl Journal of Medicinal Chemistry (2012) Article ID 412614). Neither publication disclosed activity of any of the compounds below against c-FMS, c-KIT or PDGFR-b kinases or teach that the compounds possessed such activity. The compounds of US2008/0255155 differ from the compounds of Formula I by the presence of an aromatic "A" moiety (e.g. left-most aryl ring in structures shown below). Published data from US2008/0255155 related to the inhibitory activity of these compounds against cMET and KDR kinases are collected in Table 3 below.

US2008/0255155 Example 3

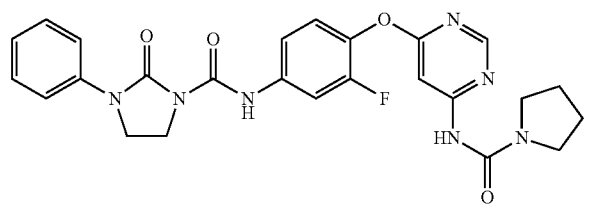

US2008/0255155 Example 5

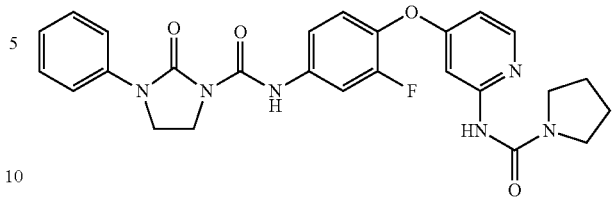

US2008/0255155 Example 6

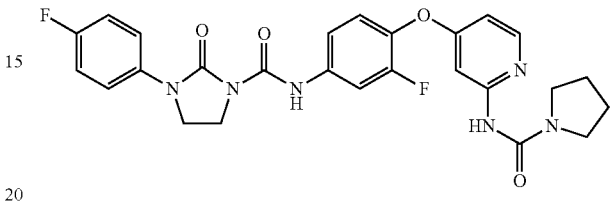

US2008/0255155 Example 10

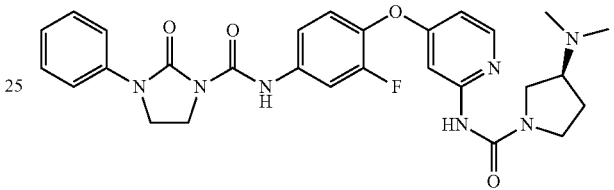

US2008/0255155 Example 11

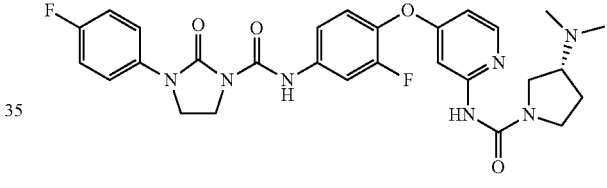

US2008/0255155 Example 12

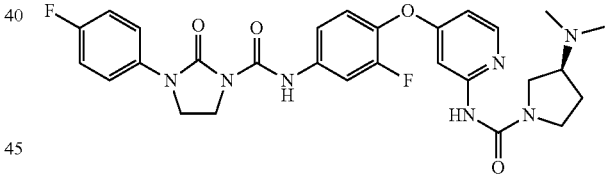

US2008/0255155 Example 70

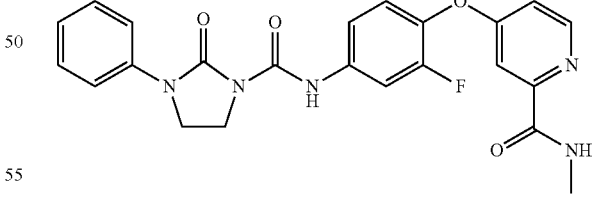

US2008/0255155 Example 71

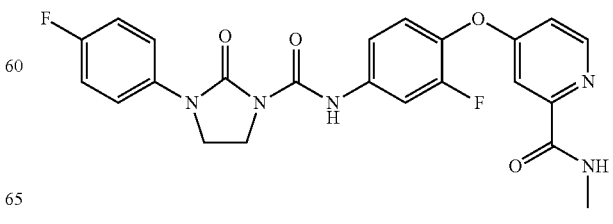

TABLE 3

| Entry | Compound | cMET IC$_{50}$ | KDR IC$_{50}$ |
|---|---|---|---|
| 1 | US2008/0255155, Ex 3 | <250 nM | <250 nM |
| 2 | US2008/0255155, Ex 5 | <250 nM | <500 nM |
| 3 | US2008/0255155, Ex 6 | <250 nM | <250 nM |
| 4 | US2008/0255155, Ex 10 | <250 nM | <250 nM |
| 5 | US2008/0255155, Ex 11 | <250 nM | <250 nM |
| 6 | US2008/0255155, Ex 12 | <250 nM | <250 nM |
| 7 | US2008/0255155, Ex 70 | <500 nM | <500 nM |
| 8 | US2008/0255155, Ex 71 | <1000 nM | >1000 nM |

Data for compound A, which contains a phenyl "A-ring" similar to the compounds of US2008/0255155, as well as compounds of the present invention are shown below. Surprisingly, compounds of Formula I (A is non-aromatic moiety) potently inhibit c-FMS kinase but do not readily inhibit cMET or KDR kinases, as illustrated in Table 4. Such results could not have been predicted from the teachings of US2008/0255155.

Compound A

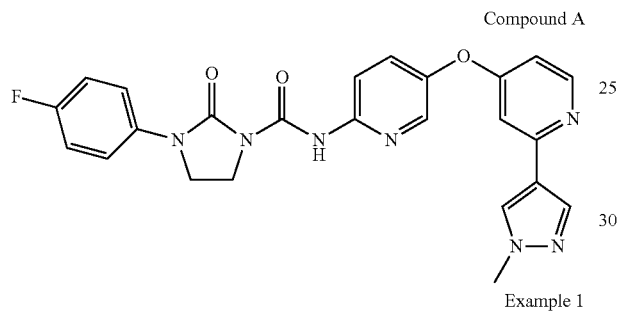

Example 1

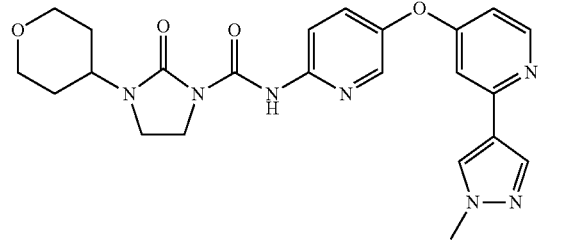

Example 91

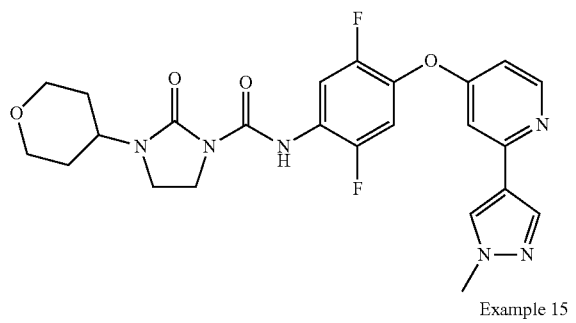

Example 15

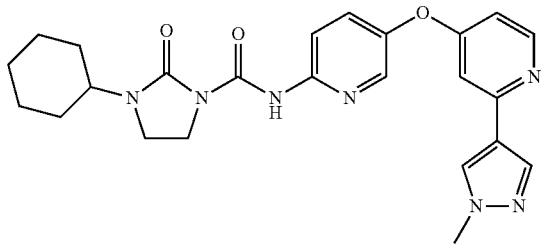

Example 16

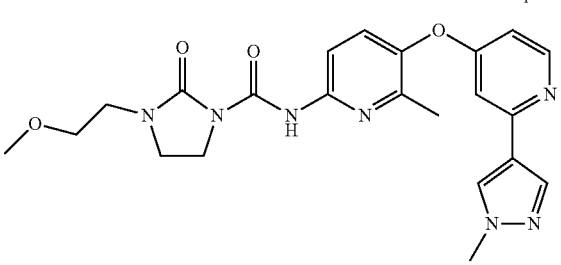

Example 29

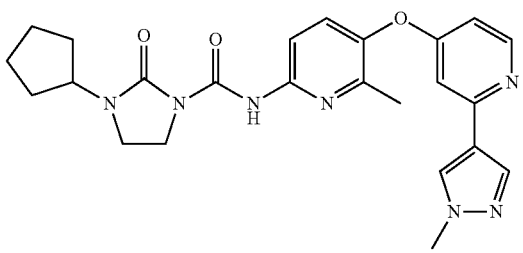

Example 42

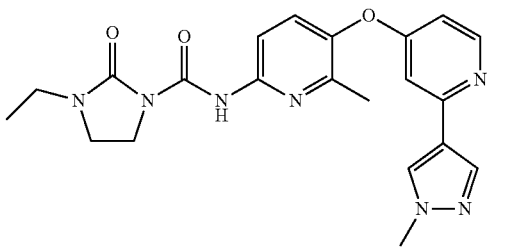

Example 101

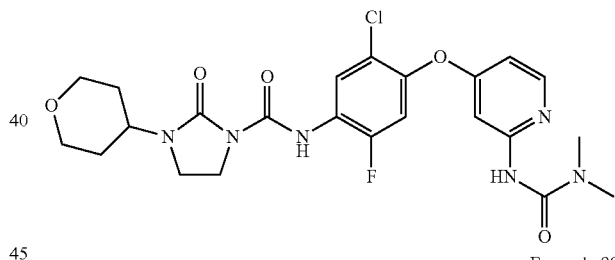

Example 90

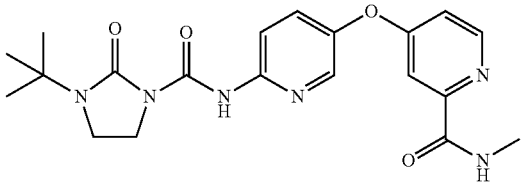

TABLE 4

| Entry | Compound | c-FMS IC$_{50}$ | cMET IC$_{50}$ | KDR IC$_{50}$ |
|---|---|---|---|---|
| 1 | Compound A | 13 nM | 196 nM | 990 nM |
| 2 | Example 1 | 6 nM | >5,000 nM | >3,300 nM |
| 3 | Example 91 | 7 nM | >5,000 nM | >3,300 nM |
| 4 | Example 15 | 3 nM | 370 nM | 670 nM |
| 5 | Example 18 | 20 nM | >5,000 nM | >3,300 nM |
| 6 | Example 29 | 2 nM | 898 nM | >3,300 nM |
| 7 | Example 42 | 8 nM | >5,000 nM | >10,000 |
| 8 | Example 101 | 8 nM | 4,000 | >3,300 nM |
| 9 | Example 90 | 5 nM | >5,000 nM | 3,300 |

Equivalents

Those skilled in the art will recognize, or be able to ascertain, using no more than routine experimentation, numerous equivalents to the specific embodiments described specifically in this disclosure. Such equivalents are intended to be encompassed in the scope of the following claims.

---

The invention claimed is:

1. A compound of Formula I,

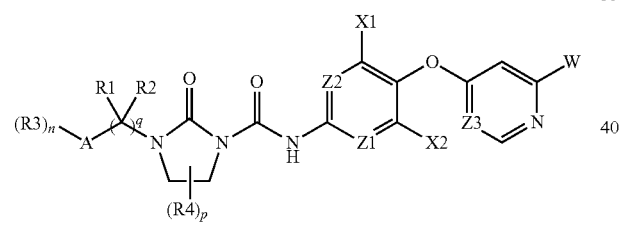

Formula I or a pharmaceutically acceptable salt, enantiomer, stereoisomer, or tautomer thereof, wherein A is selected from the group consisting of C1-C6 alkyl, deutero-C1-C6 alkyl wherein the alkyl chain is partially or completely deuterated, branched C3-C8alkyl, fluoroC 1 -C6alkyl wherein the alkyl is fully or partially fluorinated, C3-C8carbocyclyl, and a 4-8 membered heterocyclic ring, and wherein the A moiety may be further substituted with one, two, or three R3 moieties;

W is C5-C6heteroaryl, —NHC(O)R6, —NHC(O)R7, —NHC(O)N(R8)R9, —C(O)R11, or phenyl, wherein the C5-C6heteroaryl and phenyl moieties are optionally substituted by one, two, or three R5;

each X1, X2, X3 and X4 is individually and independently hydrogen, C1-C6 alkyl, halogen, or fluoro-C1-C6 alkyl wherein the alkyl chain is partially or completely fluorinated;

Z1 is N or CX3;

Z2 is CX4 or N;

Z3 is CH or N;

each R1 and R2 is individually and independently H, C1-C6 alkyl, fluoroC1-C6alkyl wherein the alkyl is fully or partially fluorinated, hydroxyl, C1-C6 alkoxy, fluoroC1-C6alkoxy wherein the alkyl group is fully or partially fluorinated, or cyano;

each R3 is individually and independently H, halogen, C1-C6 alkyl, fluoro-C1-C6 alkyl wherein the alkyl chain is partially or completely fluorinated, branched C3-C8 alkyl, C3-C8 cycloalkyl, C1-C6 alkoxy, fluoro-C1-C6 alkoxy wherein the alkyl chain is partially or completely fluorinated, branched C3-C6 alkoxy, hydroxyl, or cyano;

each R4 is individually and independently hydrogen, C1-C6 alkyl, or branched C3-C8 alkyl;

each R5 is individually and independently hydrogen, C1-C6 alkyl, deutero-C1-C6 alkyl wherein the alkyl chain is partially or completely deuterated, branched C3-C8 alkyl, halogen, cyano, fluoro-C1-C6 alkyl wherein the alkyl chain is partially or completely fluorinated, —(CH$_2$)$_m$—C(O)NR8(R9), —(CH$_2$)$_m$—C(O)R7, —(CH$_2$)$_m$—C(O)R6, —(CH$_2$)$_m$—CN, —(CH$_2$)$_m$—OR8, —(CH$_2$)$_m$—NR8(R9), or —(CH$_2$)$_m$—R7, wherein each alkylene may be further substituted with one or more C1-C6alkyl;

each R6 is individually and independently hydrogen, C1-C6 alkyl, branched C3-C8 alkyl, C3-C8 cycloalkyl, —(CH$_2$)$_m$—CN, —(CH$_2$)$_m$—OR8, —(CH$_2$)$_m$—NR8(R9), or —(CH$_2$)$_m$—R7, wherein each alkylene may be further substituted with one or more C1-C6alkyl;

each R7 is independently and individually selected from the group consisting of

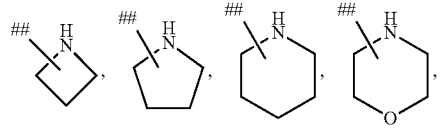

-continued

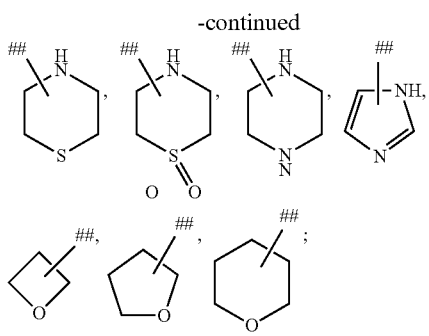

and wherein the symbol (##) is the point of attachment to respective R5 or R6 moieties containing a R7 moiety;
each R7 is optionally substituted with —(R10)$_p$;
each R8 and R9 is individually and independently H, C1-C6 alkyl, fluoro-C1-C6 alkyl wherein the alkyl chain is partially or completely fluorinated, or branched C3-C8 alkyl;
each R10 is individually and independently C1-C6 alkyl, —(CH$_2$)$_m$—CN, —(CH$_2$)$_m$—OR3, —(CH$_2$)$_m$—NR8(R9), or —(CH$_2$)$_m$—C(O)—R6, wherein each alkyl or alkylene is optionally substituted with one or two C1-C6 alkyl;
R11 is —N(R8)R9 or R7;
each m is individually and independently 0, 1, 2, or 3;
each n is individually and independently 0, 1, 2, or 3;
each p is individually and independently 0, 1, 2, or 3; and
each q is individually and independently 0, 1, 2, or 3.

2. The compound of claim 1, wherein W is selected from the group consisting of pyrazolyl, imidazolyl, isoxazolyl, oxazolyl, thiazolyl, triazolyl, pyridinyl, —NHC(O)R6, —NHC(O)R7, —NHC(O)N(R8)R9, —C(O)N(R8)R9 and phenyl.

3. The compound of claim 2, wherein the compound is a compound of Formula Ia,

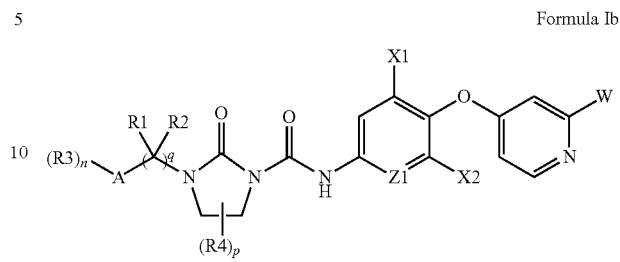

Formula Ia or a pharmaceutically acceptable salt, enantiomer, stereoisomer, or tautomer thereof,
wherein the A moiety is selected from the group consisting of C1-C6 alkyl, branched C3-C8alkyl, fluoroC1-C6alkyl wherein the alkyl is fully or partially fluorinated, C3-C8-carbocyclyl, and a 4-8 membered heterocyclic ring.

4. The compound of claim 3, wherein W is pyrazolyl, optionally substituted with —(R5)$_p$.

5. The compound of claim 4, wherein Z1 is N and X1 and X2 are independently selected from C1-C6alkyl and hydrogen.

6. The compound of claim 4, wherein Z1 is CX3 and X1, X2 and X3 are individually and independently halogen, hydrogen, or C1-C6 alkyl.

7. The compound of claim 2, wherein the compound is a compound of Formula Ib,

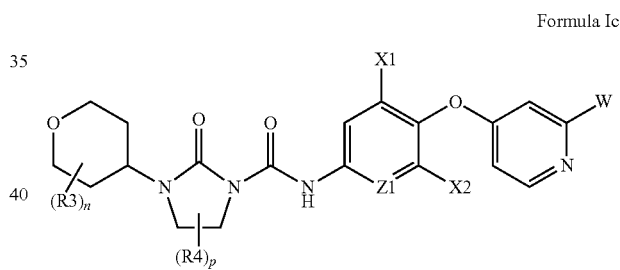

Formula Ib or a pharmaceutically acceptable salt, enantiomer, stereoisomer, or tautomer thereof,
wherein A is C1-C6 alkyl, branched C3-C8alkyl, fluoroC1-C6alkyl wherein the alkyl is fully or partially fluorinated, C3-C8carbocyclyl, or a 4-8 membered heterocyclic ring and q is 0 or 1.

8. The compound of claim 7, wherein W is pyrazolyl, optionally substituted with —(R5)$_p$.

9. The compound of claim 8, wherein Z1 is N and X1 and X2 are independently selected from C1-C6alkyl or hydrogen.

10. The compound of claim 8, wherein Z1 is CX3 and X1, X2 and X3 are individually and independently halogen, hydrogen, or C1-C6 alkyl.

11. The compound of claim 3, wherein the compound is a compound of Formula Ic,

Formula Ic or a pharmaceutically acceptable salt, enantiomer, stereoisomer, or tautomer thereof.

12. The compound of claim 11, wherein W is pyrazolyl, optionally substituted with —(R5)$_p$.

13. The compound of claim 12, wherein Z1 is N and X1 and X2 are independently selected from C1-C6alkyl or hydrogen.

14. The compound of claim 12, wherein Z1 is CX3 and X1, X2 and X3 are individually and independently halogen, hydrogen, or C1-C6 alkyl.

15. The compound of claim 1 selected from the group consisting of N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(6-methyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-ethyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1H-pyrazol-4-yl)pyridin-4-yl)oxy)pyridin-2-yl)-2-oxo-3-(tetrahydro-2H-pyran-4-yl)imidazolidine-1-carboxamide, 2-oxo-3-(tetrahydro-2H-pyran-4-yl)-N-(5-((2-(1-(trideuteromethyl)-1H-pyrazol-4-yl)pyridin-4-yl)oxy)pyridin-2-yl)imidazolidine-1-carboxamide, N-(5-((2-(3-methylisoxazol-5-yl)pyridin-4-yl)

oxy)pyridin-2-yl)-2-oxo-3-(tetrahydro-2H-pyran-4-yl)imidazolidine-1-carboxamide, N-(5-((6-(1-methyl-1H-pyrazol-4-yl)pyrimidin-4-yl)oxy)pyridin-2-yl)-2-oxo-3-(tetrahydro-2H-pyran-4-yl)imidazolidine-1-carboxamide, N-(5-((2-(1H-pyrazol-4-yl)pyridin-4-yl)oxy)-6-methylpyridin-2-yl)-2-oxo-3-(tetrahydro-2H-pyran-4-yl)imidazolidine-1-carboxamide, 3-(2-methoxyethyl)-N-(5-((2-(1-methyl-1H-pyrazol-4-yl)pyridin-4-yl)oxy)pyridin-2-yl)-2-oxoimidazolidine-1-carboxamide, 3-(3-methoxypropyl)-N-(5-((2-(1-methyl-1H-pyrazol-4-yl)pyridin-4-yl)oxy)pyridin-2-yl)-2-oxoimidazolidine-1-carboxamide, (S)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(2,2-dimethyltetrahydro-2H-pyran-4-yl)-N-(5-((2-(1-methyl-1H-pyrazol-4-yl)pyridine-4-yl)oxy)pyridin-2-yl)-2-oxoimidazolidine-1-carboxamide, N-(6-methyl-5-((2-(3-methylisoxazol-5-yl)pyridin-4-yl)oxy)pyridin-2-yl)-2-oxo-3-(tetrahydro-2H-pyran-4-yl)imidazolidine-1-carboxamide, 3-cyclohexyl-N-(5-((2-(1-methyl-1H-pyrazol-4-yl)pyridin-4-yl)oxy)pyridin-2-yl)-2-oxoimidazolidine-1-carboxamide, (S)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide, 3-(2-(1-methoxycyclopropyl)ethyl)-N-(5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide, 3-(3-methoxypropyl)-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2-(1-methyl-1H-pyrazol-4-yl)pyridin-4-yl)oxy)pyridin-2-yl)-2-oxo-3-(2-(trifluoromethoxy)ethyl)imidazolidine-1-carboxamide, 3-cyclohexyl-N-(6-methyl-5-((2-(1-methyl-1H-pyrazol-4-yl)pyridin-4-yl)oxy)pyridin-2-yl)-2-oxoimidazolidine-1-carboxamide, (S)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-(3-methoxy-3-methylbutyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(5-((2-(1-methyl-1H-pyrazol-4-yl)pyridin-4-yl)oxy)pyridin-2-yl)-2-oxoimidazolidine-1-carboxamide, 3-(4,4-difluorocyclohexyl)-N-(6-methyl-5-((2-(1-methyl-1H-pyrazol-4-yl)pyridin-4-yl)oxy)pyridin-2-yl)-2-oxoimidazolidine-1-carboxamide, (R)—N-(5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, (R)—N-(6-methyl-5-((2-(1-methyl-1H-pyrazol-4-yl)pyridin-4-yl)oxy)pyridin-2-yl)-2-oxo-3-(tetrahydrofuran-3-yl)imidazolidine-1-carboxamide, 3-cyclopentyl-N-(6-methyl-5-((2-(1-methyl-1H-pyrazol-4-yl)pyridin-4-yl)oxy)pyridin-2-yl)-2-oxoimidazolidine-1-carboxamide, 3-cyclopentyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(5-((2-(1-methyl-1H-pyrazol-4-yl)pyridin-4-yl)oxy)pyridin-2-yl)-2-oxoimidazolidine-1-carboxamide, 3-cyclohexyl-4,4-dimethyl-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(5-((2-(1-methyl-1H-pyrazol-4-yl)pyridin-4-yl)oxy)pyridin-2-yl)-2-oxoimidazolidine-1-carboxamide, 3-isopropyl-N-(6-methyl-5-((2-(1-methyl-1H-pyrazol-4-yl)pyridin-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyridin-2-yl)-2-oxoimidazolidine-1-carboxamide, (R)—N-(6-methyl-5-((2-(1-(trideuteromethyl)-1H-pyrazol-4-yl)pyridin-4-yl)oxy)pyridine-2-yl)-2-oxo-3-(tetrahydrofuran-3-yl)imidazolidine-1-carboxamide, (S)-3-(1-methoxypropan-2-yl)-N-(6-methyl-5-((2-(1-methyl-1H-pyrazol-4-yl)pyridine-4-yl)oxy)pyridin-2-yl)-2-oxoimidazolidine-1-carboxamide, 3-(2-methoxyethyl)-N-(6-methyl-5-((2-(1-(trideuteromethyl)-1H-pyrazol-4-yl)pyridin-4-yl)oxy)pyridin-2-yl)-2-oxoimidazolidine-1-carboxamide, 4-methyl-N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, 3-methyl-N-(6-methyl-5-((2-(1-methyl-1H-pyrazol-4-yl)pyridin-4-yl)oxy)pyridin-2-yl)-2-oxoimidazolidine-1-carboxamide, 3-ethyl-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-methyl-N-(5-((2-(1-methyl-1H-pyrazol-4-yl)pyridin-4-yl)oxy)pyridin-2-yl)-2-oxoimidazolidine-1-carboxamide, 3-ethyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(1-methyl-1H-pyrazol-4-yl)pyridin-4-yl)oxy)pyridin-2-yl)-2-oxoimidazolidine-1-carboxamide, N-(5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, N-(6-ethyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-pyrazol-4-yl)pyridin-4-yl)oxy)pyridin-2-yl)-3-(oxetan-3-yl)-2-oxoimidazolidine-1-carboxamide, N-(5-((2'-methyl-[2,4'-bipyridin]-4-yl)oxy)pyridin-2-yl)-2-oxo-3-(tetrahydro-2H-pyran-4-yl)imidazolidine-1-carboxamide, N-(5-((6'-methyl-[2,3'-bipyridin]-4-yl)oxy)pyridin-2-yl)-2-oxo-3-(tetrahydro-2H-pyran-4-yl)imidazolidine-1-carboxamide, N-(6-methyl-5-((6'-methyl-[2,3'-bipyridin]-4-yl)oxy)pyridin-2-yl)-2-oxo-3-(2,2,2-trifluoroethyl)imidazolidine-1-carboxamide, N-(6-methyl-5-((6'-methyl-[2,3'-bipyridin]-4-yl)oxy)pyridin-2-yl)-2-oxo-3-(tetrahydro-2H-pyran-4-yl)imidazolidine-1-carboxamide, 3-(cyanomethyl)-N-(5-((2-(1-methyl-1H-pyrazol-4-yl)pyridin-4-yl)oxy)pyridin-2-yl)-2-oxoimidazolidine-1-carboxamide, N-(6-ethyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-cyclopentyl-N-(6-ethyl-5-((2-(1-methyl-1H-pyrazol-4-yl)pyridin-4-yl)oxy)pyridin-2-yl)-2-oxoimidazolidine-1-carboxamide, 3-cyclopentyl-N-(6-ethyl-5-((2-(1-methyl-1H-pyrazol-4-yl)pyridin-4-yl)oxy)pyridin-2-yl)-2-oxoimidazolidine-1-carboxamide (R)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide, N-(5-((2-(2-methylthiazol-5-yl)pyridin-4-yl)oxy)pyridin-2-yl)-2-oxo-3-(tetrahydro-2H-pyran-4-yl)imidazolidine-1-carboxamide, 3-ethyl-N-(6-methyl-5-((2-(4-(1-methylpiperidin-4-yl)phenyl)pyridin-4-yl)oxy)pyridin-2-yl)-2-oxoimidazolidine-1-carboxamide, 3-(2-methoxyethyl)-N-(5-((2-(2-methylthiazol-5-yl)pyridin-4-yl)oxy)pyridin-2-yl)-2-oxoimidazolidine-1-carboxamide, N-(6-ethyl-5-((6'-methyl-[2,3'-bipyridin]-4-yl)oxy)pyridin-2-yl)-2-oxo-3-(tetrahydro-2H-pyran-4-yl)imidazolidine-1-carboxamide, N-(6-ethyl-5-((2'-methyl-[2,4'-bipyridin]-4-yl)oxy)pyridin-2-yl)-2-oxo-3-(tetrahydro-2H-pyran-4-yl)imidazolidine-1- carboxamide, 3-cyclopropyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(tetrahydro-2H-pyran-4-yl)imidazolidine-1-carboxamide, 3-(2-methoxyethyl)-N-(6-methyl-5-((2-(2-methylthiazol-5-yl)pyridin-4-yl)oxy)pyridin-2-yl)-2-oxoimidazolidine-1-carboxamide, 3-ethyl-N-(6-methyl-5-((2-(4-(4-methylpiperazin-1-yl)phenyl)pyridin-4-yl)oxy)pyridine -2-yl)-2-oxoimidazolidine-1-carboxamide, 3-ethyl-N-(5-((2-(2-methylthiazol-5-yl)pyridin-4-yl)oxy)pyridin-2-yl)-2-oxoimidazolidine-1-carboxamide, 3-ethyl-N-(6-methyl-5-((2-(2-methylthiazol-5-yl)pyridin-4-yl)oxy)pyridin-2-yl)-2-oxoimidazolidine-1-carboxamide, 3-cyclopropyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-cyclopentyl-N-(4,6-dimethyl-5-((2-(1-methyl-1H-pyrazol-4-yl)pyridin-4-yl)oxy)pyridin-2-yl)-2-oxoimidazolidine-1-carboxamide, 3-methyl-N-(6-methyl-5-((2-(2-methylthiazol-5-yl)pyridin-4-yl)oxy)pyridin-2-yl)-2-oxoimidazolidine-1-carboxamide, N-(6-methyl-5-((2-(2-methylthiazol-5-yl)pyridin-4-yl)oxy)pyridin-2-yl)-2-oxo-3-(2,2,2-trifluoroethyl)imidazolidine-1-carboxamide, 3-cyclopentyl-N-(6-methyl-5-((2-(2-methylthiazol-5-yl)pyridin-4-yl)oxy)pyridin-2-yl)-2-oxoimidazolidine-1-carboxamide, N-(5-((2-(4-methyl-1H-imidazol-1-yl)pyridin-4-yl)oxy)pyridin-2-yl)-2-oxo-3-(2,2,2-trifluoroethyl)imidazolidine-1-carboxamide, N-(5-((2-(4-methyl-1H-imidazol-1-yl)pyridin-4-yl)oxy)pyridin-2-yl)-2-oxo-3-(tetrahydro-2H-pyran-4-yl)imidazolidine-1-carboxamide, 3-cyclopentyl-N-(6-ethyl-5-((2-(2-methylthiazol-5-yl)pyridin-4-yl)oxy)pyridin-2-yl)-2-oxoimidazolidine-1-carboxamide, 3-ethyl-N-(5-((2-(4-methyl-1H-imidazol-1-yl)pyridin-4-yl)oxy)pyridin-2-yl)-2-oxoimidazolidine-1-carboxamide, 3-(2-methoxyethyl)-N-(6-methyl-5-((2-(4-(1-methylpiperidin-4-yl)phenyl)pyridin-4-yl)oxy)pyridin-2-yl)-2-oxoimidazolidine-1-carboxamide, 3-(2-methoxyethyl)-N-(6-methyl-5-((2-(1-methyl-1H-imidazol-4-yl)pyridin-4-yl)oxy)pyridin-2-yl)-2-oxoimidazolidine-1-carboxamide, 3-ethyl-N-(5-((2-(1-methyl-1H-imidazol-4-yl)pyridin-4-yl)oxy)pyridin-2-yl)-2-oxoimidazolidine-1-carboxamide, N-(5-((2-(1-methyl-1H-imidazol-4-yl)pyridin-4-yl)oxy)pyridin-2-yl)-2-oxo-3-(tetrahydro-2H-pyran-4-yl)imidazolidine-1-carboxamide, N-(5-((2-(1-methyl-1H-imidazol-4-yl)pyridin-4-yl)oxy)pyridin-2-yl)-2-oxo-3-(2,2,2-trifluoroethyl)imidazolidine-1-carboxamide, 3-methyl-N-(4-methyl-5-((2-(1-methyl-1H-pyrazol-4-yl)pyridin-4-yl)oxy)pyridin-2-yl) -2-oxoimidazolidine-1-carboxamide, 3-cyclopropyl-N-(6-methyl-5-((2-(4-(1-methylpiperidin-4-yl)phenyl)pyridin-4-yl)oxy)pyridin-2-yl)-2-oxoimidazolidine-1-carboxamide, N-(6-methyl-5-((2'-methyl-[2,4'-bipyridin]-4-yl)oxy)pyridin-2-yl)-2-oxo-3-(tetrahydro -2H-pyran-4-yl)imidazolidine-1-carboxamide, 3-ethyl-N-(4-methyl-5-((2-(4-methyl-1H-imidazol-1-yl)pyridin-4-yl)oxy)pyridin-2-yl)-2-oxoimidazolidine-1-carboxamide, 3-methyl-N-(4-methyl-5-((2-(4-methyl-1H-imidazol-1-yl)pyridin-4-yl)oxy)pyridin-2-yl) -2 -oxoimidazolidine-1-carboxamide, 4-((6-(3-(tert-butyl)-2-oxoimidazolidine-1-carboxamido)pyridin-3-yl)oxy)-N -methylpicolinamide, N-(2,5-difluoro-4-((2-(1-methyl-1H-pyrazol-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-2-oxo -3-(tetrahydro-2H-pyran-4-yl)imidazolidine-1-carboxamide, N-(2-fluoro-3-methyl-4-((2-(1-methyl-1H-pyrazol-4-yl)pyridin-4-yl)oxy)phenyl)-2-oxo -3-(tetrahydro-2H-pyran-4-yl)imidazolidine-1-carboxamide, N-(4-((2-(1H-pyrazol-4-yl)pyridin-4-yl)oxy)-5-chloro-2-fluorophenyl)-2-oxo-3-(tetrahydro-2H-pyran-4-yl)imidazolidine-1-carboxamide, N-(2-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(3-chloro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(4-((2-acetamidopyridin-4-yl)oxy)-5-chloro-2-fluorophenyl)-2-oxo-3-(tetrahydro-2H -pyran-4-yl)imidazolidine-1-carboxamide, N-(2,5-difluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-(1-methoxycyclopropyl)ethyl)-2-oxoimidazolidine-1-carboxamide, N-(5-chloro-2-fluoro-4-((2-(1-methyl-1H-pyrazol-4-yl)pyridin-4-yl)oxy)phenyl)-3-(2-methoxyethyl)-2-oxoimidazolidine-1-carboxamide, N-(5-chloro-4-((2-(3,3-dimethylureido)pyridin-4-yl)oxy)-2-fluorophenyl)-2-oxo-3-(tetrahydro-2H-pyran-4-yl)imidazolidine-1-carboxamide, N-(3-fluoro-4-((2-(1-methyl-1H-pyrazol-4-yl)pyridin-4-yl)oxy)phenyl)-2-oxo-3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(3-methoxypropyl)-2-oxoimidazolidine-1-carboxamide, N-(5-chloro-2-fluoro-4-((2-(1-methyl-1H-pyrazol-4-yl)pyridin-4-yl)oxy)phenyl)-3-(oxetan-3-yl)-2-oxoimidazolidine-1-carboxamide, (S)—N-(5-chloro-2-fluoro-4-((2-(1-methyl-1H-pyrazol-4-yl)pyridin-4-yl)oxy)phenyl)-3-(1-methoxypropan-2-yl)-2-oxoimidazolidine-1-carboxamide, N-(5-chloro-2-fluoro-4-((2-(1-methyl-1H-pyrazol-4-yl)pyridin-4-yl)oxy)phenyl)-2-oxo -3-(2-(trifluoromethoxy)ethyl)imidazolidine-1-carboxamide, N-(5-chloro-2-fluoro-4-((2-(1-methyl-1H-pyrazol-4-yl)pyridin-4-yl)oxy)phenyl)-3-cyclohexyl-2-oxoimidazolidine-1-carboxamide, N-(5-chloro-2-fluoro-4-((2-(1-methyl-1H-pyrazol-4-yl)pyridin-4-yl)oxy)phenyl)-3-(3-methoxy-3-methylbutyl)-2-oxoimidazolidine-1-carboxamide, N-(5-bromo-2-fluoro-4-((2-(1-methyl-1H-pyrazol-4-yl)pyridin-4-yl)oxy)phenyl)-2-oxo -3-(tetrahydro-2H-pyran-4-yl)imidazolidine-1-carboxamide, N-(5-chloro-2-fluoro-4-((2-(1-methyl-1H-pyrazol-4-yl)pyridin-4-yl)oxy)phenyl)-3-(4,4-difluorocyclohexyl)-2-oxoimidazolidine-1-carboxamide, N-(5-chloro-2-fluoro-4-((2-(1-methyl-1H-pyrazol-4-yl)pyridin-4-yl)oxy)phenyl)-3-cyclopentyl-2-oxoimidazolidine-1-carboxamide, N-(5-chloro-2-fluoro-4-((2-(1-methyl-1H-pyrazol-4-yl)pyridin-4-yl)oxy)phenyl)-3-(2-hydroxy-3,3-dimethylbutyl)-2-oxoimidazolidine-1-carboxamide, N-(3-chloro-2-fluoro-4-((2-(1-methyl-1H-pyrazol-4-yl)pyridin-4-yl)oxy)phenyl)-2-oxo -3-(tetrahydro-2H-pyran-4-yl) imidazolidine-1-carboxamide, N-(5-chloro-4-((2-(2-cyanoacetamido)pyridin-4-yl)oxy)-2-fluorophenyl)-2-oxo-3-(tetrahydro-2H-pyran-4-yl)imidazolidine-1-carboxamide, 4-((6-(3-ethyl-2-oxoimidazolidine-1-carboxamido)pyridin-3-yl)oxy)-N -methylpicolinamide, N-(5-((2-(3,3-dimethylureido)pyridin-4-yl)oxy)pyridin-2-yl)-3-(2-methoxyethyl)-2-oxoimidazolidine-1-carboxamide, 3-ethyl-N-(5-((2-(2-methyloxazol-5-yl)pyridin-4-yl)oxy)pyridin-2-yl)-2-oxoimidazolidine-1-carboxamide, 3-ethyl-N-(6-methyl-5-((2'-methyl-[2,4'-bipyridin]-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyrimidin-2-yl)-2-oxoimidazolidine-1-carboxamide, N-(5-((2-acetamidopyridin-4-yl)oxy)pyridin-2-yl)-2-oxo-3-(tetrahydro-2H-pyran-4-yl)imidazolidine-1-carboxamide, N-(5-((2-(3,3-dimethylureido)pyridin-4-yl)oxy)pyridin-2-yl)-2-oxo-3-(tetrahydro-2H -pyran-4-yl)imidazolidine-1-carboxamide, N-(5-((2-acetamidopyridin-4-yl)oxy)-6-methylpyridin-2-yl)-2-oxo-3-(tetrahydro-2H-pyran-4-yl)imidazolidine-1-carboxamide, and N-(5-((2-acetamidopyridin-4-yl)oxy)-6-methylpyridin-2-yl)-3-ethyl-2-oxoimidazolidine-1-carboxamide.

16. A pharmaceutical composition, comprising a compound of claim 15 and a pharmaceutically acceptable carrier.

17. A compound selected from the group consisting of 3-(tert-butyl)-N-(6-methyl-5-((2-(1-methyl-1H-pyrazol-4-yl)pyridin-4-yl)oxy)pyridin-2-yl)-2-oxoimidazolidine-1-carboxamide, 3-(tert-butyl)-N-(5-((2-(1-methyl-1H-pyrazol-4-yl)pyridin-4-yl)oxy)pyridin-2-yl)-2-oxoimidazolidine-1-carboxamide, 3-isopropyl-N-(6-methyl-5-((2-(1-methyl-1H-pyrazol-4-yl)pyridin-4-yl)oxy)pyridin-2-yl)-2-oxoimidazolidine-1-carboxamide, 3-isopropyl-N-(5-((2-(1-methyl-1H-pyrazol-4-yl)pyridin-4-yl)oxy)pyridin-2-yl)-2-oxoimidazolidine-1-carboxamide, 3-methyl-N-(6-methyl-5-((2-(1-methyl-1H-pyrazol-4-yl)pyridin-4-yl)oxy)pyridin-2-yl)-2-oxoimidazolidine-1-carboxamide, 3-ethyl-N-(6-methyl-5-((2-(1-methyl-1H-pyrazol-4-yl)pyridin-4-yl)oxy)pyridin-2-yl)-2-oxoimidazolidine-1-carboxamide, N-(6-methyl-5-((2-(1-methyl-1H-pyrazol-4-yl)pyridin-4-yl)oxy)pyridin-2-yl)-2-oxo-3-(2,2,2-trifluoroethyl)imidazolidine-1-carboxamide, 3-ethyl-N-(5-((2-(1-methyl-1H-pyrazol-4-yl)pyridin-4-yl)oxy)pyridin-2-yl)-2-oxoimidazolidine-1-carboxamide, 3-cyclopropyl-N-(6-methyl-5-((2-(1-methyl-1H-pyrazol-4-yl)pyridin-4-yl)oxy)pyridin-2-yl)-2-oxoimidazolidine-1-carboxamide, 3-ethyl-N-(6-methyl-5-((2-(4-(1-methylpiperidin-4-yl)phenyl)pyridin-4-yl)oxy)pyridin-2-yl)-2-oxoimidazolidine-1-carboxamide, 3-ethyl-N-(6-methyl-5-((2-(4-(4-methylpiperazin-1-yl)phenyl)pyridin-4-yl)oxy)pyridine-2-yl)-2-oxoimidazolidine-1-carboxamide, 3-ethyl-N-(5-((2-(2-methylthiazol-5-yl)pyridin-4-yl)oxy)pyridin-2-yl)-2-oxoimidazolidine-1-carboxamide, N-(5-((2-(1-methyl-1H-imidazol-4-yl)pyridin-4-yl)oxy)pyridin-2-yl)-2-oxo-3-(2,2,2-trifluoroethyl)imidazolidine-1-carboxamide, and 3-ethyl-N-(4-methyl-5-((2-(4-methyl-1H-imidazol-1-yl)pyridin-4-yl)oxy)pyridin-2-yl)-2-oxoimidazolidine-1-carboxamide.

18. A pharmaceutical composition, comprising a compound of claim 17 and a pharmaceutically acceptable carrier.

19. A compound selected from the group consisting of 3-(2-methoxyethyl)-N-(5-((2-(1-methyl-1H-pyrazol-4-yl)pyridin-4-yl)oxy)pyridin-2-yl)-2-oxoimidazolidine-1-carboxamide, 3-(3-methoxypropyl)-N-(5-((2-(1-methyl-1H-pyrazol-4-yl)pyridin-4-yl)oxy)pyridin-2-yl)-2-oxoimidazolidine-1-carboxamide, (S)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide, 3-(3-methoxypropyl)-N-(6-methyl-5-((2-(1-methyl-1H-pyrazol-4-yl)pyridin-4-yl)oxy)pyridin-2-yl)-2-oxoimidazolidine-1-carboxamide, (S)-3-(1-methoxypropan-2-yl)-N-(6-methyl-5-((2-(1-methyl-1H-pyrazol-4-yl)pyridin-4-yl)oxy)pyridin-2-yl)-2-oxoimidazolidine-1-carboxamide, 3-(2-methoxyethyl)-N-(6-methyl-5-((2-(1-(trideuteromethyl)-1H-pyrazol-4-yl)pyridin-4-yl)oxy)pyridin-2-yl)-2-oxoimidazolidine-1-carboxamide, and (R)-3-(1-methoxypropan-2-yl)-N-(5-((2-(1-methyl-1H-pyrazol-4-yl)pyridin-4-yl)oxy)pyridin-2-yl)-2-oxoimidazolidine-1-carboxamide.

20. A pharmaceutical composition, comprising a compound of claim 19 and a pharmaceutically acceptable carrier.

21. A compound selected from the group consisting of N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(6-methyl-5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide, N-(5-((2-(1-ethyl-1H-pyrazol-4-yl)pyridin-4-yl)oxy)pyridin-2-yl)-2-oxo-3-(tetrahydro-2H-pyran-4-yl)imidazolidine-1-carboxamide, 2-oxo-3-(tetrahydro-2H-pyran-4-yl)-N-(5-((2-(1-(trideuteromethyl)-1H-pyrazol-4-yl)pyridin-4-yl)oxy)pyridin-2-yl)imidazolidine-1-carboxamide, N-(5-((2-(3-methylisoxazol-5-yl)pyridin-4-yl)oxy)pyridin-2-yl)-2-oxo-3-(tetrahydro-2H-pyran-4-yl)imidazolidine-1-carboxamide, N-(5-((6-(1-methyl-1H-pyrazol-4-yl)pyrimidin-4-yl)oxy)pyridin-2-yl)-2-oxo-3-(tetrahydro-2H-pyran-4-yl)imidazolidine-1-carboxamide, and N-(6-methyl-5-((2-(3-methylisoxazol-5-yl)pyridin-4-yl)oxy)pyridin-2-yl)-2-oxo-3-(tetrahydro-2H-pyran-4-yl)imidazolidine-1-carboxamide.

22. A pharmaceutical composition, comprising a compound of claim 21 and a pharmaceutically acceptable carrier.

23. The compound of claim 1 which is 3-ethyl-N-(6-methyl-5-((2-(1-methyl-1H-pyrazol-4-yl)pyridin-4-yl)oxy)pyridin-2-yl)-2-oxoimidazolidine-1-carboxamide.

24. A pharmaceutical composition, comprising the compound of claim 23 and a pharmaceutically acceptable carrier.

25. The compound of claim 1 which is 3-(2-methoxyethyl)-N-(6-methyl-5-((2-(1-methyl-1H-pyrazol-4-yl)pyridin-4-yl)oxy)pyridin-2-yl)-2-oxoimidazolidine-1-carboxamide.

26. A pharmaceutical composition, comprising the compound of claim 25 and a pharmaceutically acceptable carrier.

27. The compound of claim 1 which is 3-methyl-N-(6-methyl-5-((2-(1-methyl-1H-pyrazol-4-yl)pyridin-4-yl)oxy)pyridin-2-yl)-2-oxoimidazolidine-1-carboxamide.

28. A pharmaceutical composition, comprising the compound of claim 27 and a pharmaceutically acceptable carrier.

29. The compound of claim 1 which is N-(5-((2-(1-methyl-1H-pyrazol-4-yl)pyridin-4-yl)oxy)pyridin-2-yl)-2-oxo-3-(tetrahydro-2H-pyran-4-yl)imidazolidine-1-carboxamide.

30. A pharmaceutical composition, comprising the compound of claim 29 and a pharmaceutically acceptable carrier.

31. A pharmaceutical composition, comprising a compound of claim 1 and a pharmaceutically acceptable carrier.

32. The composition of claim 31 further comprising an additive selected from adjuvants, excipients, diluents, or stabilizers.

* * * * *